United States Patent
Blokker et al.

(10) Patent No.: US 12,251,391 B2
(45) Date of Patent: Mar. 18, 2025

(54) METHODS OF SUPPORTING GASTROINTESTINAL HOMEOSTASIS

(71) Applicant: DSM IP Assets B.V., Heerlen (NL)

(72) Inventors: Britta Blokker, Saint-Louis (FR); Stephane Duval, Carspach (FR); John Michael Geremia, Watertown, MA (US); Estefania Perez Calvo, Rosenau (FR); Nathalie Richard, Mulhouse (FR); Jerome Schmeisser, Mulhouse (FR); Nicole Seifert, Rheinfelden (CH); Viviane Verlhac, Dietwiller (FR)

(73) Assignee: DSM IP ASSETS B.V., Heerlen (NL)

( * ) Notice: Subject to any disclaimer, the term of this patent is extended or adjusted under 35 U.S.C. 154(b) by 983 days.

(21) Appl. No.: 17/291,481

(22) PCT Filed: Nov. 8, 2019

(86) PCT No.: PCT/US2019/060443
§ 371 (c)(1),
(2) Date: May 5, 2021

(87) PCT Pub. No.: WO2020/097446
PCT Pub. Date: May 14, 2020

(65) Prior Publication Data
US 2022/0000891 A1    Jan. 6, 2022

Related U.S. Application Data

(60) Provisional application No. 62/757,500, filed on Nov. 8, 2018, provisional application No. 62/757,465, filed on Nov. 8, 2018.

(51) Int. Cl.
| A61K 31/702 | (2006.01) |
| A23K 20/163 | (2016.01) |
| A23K 50/30 | (2016.01) |
| A23K 50/75 | (2016.01) |
| A61K 9/00 | (2006.01) |
| A61P 1/00 | (2006.01) |

(52) U.S. Cl.
CPC .......... *A61K 31/702* (2013.01); *A23K 20/163* (2016.05); *A23K 50/30* (2016.05); *A23K 50/75* (2016.05); *A61K 9/0053* (2013.01); *A61P 1/00* (2018.01)

(58) Field of Classification Search
None
See application file for complete search history.

(56) References Cited

U.S. PATENT DOCUMENTS

| 2008/0260696 A1 | 10/2008 | Massimino |
| 2012/0196811 A1 | 8/2012 | Dikovskiy |
| 2016/0213702 A1 | 7/2016 | Von Maltzahn |
| 2016/0366909 A1 | 12/2016 | Geremia |

FOREIGN PATENT DOCUMENTS

| CN | 102091089 | 6/2011 | |
| CN | 107897512 | 4/2013 | |
| DE | 10104055 | 8/2002 | |
| JP | 2010-519921 | 6/2010 | |
| JP | 2018-509176 | 4/2018 | |
| WO | 2017125929 A1 | 7/2017 | |
| WO | WO 2018/091759 | 5/2018 | |
| WO | WO-2018157900 A1 * | 9/2018 | ........... A23L 33/125 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*

San In Lee et al., Difructose dianhydride improves intestinal calcium absorption, wound healing, and barrier function, Scientific Reports, (2018) 8:7813.

International Search Report issued by the International Searching Authority in International Application No. PCT/US19/60443, dated Jan. 30, 2020 (3 pages).

Written Opinion of the International Searching Authority issued by the International Searching Authority in International Application No. PCT/US19/60443, dated Jan. 30, 2020 (6 pages).

\* cited by examiner

*Primary Examiner* — Dale R Miller

(74) *Attorney, Agent, or Firm* — NIXON & VANDERHYE P.C.

(57) ABSTRACT

The present disclosure relates to methods of feeding animals by providing feed additives that modulate the gut microbiome to prevent or treat dysfunctions in a gastrointestinal barrier. The present disclosure further relates to methods of feeding animals by providing feed additives that modulate the gut microbiome to prevent or treat infections.

13 Claims, 46 Drawing Sheets

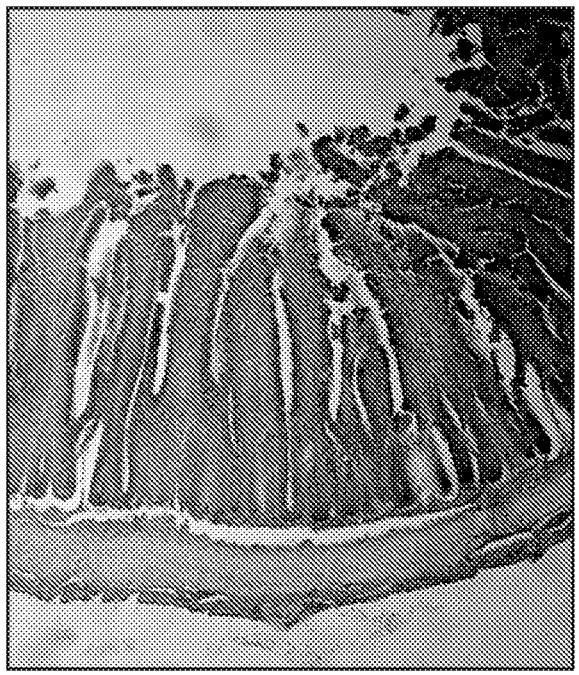 
Treatment B
(Challenge)
Treatment D
(Oligo from Example 9.2)
FIG. 24

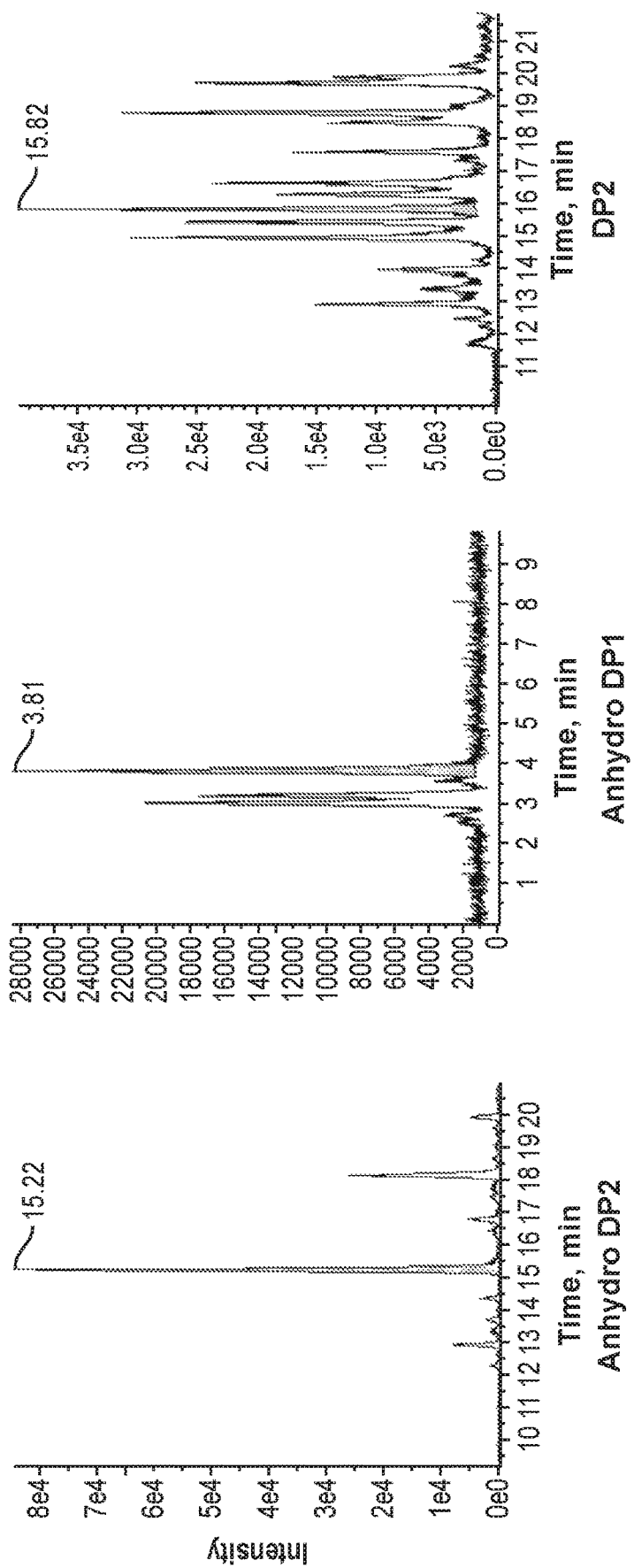
FIG. 34A Anhydro DP2
FIG. 34B Anhydro DP1
FIG. 34C DP2

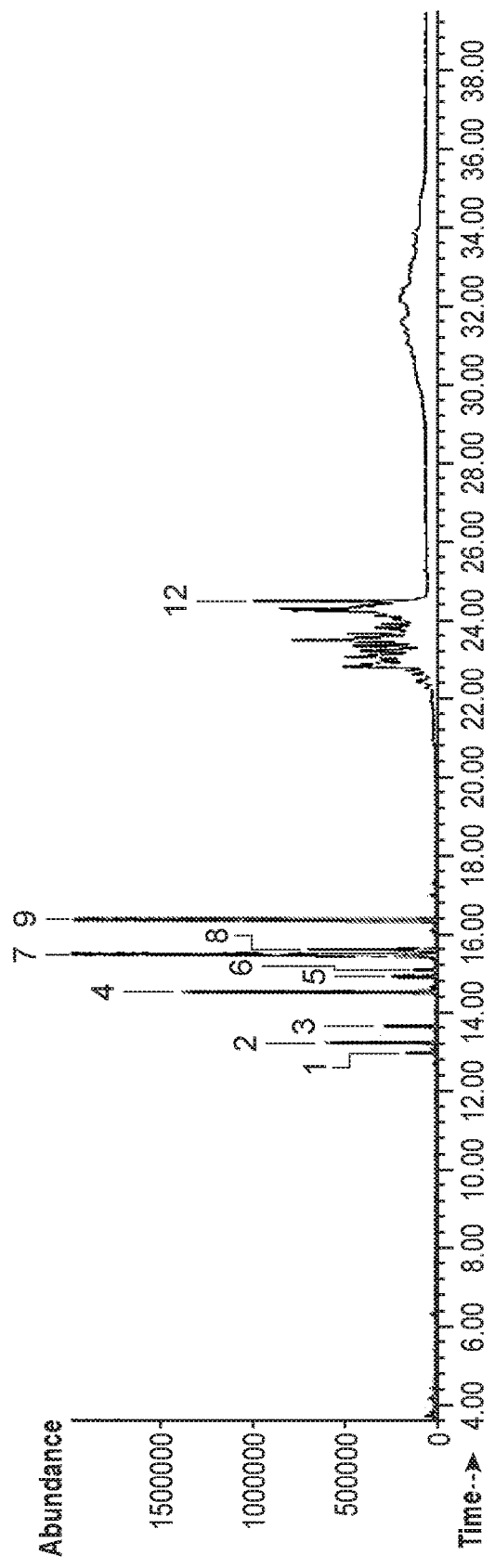
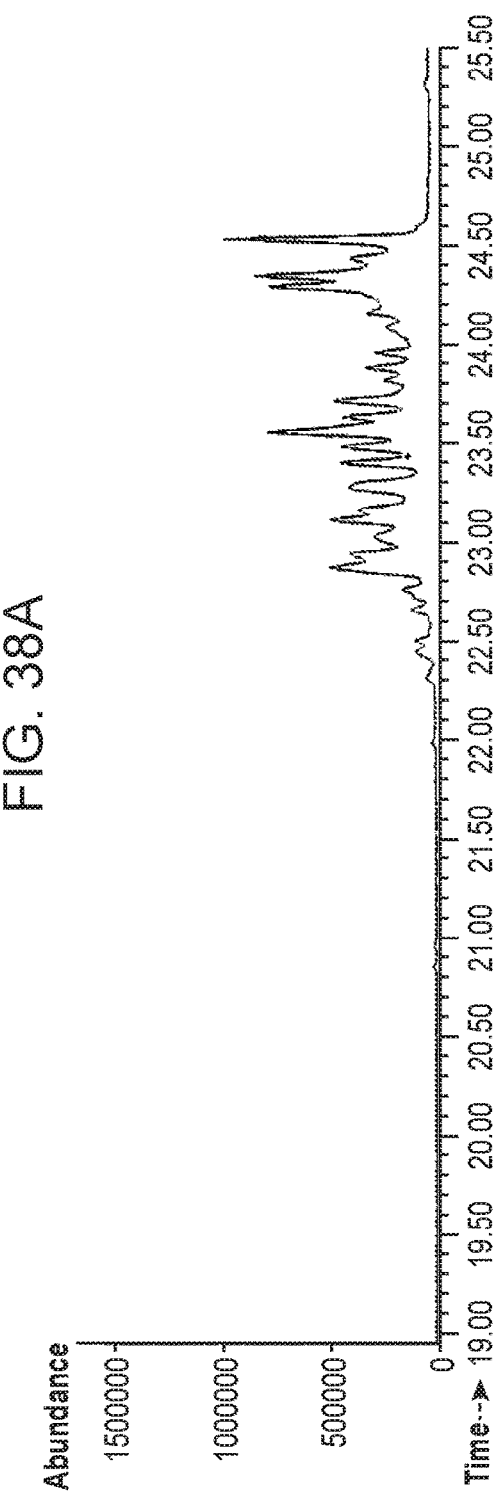
FIG. 38A
FIG. 38B

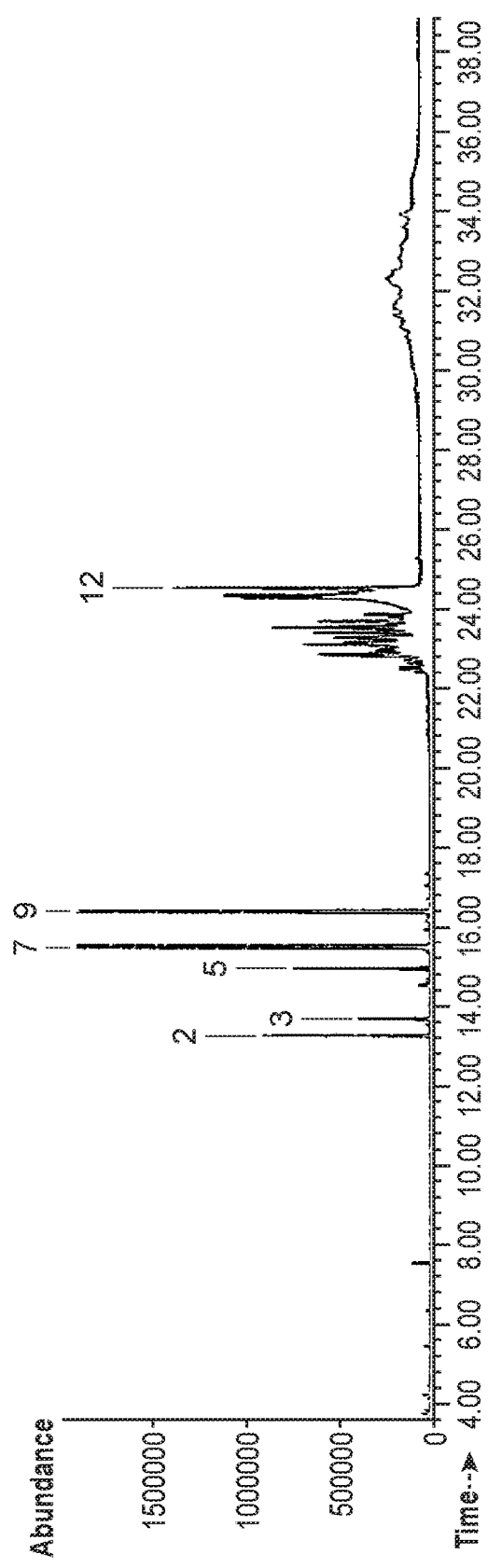
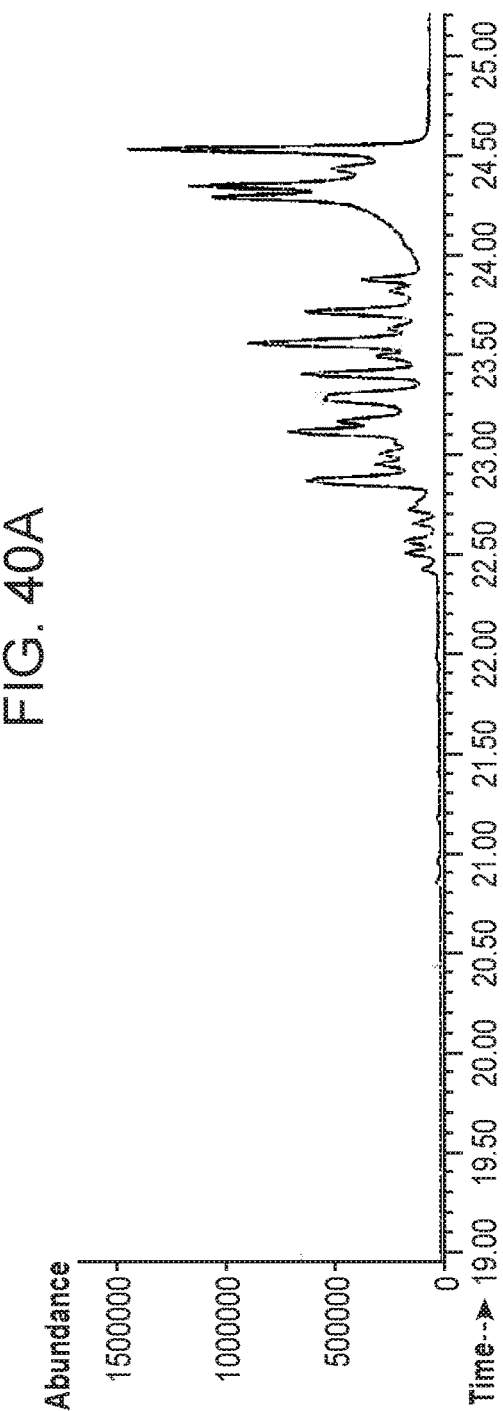
FIG. 40A
FIG. 40B

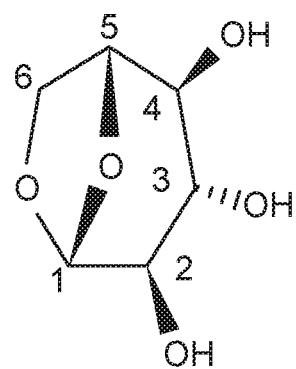
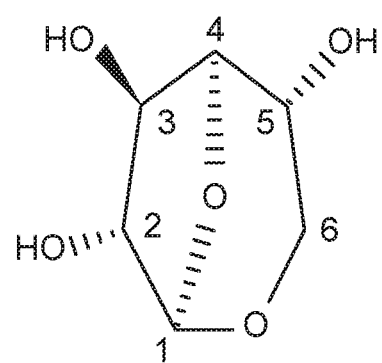
1,6-Anhydro-beta-D-glucofuranose
1,6-Anhydro-beta-D-glucopyranose
FIG. 42

METHODS OF SUPPORTING GASTROINTESTINAL HOMEOSTASIS

CROSS-REFERENCE TO RELATED APPLICATIONS

This application is a US National Stage of International Application No. PCT/US2019/060443, filed Nov. 8, 2019, which designated the US and claims the benefit of the filing date of U.S. Provisional Patent Application No. 62/757,500 filed on Nov. 8, 2018, and U.S. Provisional Application No. 62/757,465 filed on Nov. 8, 2018, the contents of each of which are hereby incorporated by reference in their entirety.

BACKGROUND

The animal gastrointestinal system is the largest surface area interface between the animal's internal anatomy and the outside world. It is responsible for digesting and absorbing nutrients and for providing an effective barrier against environmental pathogens. The gastrointestinal track (GIT) interfaces strongly with the host animal immune system and is home to the animal gut microbiome, which comprises the various microorganisms (bacteria, fungi, mold, viruses, etc.) that inhabit the digestive track.

In healthy animals, the gastrointestinal system maintains homeostasis via a complex interaction between the host animal's immune function, physiology of the intestinal mucosal layer and endothelium, and the biochemistry of the gut microbiome. Mucin and mucus production by intestinal goblet cells, non-specific immune system activity, chemokine and cytokine-mediated and inflammatory modulation, and tight-junctions between the cells of the intestinal lining promote healthy absorption of nutrients and protection against pathogens and toxins.

Disruption of gastrointestinal homeostasis results in negative health and nutritional consequences for the animal. For example, disruption of healthy barrier function enables translocation of intestinal contents to the host circulation, e.g. allowing pathogens and toxins to permeate the mucosal and endothelial layer and negatively impact the host animal. Inflammation and/or damage to the epithelial intestinal cells reduces the ability of the animal to absorb nutrients. For production animals, maintaining healthy gastrointestinal homeostasis gastrointestinal system exhibit poor nutritional and health outcomes, resulting in reduced weight gain, reduced feed efficiency, reduced meat yield, lower meat quality, and higher mortality. For companion animals, disruption of gastrointestinal homeostasis can degrade quality of life and overall health. There is therefore a considerable need to provide nutritional compositions, including animal feeds, which prevent and/or treat gastrointestinal barrier dysfunction.

SUMMARY

In one aspect, provided herein are methods of treating or preventing a gastrointestinal barrier dysfunction in an animal in need thereof, the method comprising: administering a nutritional composition that comprises a base nutritional composition and a synthetic oligosaccharide preparation to said animal, at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry, to thereby treat or prevent said gastrointestinal barrier dysfunction.

In some embodiments, permeability of a gastrointestinal barrier of said animal is decreased relative to permeability of said gastrointestinal barrier of said animal prior to said administering said synthetic oligosaccharide preparation.

In some embodiments, said decrease is at least about a 0.5%, 1%, 2%, 3%, 4%, 5%, 10%, 15%, 20%, 25%, or 30% decrease relative to said permeability of said gastrointestinal barrier of said animal prior to said administering said synthetic oligosaccharide preparation. In some embodiments, said decrease is a decrease from about 0.5-30%, 0.5-20%, 0.5-10%, 0.5-5%, 0.5-4%, 0.5-3%, 0.5-2%, 0.5-1%, 1-30%, 1-20%, 1-10%, 1-5%, 10-4%, 1-3%, or 1-2% relative to said permeability of said gastrointestinal barrier of said animal prior to said administering said synthetic oligosaccharide preparation.

In some embodiments, said decrease is a larger decrease compared to a decrease in permeability of a gastrointestinal barrier of a comparable control animal administered a nutritional composition lacking said synthetic oligosaccharide preparation. In some embodiments, said decrease is at least about a 0.5%, 1%, 2%, 3%, 4%, 5%, 10%, 15%, 20%, 25%, 30%, 40%, 50%, or 60% greater decrease compared to a decrease in permeability of a gastrointestinal barrier of a comparable control animal administered a nutritional composition lacking said synthetic oligosaccharide preparation.

In some embodiments, permeability of a gastrointestinal barrier of said animal is decreased relative to permeability of said gastrointestinal barrier of said animal prior to said administering said synthetic oligosaccharide preparation.

In some embodiments, said decrease is at least about a 0.5%, 1%, 2%, 3%, 4%, 5%, 10%, 15%, 20%, 25%, or 30% decrease relative to permeability of said gastrointestinal barrier of said animal prior to said administering said synthetic oligosaccharide preparation. In some embodiments, said decrease is a decrease from about 0.5-30%, 0.5-20%, 0.5-10%, 0.5-5%, 0.5-4%, 0.5-3%, 0.5-2%, 0.5-1%, 1-30%, 1-20%, 1-10%, 1-5%, 10-4%, 1-3%, or 1-2% relative to permeability of said gastrointestinal barrier of said animal prior to said administering said synthetic oligosaccharide preparation.

In some embodiments, said permeability of said gastrointestinal barrier is determined from a sample of said gastrointestinal barrier from said animal. In some embodiments, said permeability is measured by histologic analysis, staining, or any combination thereof.

In some embodiments, said method further comprises evaluating mucosal morphology of said gastrointestinal barrier. In some embodiments, said evaluating comprises determining villus length, crypt length, a level of inflammatory cell infiltration, or any combination thereof.

In some embodiments, said permeability of said gastrointestinal barrier is determined from a blood, fecal, or urine sample from said animal. In some embodiments, said permeability is measured by determining a level of a tracer administered orally to said animal in said sample. In some embodiments, said tracer is a non-digestible sugar, a polyethylene glycol (PEG), a fluorescently labeled dextran, or a radioisotope. In some embodiments, said permeability is measured by determining a level of at least one microbial species in said blood, fecal, or urine sample.

In some embodiments, said permeability is measured by determining a level of an antibody that binds at least one microbial species in said sample. In some embodiments, said at least one microbial species is present in said animal's gastrointestinal tract.

In some embodiments, said decrease in permeability of said gastrointestinal barrier is mediated directly by said synthetic oligosaccharide preparation. In some embodiments, said decrease permeability of said gastrointestinal barrier is mediated indirectly by said synthetic oligosaccharide preparation. In some embodiments, said synthetic oligosaccharide preparation is processed in vivo into at least one secondary species. In some embodiments, said synthetic oligosaccharide preparation is processed in vivo by a component of said animal's gastrointestinal microbiome. In some embodiments, said synthetic oligosaccharide preparation is processed in vivo by a bacterium present in the gastrointestinal tract of said animal. In some embodiments, said decrease in gastrointestinal permeability is mediated directly by said at least one secondary species.

In some embodiments, said gastrointestinal barrier dysfunction is a hyper-permeable gastrointestinal barrier. In some embodiments, said hyper-permeable gastrointestinal barrier allows translocation of intestinal contents from an intraluminal space into circulation of the animal. In some embodiments, said intestinal contents comprises food particles, microorganisms, toxins, or any combination thereof.

In some embodiments, at least one symptom associated with said gastrointestinal barrier dysfunction is ameliorated or prevented. In some embodiments, said at least one symptom is decreased mucus synthesis, decreased mucin synthesis, decreased mucus secretion, decreased mucin secretion, decreased nutrient absorption, increased inflammation, decreased resistance to infection, decreased proliferation of intestinal epithelial cells, decreased maturation of intestinal epithelial cells, increased immune cells in gastrointestinal tract, increased level of pro-inflammatory cytokines or chemokines in the blood or gastrointestinal tract, irritable bowel syndrome, inflammatory bowel syndrome, rectal inflammation, system infection, system inflammation, malnutrition, decreased weight gain, weight loss, increased feed conversion ratio, decreased feed efficiency, hair loss, fecal inconsistency, or diarrhea, relative to a comparable control animal lacking said gastrointestinal barrier dysfunction.

In some embodiments, said animal has an infection. In some embodiments, said gastrointestinal barrier dysfunction is associated with or caused by an infection. In some embodiments, said infection is a parasitic, bacterial, fungal, or viral infection. In some embodiments, said infection is a parasitic infection.

In some embodiments, said parasitic infection is a Coccidiosis infection. In some embodiments, said Coccidiosis infection is an *Eimeria* infection, *Toxoplasma* infection, a *Cryptosporidium* infection, *Isospora* infection, or a *Hammondia* infection. In some embodiments, said Coccidiosis infection is an *Eimeria* infection. In some embodiments, said *Eimeria* infection is an *E. mivati, E. tenella, E. acervulina*, or *E. maxima* infection. In some embodiments, said Coccidiosis infection is a *Toxoplasma* infection. In some embodiments, said *Toxoplasma* infection is *Toxoplasma gondii*. In some embodiments, said Coccidiosis infection is a *Cryptosporidium* infection. In some embodiments, said *Cryptosporidium* infection is a *Cryptosporidium parvum, Cryptosporidium muris*, or *Cryptosporidium hominis* infection. In some embodiments, said Coccidiosis infection is an *Isospora* infection.

In some embodiments, said *Isospora* infection is an *Isospora canis, Isospora ohioensis, Isospora burrosi*, or *Isospora felis* infection. In some embodiments, said Coccidiosis infection is a *Hammondia* infection. In some embodiments, said *Hammondia* infection is a *Hammondia* spp infection. In some embodiments, said Coccidiosis infection is *Eimeria acervuline, Eimeria maxima, Eimeria mitis, Eimeria tenella, Toxoplasma gondii, Hammondia* spp. *Cryptosporidium parvum, Cryptosporidium muris, Cryptosporidium hominis, Isospora canis, Isospora ohioensis, Isospora burrosi*, or *Isospora felis* infection.

In some embodiments, said infection is a bacterial infection. In some embodiments, said bacterial infection is a Staphylococcal infection, *Shigella* infection, *Campylobacter* infection, *Salmonella* infection, *Escherichia* infection, or *Yersinia* infection.

In some embodiments, said infection causes an increase in inflammation of gastrointestinal tract, a decrease in the number of goblet cells in the gastrointestinal tract of said animal, a decrease in mucus secretion in the gastrointestinal tract of said animal, a decrease in the length of villi of a gastrointestinal barrier of said animal, damage to the villi of a gastrointestinal barrier of said animal, an increased level of immune cells in the gastrointestinal tract of said animal, an increased level of CD8+ T cells in the gastrointestinal tract of said animal, an increase in level of hepatic protein APG (alpha glycoprotein), an increase in a level of circulating antibodies, an increase in a level of circulating IgA antibodies, or a decrease in a level of circulating diamine oxidase, or any combination thereof, relative to a comparable animal without said infection.

In some embodiments, said animal has decreased inflammation of a gastrointestinal barrier relative to inflammation of said gastrointestinal barrier prior to said administering said synthetic oligosaccharide preparation. In some embodiments, said animal has decreased inflammation of a gastrointestinal barrier relative to inflammation of said gastrointestinal barrier of a comparable control animal administered a nutritional composition lacking said synthetic oligosaccharide preparation. In some embodiments, said inflammation is measured by an increase in a level of at least one anti-inflammatory cytokine. In some embodiments, said anti-inflammatory cytokine is IL1B, IL4, IL10, IL-6, IL-11, IL-13, IL1RA, or TGF-β. In some embodiments, said anti-inflammatory cytokine is IL1B, IL4, or IL10.

In some embodiments, said animal exhibits a decrease in CD8+ T cells, an increase in CD4+ T cells, an increase in a level of circulating diamine oxidase, or a decrease in circulating antibody levels (e.g., IgA), relative to said animal prior to said administering said synthetic oligosaccharide preparation. In some embodiments, said animal exhibits a decrease in CD8+ T cells, an increase in CD4+ T cells, an increase in a level of circulating diamine oxidase, or a decrease in circulating antibody levels (e.g., IgA), relative to a comparable control animal administered a nutritional composition lacking said synthetic oligosaccharide preparation.

In some embodiments, said animal exhibits increased nutrient absorption via a gastrointestinal barrier relative to said gastrointestinal barrier prior to said administering said synthetic oligosaccharide preparation. In some embodiments, said animal exhibits increased nutrient absorption via a gastrointestinal barrier relative to a gastrointestinal barrier of a comparable control animal administered a nutritional composition lacking said synthetic oligosaccharide preparation.

In some embodiments, said nutrient absorption is measured by an increase in a level of at least one gastrointestinal protein associated with nutrient absorption. In some embodiments, said protein is SI (sucrase-isomaltase), SLC5A10, SLC34A1, SLC2A2, SLC34A2, SLC23A1, SLC23A2, SLC5A8, SLC16A3, SLC4, SLC4A9, SLC4A2, SLC4A3, NPC1L1, C6orf58, DDC, MCT1, MCT4, NaS1, DTDST, PAT1, DRA, CLD, SAT1, SUT2, SGLT1, GLUT2, B⁰AT1, ATB0+, SIT1, TAUT, EAAC1, ASCT2, SN1, SN2, PEPT1, SNAT2, GLYT1, y+LAT1, y+LAT2, CD36, LFABP, NPC1L1, ABCG5, ABCG8, SVCT1, SVCT2, SMVT, GIF, AMN, CUBL, MRP1, FOLT, PCFT, FOLR1, OAT10, RFVT1, RFVT2, THTR1, THTR2, VDR, DCYTB, DMT1, HCP1, FPN1, HEPH, HAMP, ZIP4, ZIP11, ZIP8, ZIP14A, ZIP14B, ZnT1, ZnT2, CTR1, SLC3A1, SLC1A4, ALPI, C17orf78, MUC17, DEFA5, RBP2, DEFA6, MLN, MEP1B, LCT, TM4SF20, or FABP6. In some embodiments, said protein is SI, SLC5A10 or SLC34A1.

In some embodiments, said animal has an increased body weight relative to a body weight of said animal prior to administration of said synthetic oligosaccharide preparation. In some embodiments, said body weight of said animal is at least 1%, 2%, 3%, 4%, 5%, 6%, 7%, 8%, 9%, or 10% increased relative to said body weight of said animal prior to administration of said nutritional composition comprising said synthetic oligosaccharide preparation. In some embodiments, said body weight of said animal is from about 1-40%, 1-30%, 1-20%, 1-10%, 1-5%, 1-4%, 1-3%, or 1-2%, increased relative to said body weight of said animal prior to administration of said nutritional composition comprising said synthetic oligosaccharide preparation. In some embodiments, said increase in body weight is a larger increase relative to an increase in body weight in a comparable control animal administered a comparable nutritional composition lacking said synthetic oligosaccharide preparation. In some embodiments, said increase in body weight is at least a 1%, 2%, 3%, 4%, 5%, 6%, 7%, 8%, 9%, or 10% larger increase relative to an increase in body weight in a comparable control animal administered a comparable nutritional composition lacking said synthetic oligosaccharide preparation. In some embodiments, said increase in body weight is a from about 1-40%, 1-30%, 1-20%, 1-10%, 1-5%, 1-4%, 1-3%, or 1-2% larger increase relative to an increase in body weight in a comparable control animal administered a comparable nutritional composition lacking said synthetic oligosaccharide preparation.

In some embodiments, said animal has an increased feed efficiency relative to a feed efficiency of said animal prior to administration of said synthetic oligosaccharide preparation. In some embodiments, said feed efficiency of said animal is at least 1%, 2%, 3%, 4%, 5%, 6%, 7%, 8%, 9%, or 10% increased relative to said feed efficiency of said animal prior to administration of said nutritional composition comprising said synthetic oligosaccharide preparation. In some embodiments, said feed efficiency of said animal is from about 1-40%, 1-35%, 1-30%, 1-25%, 1-20%, 1-15%, 1-10%, 1-5%, 1-4%, 1-3%, or 1-2%, increased relative to said body weight of said animal prior to administration of said nutritional composition comprising said synthetic oligosaccharide preparation. In some embodiments, said increase in feed efficiency is a larger increase relative to a comparable control animal administered a comparable nutritional composition lacking said synthetic oligosaccharide preparation. In some embodiments, said increase in feed efficiency is at least a 1%, 2%, 3%, 4%, 5%, 6%, 7%, 8%, 9%, or 10% larger increase relative to said increase in feed efficiency in said comparable control animal administered said comparable nutritional composition lacking said synthetic oligosaccharide preparation. In some embodiments, said increase in feed efficiency is a from about 1-40%, 1-30%, 1-20%, 1-10%, 1-5%, 1-4%, 1-3%, or 1-2% larger increase relative to said increase in feed efficiency in said comparable control animal administered said comparable nutritional composition lacking said synthetic oligosaccharide preparation.

In some embodiments, said animal has a decreased feed conversion ratio (FCR) relative to an FCR of said animal prior to administration of said synthetic oligosaccharide preparation. In some embodiments, said feed conversion ratio of said animal is at least 1%, 2%, 3%, 4%, 5%, 6%, 7%, 8%, 9%, or 10% decreased relative to the feed conversion ratio of said animal prior to administration of said nutritional composition comprising said synthetic oligosaccharide preparation. In some embodiments, said feed conversion ratio (FCR) of said animal is from about 1-40%, 1-35%, 1-30%, 1-25%, 1-20%, 1-15%, 1-10%, 1-5%, 1-4%, 1-3%, or 1-2%, decreased relative to said body weight of said animal prior to administration of said nutritional composition comprising said synthetic oligosaccharide preparation. In some embodiments, said animal has said decrease in feed conversion ratio is a larger decrease relative to a comparable control animal administered a comparable nutritional composition lacking said synthetic oligosaccharide preparation. In some embodiments, said decrease in feed conversion ratio is at least a 1%, 2%, 3%, 4%, 5%, 6%, 7%, 8%, 9%, or 10% larger decrease relative to said decrease in feed conversion ratio in said comparable control animal administered said comparable nutritional composition lacking said synthetic oligosaccharide preparation. In some embodiments, said decrease in feed conversion ratio is a from about 1-40%, 1-30%, 1-20%, 1-10%, 1-5%, 1-4%, 1-3%, or 1-2% larger decrease relative to said decrease in feed conversion ratio in said comparable control animal administered said comparable nutritional composition lacking said synthetic oligosaccharide preparation.

In some embodiments, a life expectancy or survival rate of said animal is increased relative to a comparable control animal that was administered a comparable nutritional composition lacking said synthetic oligosaccharide preparation.

In some embodiments, said nutritional composition that comprises said synthetic oligosaccharide preparation is administered to said animal in an amount sufficient to treat or prevent said gastrointestinal barrier dysfunction.

In some embodiments, said nutritional composition that comprises said synthetic oligosaccharide preparation is administered to said animal for at least 1, 7, 10, 14, 30, 45, 60, 90, or 120 days. In some embodiments, said nutritional composition that comprises said synthetic oligosaccharide preparation is administered to said animal at least once, twice, three, four, or five times a day. In some embodiments, said administering comprises providing said nutritional composition that comprises said synthetic oligosaccharide preparation to said animal to ingest at will. In some embodiments, said animal ingests at least a portion of said nutritional composition that comprises said synthetic oligosaccharide preparation in over at least 1, 2, 3, 4, 5, 6, 7, 8, 9, 10, 20, 30, 40, 50, 60, 90, or 120 twenty-four-hour periods.

In some embodiments, said nutritional composition comprises at least 100 ppm, 200 ppm, 300 ppm, 400 ppm, 500 ppm, 600 ppm, 700 ppm, 800 ppm, 900 ppm, 1000 ppm, 1500 ppm, or 2000 ppm of said synthetic oligosaccharide preparation. In some embodiments, said nutritional composition comprises about 100 ppm, 200 ppm, 300 ppm, 400 ppm, 500 ppm, 600 ppm, 700 ppm, 800 ppm, 900 ppm, 1000 ppm, 1500 ppm, or 2000 ppm of said synthetic oligosaccharide preparation. In some embodiments, said nutritional composition comprises about 500 ppm of said synthetic oligosaccharide preparation. In some embodiments, said nutritional composition comprises from about 100 ppm-2000 ppm, 100 ppm-1500 ppm, 100 ppm-1000 ppm, 100 ppm-900 ppm, 100 ppm-800 ppm, 100 ppm-700 ppm, 100 ppm-600 ppm, 100 ppm-500 ppm, 100 ppm-400 ppm, 100 ppm-300 ppm, 100 ppm-200 ppm, 200 ppm-1000 ppm, 200 ppm-800 ppm, 200 ppm-700 ppm, 200 ppm-600 ppm, 200 ppm-500 ppm, 300 ppm-1000 ppm, 300 ppm-700 ppm, 300 ppm-600 ppm, or 300 ppm-500 ppm of said synthetic oligosaccharide preparation. In some embodiments, said nutritional composition comprises from about 300 ppm-600 ppm of said synthetic oligosaccharide preparation.

In some embodiments, the animal is a poultry, seafood, sheep, cow, cattle, buffalo, bison, pig, cat, dog, rabbit, goat, guinea pig, donkey, camel, horse, pigeon, ferret, gerbil, hamster, mouse, rat, fish, shrimp, or bird.

In some embodiments, the animal is poultry. In some embodiments, the animal is a chicken, turkey, duck, or goose. In some embodiments, said chicken is a broiler chicken, a layer chicken, or a breeder chicken.

In some embodiments, the animal is a pig. In some embodiments, said pig is a nursery pig, a grower pig, or a finisher pig.

In some embodiments, said animal is a fish. In some embodiments, said fish is a salmon, a tilapia, or a tropical fish.

In some embodiments, said nutritional composition is an animal feed composition. In some embodiments, said base nutritional composition is base animal feed.

In some embodiments, said relative abundance is determined by LC-MS/MS.

In some embodiments, said relative abundance of oligosaccharides in at least 5, 10, 20, or 30 DP fractions decreases monotonically with its degree of polymerization. In some embodiments, said relative abundance of oligosaccharides in each of the n fractions decreases monotonically with its degree of polymerization.

In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In some embodiments, said DP2 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance.

In some embodiments, said DP2 fraction comprises from about 5% to about 10% of anhydro-subunit containing oligosaccharides by relative abundance. In some embodiments, said DP2 fraction comprises from about 1% to about 10% of anhydro-subunit containing oligosaccharides by relative abundance. In some embodiments, said DP2 fraction comprises from about 0.5% to about 10% of anhydro-subunit containing oligosaccharides by relative abundance. In some embodiments, said DP2 fraction comprises from about 2% to about 12% of anhydro-subunit containing oligosaccharides by relative abundance.

In some embodiments, said DP1 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP1 fraction comprises from about 2% to about 12% of anhydro-subunit containing oligosaccharides by relative abundance. In some embodiments, said DP1 fraction comprises from about 1% to about 10% of anhydro-subunit containing oligosaccharides by relative abundance. In some embodiments, said DP1 fraction comprises from about 0.5% to about 10% of anhydro-subunit containing oligosaccharides by relative abundance. In some embodiments, said DP1 fraction comprises from about 5% to about 10% of anhydro-subunit containing oligosaccharides by relative abundance.

In some embodiments, said DP3 fraction comprises less than 15%, less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP3 fraction comprises from about 2% to about 12% of anhydro-subunit containing oligosaccharides by relative abundance. In some embodiments, said DP3 fraction comprises from about 1% to about 10% of anhydro-subunit containing oligosaccharides by relative abundance. In some embodiments, said DP3 fraction comprises from about 0.5% to about 10% of anhydro-subunit containing oligosaccharides by relative abundance. In some embodiments, said DP3 fraction comprises from about 5% to about 10% of anhydro-subunit containing oligosaccharides by relative abundance.

In some embodiments, said oligosaccharide preparation comprises from about 2% to about 12% anhydro-subunit containing oligosaccharides by relative abundance. In some embodiments, said oligosaccharide preparation comprises from about 0.5% to about 10% anhydro-subunit containing oligosaccharides by relative abundance. In some embodiments, said oligosaccharide preparation comprises from about 1% to about 10% anhydro-subunit containing oligosaccharides by relative abundance. In some embodiments, said oligosaccharide preparation comprises from about 5% to about 10% anhydro-subunit containing oligosaccharides by relative abundance.

In some embodiments, said DP2 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP1 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP3 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation comprises greater than 0.5%, 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation has a DP1 fraction content of from about 1% to about 40% by weight as determined by liquid chromatography.

In some embodiments, said oligosaccharide preparation has a DP2 fraction content of from about 1% to about 35% by weight as determined by liquid chromatography.

In some embodiments, said oligosaccharide preparation has a DP3 fraction content of from about 1% to about 30% by weight as determined by liquid chromatography.

In some embodiments, said oligosaccharide preparation has a DP4 fraction content of from about 0.1% to about 20% by weight as determined by liquid chromatography In some embodiments, said oligosaccharide preparation has a DP5 fraction content of from about 0.1% to about 15% by weight as determined by liquid chromatography.

In some embodiments, a ratio of the DP2 fraction to the DP1 fraction is from about 0.02 to about 0.40 as determined by liquid chromatography.

In some embodiments, a ratio of the DP3 fraction to the DP2 fraction is from about 0.01 to about 0.30 as determined by liquid chromatography.

In some embodiments, an aggregate content of the DP1 and the DP2 fractions in the oligosaccharide preparation is less than 50%, less than 40%, or less than 30% as determined by liquid chromatography.

In some embodiments, said oligosaccharide preparation comprises at least 103, at least 104, at least 105, at least 106 or at least 109 different oligosaccharide species.

In some embodiments, two or more independent oligosaccharides comprise different anhydro-subunits.

In some embodiments, each of said anhydro-subunit containing oligosaccharides comprises one or more anhydro-subunits that are products of thermal dehydration of monosaccharides.

In some embodiments, said oligosaccharide preparation comprises one or more anhydro-subunits selected from anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, and anhydro-xylose.

In some embodiments, said oligosaccharide preparation comprises one or more anhydro-glucose, anhydro-galactose, anhydro-mannose, or anhydro-fructose subunits.

In some embodiments, said DP1 fraction comprises 1,6-anhydro-β-D-glucofuranose or 1,6-anhydro-β-D-glucopyranose anhydro-subunits. In some embodiments, said DP1 fraction comprises both 1,6-anhydro-β-D-glucofuranose and 1,6-anhydro-β-D-glucopyranose anhydro-subunits.

In some embodiments, a ratio of the 1,6-anhydro-β-D-glucofuranose to the 1,6-anhydro-β-D-glucopyranose is from about 10:1 to 1:10, from about 9:1 to about 1:10, from about 8:1 to about 1:10, from about 7:1 to about 1:10, from about 6:1 to about 1:10, from about 5:1 to about 1:10, from about 4:1 to about 1:10, from about 3:1 to about 1:10, from about 2:1 to about 1:10, from about 10:1 to about 1:9, from about 10:1 to about 1:8, from about 10:1 to about 1:7, from about 10:1 to about 1:6, from about 10:1 to about 1:5, from about 10:1 to about 1:4, from about 10:1 to about 1:3, from about 10:1 to about 1:2, or from about 1:1 to about 3:1 in the oligosaccharide reparation. In some embodiments, a ratio of the 1,6-anhydro-β-D-glucofuranose to the 1,6-anhydro-β-D-glucopyranose is about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 in the oligosaccharide preparation. In some embodiments, a ratio of the 1,6-anhydro-β-D-glucofuranose to the 1,6-anhydro-β-D-glucopyranose is about 2:1 in the oligosaccharide preparation.

In some embodiments, said DP2 fraction comprises at least 5 species of anhydro-subunit containing oligosaccharides. In some embodiments, said DP2 fraction comprises about 5 to 10 species of anhydro-subunit containing oligosaccharides.

In some embodiments, said oligosaccharide preparation comprises one or more sugar caramelization products. In some embodiments, said sugar caramelization products are selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf).

In some embodiments, greater than 50%, 60%, 70%, 80%, 90%, 95%, or 99% of the anhydro-subunit containing oligosaccharides comprise a chain-end anhydro-subunit.

In some embodiments, said oligosaccharide preparation has a weight average molecular weight of from about 300 to about 5000 g/mol as determined by high-performance liquid chromatography (HPLC). In some embodiments, said oligosaccharide preparation has a weight average molecular weight of from about 300 to about 2500 g/mol as determined by HPLC. In some embodiments, said oligosaccharide preparation has a weight average molecular weight of from about 500 to about 2000 g/mol as determined by HPLC. In some embodiments, said oligosaccharide preparation has a weight average molecular weight of from about 500 to about 1500 g/mol as determined by HPLC. In some embodiments, said oligosaccharide preparation has a number average molecular weight of from about 300 to about 5000 g/mol as determined by HPLC. In some embodiments, said oligosaccharide preparation has a number average molecular weight of from about 300 to about 2500 g/mol as determined by HPLC. In some embodiments, said oligosaccharide preparation has a number average molecular weight of from about 500 to about 2000 g/mol as determined by HPLC. In some embodiments, said oligosaccharide preparation has a number average molecular weight of from about 500 to about 1500 g/mol as determined by HPLC.

In some embodiments, said oligosaccharide preparation has a weight average molecular weight of from about 2000 to about 2800 g/mol. In some embodiments, said oligosaccharide preparation has a number average molecular weight of from about 1000 to about 2000 g/mol.

In one aspect, provided herein are methods of treating or preventing an infection in an animal in need thereof, the method comprising administering a nutritional composition comprising a base nutritional composition and a synthetic oligosaccharide preparation to said animal, at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry; to thereby treat or prevent said infection.

In some embodiments, a level of at least one immune cell in a sample from said animal is increased relative to a level of said at least one immune cell in a sample from said animal prior to administration of said nutritional composition that comprises said synthetic oligosaccharide preparation. In some embodiments, said increase is at least 1%, 2%, 3%, 4%, 5%, 6%, 7%, 8%, 9%, or 10% increased relative to said level of said at least one immune cell prior to administration of said nutritional composition comprising said synthetic oligosaccharide preparation. In some embodiments, said increase from about 1-40%, 1-35%, 1-30%, 1-25%, 1-20%, 1-15%, 1-10%, 1-5%, 1-4%, 1-3%, or 1-2%, increased relative to said level of said at least one immune cell prior to administration of said nutritional composition comprising said synthetic oligosaccharide preparation.

In some embodiments, a level of at least one immune cell in a sample from said animal is increased relative to a level of said at least one immune cell in a sample from a comparable control animal that has been administered a comparable nutritional composition lacking said synthetic oligosaccharide preparation. In some embodiments, said increase is at least 1%, 2%, 3%, 4%, 5%, 6%, 7%, 8%, 9%, or 10% increased relative to said level of said at least one immune cell in said sample from said comparable control animal that has been administered a comparable nutritional composition lacking said synthetic oligosaccharide preparation. In some embodiments, said increase from about 1-40%, 1-35%, 1-30%, 1-25%, 1-20%, 1-15%, 1-10%, 1-5%, 1-4%, 1-3%, or 1-2%, increased relative to said level of said at least one immune cell in said sample from said comparable control animal that has been administered a comparable nutritional composition lacking said synthetic oligosaccharide preparation.

In some embodiments, said at least one immune cell is a neutrophil, eosinophil, basophil, mast cell, T cell, B cell, macrophage, monocyte, granulocyte, or dendritic cell. In some embodiments, said immune cell is a phagocytic cell. In some embodiments, said phagocytic cells is a neutrophil, eosinophil, basophil, mast cell, macrophage, monocyte, or dendritic cell. In some embodiments, said immune cell is a T cell. In some embodiments, the immune cell is a granulocyte.

In some embodiments, a level of at least one pro-inflammatory cytokine in a sample from said animal is increased relative to a level of said at least one pro-inflammatory cytokine in a sample from said animal prior to administration of said nutritional composition that comprises said synthetic oligosaccharide preparation. In some embodiments, a level of at least one pro-inflammatory cytokine in a sample from said animal is increased relative to a level of said at least one pro-inflammatory cytokine in a sample from a comparable control animal that has been administered a comparable nutritional composition lacking said synthetic oligosaccharide preparation. In some embodiments, said at least one pro-inflammatory cytokine is IL1, IL-12, IL18, TNFA, IFNG, GM-CSF, IL-1β, IL6, RANTES, MCP1, IL8, MIP-1α, MIP-1β, lymphotactin, fractalkine, or GRO/KC.

In some embodiments, permeability of a gastrointestinal barrier of said animal is decreased relative to permeability of said gastrointestinal barrier of said animal prior to said administering said synthetic oligosaccharide preparation. In some embodiments, said decrease is at least about a 0.5%, 1%, 2%, 3%, 4%, 5%, 10%, 15%, 20%, 25%, or 30% decrease relative to said permeability of said gastrointestinal barrier of said animal prior to said administering said synthetic oligosaccharide preparation; or said decrease is a decrease from about 0.5-30%, 0.5-20%, 0.5-10%, 0.5-5%, 0.5-4%, 0.5-3%, 0.5-2%, 0.5-1%, 1-30%, 1-20%, 1-10%, 1-5%, 10-4%, 1-3%, or 1-2% relative to said permeability of said gastrointestinal barrier of said animal prior to said administering said synthetic oligosaccharide preparation. In some embodiments, said decrease is a larger decrease compared to a decrease in permeability of a gastrointestinal barrier of a comparable control animal administered a nutritional composition lacking said synthetic oligosaccharide preparation. In some embodiments, said decrease is at least about a 0.5%, 1%, 2%, 3%, 4%, 5%, 10%, 15%, 20%, 25%, 30%, 40%, 50%, or 60% greater decrease compared to a decrease in permeability of a gastrointestinal barrier of a comparable control animal administered a nutritional composition lacking said synthetic oligosaccharide preparation.

In some embodiments, permeability of a gastrointestinal barrier of said animal is decreased relative to permeability of said gastrointestinal barrier of said animal prior to said administering said synthetic oligosaccharide preparation. In some embodiments, said decrease is at least about a 0.5%, 1%, 2%, 3%, 4%, 5%, 10%, 15%, 20%, 25%, or 30% decrease relative to permeability of said gastrointestinal barrier of said animal prior to said administering said synthetic oligosaccharide preparation. In some embodiments, said decrease is a decrease from about 0.5-30%, 0.5-20%, 0.5-10%, 0.5-5%, 0.5-4%, 0.5-3%, 0.5-2%, 0.5-1%, 1-30%, 1-20%, 1-10%, 1-5%, 10-4%, 1-3%, or 1-2% relative to permeability of said gastrointestinal barrier of said animal prior to said administering said synthetic oligosaccharide preparation.

In some embodiments, said gastrointestinal barrier dysfunction is associated with or caused by an infection. In some embodiments, said infection is a parasitic, bacterial, fungal, or viral infection.

In some embodiments, said infection is a parasitic infection. In some embodiments, said parasitic infection is a Coccidiosis infection. In some embodiments, said Coccidiosis infection is an *Eimeria* infection, *Toxoplasma* infection, a *Cryptosporidium* infection, *Isospora* infection, or a *Hammondia* infection. In some embodiments, said Coccidiosis infection is an *Eimeria* infection. In some embodiments, said *Eimeria* infection is an *E. mivati, E. tenella, E. acervulina*, or *E. maxima* infection. In some embodiments, said Coccidiosis infection is a *Toxoplasma* infection. In some embodiments, said *Toxoplasma* infection is *Toxoplasma gondii*. In some embodiments, said Coccidiosis infection is a *Cryptosporidium* infection. In some embodiments, said *Cryptosporidium* infection is a *Cryptosporidium parvum, Cryptosporidium muris*, or *Cryptosporidium hominis* infection. In some embodiments, said Coccidiosis infection is an *Isospora* infection. In some embodiments, said *Isospora* infection is an *Isospora canis, Isospora ohioensis, Isospora burrosi*, or *Isospora felis* infection. In some embodiments, said Coccidiosis infection is a *Hammondia* infection. In some embodiments, said *Hammondia* infection is a *Hammondia* spp infection. In some embodiments, said Coccidiosis infection is *Eimeria* acervuline, *Eimeria maxima, Eimeria mitis, Eimeria tenella, Toxoplasma gondii, Hammondia* spp. *Cryptosporidium parvum, Cryptosporidium muris, Cryptosporidium hominis, Isospora canis, Isospora ohioensis, Isospora burrosi*, or *Isospora felis* infection.

In some embodiments, said infection is a bacterial infection. In some embodiments, said bacterial infection is a Staphylococcal infection, *Shigella* infection, *Campylobacter* infection, *Salmonella* infection, *Escherichia* infection, or *Yersinia* infection.

In some embodiments, wherein said nutritional composition that comprises said synthetic oligosaccharide preparation is administered to said animal in an amount sufficient to treat or prevent said infection. In some embodiments, said nutritional composition that comprises said synthetic oligosaccharide preparation is administered to said animal for at least 1, 7, 10, 14, 30, 45, 60, 90, or 120 days. In some embodiments, said nutritional composition that comprises said synthetic oligosaccharide preparation is administered to said animal at least once, twice, three, four, or five times a day. In some embodiments, said administering comprises providing said nutritional composition that comprises said synthetic oligosaccharide preparation to said animal to ingest at will. In some embodiments, said animal ingests at least a portion of said nutritional composition that comprises said synthetic oligosaccharide preparation in over at least 1, 2, 3, 4, 5, 6, 7, 8, 9, 10, 20, 30, 40, 50, 60, 90, or 120 twenty-four-hour periods.

In some embodiments, said nutritional composition comprises at least 100 ppm, 200 ppm, 300 ppm, 400 ppm, 500 ppm, 600 ppm, 700 ppm, 800 ppm, 900 ppm, 1000 ppm, 1500 ppm, or 2000 ppm of said synthetic oligosaccharide preparation. In some embodiments, said nutritional composition comprises about 100 ppm, 200 ppm, 300 ppm, 400 ppm, 500 ppm, 600 ppm, 700 ppm, 800 ppm, 900 ppm, 1000 ppm, 1500 ppm, or 2000 ppm of said synthetic oligosaccharide preparation. In some embodiments, said nutritional composition comprises about 500 ppm of said synthetic oligosaccharide preparation. In some embodiments, said nutritional composition comprises from about 100 ppm-2000 ppm, 100 ppm-1500 ppm, 100 ppm-1000 ppm, 100 ppm-900 ppm, 100 ppm-800 ppm, 100 ppm-700 ppm, 100 ppm-600 ppm, 100 ppm-500 ppm, 100 ppm-400 ppm, 100 ppm-300 ppm, 100 ppm-200 ppm, 200 ppm-1000 ppm, 200 ppm-800 ppm, 200 ppm-700 ppm, 200 ppm-600 ppm, 200 ppm-500 ppm, 300 ppm-1000 ppm, 300 ppm-700 ppm, 300 ppm-600 ppm, or 300 ppm-500 ppm of said synthetic oligosaccharide preparation. In some embodiments, said nutritional composition comprises from about 300 ppm-600 ppm of said synthetic oligosaccharide preparation.

In some embodiments, the animal is a poultry, seafood, sheep, cow, cattle, buffalo, bison, pig, cat, dog, rabbit, goat, guinea pig, donkey, camel, horse, pigeon, ferret, gerbil, hamster, mouse, rat, fish, shrimp, or bird.

In some embodiments, the animal is poultry. In some embodiments, the animal is a chicken, turkey, duck, or goose. In some embodiments, said chicken is a broiler chicken, a layer chicken, or a breeder chicken.

In some embodiments, the animal is a pig. In some embodiments, said pig is a nursery pig, a grower pig, or a finisher pig.

In some embodiments, said animal is a fish. In some embodiments, said fish is a salmon, a tilapia, or a tropical fish.

In some embodiments, said nutritional composition is an animal feed composition. In some embodiments, said base nutritional composition is base animal feed.

In some embodiments, said relative abundance is determined by LC-MS/MS.

In some embodiments, said relative abundance of oligosaccharides in at least 5, 10, 20, or 30 DP fractions decreases monotonically with its degree of polymerization. In some embodiments, said relative abundance of oligosaccharides in each of the n fractions decreases monotonically with its degree of polymerization.

In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In some embodiments, said DP2 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance.

In some embodiments, said DP2 fraction comprises from about 5% to about 10% of anhydro-subunit containing oligosaccharides by relative abundance. In some embodiments, said DP2 fraction comprises from about 1% to about 10% of anhydro-subunit containing oligosaccharides by relative abundance. In some embodiments, said DP2 fraction comprises from about 0.5% to about 10% of anhydro-subunit containing oligosaccharides by relative abundance. In some embodiments, said DP2 fraction comprises from about 2% to about 12% of anhydro-subunit containing oligosaccharides by relative abundance.

In some embodiments, said DP1 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP1 fraction comprises from about 2% to about 12% of anhydro-subunit containing oligosaccharides by relative abundance. In some embodiments, said DP1 fraction comprises from about 1% to about 10% of anhydro-subunit containing oligosaccharides by relative abundance. In some embodiments, said DP1 fraction comprises from about 0.5% to about 10% of anhydro-subunit containing oligosaccharides by relative abundance. In some embodiments, said DP1 fraction comprises from about 5% to about 10% of anhydro-subunit containing oligosaccharides by relative abundance.

In some embodiments, said DP3 fraction comprises less than 15%, less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP3 fraction comprises from about 2% to about 12% of anhydro-subunit containing oligosaccharides by relative abundance. In some embodiments, said DP3 fraction comprises from about 1% to about 10% of anhydro-subunit containing oligosaccharides by relative abundance. In some embodiments, said DP3 fraction comprises from about 0.5% to about 10% of anhydro-subunit containing oligosaccharides by relative abundance. In some embodiments, said DP3 fraction comprises from about 5% to about 10% of anhydro-subunit containing oligosaccharides by relative abundance.

In some embodiments, said oligosaccharide preparation comprises from about 2% to about 12% anhydro-subunit containing oligosaccharides by relative abundance. In some embodiments, said oligosaccharide preparation comprises from about 0.5% to about 10% anhydro-subunit containing oligosaccharides by relative abundance. In some embodiments, said oligosaccharide preparation comprises from about 1% to about 10% anhydro-subunit containing oligosaccharides by relative abundance. In some embodiments, said oligosaccharide preparation comprises from about 5% to about 10% anhydro-subunit containing oligosaccharides by relative abundance.

In some embodiments, said DP2 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP1 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP3 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation comprises greater than 0.5%, 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation has a DP1 fraction content of from about 1% to about 40% by weight as determined by liquid chromatography.

In some embodiments, said oligosaccharide preparation has a DP2 fraction content of from about 1% to about 35% by weight as determined by liquid chromatography.

In some embodiments, said oligosaccharide preparation has a DP3 fraction content of from about 1% to about 30% by weight as determined by liquid chromatography.

In some embodiments, said oligosaccharide preparation has a DP4 fraction content of from about 0.1% to about 20% by weight as determined by liquid chromatography In some embodiments, said oligosaccharide preparation has a DP5 fraction content of from about 0.1% to about 15% by weight as determined by liquid chromatography.

In some embodiments, a ratio of the DP2 fraction to the DP1 fraction is from about 0.02 to about 0.40 as determined by liquid chromatography.

In some embodiments, a ratio of the DP3 fraction to the DP2 fraction is from about 0.01 to about 0.30 as determined by liquid chromatography.

In some embodiments, an aggregate content of the DP1 and the DP2 fractions in the oligosaccharide preparation is less than 50%, less than 40%, or less than 30% as determined by liquid chromatography.

In some embodiments, said oligosaccharide preparation comprises at least 103, at least 104, at least 105, at least 106 or at least 109 different oligosaccharide species.

In some embodiments, two or more independent oligosaccharides comprise different anhydro-subunits.

In some embodiments, each of said anhydro-subunit containing oligosaccharides comprises one or more anhydro-subunits that are products of thermal dehydration of monosaccharides.

In some embodiments, said oligosaccharide preparation comprises one or more anhydro-subunits selected from anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, and anhydro-xylose.

In some embodiments, said oligosaccharide preparation comprises one or more anhydro-glucose, anhydro-galactose, anhydro-mannose, or anhydro-fructose subunits.

In some embodiments, said DP1 fraction comprises 1,6-anhydro-β-D-glucofuranose or 1,6-anhydro-β-D-glucopyranose anhydro-subunits. In some embodiments, said DP1 fraction comprises both 1,6-anhydro-β-D-glucofuranose and 1,6-anhydro-β-D-glucopyranose anhydro-subunits.

In some embodiments, a ratio of the 1,6-anhydro-β-D-glucofuranose to the 1,6-anhydro-β-D-glucopyranose is from about 10:1 to 1:10, from about 9:1 to about 1:10, from about 8:1 to about 1:10, from about 7:1 to about 1:10, from about 6:1 to about 1:10, from about 5:1 to about 1:10, from about 4:1 to about 1:10, from about 3:1 to about 1:10, from about 2:1 to about 1:10, from about 10:1 to about 1:9, from about 10:1 to about 1:8, from about 10:1 to about 1:7, from about 10:1 to about 1:6, from about 10:1 to about 1:5, from about 10:1 to about 1:4, from about 10:1 to about 1:3, from about 10:1 to about 1:2, or from about 1:1 to about 3:1 in the oligosaccharide reparation. In some embodiments, a ratio of the 1,6-anhydro-β-D-glucofuranose to the 1,6-anhydro-β-D-glucopyranose is about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 in the oligosaccharide preparation. In some embodiments, a ratio of the 1,6-anhydro-β-D-glucofuranose to the 1,6-anhydro-β-D-glucopyranose is about 2:1 in the oligosaccharide preparation.

In some embodiments, said DP2 fraction comprises at least 5 species of anhydro-subunit containing oligosaccharides. In some embodiments, said DP2 fraction comprises about 5 to 10 species of anhydro-subunit containing oligosaccharides.

In some embodiments, said oligosaccharide preparation comprises one or more sugar caramelization products. In some embodiments, said sugar caramelization products are selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf).

In some embodiments, greater than 50%, 60%, 70%, 80%, 90%, 95%, or 99% of the anhydro-subunit containing oligosaccharides comprise a chain-end anhydro-subunit.

In some embodiments, said oligosaccharide preparation has a weight average molecular weight of from about 300 to about 5000 g/mol as determined by high-performance liquid chromatography (HPLC). In some embodiments, said oligosaccharide preparation has a weight average molecular weight of from about 300 to about 2500 g/mol as determined by HPLC. In some embodiments, said oligosaccharide preparation has a weight average molecular weight of from about 500 to about 2000 g/mol as determined by HPLC. In some embodiments, said oligosaccharide preparation has a weight average molecular weight of from about 500 to about 1500 g/mol as determined by HPLC. In some embodiments, said oligosaccharide preparation has a number average molecular weight of from about 300 to about 5000 g/mol as determined by HPLC. In some embodiments, said oligosaccharide preparation has a number average molecular weight of from about 300 to about 2500 g/mol as determined by HPLC. In some embodiments, said oligosaccharide preparation has a number average molecular weight of from about 500 to about 2000 g/mol as determined by HPLC. In some embodiments, said oligosaccharide preparation has a number average molecular weight of from about 500 to about 1500 g/mol as determined by HPLC.

In some embodiments, said oligosaccharide preparation has a weight average molecular weight of from about 2000 to about 2800 g/mol. In some embodiments, said oligosaccharide preparation has a number average molecular weight of from about 1000 to about 2000 g/mol.

The disclosure is based, at least in part, on the discovery that oligosaccharides comprising one or more anhydro-subunit decrease the permeability of the gastrointestinal barrier. Accordingly, the disclosure features, inter alia, methods of preventing gastrointestinal dysfunction in an animal comprising administering an oligosaccharide preparation described herein.

In some embodiments, the relative abundance of oligosaccharides in at least 5, 10, 20, or 30 DP fractions of said oligosaccharide preparation decreases monotonically with its degree of polymerization. In some embodiments, the relative abundance of oligosaccharides in each of the n fractions of said oligosaccharide preparation decreases monotonically with its degree of polymerization. In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In some embodiments, at least one fraction of said oligosaccharide preparation comprises less than 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, said oligosaccharide preparation comprises less than 80%, 70%, 60%, 50%0, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, each fraction of said oligosaccharide preparation comprises less than 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, at least one fraction of said oligosaccharide preparation comprises less than 10%, 9%, 8%, 7%, 6%, 5%, 4%, 3%, or 2% anhydro-subunit containing oligosaccharides by relative abundance. In some embodiments, said oligosaccharide preparation comprises less than 10%, 9%, 8%, 7%, 6%, 5%, 4%, 3%, or 2% anhydro-subunit containing oligosaccharides by relative abundance. In some embodiments, each fraction of said oligosaccharide preparation comprises less than 10%, 9%, 8%, 7%, 6%, 5%, 4%, 3%, or 2% anhydro-subunit containing oligosaccharides by relative abundance. In some embodiments, at least one fraction of said oligosaccharide comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% anhydro-subunit containing oligosaccharides by relative abundance. In some embodiments, said oligosaccharide preparation comprises greater than 2%, 3%, 4%, 5%, 6%, 7%, 8%, 9%, 10%, 11%, 12%, 13%, 14%, 15%, 6%1, 7%1, 8%1, 19%, 20%, 30%, 40%, 50%, 60%, 70%, or 80% anhydro-subunit containing oligosaccharides by relative abundance. In some embodiments, each fraction of said oligosaccharide preparation comprises greater than 2%, 3%, 4%, 5%, 6%, 7%, 8%, 9%, 10%, 11%, 12%1, 3%, 14%, 15%, 6%1, 7%1, 8%1, 19%, 20%, 30%, 40%, 50%, 60%, 70%, or 80% anhydro-subunit containing oligosaccharides by relative abundance. In some embodiments, at least one fraction of said oligosaccharide preparation comprises greater than 20%, 21%, 22%, 23%, 24%, or 25% anhydro-subunit containing oligosaccharides by relative abundance. In some embodiments, said oligosaccharide preparation comprises greater than 20%, 21%, 22%, 23%, 24%, or 25% anhydro-subunit containing oligosaccharides by relative abundance. In some embodiments, each fraction of said oligosaccharide preparation comprises greater than 20%, 21%, 22%, 23%, 24%, or 25% anhydro-subunit containing oligosaccharides by relative abundance. In some embodiments, more than 99%, 95%, 90%, 85%, 80%, 75%, 70%, 65%, 60%, 55%, 50%, 45%, 40%, 35%, or 30% of the anhydro-subunit containing oligosaccharides have only one anhydro-subunit.

In some embodiments, said oligosaccharide preparation has a DP1 fraction content from 1 to 40% by relative abundance. In some embodiments, said oligosaccharide preparation has a DP2 fraction content from 1 to 35% by relative abundance. In some embodiments, said oligosaccharide preparation has a DP3 fraction content from 1 to 30% by relative abundance. In some embodiments, said oligosaccharide preparation has a DP4 fraction content from 0.1 to 20% by relative abundance. In some embodiments, said oligosaccharide preparation comprises a DP5 fraction content from 0.1 to 15% by relative abundance. In some embodiments, said oligosaccharide preparation comprises a DP2 fraction and a DP1 fraction, wherein the ratio of said DP2 fraction to said DP1 fraction is 0.02-0.40 by relative abundance. In some embodiments, said oligosaccharide preparation comprises a DP3 fraction and a DP2 fraction, wherein the ratio of said DP3 fraction to said DP2 fraction in said oligosaccharide preparation is 0.01-0.30 by relative abundance. In some embodiments, said oligosaccharide preparation comprises a DP1 fraction and a DP2 fraction, wherein the aggregate content of said DP1 and said DP2 fractions in said oligosaccharide preparation is less than 50, 30, or 10% by relative abundance. In some embodiments, said oligosaccharide preparation comprises at least 25, 50, 75, 100, 103, 104, 105, 106, 109, 110, 120, 150, or 200 different oligosaccharide species.

In some embodiments, at least two independent oligosaccharides of said oligosaccharide preparation comprise different anhydro-subunits. In some embodiments, said oligosaccharide preparation comprises at least one anhydro-subunit that is a product of reversible thermal dehydration of a monosaccharide. In some embodiments, said oligosaccharide preparation comprises at least one anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, or anhydro-xylose subunit. In some embodiments, said oligosaccharide preparation comprises at least one anhydro-glucose, anhydro-galactose, anhydro-mannose, or anhydro-fructose subunit.

In some embodiments, said oligosaccharide preparation comprises at least one 1,6-anhydro-β-D-glucofuranose or 1,6-anhydro-β-D-glucopyranose subunit. In some embodiments, said oligosaccharide preparation comprises at least one 1,6-anhydro-β-D-glucofuranose subunit and at least one 1,6-anhydro-β-D-glucopyranose anhydro-subunit. In some embodiments, a ratio of 1,6-anhydro-β-D-glucofuranose to 1,6-anhydro-β-D-glucopyranose in said oligosaccharide preparation is from about 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1. In some embodiments, a ratio of 1,6-anhydro-β-D-glucofuranose to 1,6-anhydro-β-D-glucopyranose in said oligosaccharide preparation is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10. In some embodiments, a ratio of 1,6-anhydro-β-D-glucofuranose to 1,6-anhydro-β-D-glucopyranose in said oligosaccharide preparation is about 2:1. In some embodiments, the ratio of 1,6-anhydro-β-D-glucofuranose to 1,6-anhydro-β-D-glucopyranose is about from 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in each fraction. In some embodiments, a ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 in each fraction of said oligosaccharide preparation. In some embodiments, a ratio of 1,6-anhydro-β-D-glucofuranose to 1,6-anhydro-β-D-glucopyranose is about 2:1 in each fraction of said oligosaccharide preparation. In some embodiments, at least 1%, 5%, 10%, 20%, 30%, 40%, 50%, 60%, 70%, 80%, or 90% of said anhydro-subunits in said oligosaccharide preparation are selected from a group consisting of 1,6-anhydro-β-D-glucofuranose and 1,6-anhydro-β-D-glucopyranose.

In some embodiments, said oligosaccharide preparation comprises at least one anhydro-subunit that is a sugar caramelization product. In some embodiments, said sugar caramelization product is selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf). In some embodiments, from about 0.1% to 5%, 0.1% to 2%, or 0.1% to 1% of said anhydro-subunits in said oligosaccharide preparation are caramelization products.

In some embodiments, at least 30%, 40%, 50%, 60%, 70%, 80%, 90%, 95%, or 99% of the anhydro-subunit containing oligosaccharides in said oligosaccharide preparation comprise a chain-end anhydro-subunit.

In some embodiments, the weight average molecular weight of said oligosaccharide preparation is from about 300 to 5000 g/mol, 500 to 5000 g/mol, 700 to 5000 g/mol, 500 to 2000 g/mol, 700 to 2000 g/mol, 700 to 1500 g/mol, 300 to 1500 g/mol, 300 to 2000 g/mol, 400 to 1300 g/mol, 400 to 1200 g/mol, 400 to 1100 g/mol, 500 to 1300 g/mol, 500 to 1200 g/mol, 500 to 1100 g/mol, 600 to 1300 g/mol, 600 to 1200 g/mol, or 600 to 1100 g/mol. In some embodiments, the number average molecular weight of said oligosaccharide preparation is from about 300 to 5000 g/mol, 500 to 5000 g/mol, 700 to 5000 g/mol, 500 to 2000 g/mol, 700 to 2000 g/mol, 700 to 1500 g/mol, 300 to 1500 g/mol, 300 to 2000 g/mol, 400 to 1000 g/mol, 400 to 900 g/mol, 400 to 800 g/mol, 500 to 900 g/mol, or 500 to 800 g/mol. In some embodiments, the weight average molecular weight of said oligosaccharide preparation is from about 2000 to 2800 g/mol, 2100 to 2700 g/mol, 2200 to 2600 g/mol, 2300 to 2500 g/mol, or 2320 to 2420 g/mol. In some embodiments, the number average molecular weight of said oligosaccharide preparation is from about 1000 to 2000 g/mol, 1100 to 1900 g/mol, 1200 to 1800 g/mol, 1300 to 1700 g/mol, 1400 to 1600 g/mol, or 1450 to 1550 g/mol.

In one aspect, provided herein are methods of preventing gastrointestinal barrier dysfunction in an animal, comprising: administering a nutritional composition comprising a base nutritional composition and a synthetic oligosaccharide preparation to the animal, wherein the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the permeability of the gastrointestinal barrier is lower than the permeability of the gastrointestinal barrier of an animal administered a nutritional composition lacking the synthetic oligosaccharide preparation. In some embodiments, the gastrointestinal barrier dysfunction is hyper-permeability (leaky gut).

In some embodiments, the permeability of the gastrointestinal barrier is at least about 0.5%, 1%, 2%, 3%, 4%, 5%, 10, 15%, 20%, 25%, or 30% less than the permeability of the gastrointestinal barrier of an animal administered a nutritional composition lacking the synthetic oligosaccharide preparation. In some embodiments, the permeability of the gastrointestinal barrier is about 0.5-40%, 0.5-30%, 0.5-20%, 0.5-10%, 0.5-5%, 0.5-1%, 1-40%, 1-30%, 1-20%, 1-10%, 1-5%, 1-2%, 5-40%, 5-30%, 5-20%, 5-10%, 10-40%, 10-30%, or 10-20% less than the permeability of the gastrointestinal barrier of an animal administered a nutritional composition lacking the synthetic oligosaccharide preparation.

In some embodiments, the decrease in gastrointestinal permeability is mediated directly by the synthetic oligosaccharide preparation. In some embodiments, the decrease in gastrointestinal permeability is mediated indirectly by the synthetic oligosaccharide preparation. In some embodiments, the oligosaccharide preparation is processed in vivo into one or more secondary species. In some embodiments, the synthetic oligosaccharide preparation is processed by a component of the animal's gastrointestinal microbiota. In some embodiments, the component is a gastrointestinal bacterium. In some embodiments, the decrease in gastrointestinal permeability is mediated directly by one or more of the secondary species.

In some embodiments, the animal has a decreased likelihood of developing a gastrointestinal barrier dysfunction relative to an animal administered a nutritional composition lacking the synthetic oligosaccharide preparation.

In some embodiments, the animal has a higher body weight relative to the body weight of an animal administered a nutritional composition lacking the synthetic oligosaccharide preparation. In some embodiments, the animal has a higher feed efficiency relative to the feed efficiency of an animal administered a nutritional composition lacking the synthetic oligosaccharide preparation. In some embodiments, the animal has a lower feed conversion ratio relative to the feed conversion ratio of an animal administered a nutritional composition lacking the synthetic oligosaccharide preparation.

In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig).

In some embodiments, the nutritional composition is an animal feed composition. In some embodiments, the base nutritional composition is base animal feed.

Provided herein are methods of promoting goblet cell proliferation in an animal, comprising: administering a nutritional composition comprising a base nutritional composition and an oligosaccharide preparation to the animal, wherein the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the level of goblet cells in the gastrointestinal tract of the animal is higher relative to the level of goblet cells in the gastrointestinal tract of an animal administered a nutritional composition lacking the synthetic oligosaccharide preparation. In some embodiments, the level of goblet cells in the gastrointestinal tract of the animal is at least about 0.5%, 1%, 2%, 3%, 4%, 5%, 6%, 7%, 8%, 9%, 10%, 15%, or 20% greater than the level of goblet cells in the gastrointestinal tract of an animal administered a nutritional composition lacking the synthetic oligosaccharide preparation. In some embodiments, the level of goblet cells in the gastrointestinal tract of the animal is about 0.5-20%, 0.5-15%, 0.5-10%, 0.5-5%, 0.5-1%, 1-20%, 1-15%, 1-10%, 1-5%, 1-2%, 5-20%, 5-15%, or 5-10% greater relative to the level of goblet cells in a nutritional composition lacking the synthetic oligosaccharide preparations.

In some embodiments, the increase in the level of goblet cells is mediated directly by the synthetic oligosaccharide preparation. In some embodiments, the increase in the level of goblet cells is mediated indirectly by the synthetic oligosaccharide preparation. In some embodiments, the oligosaccharide preparation is processed in vivo into one or more secondary species. In some embodiments, the synthetic oligosaccharide preparation is processed by a component of the animal's gastrointestinal microbiota. In some embodiments, the component is a gastrointestinal bacterium. In some embodiments, the increase in the number of goblet cells is mediated directly by one or more of the secondary species.

In some embodiments, the animal has a higher body weight relative to the body weight of an animal administered a nutritional composition lacking the synthetic oligosaccharide preparation. In some embodiments, the animal has a higher feed efficiency relative to the feed efficiency of an animal administered a nutritional composition lacking the synthetic oligosaccharide preparation. In some embodiments, the animal has a lower feed conversion ratio relative to the feed conversion ratio of an animal administered a nutritional composition lacking the synthetic oligosaccharide preparation.

In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig). In some embodiments, the animal is livestock. In some embodiments, the animal is a companion animal.

In some embodiments, the nutritional composition is an animal feed composition. In some embodiments, the base nutritional composition is base animal feed.

Provided herein are methods of promoting mucus production in the gastrointestinal tract of an animal, comprising: administering a nutritional composition comprising a base nutritional composition and an oligosaccharide preparation to the animal, wherein the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the level of mucus in the gastrointestinal tract of the animal is higher relative to that in an animal administered a nutritional composition lacking the synthetic oligosaccharide preparation. In some embodiments, the level of mucus is at least about 0.5%, 1%, 2%, 3%, 4%, 5%, 6%, 7%, 8%, 9%, 10%, 15%, or 20% higher relative to the level of mucus in the gastrointestinal tract of an animal administered a nutritional composition lacking the synthetic oligosaccharide preparation. In some embodiments, the level of mucus is at least about 0.5-20%, 0.5-15%, 0.5-10%, 0.5-5%, 0.5-2%, 0.5-1%, 1-20%, 1-15%, 1-10%, 1-5%, 1-2%, 5-20%, 5-15%, or 5-10% higher relative to the level of mucus in the gastrointestinal tract of an animal administered a nutritional composition lacking the synthetic oligosaccharide preparation.

In some embodiments, the method comprises obtaining a gastrointestinal sample from the animal. In some embodiments, the sample is a gastrointestinal tissue (e.g., a cecal biopsy) or a fecal sample. In some embodiments, the method comprises detecting the level of mucus in the sample. In some embodiments, the level of mucus is detected by detecting a protein component of mucus. In some embodiments, the protein is mucin.

In some embodiments, the increase in the level of mucus is mediated directly by the synthetic oligosaccharide preparation. In some embodiments, the increase in the level of mucus is mediated indirectly by the synthetic oligosaccharide preparation. In some embodiments, the oligosaccharide preparation is processed in vivo into one or more secondary species. In some embodiments, the synthetic oligosaccharide preparation is processed by a component of the animal's gastrointestinal microbiota. In some embodiments, the component is a gastrointestinal bacterium. In some embodiments, the increase in the level of mucus is mediated directly by one or more of the secondary species.

In some embodiments, the animal has a higher body weight relative to the body weight of an animal administered a nutritional composition lacking the synthetic oligosaccharide preparation. In some embodiments, the animal has a higher feed efficiency relative to the feed efficiency of an animal administered a nutritional composition lacking the synthetic oligosaccharide preparation. In some embodiments, the animal has a lower feed conversion ratio relative to the feed conversion ratio of an animal administered a nutritional composition lacking the synthetic oligosaccharide preparation.

In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig). In some embodiments, the animal is livestock. In some embodiments, the animal is a companion animal.

In some embodiments, the nutritional composition is an animal feed composition. In some embodiments, the base nutritional composition is base animal feed.

Provided herein are methods of preventing an infection of an animal, comprising: administering a nutritional composition comprising a base nutritional composition and a synthetic oligosaccharide preparation to the animal, wherein the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the level of one or more type of immune cell in the gastrointestinal tract of the animal is higher relative to the level in the gastrointestinal tract of an animal administered a nutritional composition lacking the synthetic oligosaccharide preparation.

In some embodiments, the immune cell is phagocytic. In some embodiments, the immune cell is a granulocyte. In some embodiments, the level of granulocyte phagocytosis in the gastrointestinal tract of the animal is higher relative to the level in the gastrointestinal tract of an animal administered a nutritional composition lacking the synthetic oligosaccharide preparation. In some embodiments, the level of immune cells or immune cell activity is mediated is mediated directly by the synthetic oligosaccharide preparation.

In some embodiments, the level of immune cells or immune cell activity is mediated is mediated indirectly by the synthetic oligosaccharide preparation. In some embodiments, the synthetic oligosaccharide preparation is processed in vivo into one or more secondary species. In some embodiments, the synthetic oligosaccharide preparation is processed by a component of the animal's gastrointestinal microbiota. In some embodiments, the component is a gastrointestinal bacterium. In some embodiments, the level of immune cells or immune cell activity is mediated is mediated directly by one or more of the secondary species.

In some embodiments, the level of one or more pro-inflammatory cytokines or chemokines in the gastrointestinal tract of the animal is higher relative to the level in the gastrointestinal tract of an animal administered a nutritional composition lacking the synthetic oligosaccharide preparation. In some embodiments, the level of one or more anti-inflammatory cytokines or chemokines in the gastrointestinal tract of the animal is lower relative to the level in the gastrointestinal tract of an animal administered a nutritional composition lacking the synthetic oligosaccharide preparation.

In some embodiments, the permeability of the gastrointestinal barrier of the animal is lower relative to the permeability of the gastrointestinal barrier of an animal administered a nutritional composition lacking the synthetic oligosaccharide preparation.

In some embodiments, the level of mucus in the gastrointestinal tract of the animal is higher relative to the level in the gastrointestinal tract of an animal administered a nutritional composition lacking the synthetic oligosaccharide preparation.

In some embodiments, the level of goblet cells in the gastrointestinal tract of the animal is higher relative to the level in the gastrointestinal tract of an animal administered a nutritional composition lacking the synthetic oligosaccharide preparation.

In some embodiments, the animal has a higher body weight relative to the body weight of an animal administered a nutritional composition lacking the synthetic oligosaccharide preparation. In some embodiments, the animal has a higher feed efficiency relative to the feed efficiency of an animal administered a nutritional composition lacking the synthetic oligosaccharide preparation.

In some embodiments, the animal has a lower feed conversion ratio relative to the feed conversion ratio of an animal administered a nutritional composition lacking the synthetic oligosaccharide preparation.

In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig). In some embodiments, the animal is livestock. In some embodiments, the animal is a companion animal.

In some embodiments, the nutritional composition is an animal feed composition. In some embodiments, the base nutritional composition is base animal feed.

In one aspect, the disclosure is based, at least in part, on the discovery that oligosaccharides comprising one or more anhydro-subunit decrease the permeability of the gastrointestinal barrier. Accordingly, in one aspect, the disclosure features, inter alia, methods of treating gastrointestinal dysfunction in an animal comprising administering an oligosaccharide preparation described herein.

Provided herein are methods of treating a gastrointestinal barrier dysfunction in an animal, comprising: administering a nutritional composition comprising a base nutritional composition and a synthetic oligosaccharide preparation to an animal with a gastrointestinal barrier dysfunction, wherein the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the permeability of the gastrointestinal barrier of the animal is lower relative to the permeability of the gastrointestinal barrier of the animal prior to administration of the nutritional preparation comprising the synthetic oligosaccharide preparation.

In some embodiments, the method comprises the gastrointestinal barrier dysfunction is hyper-permeability (leaky gut). In some embodiments, the permeability of the gastrointestinal barrier allows for the translocation of intestinal contents (e.g., food particles, microorganism, toxins) from the intraluminal space to the circulation of the animal. In some embodiments, the permeability of the gastrointestinal barrier is at least about 0.5%, 1%, 2%, 3%, 4%, 5%, 10%, 15%, 20%, 25%, or 30% less than the permeability of the gastrointestinal barrier of the animal prior to administration of the nutritional composition comprising the synthetic oligosaccharide preparation. In some embodiments, permeability of the gastrointestinal barrier is about 0.5-40%, 0.5-30%, 0.5-20%, 0.5-10%, 0.5-5%, 0.5-1%, 1-40%, 1-30%, 1-20%, 1-10%, 1-5%, 1-2%, 5-40%, 5-30%, 5-20%, 5-10%, 10-40%, 10-30%, or 10-20% less than the permeability of the gastrointestinal barrier of the animal prior to administration of the nutritional composition comprising synthetic oligosaccharide preparation.

In some embodiments, the decrease in gastrointestinal permeability is mediated directly by the synthetic oligosaccharide preparation. In some embodiments, the decrease in gastrointestinal permeability is mediated indirectly by the synthetic oligosaccharide preparation. In some embodiments, the synthetic oligosaccharide preparation is processed in vivo into one or more secondary species. In some embodiments, the synthetic oligosaccharide preparation is processed by a component of the animal's gastrointestinal microbiota. In some embodiments, the component is a gastrointestinal bacterium. In some embodiments, the decrease in gastrointestinal permeability is mediated directly by one or more of the secondary species.

In some embodiments, one or more symptoms of the gastrointestinal barrier dysfunction are ameliorated. In some embodiments the one or more symptoms is decreased mucus synthesis, decreased mucin synthesis, decreased mucus secretion, decreased mucin secretion, decreased nutrient absorption, increased inflammation, decreased resistance to infection, decreased proliferation of intestinal epithelial cells, decreased maturation of intestinal epithelial cells, malnutrition, decreased weight gain, increased feed conversion ratio, decreased feed efficiency, increased mortality.

In some embodiments, the animal has a higher body weight relative to the body weight of the animal prior to administration of the nutritional composition comprising the synthetic oligosaccharide preparation. In some embodiments, the animal has a higher feed efficiency relative to the feed efficiency of the animal prior to administration of the nutritional composition comprising the synthetic oligosaccharide preparation. In some embodiments, the animal has a lower feed conversion ratio relative to the feed conversion ratio of the animal prior to administration of the nutritional composition comprising the synthetic oligosaccharide preparation.

In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig).

In some embodiments, the nutritional composition is an animal feed composition. In some embodiments, the base nutritional composition is base animal feed.

Provided herein are methods of treating an infection, comprising administering a nutritional composition comprising a base nutritional composition and a synthetic oligosaccharide preparation to the animal, wherein the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the level of one or more type of immune cell in the gastrointestinal tract of the animal is higher relative to the level in the gastrointestinal tract of the animal prior to administration of the nutritional composition comprising the synthetic oligosaccharide preparation.

In some embodiments, the immune cell is phagocytic. In some embodiments, the immune cell is a granulocyte. In some embodiments, the level of granulocyte phagocytosis in the gastrointestinal tract of the animal is higher relative to the level in the gastrointestinal tract of the animal prior to administration of the nutritional composition comprising the synthetic oligosaccharide preparation. In some embodiments, the level of immune cells or immune cell activity is mediated is mediated directly by the synthetic oligosaccharide preparation.

In some embodiments, the level of immune cells or immune cell activity is mediated is mediated indirectly by the synthetic oligosaccharide preparation. In some embodiments, the synthetic oligosaccharide preparation is processed in vivo into one or more secondary species. In some embodiments, the synthetic oligosaccharide preparation is processed by a component of the animal's gastrointestinal microbiota. In some embodiments, the component is a gastrointestinal bacterium. In some embodiments, the increase in the level of mucus is mediated directly by one or more of the secondary species.

In some embodiments, the level of one or more pro-inflammatory cytokines or chemokines in the gastrointestinal tract of the animal is higher relative to the level in the gastrointestinal tract of the animal prior to administration of the nutritional composition comprising the synthetic oligosaccharide preparation. In some embodiments, the level of one or more anti-inflammatory cytokines or chemokines in the gastrointestinal tract of the animal is lower relative to the level in the gastrointestinal tract of the animal prior to administration of the nutritional composition comprising the synthetic oligosaccharide preparation.

In some embodiments, the permeability of the gastrointestinal barrier of the animal is lower relative to the permeability of the gastrointestinal barrier of the animal prior to administration of the nutritional composition comprising the synthetic oligosaccharide preparation. In some embodiments, the level of mucus in the gastrointestinal tract of the animal is higher relative to the level in the gastrointestinal tract of the animal prior to administration of the nutritional composition comprising the synthetic oligosaccharide preparation. In some embodiments, the level of goblet cells in the gastrointestinal tract of the animal is higher relative to the level in the gastrointestinal tract of the animal prior to administration of the nutritional composition comprising the synthetic oligosaccharide preparation.

In some embodiments, the animal has a higher body weight relative to the body weight of the animal prior to administration of the nutritional composition comprising the synthetic oligosaccharide preparation. In some embodiments, the animal has a higher feed efficiency relative to the feed efficiency of the animal prior to administration of the nutritional composition comprising the synthetic oligosaccharide preparation. In some embodiments, the animal has a lower feed conversion ratio relative to the feed conversion ratio of the animal prior to administration of the nutritional composition comprising the synthetic oligosaccharide preparation.

In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig).

In some embodiments, the nutritional composition is an animal feed composition. In some embodiments, the base nutritional composition is base animal feed.

Provided herein are methods of enhancing or inducing an immune response, comprising: administering a nutritional composition comprising a base nutritional composition and a synthetic oligosaccharide preparation to the animal, wherein the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the level of one or more type of immune cell in the gastrointestinal tract of the animal is higher relative to the level in the gastrointestinal tract of the animal prior to administration of the nutritional composition comprising the synthetic oligosaccharide preparation.

In some embodiments, the level of one or more type of immune cell in the gastrointestinal tract of the animal is higher relative to the level in the gastrointestinal tract of the animal prior to administration of the nutritional composition comprising the synthetic oligosaccharide preparation.

In some embodiments, the immune cell is phagocytic. In some embodiments, the immune cell is a granulocyte. In some embodiments, the level of granulocyte phagocytosis in the gastrointestinal tract of the animal is higher relative to the level in the gastrointestinal tract of the animal prior to administration of the nutritional composition comprising the synthetic oligosaccharide preparation. In some embodiments, the level of immune cells or immune cell activity is mediated is mediated directly by the synthetic oligosaccharide preparation.

In some embodiments, the level of immune cells or immune cell activity is mediated is mediated indirectly by the synthetic oligosaccharide preparation. In some embodiments, the synthetic oligosaccharide preparation is processed in vivo into one or more secondary species. In some embodiments, the synthetic oligosaccharide preparation is processed by a component of the animal's gastrointestinal microbiota. In some embodiments, the component is a gastrointestinal bacterium. In some embodiments, the increase in the level of mucus is mediated directly by one or more of the secondary species.

In some embodiments, the level of one or more pro-inflammatory cytokines or chemokines in the gastrointestinal tract of the animal is higher relative to the level in the gastrointestinal tract of the animal prior to administration of the nutritional composition comprising the synthetic oligosaccharide preparation. In some embodiments, the level of one or more anti-inflammatory cytokines or chemokines in the gastrointestinal tract of the animal is lower relative to the level in the gastrointestinal tract of the animal prior to administration of the nutritional composition comprising the synthetic oligosaccharide preparation.

In some embodiments, the permeability of the gastrointestinal barrier of the animal is lower relative to the permeability of the gastrointestinal barrier of the animal prior to administration of the nutritional composition comprising the synthetic oligosaccharide preparation. In some embodiments, the level of mucus in the gastrointestinal tract of the animal is higher relative to the level in the gastrointestinal tract of the animal prior to administration of the nutritional composition comprising the synthetic oligosaccharide preparation. In some embodiments, the level of goblet cells in the gastrointestinal tract of the animal is higher relative to the level in the gastrointestinal tract of the animal prior to administration of the nutritional composition comprising the synthetic oligosaccharide preparation.

In some embodiments, the animal has a higher body weight relative to the body weight of the animal prior to administration of the nutritional composition comprising the synthetic oligosaccharide preparation. In some embodiments, the animal has a higher feed efficiency relative to the feed efficiency of the animal prior to administration of the nutritional composition comprising the synthetic oligosaccharide preparation. In some embodiments, the animal has a lower feed conversion ratio relative to the feed conversion ratio of the animal prior to administration of the nutritional composition comprising the synthetic oligosaccharide preparation.

In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig).

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawing (also "figure" and "FIG." herein), of which:

FIG. 24 is a microscopy image of ileum tissue from birds in treatment Group B and treatment Group D (Groups as defined in Table 26). The ileal histology reveals significantly less inflammation damage and improved villi length in broilers fed a diet containing oligosaccharides of Example 9.2.

FIG. 34A illustrates LC-MS/MS detection of the anhydro DP2, anhydro DP1, and DP2 species of an oligosaccharide preparation of Example 3. FIG. 34B illustrates LC-MS/MS detection of the anhydro DP2, anhydro DP1, and DP2 species of an oligosaccharide preparation of Example 3.

FIG. 34C illustrates LC-MS/MS detection of the anhydro DP2, anhydro DP1, and DP2 species of an oligosaccharide preparation of Example 3.

FIG. 38A illustrates GC-MS spectrum detection of the DP1, anhydro DP1, DP2 and anhydro DP2 fractions of an oligosaccharide preparation of Example 3. FIG. 38B illustrates an enlargement of the DP2 and anhydro DP 2 fractions as shown in FIG. 38A.

FIG. 40A illustrates GC-MS spectrum detection of the DP1, anhydro DP1, DP2 and anhydro DP2 fractions of an oligosaccharide preparation of Example 7. FIG. 40B illustrates an enlargement of the DP2 and anhydro DP 2 fractions as shown in FIG. 40A.

FIG. 42 illustrates the NMR assignments of 1,6-anhydro-beta-D-glucofuranose and 1,6-anhydro-beta-D-glucopyranose.

DETAILED DESCRIPTION

Figure 1:
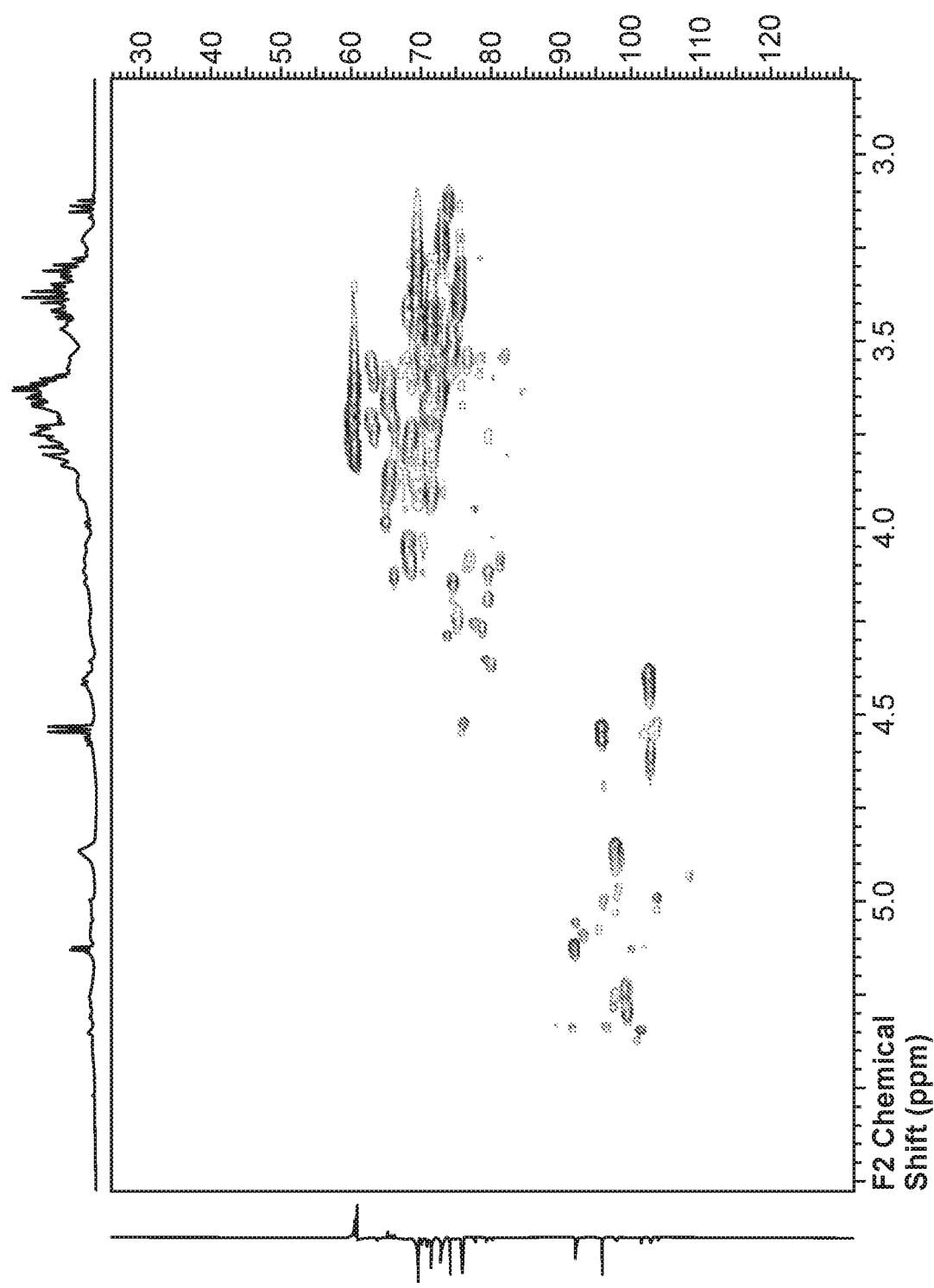
FIG. 1 illustrates part of a $^1$H, $^{13}$C-HSQC NMR spectrum of the oligosaccharide preparation of Example 9.7.

The following description and examples illustrate embodiments of the present disclosure in detail. It is to be understood that this present disclosure is not limited to the particular embodiments described herein and as such can vary. Those of skill in the art will recognize that there are numerous embodiments and modifications of this present disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure may be described in the context of a single embodiment, the features may also be provided separately or in any suitable combination. Conversely, although the present disclosure may be described herein in the context of separate embodiments for clarity, the present disclosure may also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only and is not intended to be limiting.

I. Definitions

The terminology used herein is for the purpose of describing particular cases only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

It is understood that terms such as "comprises," "comprised," "comprising," and the like have the meaning attributed to it in U.S. Patent law; i.e., they mean "includes," "included," "including," and the like and are intended to be inclusive or open ended and does not exclude additional, unrecited elements or method steps; and that terms such as "consisting essentially of" and "consists essentially of" have the meaning ascribed to them in U.S. Patent law; i.e., they allow for elements not explicitly recited, but exclude elements that are found in the prior art or that affect a basic or novel characteristic of the invention.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or B; A or C; B or C; A and B; A and C; B and C; A (alone); B (alone); and C (alone).

When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. In some embodiments, the term "about" means within 15%, 10%, 9%, 8%, 7%, 6%, 5%, 4%, 3%, 2%, 1%, 0.5%, 0.1%, or 0.05% of a given value or range.

As used herein the term "administering" includes providing a synthetic oligosaccharide preparation, a nutritional composition, a liquid, or an animal feed composition described herein, to an animal such that the animal can ingest the synthetic oligosaccharide preparation, the nutritional composition, the liquid, or the animal feed composition. In such embodiments, the animal ingests some portion of the synthetic oligosaccharide preparation, the nutritional composition, or the animal feed composition. In some embodiments, the synthetic oligosaccharide preparation, the nutritional composition, the liquid, or the animal feed composition is provided to said animal such that the animal may ingest the synthetic oligosaccharide preparation, the nutritional composition, the liquid, or the animal feed composition at will. In some embodiments, the synthetic oligosaccharide preparation, the nutritional composition, the liquid, or the animal feed composition is administered to said animal as a prescribed diet. In some embodiments, the synthetic oligosaccharide preparation, the nutritional composition, the liquid, or the animal feed composition is administered to said animal via manual feeding, e.g., an oral syringe feeding, a tube feeding, etc. In some embodiments, the synthetic oligosaccharide preparation, the nutritional composition, the liquid, or the animal feed composition is administered to said animal oral, e.g., at will or manually. In some embodiments, the animal ingests some portion of the synthetic oligosaccharide preparation, the nutritional composition, the liquid, or the animal feed composition in every 24-hour period or every other 24-hour period for at least 7 days, 14 days, 21 days, 30 days, 45 days, 60 days, 75 days, 90 days or 120 days. In some embodiments, the oligosaccharide preparation may be dissolved in water or another liquid, and the animal ingests some portion of the oligosaccharide preparation by drinking the liquid. In some embodiments, the oligosaccharide is provided to the animal via its drinking water. In some embodiments, the oligosaccharide preparation, nutritional composition, liquid, or animal feed composition is consumed at will.

As used herein the term "feed conversion ratio (FCR)," refers to the ratio of feed mass input (for example consumed by the animal) to the animal output, wherein the animal output is the target animal product. For example, the animal output for dairy animals is milk, whereas the animal output for animals raised for meat is body mass.

As used herein, "feed efficiency" refers to the ratio of the animal output to the feed mass input (for example consumed by the animal), wherein the animal output is the target animal product.

As used herein, the term "anhydro-subunit" refers to a product of thermal dehydration of a monosaccharide (or monosaccharide subunit) or a sugar caramelization product. For example, an "anhydro-subunit" can be an anhydro-monosaccharide such as anhydro-glucose. As another example, an "anhydro-subunit" can be linked with one or more regular or anhydro-monosaccharide subunits via glycosidic linkage.

The term "oligosaccharide" refers to a monosaccharide or a compound containing two or more monosaccharide subunits linked by glycosidic bonds. As such, an oligosaccharide includes a regular monosaccharide; an anhydro-monosaccharide; or a compound containing two or more monosaccharide subunits, wherein one or more monosaccharide subunits are optionally, independently replaced by one or more anhydro-subunits. An oligosaccharide can be functionalized. As used herein, the term oligosaccharide encompasses all species of the oligosaccharide, wherein each of the monosaccharide subunit in the oligosaccharide is independently and optionally functionalized and/or replaced with its corresponding anhydro-monosaccharide subunit.

As used herein, the term "oligosaccharide preparation" refers to a preparation that comprises at least one oligosaccharide.

As used herein, the term "gluco-oligosaccharide" refers to a glucose or a compound containing two or more glucose monosaccharide subunits linked by glycosidic bonds. As such, a gluco-oligosaccharide includes a glucose; an anhydro-glucose; or a compound containing two or more glucose monosaccharide subunits linked by glycosidic bonds, wherein one or more of said glucose monosaccharide subunits are each optionally and independently replaced with an anhydro-glucose subunit.

As used herein, the term "galacto-oligosaccharide" refers to a galactose or a compound containing two or more galactose monosaccharide subunits linked by glycosidic bonds. As such, a galacto-oligosaccharide includes a galactose; an anhydro-galactose or a compound containing two or more galactose monosaccharide subunits linked by glycosidic bonds, wherein at least one monosaccharide subunit is optionally replaced with an anhydro-galactose subunit.

As used herein, the term "gluco-galacto-oligosaccharide preparation" refers to a composition that is produced from a complete or incomplete sugar condensation reaction of glucose and galactose. Accordingly, in some embodiments, a gluco-galactose-oligosaccharide preparation comprises gluco-oligosaccharides, galacto-oligosaccharides, compounds containing one or more glucose monosaccharide subunits and one or more galactose monosaccharide subunits linked by glycosidic bonds, or a combination thereof. In some embodiments, a gluco-galactose-oligosaccharide preparation comprises gluco-oligosaccharides and compounds containing one or more glucose monosaccharide subunits and one or more galactose monosaccharide subunits linked by glycosidic bonds. In some embodiments, a gluco-galactose-oligosaccharide preparation comprises galacto-oligosaccharides and compounds containing one or more glucose monosaccharide subunits and one or more galactose monosaccharide subunits linked by glycosidic bonds. In some embodiments, a gluco-galactose-oligosaccharide preparation comprises compounds containing one or more glucose monosaccharide subunits and one or more galactose monosaccharide subunits linked by glycosidic bonds.

As used herein, the term "monosaccharide unit" and "monosaccharide subunit" are used interchangeably. A "monosaccharide subunit" refers to a monosaccharide monomer in an oligosaccharide. For an oligosaccharide having a degree of polymerization of 1, the oligosaccharide can be referred to as a monosaccharide subunit or monosaccharide. For an oligosaccharide having a degree of polymerization of 2 or higher, its monosaccharide subunits are linked via glycosidic bonds.

As used herein, the term "regular monosaccharide" refers to a monosaccharide that does not contain an anhydro-subunit. The term "regular disaccharide" refers to a disaccharide that does not contain an anhydro-subunit. Accordingly, the term "regular subunit" refers to a subunit that is not an anhydro-subunit.

The term "relative abundance" or "abundance," as used herein, refers to the abundance of a species in terms of how common or rare the species exists. For example, a DP1 fraction comprising 10% anhydro-subunit containing oligosaccharides by relative abundance can refer to a plurality of DP1 oligosaccharides, wherein 10% of the DP1 oligosaccharides are anhydro-monosaccharides. The relative abundance, e.g., for a certain DP fraction of oligosaccharides, can be determined by suitable analytical instrumentations, for example, mass spectrometry and liquid chromatography such as LC-MS/MS, GC-MS, HPLC-MS, and MALDI-MS. In some embodiments, the relative abundance is determined by integrating the area under the peaks of the chromatographs (e.g., LC-MS/MS, GC-MS, and HPLC-MS) that correspond to the fractions of interest. In some embodiments, the relative abundance is determined by the peak intensities (e.g., MALDI-MS). In some embodiments, the relative abundance is determined by a combination of analytical methods such as a weight determination after separation by liquid chromatography.

As used herein, the term an "anhydro DPn oligosaccharide," an "anhydro DPn species," or a "DPn anhydro-subunit containing oligosaccharide" refers to an oligosaccharide that has a degree of polymerization of n and comprises one or more anhydro-subunits. As such, an anhydro-glucose is a DP1 anhydro-subunit containing oligosaccharide and a cellotriosan is a DP3 anhydro-subunit containing oligosaccharide.

As used herein, the singular forms "a," "and," and "the" include plural referents unless the context clearly dictates otherwise. Thus, for example, reference to "an agent" includes a plurality of such agents, and reference to "the oligosaccharide" includes reference to one or more oligosaccharides (or to a plurality of oligosaccharides) and equivalents thereof known to those skilled in the art, and so forth.

II. Oligosaccharide Preparation

Disclosed herein are oligosaccharide preparations suitable for use in nutritional compositions. In some embodiments, said oligosaccharide preparation comprises at least n fractions of oligosaccharides each having a distinct degree of polymerization selected from 1 to n (DP1 to DPn fractions), wherein n is an integer greater than or equal to 2. In some embodiments, n is an integer greater than 2. In some embodiments, each of the 1 to n fraction in the oligosaccharide preparation comprises from 1% to 90% anhydro-subunit containing oligosaccharides by relative abundance as measured by mass spectrometry. In some embodiments, the relative abundance of oligosaccharides in each fraction decreases monotonically with its degree of polymerization.

In some embodiments, n is an integer greater than or equal to 3. In some embodiments, n is an integer within a range of 1 to 100, such as 4, 5, 6, 7, 8, 9, 10, 11, 12, 13, 14, 15, 16, 17, 18, 19, 20, 21, 22, 23, 24, 25, 26, 27, 28, 29, 30, 40, or 50. In some embodiments, each of the 1 to n fraction in the oligosaccharide preparation independently comprises from 0.1% to 90% anhydro-subunit containing oligosaccharides by relative abundance as measured by mass spectrometry or by LC-MS/MS or GC-MS. In some embodiments, each of the 1 to n fraction in the oligosaccharide preparation independently comprises from about 0.10% to about 15% anhydro-subunit containing oligosaccharides. In some embodiments, each of the 1 to n fraction in the oligosaccharide preparation independently comprises from about 0.5% to about 15% anhydro-subunit containing oligosaccharides. In some embodiments, the DP1 and DP2 fractions each independently comprises from about 0.1% to about 15% of anhydro-subunit containing oligosaccharides by relative abundance as measured by mass spectrometry such as MALDI-MS or by LC-MS/MS or GC-MS. In some embodiments, the DP1 and DP2 fractions each independently comprises from about 0.5% to about 15% of anhydro-subunit containing oligosaccharides. In some embodiments, the DP1 and DP2 fractions each independently comprises from about 0.1%, 0.2%, 0.3%, 0.4%, 0.5%, 0.8%, 1%, 2% or 3% to about 8%, 9%, 10%, 11%, 12%, 13%, 14%, or 15% of anhydro-subunit containing oligosaccharides by relative abundance as measured by mass spectrometry, LC-MS/MS or GC-MS. In some embodiments, the relative abundance of oligosaccharides in each fraction decreases monotonically with its degree of polymerization.

In some embodiments, the oligosaccharide preparation is a synthetic oligosaccharide preparation. In some embodiments, a synthetic oligosaccharide preparation refers to a plurality of oligosaccharides produced by a process that does not require live organisms. In some embodiments, a synthetic oligosaccharide preparation refers to a plurality of oligosaccharides produced by a process that does not require enzymes. In some embodiments, a synthetic oligosaccharide preparation refers to a plurality of oligosaccharides produced by a chemical process. In certain embodiments, a synthetic oligosaccharide preparation refers to a plurality of oligosaccharides produced by the condensation of sugars.

A. Prebiotic Utility of Oligosaccharides

Disclosed herein are oligosaccharide preparations comprising anhydro-sugar components and/or sugar dehydration product components that exhibit complex functional modulation of a microbial community, such as the animal gut microbiome. The oligosaccharide preparations provide a utility to regulate the utilization of fermentable carbon by microflora and direct metabolic flux to beneficial species, thus providing a microbiome-mediated health or nutritional benefit.

Indigestible carbohydrates can act as prebiotics by providing a fermentable carbon source to a microbial community. For example, diets rich in soluble plant fiber have been identified for their ability to nourish the gut microflora. Additionally, bifidogenic prebiotics support the growth of bifidobacteria (e.g., members of genus *Bifidobacterium*) and lactogenic prebiotics support the growth of *Lactobacillus* species.

Prebiotic fiber may be fermented into beneficial chemical species such as short chain fatty acids (SCFAs). Prebiotic fibers include: resistant starches; cellulose; pectins such as rhamnogalactans, arabinogalactans, arabinans; hemicelluloses such as arabinoxylans, xyloglucans, glucomannans, galactomannans; xylans such as corn cob oligosaccharides; b-glucans such as cereal b-glucans, yeast b-glucans, bacterial b-glucans; polyfructans such as inulin and levan; and gums such as alginate. Inulin is a common bifidogenic prebiotic fiber.

In other cases, prebiotics act by hindering the ability of pathogenic bacteria to engraft and thus infect a host organism via anti-adherence mechanisms such as the competitive binding of cell surface receptor cites. Certain galacto-oligosaccharides provide effective anti-adherence of various enteropathogenic organisms, such as *Escherichia* species.

Prebiotics are typically provided to a host animal by incorporation into the diet, upon which they exhibit a dose-dependent response (at least up to a saturation threshold). For example, providing a higher dose of a bifidogenic prebiotic such as inulin tends to provide a larger increase in the population of *Bifidobacterium* species. Higher doses of inulin correspond to higher production of SCFAs through fermentation. This is because the prebiotic provides a metabolic carbon source and more carbon translates to more fermented product. Similarly, providing a higher dose of an anti-adherence prebiotic provides a likelihood of competitively binding surface receptor sites.

Certain carbohydrate species comprising modified monomeric subunits may affect the manner in which microbial systems utilize other carbohydrates otherwise available to them as a prebiotic source. For example, such carbohydrate species may be a modified carbohydrate species that modulate the bacterial starch utilization system (SUS), i.e., proteins responsible for the cell-surface recognition, glycosidic cleavage, and importation of starch metabolites.

Carbohydrate compositions capable of complex modulation of the microbiota of animals have utility as feed additives that improve animal health and nutrition via their impact on the animal microbiome. For example, modulation of butyrate production by the gut microflora confers health benefits to the animal by promoting a healthy gut mucosa, barrier function, and via anti-inflammatory effects. Modulation of propionic acid production affects the metabolic energy extracted from the animal's diet via increased gluconeogenesis. Relevant microbial communities include, for example, ileal, jejunal, and cecal and/or fecal microbiota in poultry, pigs, dogs, cats, horses, or the ruminant microbiota of cattle, cows, sheep, etc. Other microbial communities include the skin microflora, nasal microflora, etc.

Further, herein disclosed oligosaccharide preparations are advantageous in that they can be selectively analyzed and quantified in a complex nutritional composition such as complete animal feed due to the presence of anhydro-subunits. It is of commercial utility to assay for the presence and/or concentration of feed additives such as oligosaccharide preparations. Such assay may be performed for the purpose of quality control, to determine whether the additive was blended consistently with the base nutritional composition to provide a final nutritional composition comprising the additive at the intended dose or level of inclusion.

However, the nutritional compositions themselves comprise a large quantity and diversity of carbohydrate structures (e.g., starch, plant fibers and pectins). It is therefore particularly challenging to distinguish small quantities of oligosaccharide-based feed additives from the vast sea of other carbohydrates present as base of the nutritional composition. As such, the herein disclosed oligosaccharide preparation provides a means to distinguish itself from other carbohydrates sources in the nutritional composition through the anhydro-subunits.

B. Degree of Polymerization (DP) Distribution

In some embodiments, the oligosaccharide preparation comprises at least n fractions of oligosaccharides each having a distinct degree of polymerization selected from 1 to n (DP1 to DPn fractions). In some embodiments, the oligosaccharide preparation comprises n fractions of oligosaccharides each having a distinct degree of polymerization selected from 1 to n (DP1 to DPn fractions). For example, in some embodiments, the DP1 fraction comprises one or more monosaccharides and/or one or more anhydro-monosaccharides. As another example, in some embodiments, the DP1 fraction comprises glucose, galactose, fructose, 1,6-anhydro-β-D-glucofuranose, 1,6-anhydro-β-D-glucopyranose, or any combination thereof. As yet another example, in some embodiments, the DP2 fraction comprises one or more regular disaccharides and one or more anhydro-subunit containing disaccharides. In some embodiments, the DP2 fraction comprises lactose.

In some embodiments, n is at least 2, at least 3, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, or at least 100. In some embodiments, n is 2, 3, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In some embodiments, n is less than 10, less than 11, less than 12, less than 13, less than 14, less than 15, less than 16, less than 17, less than 18, less than 19, less than 20, less than 21, less than 22, less than 23, less than 24, less than 25, less than 26, less than 27, less than 28, less than 29, less than 30, less than 31, less than 32, less than 33, less than 34, less than 35, less than 36, less than 37, less than 38, less than 39, less than 40, less than 41, less than 42, less than 43, less than 44, less than 45, less than 46, less than 47, less than 48, less than 49, less than 50, less than 51, less than 52, less than 53, less than 54, less than 55, less than 56, less than 57, less than 58, less than 59, less than 60, less than 61, less than 62, less than 63, less than 64, less than 65, less than 66, less than 67, less than 68, less than 69, less than 70, less than 71, less than 72, less than 73, less than 74, less than 75, less than 76, less than 77, less than 78, less than 79, less than 80, less than 81, less than 82, less than 83, less than 84, less than 85, less than 86, less than 87, less than 88, less than 89, less than 90, less than 91, less than 92, less than 93, less than 94, less than 95, less than 96, less than 97, less than 98, less than 99, or less than 100. In some embodiments, n is from 2 to 100, from 5 to 90, from 10 to 90, from 10 to 80, from 10 to 70, from 10 to 60, from 10 to 50, from 10 to 40, from 10 to 30, from 15 to 60, from 15 to 50, from 15 to 45, from 15 to 40, from 15 to 35, or from 15 to 30.

Figure 2:
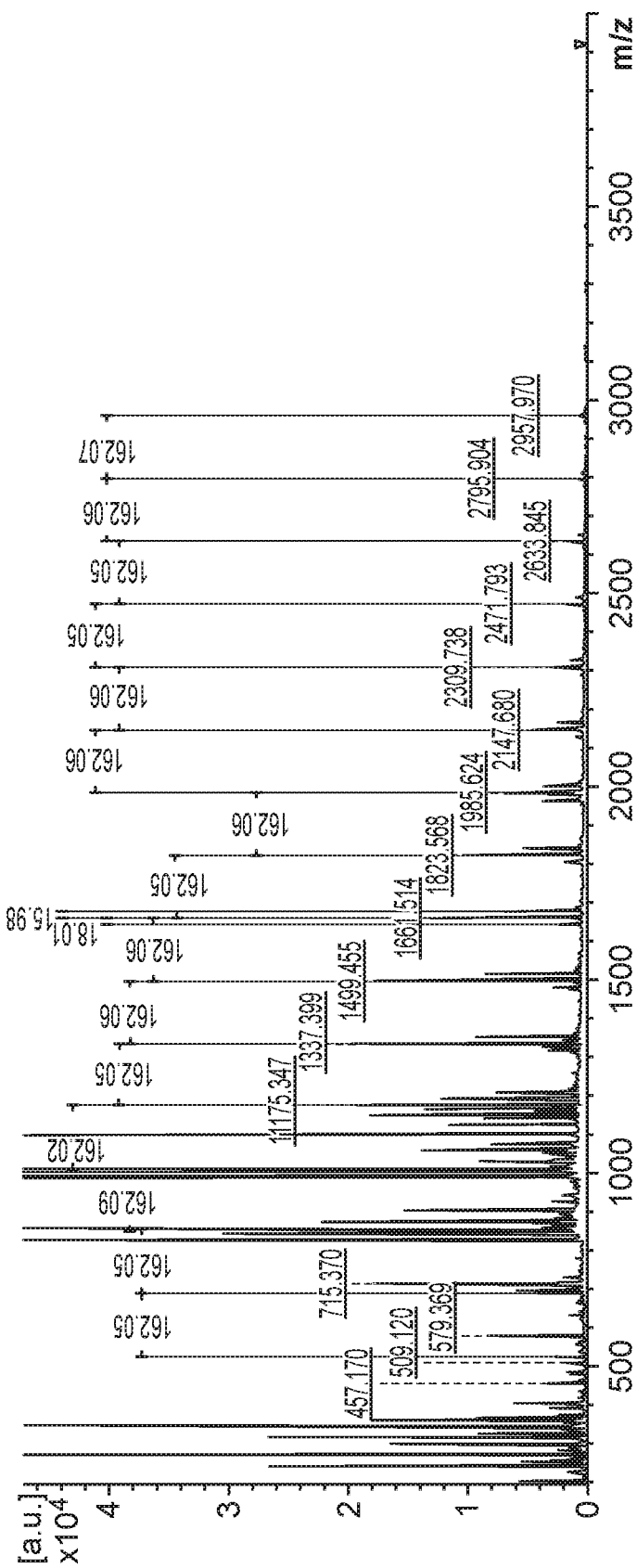
FIG. 2 illustrates a MALDI-MS spectrum of an oligosaccharide preparation from Example 9.7 that demonstrates the presence of anhydro-subunits.

A distribution of the degree of polymerization of the oligosaccharide preparation can be determined by any suitable analytical method and instrumentation, including but not limited to end group method, osmotic pressure (osmometry), ultracentrifugation, viscosity measurements, light scattering method, size exclusion chromatography (SEC), SEC-MALLS, field flow fractionation (FFF), asymmetric flow field flow fractionation (A4F), high-performance liquid chromatography (HPLC), and mass spectrometry (MS). For example, the distribution of the degree of polymerization may be determined and/or detected by mass spectrometry, such as matrix-assisted laser desorption/ionization (MALDI)-MS, liquid chromatography (LC)-MS, or gas chromatography (GC)-MS. For another example, the distribution of the degree of polymerization can be determined and/or detected by SEC, such as gel permeation chromatography (GPC). As yet another example, the distribution of the degree of polymerization can be determined and/or detected by HPLC, FFF, or A4F. In some embodiments, the distribution of the degree of polymerization is determined and/or detected by MALDI-MS. In some embodiments, the distribution of the degree of polymerization is determined and/or detected by GC-MS or LC-MS. In some embodiments, the distribution of the degree of polymerization is determined and/or detected by SEC. In some embodiments, the distribution of the degree of polymerization is determined and/or detected by HPLC. In some embodiments, the distribution of the degree of polymerization is determined and/or detected by a combination of analytical instrumentations such as MALDI-MS and SEC. In some embodiments, the degree of polymerization of the oligosaccharide preparation can be determined based on its molecular weight and molecular weight distribution. For example, FIG. 2 shows a MALDI-MS spectrum that illustrates the degrees of polymerizations of various fractions and the presence of anhydro-subunit containing oligosaccharides (the −18 g/mol MW offset peaks) in all of the observed fractions.

In some embodiments, the relative abundance of oligosaccharides in a majority of the fractions decreases monotonically with its degree of polymerization. In some embodiments, the relative abundance of oligosaccharides of less than 6, less than 5, less than 4, less than 3, or less than 2 fractions of the oligosaccharide preparation do not decrease monotonically with its degree of polymerization.

In some embodiments, the relative abundance of oligosaccharides in at least 5, at least 10, at least 15, at least 20, at least 25, at least 30, at least 35, at least 40, at least 45, or at least 50 DP fractions decreases monotonically with its degree of polymerization. In some embodiments, the relative abundance of oligosaccharides in at least 5, at least 10, at least 15, at least 20, at least 25, at least 30, at least 35, at least 40, at least 45, or at least 50 consecutive DP fractions decreases monotonically with its degree of polymerization. In some embodiments, the relative abundance of oligosaccharides in at least 5, at least 10, at least 20, or at least 30 DP fractions decreases monotonically with its degree of polymerization. In some embodiments, the relative abundance of oligosaccharides in at least 5, at least 10, at least 20, or at least 30 consecutive DP fractions decreases monotonically with its degree of polymerization.

Figure 15:
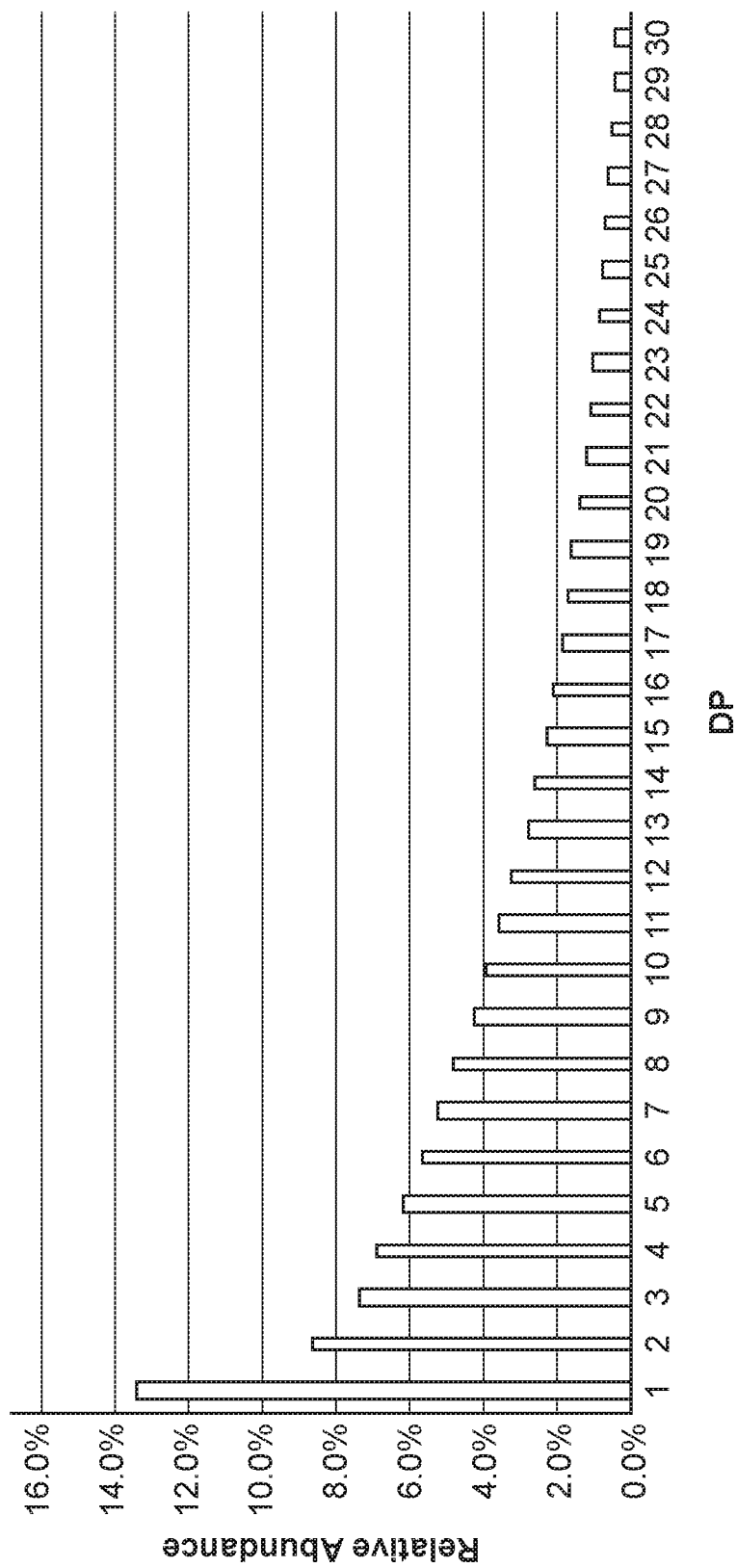
FIG. 15 shows a graph of the relative abundance versus degree of polymerization (DP) of an oligosaccharide of Example 9. The graph shows the oligosaccharide preparation has monotonically decreasing DP distribution.
Figure 16:
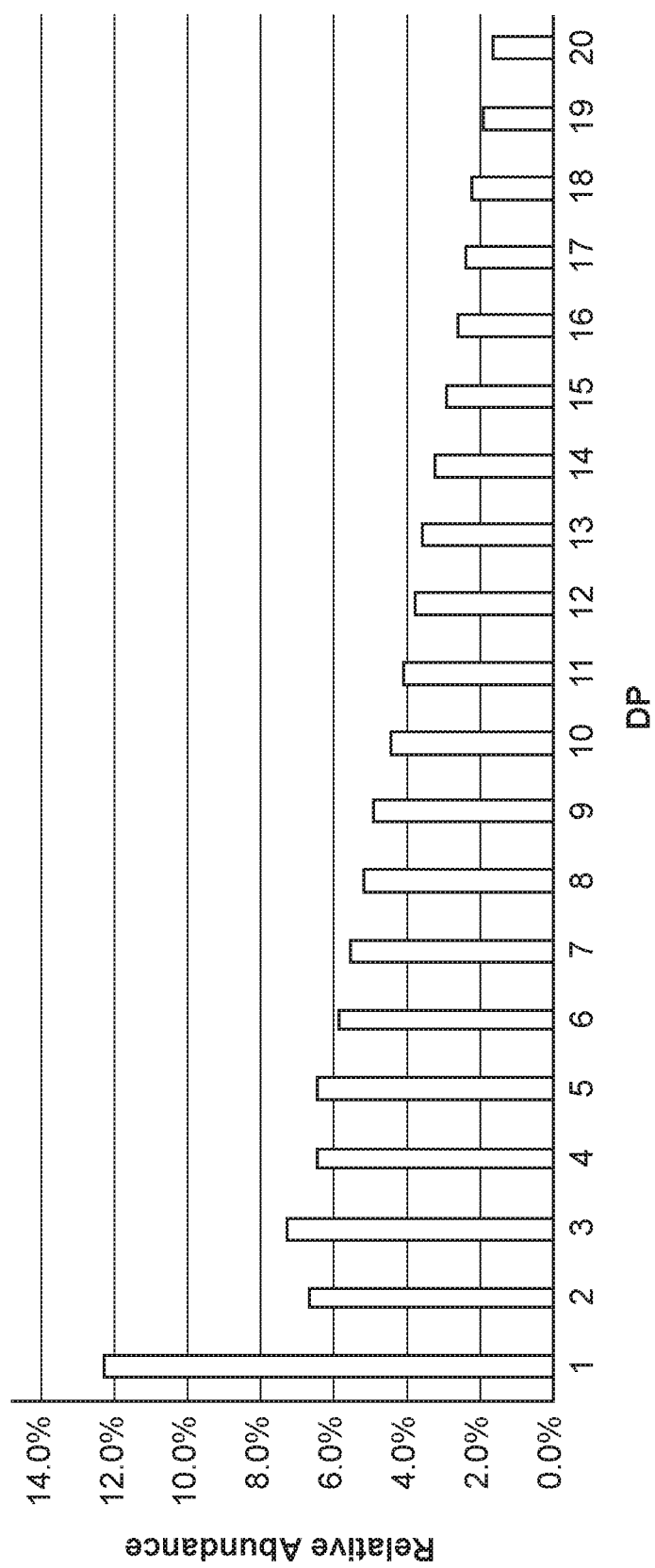
FIG. 16 shows a graph of the relative abundance versus degree of polymerization of an oligosaccharide of Example 9. The graph shows the oligosaccharide preparation has non-monotonically decreasing DP distribution.
Figure 17:
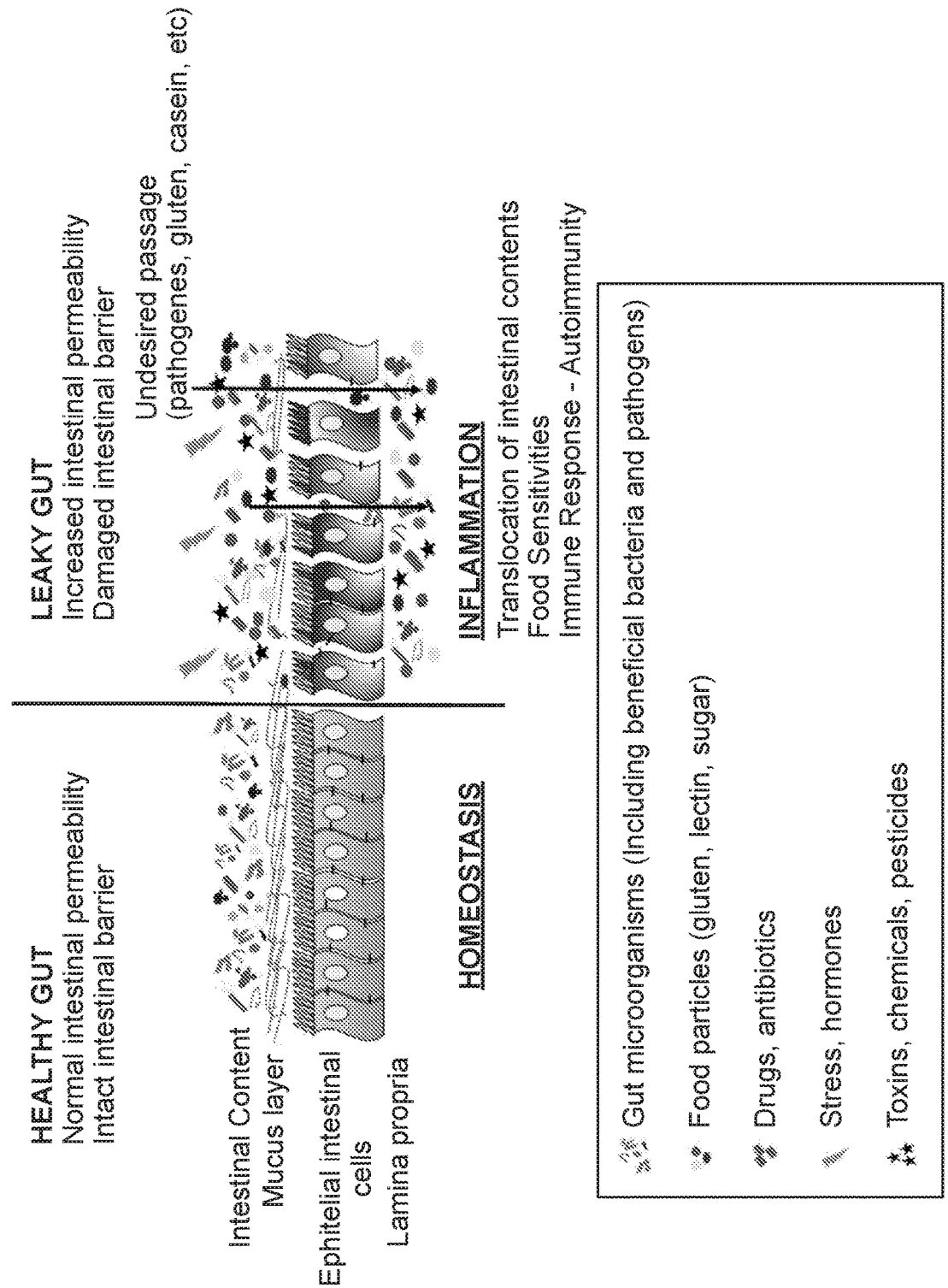
FIG. 17 shows a graphic depiction of a healthy gastrointestinal barrier and a leaky gastrointestinal barrier.

In some embodiments, the relative abundance of oligosaccharides in each of the n fractions decreases monotonically with its degree of polymerization. For example, FIG. 15 provides an example of a DP distribution where the relative abundance of oligosaccharides in each of the n fractions decrease monotonically with its DP. For example, in some embodiments, only the relative abundance of oligosaccharides in the DP3 fraction does not decrease monotonically with its degree of polymerization, i.e., the relative abundance of oligosaccharides in the DP3 fraction is lower than the relative abundance of oligosaccharides in the DP4 fraction. In some embodiments, the relative abundance of oligosaccharides in the DP2 fraction is lower than the relative abundance of oligosaccharides in the DP3 fraction. For example, FIG. 16 illustrates a degree of polymerization distribution wherein the relative abundance of oligosaccharides in the DP2 fraction does not decrease monotonically with its degree of polymerization.

In some embodiments, a herein described oligosaccharide preparation has a DP1 fraction content of from about 1% to about 50%, from about 1% to about 40%, from about 1% to about 35%, from about 1% to about 30%, from about 1% to about 25%, from about 1% to about 20%, from about 1% to about 15%, from about 5% to about 50%, from about 5% to about 40%, from about 5% to about 35%, from about 5% to about 30%, from about 5% to about 25%, from about 5% to about 20%, from about 5% to about 15%, from about 10% to about 50%, from about 10% to about 40%, from about 10% to about 35%, from about 10% to about 30%, from about 10% to about 25%, from about 10% to about 20%, or from about 10% to about 15% by weight or by relative abundance. In some embodiments, the oligosaccharide preparation has a DP1 fraction content of from about 10% to about 35%, from about 10% to about 20%, or from about 10% to about 15% by weight or by relative abundance. In some embodiments, the content of the DP1 fraction is determined by MALDI-MS. In some embodiments, the content of the DP1 fraction is determined by HPLC. In some embodiments, the content of the DP1 fraction is determined by LC-MS/MS or GC-MS.

In some embodiments, a herein described oligosaccharide preparation has a DP2 fraction content of from about 1% to about 35%, from about 1% to about 30%, from about 1% to about 25%, from about 1% to about 20%, from about 1% to about 15%, from about 1% to about 10%, from about 5% to about 30%, from about 5% to about 25%, from about 5% to about 20%, from about 5% to about 15%, or from about 5% to about 10% by weight or by relative abundance. In some embodiments, the oligosaccharide preparation has a DP2 fraction content of from about 5% to about 25%, from about 5% to about 20%, from about 5% to about 15%, or from about 5% to about 10% by weight or by relative abundance. In some embodiments, the content of the DP2 fraction is determined by MALDI-MS. In some embodiments, the content of the DP2 fraction is determined by HPLC. In some embodiments, the content of the DP2 fraction is determined by LC-MS/MS or GC-MS.

In some embodiments, a herein described oligosaccharide preparation has a DP3 fraction content of from about 1% to about 30%, from about 1% to about 25%, from about 1% to about 20%, from about 1% to about 15%, from about 1% to about 10%, from about 5% to about 30%, from about 5% to about 25%, from about 5% to about 20%, from about 5% to about 15%, or from about 5% to about 10% by weight or by relative abundance. In some embodiments, the oligosaccharide preparation has a DP3 fraction content of from about 1% to about 15%, from about 1% to about 10%, from about 5% to about 15%, or from about 5% to about 10% by weight or by relative abundance. In some embodiments, the content of the DP3 fraction is determined by MALDI-MS. In some embodiments, the content of the DP3 fraction is determined by HPLC. In some embodiments, the content of the DP3 fraction is determined by LC-MS/MS or GC-MS.

In some embodiments, a herein described oligosaccharide preparation has a DP4 fraction content of from about 0.1% to about 20%, from about 0.1% to about 15%, from about 0.1% to about 10%, from about 0.1% to about 5%, from about 1% to about 20%, from about 1% to about 15%, from about 1% to about 10%, or from about 1% to about 5% by weight or by relative abundance. In some embodiments, the oligosaccharide preparation has a DP4 fraction content of from about 1% to about 15%, from about 1% to about 10%, or from about 1% to about 5% by weight or by relative abundance. In some embodiments, a herein described oligosaccharide preparation has a DP5 fraction content of from about 0.1% to about 15%, from about 0.1% to about 10%, from about 0.1% to about 5%, from about 1% to about 15%, from about 1% to about 10%, or from about 1% to about 5% by weight or by relative abundance. In some embodiments, the oligosaccharide preparation has a DP5 fraction content of from about 1% to about 10% or from about 1% to about 5% by weight or by relative abundance. In some embodiments, the content of the DP4 and/or the DP5 fraction is determined by MALDI-MS. In some embodiments, the content of the DP4 and/or the DP5 fraction is determined by HPLC. In some embodiments, the content of the DP4 and/or the DP5 fraction is determined by LC-MS/MS or GC-MS.

In some embodiments, the ratio of DP2 fraction to DP1 fraction in the oligosaccharide preparation is from about 0.01 to about 0.8, from about 0.02 to about 0.7, from about 0.02 to about 0.6, from about 0.02 to about 0.5, from about 0.02 to about 0.4, from about 0.02 to about 0.3, from about 0.02 to about 0.2, from about 0.1 to about 0.6, from about 0.1 to about 0.5, from about 0.1 to about 0.4, or from about 0.1 to about 0.3 by their weight or relative abundance. In some embodiments, the ratio of DP2 fraction to DP1 fraction in the oligosaccharide preparation is from about 0.02 to about 0.4 by their weight or relative abundance.

In some embodiments, the ratio of DP3 fraction to DP2 fraction in the oligosaccharide preparation is from about 0.01 to about 0.7, from about 0.01 to about 0.6, from about 0.01 to about 0.5, from about 0.01 to about 0.4, from about 0.01 to about 0.3, or from about 0.01 to about 0.2 by their weight or relative abundance. In some embodiments, the ratio of DP3 fraction to DP2 fraction in the oligosaccharide preparation is from about 0.01 to about 0.3 by their weight or relative abundance.

In some embodiments, the aggregate content of DP1 and DP2 fractions in the oligosaccharide preparation is less than 70%, less than 60%, less than 50%, less than 40%, less than 30%, less than 20%, or less than 10% by weight or by relative abundance. In some embodiments, the aggregate content of DP1 and DP2 fractions in the oligosaccharide preparation is less than 50%, less than 30%, or less than 10% by weight or by relative abundance.

In some embodiments, an oligosaccharide preparation described herein has a mean DP value within a range of 2 to 10. In some embodiments, the oligosaccharide preparation has a mean DP value of from about 2 to about 8, from about 2 to about 5, or from about 2 to about 4. In some embodiments, the oligosaccharide preparation has a mean DP value of about 3.5. The mean DP value can be determined by SEC or by elemental analysis.

C. Anhydro-Subunit Level

In some embodiments, each of the n fractions of oligosaccharides independently comprises an anhydro-subunit level. For instance, in some embodiments, the DP1 fraction comprises 10% anhydro-subunit containing oligosaccharides by relative abundance, and the DP2 fraction comprises 15% anhydro-subunit containing oligosaccharides by relative abundance. For another example, in some embodiments, DP1, DP2, and DP3 fraction each comprises 5%, 10%, and 2% anhydro-subunit containing oligosaccharides by relative abundance, respectively. In other embodiments, two or more fractions of oligosaccharides may comprise similar level of anhydro-subunit containing oligosaccharides. For example, in some embodiments, the DP1 and DP3 fraction each comprises about 5% anhydro-subunit containing oligosaccharides by relative abundance.

In some embodiments, each of the 1 to n fractions in a herein described oligosaccharide preparation independently comprises from about 0.1% to 15% of anhydro-subunit containing oligosaccharides by relative abundance as measured by mass spectrometry, LC-MS/MS or GC-MS. In some embodiments, each of the 1 to n fractions in the oligosaccharide preparation independently comprises from about 0.5% to 15% of anhydro-subunit containing oligosaccharides by relative abundance as measured by mass spectrometry, LC-MS/MS or GC-MS. In some embodiments, LC-MS/MS is used to determine the relative abundance for oligosaccharides in the DP1, DP2, and/or DP3 fractions. In some embodiments, GC-MS is used to determine the relative abundance for oligosaccharides in the DP1, DP2, and/or DP3 fractions. In some embodiments, MALDI-MS is used to determine the relative abundance for oligosaccharides in the DP4 fraction or in a higher DP fraction. In some embodiments, the relative abundance of a certain fraction is determined by integrating the area under the peaks of the LC-MS/MS chromatogram that are designated as corresponding to that fraction. In some embodiments, the relative abundance of a certain fraction is determined by integrating the area under the peaks of the GC-MS chromatogram that are designated as corresponding to that fraction.

The level of anhydro-subunits can be determined by any suitable analytical methods, such as nuclear magnetic resonance (NMR) spectroscopy, mass spectrometry, HPLC, FFF, A4F, or any combination thereof. In some embodiments, the level of anhydro-subunits is determined, at least in part, by mass spectrometry such as MALDI-MS. In some embodiments, the level of anhydro-subunits is determined, at least in part, by NMR. In some embodiments, the level of anhydro-subunits containing oligosaccharides is determined, at least in part, by HPLC. In some embodiments, the level of anhydro-subunits containing oligosaccharides is determined by MALDI-MS, as illustrated by the −18 g/mol MW offset peaks in FIG. 2. In some embodiments, the presence and the type of species of anhydro-subunits can be determined and/or detected by NMR, as illustrated by Example 11, FIG. 3, and FIG. 4. In some embodiments, the relative abundance of anhydro-subunit containing oligosaccharides is determined by MALDI-MS. In some embodiments, the relative abundance of anhydro-subunit containing oligosaccharides is determined by LC-MS/MS, as illustrated in FIGS. 33A-33C, 34A-34C, 35A-35C and 36A-36C. In some embodiments, the relative abundance of anhydro-subunit containing oligosaccharides is determined by GC-MS, as illustrated in FIGS. 37A-37B, 38A-38B, 39A-39B and 40A-40B.

In some embodiments, at least one fraction of a herein described oligosaccharide preparation comprises less than 80%, less than 70%, less than 60%, less than 50%, less than 40%, less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, at least one fraction of a herein described oligosaccharide preparation comprises less than 10%, less than 9%, less than 8%, less than 7%, less than 6%, less than 5%, less than 4%, less than 3%, or less than 2% of anhydro-subunit containing oligosaccharides by relative abundance. In other embodiments, at least one fraction of a herein described oligosaccharide preparation comprises greater than 0.5%, greater than 0.8%, greater than 1%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, greater than 15%, greater than 16%, greater than 17%, greater than 18%, greater than 19%, greater than 20%, greater than 30%, greater than 40%, greater than 50%, greater than 60%, greater than 70%, or greater than 80% of anhydro-subunit containing oligosaccharides by relative abundance. In other embodiments, at least one fraction of a herein described oligosaccharide preparation comprises greater than 20%, greater than 21%, greater than 22%, greater than 23%, greater than 24%, greater than 25%, greater than 26%, greater than 27%, greater than 28%, greater than 29%, or greater than 30% of anhydro-subunit containing oligosaccharides by relative abundance. In some embodiments, at least one fraction (such as DP1, DP2, and/or DP3) of the oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, or about 30% of anhydro-subunit containing oligosaccharides by relative abundance. In some embodiments, at least one fraction (such as DP1, DP2, and/or DP3) of the oligosaccharide preparation comprises about 0.1%, about 0.2%, about 0.3%, about 0.4%, about 0.5%, about 0.6%, about 0.7%, about 0.8%, about 0.9%, about 1%, about 1.5%, about 2%, about 3%, about 4%, about 5%, about 6%, about 7%, about 8%, about 9%, or about 10% of anhydro-subunit containing oligosaccharides by relative abundance. In some embodiments, at least one fraction (such as DP1, DP2, and/or DP3) of the oligosaccharide preparation comprises from about 0.1% to about 90%, from about 0.5% to about 90%, from about 0.5% to about 80%, from about 0.5% to about 70%, from about 0.5% to about 60%, from about 0.5% to about 50%, from about 0.5% to about 40%, from about 0.5% to about 30%, from about 0.5% to about 20%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 1% to about 10%, from about 2% to about 9%, from about 2% to about 8%, from about 2% to about 7%, from about 2% to about 6%, from about 2% to about 5%, from about 2% to about 4%, from about 2% to about 3%, or from about 5% to about 10% of anhydro-subunit containing oligosaccharides by relative abundance. In some embodiments, the DP1 and DP2 fractions of the oligosaccharide preparation each independently comprises anhydro-subunit containing oligosaccharides within a range of from about 0.1%, 0.5%, 0.6%, 0.7%, 0.8%, 0.9%, 1%, 1.1%, 1.2%, 1.3%, 1.4%, or 1.5% to about 8%, 9%, 10%, 11%, 12%, or 15% by relative abundance as measured by mass spectrometry, LC-MS/MS, or GC-MS. In some embodiments, the DP1 and DP2 fractions each independently comprises from about 0.5% to about 15% of anhydro-subunit containing oligosaccharides by relative abundance as measured by mass spectrometry or by LC-MS/MS or GC-MS.

In some embodiments, each fraction of a herein described oligosaccharide preparation comprises less than 80%, less than 70%, less than 60%, less than 50%, less than 40%, less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, or less than 2% of anhydro-subunit containing oligosaccharides by relative abundance. In some embodiments, each fraction of a herein described oligosaccharide preparation comprises less than 10%, 9%, 8%, 7%, 6%, 5%, 4%, 3%, or 2% anhydro-subunit containing oligosaccharides by relative abundance. In other embodiments, each fraction of a herein described oligosaccharide preparation comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% of anhydro-subunit containing oligosaccharides by relative abundance. In other embodiments, each fraction of a herein described oligosaccharide preparation comprises greater than 20%, 21%, 22%, 23%, 24%, 25%, 26%, 27%, 28%, 29%, or 30% anhydro-subunit containing oligosaccharides by relative abundance. In some embodiments, each fraction of a herein described oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, or about 30% of anhydro-subunit containing oligosaccharides by relative abundance. In some embodiments, each fraction of a herein described oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% of anhydro-subunit containing oligosaccharides by relative abundance. In some embodiments, each fraction of a herein described oligosaccharide preparation comprises from about 0.1% to about 90%, from about 0.1% to about 15%, from about 0.5% to about 90%, from about 0.5% to about 80%, from about 0.5% to about 70%, from about 0.5% to about 60%, from about 0.5% to about 50%, from about 0.5% to about 40%, from about 0.5% to about 30%, from about 0.5% to about 20%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 2% to about 9%, from about 2% to about 8%, from about 2% to about 7%, from about 2% to about 6%, from about 2% to about 5%, from about 2% to about 4%, from about 2% to about 3%, or from about 5% to about 10% of anhydro-subunit containing oligosaccharides by relative abundance.

In some embodiments, a herein described oligosaccharide preparation comprises less than 80%, less than 70%, less than 60%, less than 50%, less than 40%, less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, the oligosaccharide preparation comprises less than 10%, 9%, 8%, 7%, 6%, 5%, 4%, 3%, or 2% anhydro-subunit containing oligosaccharides by relative abundance. In other embodiments, the oligosaccharide preparation comprises greater than 0.5%, greater than 0.8%, greater than 1%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, greater than 15%, greater than 16%, greater than 17%, greater than 18%, greater than 19%, greater than 20%, greater than 30%, greater than 40%, greater than 50%, greater than 60%, greater than 70%, or greater than 80% anhydro-subunit containing oligosaccharides by relative abundance. In other embodiments, the oligosaccharide preparation comprises greater than 20%, 21%, 22%, 23%, 24%, 25%, 26%, 27%, 28%, 29%, or 30% anhydro-subunit containing oligosaccharides by relative abundance. In some embodiments, the oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, or about 30% of anhydro-subunit containing oligosaccharides by relative abundance. In some embodiments, the oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% of anhydro-subunit containing oligosaccharides by relative abundance. In some embodiments, the oligosaccharide preparation comprises from about 0.1% to about 90%, from about 0.1% to about 15%, from about 0.5% to about 90%, from about 0.5% to about 80%, from about 0.5% to about 70%, from about 0.5% to about 60%, from about 0.5% to about 50%, from about 0.5% to about 40%, from about 0.5% to about 30%, from about 0.5% to about 20%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 2% to about 9%, from about 2% to about 8%, from about 2% to about 7%, from about 2% to about 6%, from about 2% to about 5%, from about 2% to about 4%, from about 2% to about 3%, or from about 5% to about 10% of anhydro-subunit containing oligosaccharides by relative abundance.

In some embodiments, the DP1 fraction of a herein described oligosaccharide preparation comprises less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, the DP1 fraction of a herein described oligosaccharide preparation comprises greater than 0.1%, greater than 0.5%, greater than 0.8%, greater than 1%, greater than 1.5%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, or greater than 15% of anhydro-subunit containing oligosaccharides by relative abundance. In some embodiments, the DP1 fraction of a herein described oligosaccharide preparation comprises about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of anhydro-subunit containing oligosaccharides by relative abundance. In some embodiments, the DP1 fraction of a herein described oligosaccharide preparation comprises from about 0.1% to about 15%, from about 0.1% to about 20%, from about 0.5% to about 20%, from 0.5% to about 10%, from about 0.5% to about 15%, from about 1% to about 20%, from about 1% to about 15%, from about 1% to about 10%, from about 2% to about 14%, from about 3% to about 13%, from about 4% to about 12%, from about 5% to about 11%, from about 5% to about 10%, from about 6% to about 9%, or from about 7% to about 8% of anhydro-subunit containing oligosaccharides by relative abundance, or any ranges therebetween. In some embodiments, the DP1 fraction of a herein described oligosaccharide preparation comprises from about 0.5% to about 10% of anhydro-subunit containing oligosaccharides by relative abundance. In some embodiments, the relative abundance of anhydro-subunit containing oligosaccharides is determined by mass spectrometry such as MALDI-MS. In some embodiments, the relative abundance of anhydro-subunit containing oligosaccharides is determined by LC-MS/MS. In some embodiments, the relative abundance of anhydro-subunit containing oligosaccharides is determined by GC-MS.

In some embodiments, the DP2 fraction of a herein described oligosaccharide preparation comprises less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, the DP2 fraction of a herein described oligosaccharide preparation comprises greater than 0.1%, greater than 0.5%, greater than 0.8%, greater than 1%, greater than 1.5%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, or greater than 15% of anhydro-subunit containing oligosaccharides by relative abundance. In some embodiments, the DP2 fraction of a herein described oligosaccharide preparation comprises about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of anhydro-subunit containing oligosaccharides by relative abundance. In some embodiments, the DP2 fraction of a herein described oligosaccharide preparation comprises from about 0.1% to about 15%, from about 0.1% to about 20%, from about 0.5% to about 20%, from 0.5% to about 10%, from about 0.5% to about 15%, from about 1% to about 20%, from about 1% to about 15%, from about 1% to about 10%, from about 2% to about 14%, from about 3% to about 13%, from about 4% to about 12%, from about 5% to about 11%, from about 0.5% to about 10%, from about 6% to about 9%, or from about 7% to about 8% of anhydro-subunit containing oligosaccharides by relative abundance, or any ranges therebetween. In some embodiments, the DP2 fraction of a herein described oligosaccharide preparation comprises from about 5% to about 10% of anhydro-subunit containing oligosaccharides by relative abundance. In some embodiments, the relative abundance of anhydro-subunit containing oligosaccharides is determined by mass spectrometry such as MALDI-MS. In some embodiments, the relative abundance of anhydro-subunit containing oligosaccharides is determined by LC-MS/MS. In some embodiments, the relative abundance of anhydro-subunit containing oligosaccharides is determined by GC-MS.

In some embodiments, the DP3 fraction of a herein described oligosaccharide preparation comprises less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, the DP3 fraction of a herein described oligosaccharide preparation comprises greater than 0.1%, greater than 0.5%, greater than 0.8%, greater than 1%, greater than 1.5%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, or greater than 15% of anhydro-subunit containing oligosaccharides by relative abundance. In some embodiments, the DP3 fraction of a herein described oligosaccharide preparation comprises about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of anhydro-subunit containing oligosaccharides by relative abundance. In some embodiments, the DP3 fraction of a herein described oligosaccharide preparation comprises from about 0.1% to about 15%, from about 0.1% to about 20%, from about 0.5% to about 20%, from 0.5% to about 10%, from about 0.5% to about 15%, from about 1% to about 20%, from about 1% to about 15%, from about 1% to about 10%, from about 2% to about 14%, from about 3% to about 13%, from about 4% to about 12%, from about 5% to about 11%, from about 5% to about 10%, from about 6% to about 9%, or from about 7% to about 8% of anhydro-subunit containing oligosaccharides by relative abundance, or any ranges therebetween. In some embodiments, the DP3 fraction of a herein described oligosaccharide preparation comprises from about 0.5% to about 10% of anhydro-subunit containing oligosaccharides by relative abundance. In some embodiments, the relative abundance of anhydro-subunit containing oligosaccharides is determined by mass spectrometry such as MALDI-MS. In some embodiments, the relative abundance of anhydro-subunit containing oligosaccharides is determined by LC-MS/MS. In some embodiments, the relative abundance of anhydro-subunit containing oligosaccharides is determined by GC-MS.

In some embodiments, an anhydro-subunit containing oligosaccharide comprises one or more anhydro-subunits. For instance, a DP1 anhydro-subunit containing oligosaccharide comprises one anhydro-subunit. In some embodiments, a DPn anhydro-subunit containing oligosaccharide may comprise from 1 to n anhydro-subunits. For example, in some embodiments, a DP2 anhydro-subunit containing oligosaccharide comprises one or two anhydro-subunits. In some embodiments, each oligosaccharide in the oligosaccharide preparation independently comprises zero, one, or two anhydro-subunits. In some embodiments, more than 99%, 95%, 90%, 85%, 80%, 75%, 70%, 65%, 60%, 55%, 50%, 45%, 40%, 35%, or 30% of the anhydro-subunit containing oligosaccharides have only one anhydro-subunit. In some embodiments, more than 99%, 95%, 90%, 85%, or 80% of the anhydro-subunit containing oligosaccharides have only one anhydro-subunit.

In some embodiments, one or more oligosaccharides in the oligosaccharide preparation or in each fraction of the oligosaccharide preparation comprise 1, 2, 3, 4, 5, 6, 7, 8, 9, or 10 anhydro-subunits each linked via a glycosidic bond, wherein the glycosidic bonds linking each anhydro-subunit are independently chosen. In some embodiments, one or more oligosaccharides in the oligosaccharide preparation or in each fraction of the oligosaccharide preparation comprise 1, 2, or 3 anhydro-subunits each linked via a glycosidic bond, wherein the glycosidic bond linking each anhydro-subunit are independently chosen. In some embodiments, greater than 50%, 60%, 70%, 80%, 90%, or 99% of oligosaccharides in the oligosaccharide preparation or in each fraction comprise 1, 2, or 3 anhydro-subunits each linked via a glycosidic bond, wherein the glycosidic bond linking each anhydro-subunit are independently chosen. In some embodiments, one or more oligosaccharides in the oligosaccharide preparation or in each fraction comprise 1 anhydro-subunit linked via a glycosidic bond. In some embodiments, greater than 50%, greater than 60%, greater than 70%, greater than 80%, greater than 90%, or greater than 99% of oligosaccharides in the oligosaccharide preparation or in each fraction comprise 1 anhydro-subunit linked via a glycosidic bond.

D. Anhydro-Subunit Species

Figure 30:
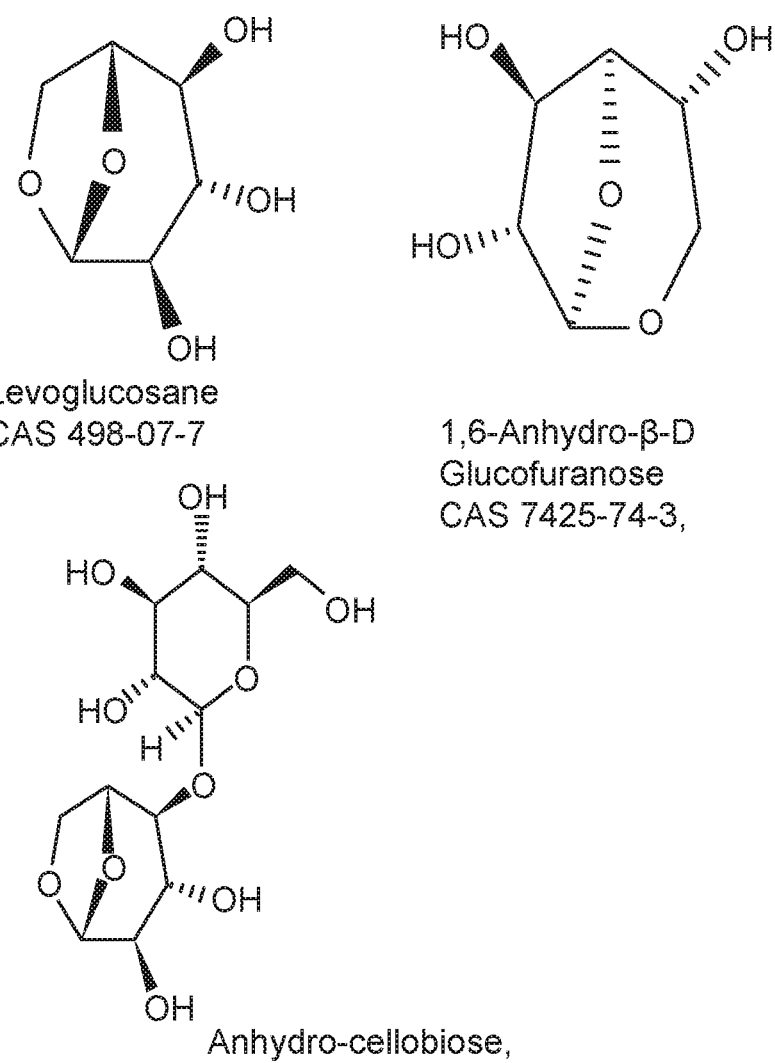
FIG. 30 illustrates two DP1 and one DP2 anhydro-subunit containing oligosaccharides.
Figure 31:
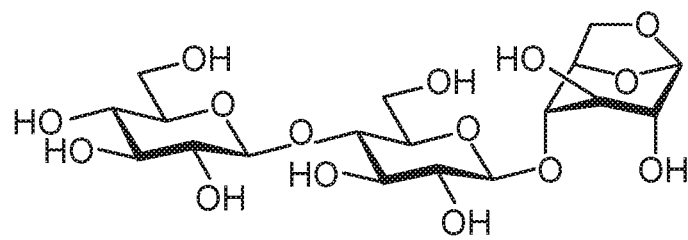
FIG. 31 illustrates an anhydro-subunit containing oligosaccharide (cellotriosan).

In some embodiments, the oligosaccharide preparation comprises different species of anhydro-subunits. In some embodiments, exemplary anhydro-subunit containing oligosaccharides are illustrated in FIG. 42, FIG. 30, and FIG. 31. In some embodiments, the oligosaccharide preparation comprises one or more anhydro-subunits that are products of thermal dehydration of monosaccharides, i.e., anhydro-monosaccharide subunits. In some embodiments, the oligosaccharide preparation comprises one or more anhydro-subunits that are products of reversible thermal dehydration of monosaccharides.

It is to be understood that an anhydro-monosaccharide (or an anhydro-monosaccharide subunit) refers to one or more species of the thermal dehydration products of the monosaccharide. For example, in some embodiments, an anhydro-glucose refers to 1,6-anhydro-β-D-glucopyranose (levoglucosan) or 1,6-anhydro-β-D-glucofuranose. In some embodiments, a plurality of anhydro-glucose refer to a plurality of 1,6-anhydro-β-D-glucopyranose (levoglucosan), a plurality of 1,6-anhydro-β-D-glucofuranose, a plurality of other thermal dehydration products of glucose, or any combination thereof. Similarly, in some embodiments, a plurality of anhydro-galactose refers to a plurality of any thermal dehydration products of galactose, or any combination thereof.

In some embodiments, an oligosaccharide preparation as described herein comprises one or more anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, anhydro-xylose, or any combination of these subunits. In some embodiments, the oligosaccharide preparation comprises one or more anhydro-glucose, anhydro-galactose, anhydro-mannose, or anhydro-fructose subunits. In some embodiments, an oligosaccharide preparation as described herein comprises one or more of: 1,6-anhydro-3-O-β-D-glucopyranosyl-β-D-glucopyranose, 1,6-anhydro-3-O-α-D-glucopyranosyl-β-D-glucopyranose, 1,6-anhydro-2-O-β-D-glucopyranosyl-β-D-glucopyranose, 1,6-anhydro-2-O-α-D-glucopyranosyl-β-D-glucopyranose, 1,6-anhydro-β-D-cellobiose (cellobiosan), 1,6-anhydro-β-D-cellotriose (cellotriosan), 1,6-anhydro-β-D-cellotetraose (cellotetraosan), 1,6-anhydro-β-D-cellopentaose (cellopentaosan), and 1,6-anhydro-β-D-maltose (maltosan).

In some embodiments, the oligosaccharide preparation comprises one or more 1,6-anhydro-β-D-glucofuranose subunits. In some embodiments, the oligosaccharide preparation comprises one or more 1,6-anhydro-β-D-glucopyranose (levoglucosan) subunits. For example, FIG. 42 illustrates two DP1 anhydro-subunit containing oligosaccharides (levoglucosan and 1,6-anhydro-β-D-glucofuranose) and a DP2 anhydro-subunit containing oligosaccharide (anhydro-cellobiose).

The presence and the level of a species of anhydro-subunit may vary based on the feed sugars used to manufacture the oligosaccharide. For instance, in some embodiments, gluco-oligosaccharides comprise anhydro-glucose subunits, galacto-oligosaccharides comprise anhydro-galactose subunits, and gluco-galacto-oligosaccharides comprise anhydro-glucose and anhydro-galactose subunits.

In some embodiments, the oligosaccharide preparation comprises both 1,6-anhydro-β-D-glucofuranose and 1,6-anhydro-β-D-glucopyranose anhydro-subunits. In some embodiments, at least 0.1%, 1%, 5%, 10%, 20%, 30%, 40%, 50%, 60%, 70%, 80%, 90%, or 99% of anhydro-subunits are selected from a group consisting of 1,6-anhydro-β-D-glucofuranose and 1,6-anhydro-β-D-glucopyranose. In some embodiments, at least 1%, 5%, 10%, 20%, 30%, 40%, 50%, 60%, 70%, 80%, or 90% of anhydro-subunits are 1,6-anhydro-β-D-glucofuranose. In some embodiments, at least 1%, 5%, 10%, 20%, 30%, 40%, 50%, or 60% of anhydro-subunits are 1,6-anhydro-β-D-glucopyranose.

In some embodiments, the ratio of 1,6-anhydro-β-D-glucofuranose to 1,6-anhydro-β-D-glucopyranose is from about 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in the preparation. In some embodiments, the ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 in the preparation. In some embodiments, the ratio of 1,6-anhydro-β-D-glucofuranose to 1,6-anhydro-β-D-glucopyranose is about 2:1 in the preparation.

In some embodiments, the ratio of 1,6-anhydro-β-D-glucofuranose to 1,6-anhydro-β-D-glucopyranose is about from 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in each fraction. In some embodiments, the ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 in each fraction. In some embodiments, the ratio of 1,6-anhydro-β-D-glucofuranose to 1,6-anhydro-β-D-glucopyranose is about 2:1 in each fraction.

In some embodiments, the ratio of 1,6-anhydro-β-D-glucofuranose to 1,6-anhydro-β-D-glucopyranose is about from 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in at least one fraction. In some embodiments, the ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 in at least one fraction. In some embodiments, the ratio of 1,6-anhydro-β-D-glucofuranose to 1,6-anhydro-β-D-glucopyranose is about 2:1 in at least one fraction.

In some embodiments, a herein described oligosaccharide preparation comprises anhydro-subunit containing DP2 oligosaccharides. In some embodiments, the oligosaccharide preparation comprises anhydro-lactose, anhydro-sucrose, anhydro-cellobiose, or a combination thereof. In some embodiment, the oligosaccharide preparation comprises from about 2 to 20, 2 to 15, 5 to 20, 5 to 15, or 5 to 10 species of DP2 anhydro-subunit containing oligosaccharides. In some embodiments, an oligosaccharide preparation described herein does not comprise cellobiosan or does not comprise a detectable level of cellobiosan.

In some embodiments, a herein described oligosaccharide preparation comprises one or more anhydro-subunits that are sugar caramelization products. In some embodiments, the oligosaccharide preparation comprises one or more anhydro-subunits are sugar caramelization products selected from the group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf). In some embodiments, the oligosaccharide preparation comprises 5-hmf anhydro-subunits.

In some embodiments, in the oligosaccharide preparation or in at least one of the DP fractions, the anhydro-subunits that are caramelization products are less abundant than the anhydro-subunits that are products of thermal dehydration of a monosaccharide. In some embodiments, in the oligosaccharide preparation or in at least one of the fractions, the anhydro-subunits that are caramelization products are more abundant than the anhydro-subunits that are products of thermal dehydration of a monosaccharide. In some embodiments, in the oligosaccharide preparation or in at least one of the fractions, anhydro-subunits that are caramelization products and anhydro-subunits that are products of thermal dehydration of a monosaccharide have similar abundance.

In some embodiments, from about 0.01% to about 50%, from about 0.01% to about 40%, from about 0.01% to about 30%, from about 0.01% to about 20%, from about 0.01% to about 10%, from about 0.01% to about 5%, from about 0.01% to about 4%, from about 0.01% to about 3%, from about 0.01% to about 2%, from about 0.01% to about 1%, from about 0.01% to about 0.5%, from about 0.10% to about 50%, from about 0.1% to about 40%, from about 0.1% to about 30%, from about 0.1% to about 20%, from about 0.1% to about 10%, from about 0.10% to about 5%, from about 0.1% to about 4%, from about 0.1% to about 3%, from about 0.1% to about 2%, from about 0.1% to about 1%, or from about 0.1% to about 0.5% of the anhydro-subunits in a herein described oligosaccharide preparation are caramelization products. In some embodiments, from about 0.1% to about 5%, from about 0.1% to about 2%, or from about 0.1% to about 1% of the anhydro-subunits in the oligosaccharide preparation are caramelization products. In some embodiments, less than 50%, less than 40%, less than 30%, less than 25%, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of the anhydro-subunits in the oligosaccharide preparation are caramelization products.

In some embodiments, from about 0.01% to about 50%, from about 0.01% to about 40%, from about 0.01% to about 30%, from about 0.01% to about 20%, from about 0.01% to about 10%, from about 0.01% to about 5%, from about 0.01% to about 4%, from about 0.01% to about 3%, from about 0.01% to about 2%, from about 0.01% to about 1%, from about 0.01% to about 0.5%, from about 0.1% to about 50%, from about 0.1% to about 40%, from about 0.1% to about 30%, from about 0.1% to about 20%, from about 0.1% to about 10%, from about 0.1% to about 5%, from about 0.1% to about 4%, from about 0.1% to about 3%, from about 0.10% to about 2%, from about 0.10% to about 1%, or from about 0.1% to about 0.5% of the anhydro-subunits in at least one fraction (e.g., DP1, DP2 and/or DP3) of a herein described preparation are caramelization products. In some embodiments, from about 0.10% to about 5%, from about 0.10% to about 2%, or from about 0.10% to about 1b % of the anhydro-subunits in at least one fraction (e.g., DP1, DP2 and/or DP3) of the preparation are caramelization products. In some embodiments, less than 50%, 40%, 30%, 25%, 20%, 15%, 14%, 13%, 12%, 11%, 10%, 9%, 8%, 7%, 6%, 5%, 4%, 3%, 2%, or 1% of the anhydro-subunits in at least one fraction of the preparation are caramelization products. In some embodiments, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of the anhydro-subunits in the DP1, DP2, and/or DP3 fractions of a herein described oligosaccharide preparation are caramelization products.

In some embodiments, from about 0.01% to about 50%, from about 0.010% to about 40%, from about 0.01% to about 30%, from about 0.01% to about 20%, from about 0.01% to about 10%, from about 0.01% to about 5%, from about 0.01% to about 4%, from about 0.01% to about 3%, from about 0.01% to about 2%, from about 0.01% to about 1%, from about 0.01% to about 0.5%, from about 0.1% to about 50%, from about 0.1% to about 40%, from about 0.1% to about 30%, from about 0.1% to about 20%, from about 0.1% to about 10%, from about 0.1% to about 5%, from about 0.1% to about 4%, from about 0.1% to about 3%, from about 0.1% to about 2%, from about 0.1% to about 1%, or from about 0.1% to about 0.5% of the anhydro-subunits in each fraction of a herein described oligosaccharide preparation are caramelization products. In some embodiments, from about 0.1% to about 5%, from about 0.1% to about 2%, or from about 0.1% to about 1% of the anhydro-subunits in each fraction of the preparation are caramelization products. In some embodiments, less than 50%, less than 40%, less than 30%, less than 20%, less than 25%, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of the anhydro-subunits in each fraction of the preparation are caramelization products.

In some embodiments, each of the oligosaccharides in a herein described oligosaccharide preparation independently and optionally comprises an anhydro-subunit. In some embodiments, two or more independent oligosaccharides comprise the same or different anhydro-subunits. In some embodiments, two or more independent oligosaccharides comprise different anhydro-subunits. For example, in some embodiments, the oligosaccharide preparation comprises a DP1 anhydro-subunit containing oligosaccharide that comprises a 1,6-anhydro-β-D-glucopyranose and a DP2 anhydro-subunit containing oligosaccharide that comprises a 1,6-anhydro-β-D-glucofuranose subunit. In some embodiments, one or more oligosaccharides in the oligosaccharide preparation comprise two or more the same or different anhydro-subunits.

In some embodiments, in any fraction of the oligosaccharide preparation that has a degree of polymerization equal or greater than 2 (i.e., DP2 to DPn fractions), an anhydro-subunit may be linked to one or more regular or anhydro-subunits. In some embodiments, in the DP2 to DPn fractions, at least one anhydro-subunit is linked to one, two, or three other regular or anhydro-subunits. In some embodiments, in the DP2 to DPn fractions, at least one anhydro-subunit is linked to one or two regular subunits. In some embodiments, in the DP2 to DPn fractions, at least one anhydro-subunit is linked to one regular subunit. In some embodiments, in any of the DP2 to DPn fractions, more than 99%, 90%, 80%, 70%, 60%, 50%, 40%, or 30% of anhydro-subunits are linked to one regular subunit. In some embodiments, in each of the DP2 to DPn fraction, more than 99%, 90%, 80%, 70%, 60%, 50%, 40%, or 30% of anhydro-subunits are linked to one regular subunit.

In some embodiments, in any fraction of the oligosaccharide preparation that has a degree of polymerization equal or greater than 2 (i.e., DP2 to DPn fractions), an anhydro-subunit can be located at a chain-end of an oligosaccharide. In some embodiments, in any fraction of the oligosaccharide preparation that has a degree of polymerization equal or greater than 3 (i.e., DP3 to DPn fractions), an anhydro-subunit can be located at a position that is not a chain-end of an oligosaccharide. In some embodiments, in the DP2 to DPn fractions, at least one of the anhydro-subunits is located at the chain-end of an oligosaccharide. In some embodiments, greater than 99%, 95%, 90%, 85%, 80%, 75%, 70%, 65%, 60%, 55%, 50%, 45%, 40%, 35%, or 30% of the anhydro-subunits in the DP2 to DPn fractions are located at the chain-end of the oligosaccharides. In some embodiments, greater than 95%, 90%, 80%, 70%, 60%, 50%, 40%, 30%, 20%, or 10% of the anhydro-subunits in the oligosaccharide preparation are located at the chain-end of the oligosaccharides. In some embodiments, greater than 30%, 40%, 50%, 60%, 70%, 80%, 90%, 95%, or 99% of the anhydro-subunit containing oligosaccharides comprise a chain-end anhydro-subunit. In some embodiments, greater than 80%, 85%, 90%, 91%, 92%, 93%, 94%, 95%, 96%, 97%, 98%, or 99% of the anhydro-subunit containing oligosaccharides comprise a chain-end anhydro-subunit.

E. Glycosidic Linkages

In some embodiments, a herein described oligosaccharide preparation comprises a variety of glycosidic linkages. The type and distribution of the glycosidic linkages can depend on the source and manufacturing method of the oligosaccharide preparation. In some embodiments, the type and distribution of various glycosidic linkages can be determined and/or detected by any suitable methods known in the art such as NMR. For example, in some embodiments, the glycosidic linkages are determined and/or detected by $^1$H NMR, $^{13}$C NMR, 2D NMR such as 2D JRES, HSQC, HMBC, DOSY, COSY, ECOSY, TOCSY, NOESY, or ROESY, or any combination thereof. In some embodiments, the glycosidic linkages are determined and/or detected, at least in part, by $^1$H NMR. In some embodiments, the glycosidic linkages are determined and/or detected, at least in part, by $^{13}$C NMR. In some embodiments, the glycosidic linkages are determined and/or detected, at least in part, by 2D $^1$H, $^{13}$C-HSQC NMR.

In some embodiments, a herein described oligosaccharide preparation comprises one or more α-(1,2) glycosidic linkages, α-(1,3) glycosidic linkages, α-(1,4) glycosidic linkages, α-(1,6) glycosidic linkages, β-(1,2) glycosidic linkages, β-(1,3) glycosidic linkages, β-(1,4) glycosidic linkages, R-(1,6) glycosidic linkages, α-(1,1)-α glycosidic linkages, α-(1,1)-β glycosidic linkages, (β-(1,1)-β glycosidic linkages, or any combination thereof.

In some embodiments, the oligosaccharide preparations have a glycosidic bond type distribution of from about 0 to about 60 mol %, from about 5% to about 55 mol %, from about 5% to about 50 mol %, from about 5% to about 45 mol %, from about 5% to about 40 mol %, from about 5% to about 35 mol %, from about 5% to about 30 mol %, from about 5% to about 25 mol %, from about 10% to about 60 mol %, from about 10% to about 55 mol %, from about 10% to about 50 mol %, from about 10% to about 45 mol %, from about 10% to about 40 mol %, from about 10% to about 35 mol %, from about 15% to about 60 mol %, from about 15% to about 55 mol %, from about 15% to about 50 mol %, from about 15% to about 45 mol %, from about 15% to about 40 mol %, from about 15% to about 35 mol %, from about 20% to about 60 mol %, from about 20% to about 55 mol %, from about 20% to about 50 mol %, from about 20% to about 45 mol %, from about 20% to about 40 mol %, from about 20% to about 35 mol %, from about 25% to about 60 mol %, from about 25% to about 55 mol %, from about 25% to about 50 mol %, from about 25% to about 45 mol %, from about 25% to about 40 mol %, or from about 25% to about 35 mol % of α-(1,6) glycosidic linkages.

In some embodiments, the oligosaccharide preparations have a glycosidic bond type distribution of from about 0 to about 50 mol %, from about 0 to about 40 mol %, from about 0 to about 35 mol %, from about 0 to about 30 mol %, from about 0 to about 25 mol %, from about 0 to about 20 mol %, from about 5% to about 40 mol %, from about 5% to about 35 mol %, from about 5% to about 30 mol %, from about 5% to about 25 mol %, from about 5% to about 20 mol %, from about 10% to about 40 mol %, from about 10% to about 35 mol %, from about 10% to about 20 mol %, from about 15% to about 40 mol %, from about 15% to about 35 mol %, from about 15% to about 30 mol %, from about 15% to about 25 mol %, or from about 15% to about 20 mol % of α-(1,3) glycosidic linkages.

In some embodiments, the oligosaccharide preparations have a glycosidic bond type distribution of from about 0 to about 40 mol %, from about 0 to about 35 mol %, from about 0 to about 30 mol %, from about 0 to about 25 mol %, from about 0 to about 20 mol %, from about 0 to about 15 mol %, from about 0 to about 10 mol %, from about 2% to about 30 mol %, from about 2% to about 25 mol %, from about 2% to about 20 mol %, from about 2% to about 15 mol %, from about 2% to about 10 mol %, from about 3% to about 30 mol %, from about 3% to about 25 mol %, from about 3% to about 20 mol %, from about 3% to about 15 mol %, from about 3% to about 10 mol %, from about 5% to about 30 mol %, from about 5% to about 25 mol %, from about 5% to about 20 mol %, from about 5% to about 15 mol %, or from about 5% to about 10 mol % of α-(1,2) glycosidic linkages.

In some embodiments, the oligosaccharide preparations have a glycosidic bond type distribution of from about 0 to about 40 mol %, from about 0 to about 30 mol %, from about 0 to about 25 mol %, from about 0 to about 20 mol %, from about 0 to about 15 mol %, from about 0 to about 10 mol %, or from about 0 to about 5 mol % of α-(1,4) glycosidic linkages. In some embodiments, the oligosaccharide preparations have a glycosidic bond type distribution of less than 40 mol %, less than 30 mol %, less than 20 mol %, less than 15 mol %, less than 10 mol %, less than 9 mol %, less than 8 mol %, less than 7 mol %, less than 6 mol %, less than 5 mol %, less than 4 mol %, less than 3 mol %, or less than 2 mol % of α-(1,4) glycosidic linkages.

In some embodiments, the oligosaccharide preparations have a glycosidic bond type distribution of from about 0 to about 40 mol %, from about 0 to about 35 mol %, from about 0 to about 30 mol %, from about 0 to about 25 mol %, from about 0 to about 20 mol %, from about 0 to about 15 mol %, from about 0 to about 10 mol %, from about 2% to about 30 mol %, from about 2% to about 25 mol %, from about 2% to about 20 mol %, from about 2% to about 15 mol %, from about 2% to about 10 mol %, from about 5% to about 30 mol %, from about 5% to about 25 mol %, from about 5% to about 20 mol %, from about 5% to about 15 mol %, from about 5% to about 10 mol %, from about 8% to about 30 mol %, from about 8% to about 25 mol %, from about 8% to about 20 mol %, from about 8% to about 15 mol %, or from about 10% to about 15 mol % of β-(1,6) glycosidic linkages.

In some embodiments, the oligosaccharide preparations have a glycosidic bond type distribution of from about 0 to about 40 mol %, from about 0 to about 35 mol %, from about 0 to about 30 mol %, from about 0 to about 25 mol %, from about 0 to about 20 mol %, from about 0 to about 15 mol %, from about 0 to about 10 mol %, from about 2% to about 30 mol %, from about 2% to about 25 mol %, from about 2% to about 20 mol %, from about 2% to about 15 mol %, from about 2% to about 10 mol %, from about 3% to about 30 mol %, from about 3% to about 25 mol %, from about 3% to about 20 mol %, from about 3% to about 15 mol %, from about 3% to about 10 mol %, from about 5% to about 30 mol %, from about 5% to about 25 mol %, from about 5% to about 20 mol %, from about 5% to about 15 mol %, or from about 5% to about 10 mol % of β-(1,4) glycosidic linkages.

In some embodiments, the oligosaccharide preparations have a glycosidic bond type distribution of from about 0 to about 40 mol %, from about 0 to about 30 mol %, from about 0 to about 25 mol %, from about 0 to about 20 mol %, from about 0 to about 15 mol %, from about 0 to about 10 mol %, from about 0 to about 5 mol %, from about 1% to about 20 mol %, from about 1% to about 15 mol %, from about 1% to about 10 mol %, from about 1% to about 5 mol %, from about 2% to about 20 mol %, from about 2% to about 15 mol %, from about 2% to about 10 mol %, or from about 2% to about 5 mol % of β-(1,2) glycosidic linkages. In some embodiments, the oligosaccharide preparations have a glycosidic bond type distribution of less than 40 mol %, less than 30 mol %, less than 20 mol %, less than 15 mol %, less than 10 mol %, less than 9 mol %, less than 8 mol %, less than 7 mol %, less than 6 mol %, less than 5 mol %, less than 4 mol %, less than 3 mol %, or less than 2 mol % of β-(1,2) glycosidic linkages.

In some embodiments, the oligosaccharide preparations have a glycosidic bond type distribution of from about 0 to about 40 mol %, from about 0 to about 30 mol %, from about 0 to about 25 mol %, from about 0 to about 20 mol %, from about 0 to about 15 mol %, from about 0 to about 10 mol %, from about 0 to about 5 mol %, from about 1% to about 20 mol %, from about 1% to about 15 mol %, from about 1% to about 10 mol %, from about 1% to about 5 mol %, from about 2% to about 20 mol %, from about 2% to about 15 mol %, from about 2% to about 10 mol %, or from about 2% to about 5 mol % of β-(1,3) glycosidic linkages. In some embodiments, the oligosaccharide preparations have a glycosidic bond type distribution of less than 40 mol %, less than 30 mol %, less than 20 mol %, less than 15 mol %, less than 10 mol %, less than 9 mol %, less than 8 mol %, less than 7 mol %, less than 6 mol %, less than 5 mol %, less than 4 mol %, less than 3 mol %, or less than 2 mol % of β-(1,3) glycosidic linkages.

In some embodiments, the oligosaccharide preparations have a glycosidic bond type distribution that is different from a glycosidic bond type distribution of non-synthetic oligosaccharide preparations. For example, in some embodiments, the oligosaccharide preparations have a glycosidic bond type distribution that is different from that of the base nutritional compositions. In some embodiments, the base nutritional compositions comprise a natural carbohydrate source, such as starch and plant fibers. Some of the natural carbohydrate sources have a high percentage of α-(1,4), α-(1,6), and/or β-(1,6) glycosidic linkages. Accordingly, in some embodiments, the oligosaccharide preparations have a lower percentage of α-(1,4) glycosidic linkages than the base nutritional composition. In some embodiments, the oligosaccharide preparations have a lower percentage of α-(1,6) glycosidic linkages than the base nutritional composition. In other embodiments, the oligosaccharide preparations have a higher percentage of α-(1,6) glycosidic linkages than the base nutritional composition. In some embodiments, the oligosaccharide preparations have a lower percentage of β-(1,6) glycosidic linkages than the base nutritional composition. In some embodiments, the oligosaccharide preparation comprises glycosidic linkages that are not readily digestible or hydrolysable by enzymes.

Specifically, in some embodiments, the α-(1,2), α-(1,3), α-(1,4), α-(1,6), β-(1,2), β-(1,3), β-(1,4), and/or β-(1,6) glycosidic linkages in the glycosidic bond type distribution of a herein described oligosaccharide preparations is at least 50 mol %, at least 40 mol %, at least 30 mol %, at least 20 mol %, at least 15 mol %, at least 10 mol %, at least 5 mol %, at least 2 mol %, or at least 1 mol % lower than that of the base nutritional composition. In some embodiments, the α-(1,2), α-(1,3), α-(1,4), α-(1,6), β-(1,2), β-(1,3), β-(1,4), and/or β-(1,6) glycosidic linkages in the glycosidic bond type distribution of the oligosaccharide preparations is at least 50 mol %, at least 40 mol %, at least 30 mol %, at least 20 mol %, at least 15 mol %, at least 10 mol %, at least 5 mol %, at least 2 mol %, or at least 1 mol % higher than that of the base nutritional composition.

It should be understood by one of skill in the art that certain types of glycosidic linkages may not be applicable to oligosaccharides comprising certain type of monosaccharides. For example, in some embodiments, the oligosaccharide preparation comprises α-(1,2) glycosidic linkages and α-(1,6) glycosidic linkages. In other embodiments, the oligosaccharide preparation comprises α-(1,2) glycosidic linkages and β-(1,3) glycosidic linkages. In some embodiments, the oligosaccharide preparation comprises α-(1,2) glycosidic linkages, α-(1,3) glycosidic linkages, and β-(1,6) glycosidic linkages. In some embodiments, the oligosaccharide preparation comprises α-(1,2) glycosidic linkages, α-(1,3) glycosidic linkages, α-(1,4) glycosidic linkages, α-(1,6) glycosidic linkages, β-(1,2) glycosidic linkages, β-(1,3) glycosidic linkages, β-(1,4) glycosidic linkages, and β-(1,6) glycosidic linkages.

F. Molecular Weight

The molecular weight and molecular weight distribution of the oligosaccharide preparation may be determined by any suitable analytical means and instrumentation, such as end group method, osmotic pressure (osmometry), ultracentrifugation, viscosity measurements, light scattering method, SEC, SEC-MALLS, FFF, A4F, HPLC, and mass spectrometry. In some embodiments, the molecular weight and molecular weight distribution are determined by mass spectrometry, such as MALDI-MS, LC-MS, or GC-MS. In some embodiments, the molecular weight and molecular weight distribution are determined by size exclusion chromatography (SEC), such as gel permeation chromatography (GPC). In other embodiments, the molecular weight and molecular weight distribution are determined by HPLC. In some embodiments, the molecular weight and molecular weight distribution are determined by MALDI-MS.

In some embodiments, a herein described oligosaccharide preparation has a weight average molecular weight of from about 100 to about 10000 g/mol, from about 200 to about 8000 g/mol, from about 300 to about 5000 g/mol, from about 500 to about 5000 g/mol, from about 700 to about 5000 g/mol, from about 900 to about 5000 g/mol, from about 1100 to about 5000 g/mol, from about 1300 to about 5000 g/mol, from about 1500 to about 5000 g/mol, from about 1700 to about 5000 g/mol, from about 300 to about 4500 g/mol, from about 500 to about 4500 g/mol, from about 700 to about 4500 g/mol, from about 900 to about 4500 g/mol, from about 1100 to about 4500 g/mol, from about 1300 to about 4500 g/mol, from about 1500 to about 4500 g/mol, from about 1700 to about 4500 g/mol, from about 1900 to about 4500 g/mol, from about 300 to about 4000 g/mol, from about 500 to about 4000 g/mol, from about 700 to about 4000 g/mol, from about 900 to about 4000 g/mol, from about 1100 to about 4000 g/mol, from about 1300 to about 4000 g/mol, from about 1500 to about 4000 g/mol, from about 1700 to about 4000 g/mol, from about 1900 to about 4000 g/mol, from about 300 to about 3000 g/mol, from about 500 to about 3000 g/mol, from about 700 to about 3000 g/mol, from about 900 to about 3000 g/mol, from about 1100 to about 3000 g/mol, from about 1300 to about 3000 g/mol, from about 1500 to about 3000 g/mol, from about 1700 to about 3000 g/mol, from about 1900 to about 3000 g/mol, from about 2100 to about 3000 g/mol, from about 300 to about 2500 g/mol, from about 500 to about 2500 g/mol, from about 700 to about 2500 g/mol, from about 900 to about 2500 g/mol, from about 1100 to about 2500 g/mol, from about 1300 to about 2500 g/mol, from about 1500 to about 2500 g/mol, from about 1700 to about 2500 g/mol, from about 1900 to about 2500 g/mol, from about 2100 to about 2500 g/mol, from about 300 to about 1500 g/mol, from about 500 to about 1500 g/mol, from about 700 to about 1500 g/mol, from about 900 to about 1500 g/mol, from about 1100 to about 1500 g/mol, from about 1300 to about 1500 g/mol, from about 2000 to about 2800 g/mol, from about 2100 to about 2700 g/mol, from about 2200 to about 2600 g/mol, from about 2300 to about 2500 g/mol, or from about 2320 to about 2420 g/mol. In some embodiments, the weight average molecular weight of the oligosaccharide preparation is from about 2000 to about 2800 g/mol, from about 2100 to about 2700 g/mol, from about 2200 to about 2600 g/mol, from about 2300 to about 2500 g/mol, or from about 2320 to about 2420 g/mol. In some embodiments, the oligosaccharide preparation has a weight average molecular weight in a range from at least 500 g/mol, 750 g/mol, 1000 g/mol, or 1500 g/mol to at most 1750 g/mol, 2000 g/mol, 2250 g/mol, 2500 g/mol, or 3000 g/mol. In some embodiments, the weight average molecular weight of a herein described oligosaccharide preparation is determined by HPLC according to Example 9.

In some embodiments, a herein described oligosaccharide preparation has a number average molecular weight of from about 100 to about 10000 g/mol, from about 200 to about 8000 g/mol, from about 300 to about 5000 g/mol, from about 500 to about 5000 g/mol, from about 700 to about 5000 g/mol, from about 900 to about 5000 g/mol, from about 1100 to about 5000 g/mol, from about 1300 to about 5000 g/mol, from about 1500 to about 5000 g/mol, from about 1700 to about 5000 g/mol, from about 300 to about 4500 g/mol, from about 500 to about 4500 g/mol, from about 700 to about 4500 g/mol, from about 900 to about 4500 g/mol, from about 1100 to about 4500 g/mol, from about 1300 to about 4500 g/mol, from about 1500 to about 4500 g/mol, from about 1700 to about 4500 g/mol, from about 1900 to about 4500 g/mol, from about 300 to about 4000 g/mol, from about 500 to about 4000 g/mol, from about 700 to about 4000 g/mol, from about 900 to about 4000 g/mol, from about 1100 to about 4000 g/mol, from about 1300 to about 4000 g/mol, from about 1500 to about 4000 g/mol, from about 1700 to about 4000 g/mol, from about 1900 to about 4000 g/mol, from about 300 to about 3000 g/mol, from about 500 to about 3000 g/mol, from about 700 to about 3000 g/mol, from about 900 to about 3000 g/mol, from about 1100 to about 3000 g/mol, from about 1300 to about 3000 g/mol, from about 1500 to about 3000 g/mol, from about 1700 to about 3000 g/mol, from about 1900 to about 3000 g/mol, from about 2100 to about 3000 g/mol, from about 300 to about 2500 g/mol, from about 500 to about 2500 g/mol, from about 700 to about 2500 g/mol, from about 900 to about 2500 g/mol, from about 1100 to about 2500 g/mol, from about 1300 to about 2500 g/mol, from about 1500 to about 2500 g/mol, from about 1700 to about 2500 g/mol, from about 1900 to about 2500 g/mol, from about 2100 to about 2500 g/mol, from about 300 to about 2000 g/mol, from about 500 to about 300 to 2000 g/mol, from about 700 to about 2000 g/mol, from about 900 to about 2000 g/mol, from about 1100 to about 2000 g/mol, from about 300 to about 1500 g/mol, from about 500 to about 1500 g/mol, from about 700 to about 1500 g/mol, from about 900 to about 1500 g/mol, from about 1100 to about 1500 g/mol, from about 1300 to about 1500 g/mol, from about 1000 to about 2000 g/mol, from about 1100 to about 1900 g/mol, from about 1200 to about 1800 g/mol, from about 1300 to about 1700 g/mol, from about 1400 to about 1600 g/mol, or from about 1450 to about 1550 g/mol. In some embodiments, the number average molecular weight of the oligosaccharide preparation is from about 1000 to about 2000 g/mol, from about 1100 to about 1900 g/mol, from about 1200 to about 1800 g/mol, from about 1300 to about 1700 g/mol, 1400 to 1600 g/mol, or 1450-1550 g/mol. In some embodiments, the oligosaccharide preparation has a number average molecular weight in a range from at least 500 g/mol, 750 g/mol, 1000 g/mol, or 1500 g/mol to at most 1750 g/mol, 2000 g/mol, 2250 g/mol, 2500 g/mol, or 3000 g/mol. In some embodiments, the number average molecular weight of a herein described oligosaccharide preparation is determined by HPLC according to Example 9.

G. Types of Oligosaccharides

The species of oligosaccharides present in an oligosaccharide preparation can depend on the type of the one or more feed sugars. For example, in some embodiments, the oligosaccharide preparations comprise a gluco-oligosaccharide when the feed sugars comprise glucose. For example, in some embodiments, the oligosaccharide preparations comprise a galacto-oligosaccharide when the feed sugars comprise galactose. For another example, in some embodiments, the oligosaccharide preparations comprise gluco-galacto-oligosaccharides when the feed sugars comprise galactose and glucose.

In some embodiments, a herein described oligosaccharide preparation comprises one or more species of monosaccharide subunits. In some embodiments, the oligosaccharide preparation comprises oligosaccharides with 1, 2, 3, 4, 5, 6, 7, 8, 9, 10, 11, 12, 13, 14, 15, 16, 17, 18, 19, 20, or more different species of monosaccharides subunits.

In some embodiments, the oligosaccharide preparation comprises oligosaccharides with 1, 2, 3, or 4 different species of monosaccharides subunits. In some embodiments, the oligosaccharide preparation comprises oligosaccharides with 1, 2, or 3 different species of monosaccharides subunits. In some embodiments, the oligosaccharide preparation comprises oligosaccharides with 3 different species of monosaccharides subunits. In some embodiments, the oligosaccharide preparation comprises oligosaccharides with 2 different species of monosaccharides subunits. In some embodiments, the oligosaccharide preparation comprises one species of monosaccharides subunits.

In some embodiments, the oligosaccharide preparation comprises different species of oligosaccharides that each oligosaccharide molecule independently comprises 1, 2, 3, 4, 5, 6, 7, 8, 9, or 10 different species of monosaccharides subunits. In some embodiments, a herein described oligosaccharide preparation comprises $10^2$, $10^1$, $10^4$, $10^5$, or more different species of oligosaccharides. In some embodiments, some of the oligosaccharides in the preparation comprise one species of monosaccharide subunits and some other oligosaccharides in the same preparation comprise two or more species of monosaccharides subunits. For instance, in some embodiments, when the feed sugars are glucose and galactose, the oligosaccharide preparation can comprise oligosaccharides that comprise only glucose subunits, oligosaccharides that comprise only galactose subunits, oligosaccharides that comprise both glucose and galactose subunits at various ratios, or any combination thereof.

In some embodiments, any or all of the n fractions of the oligosaccharide preparation comprises different species of oligosaccharides subunits that each oligosaccharide independently comprises 1, 2, 3, 4, 5, 6, 7, 8, 9, or 10 different species of monosaccharides subunits. In some embodiments, some of the oligosaccharides in a fraction of the preparation comprise one species of monosaccharide subunits and some other oligosaccharides in the same fraction of the preparation comprise two or more species of monosaccharides subunits.

In some embodiments, a herein described oligosaccharide preparation comprises one or more monosaccharide subunits selected from a group consisting of: triose, tetrose, pentose, hexose, heptose, and any combination thereof, wherein each of the said triose, tetrose, pentose, hexose, or heptose subunit is independently and optionally functionalized and/or replaced with one of its corresponding anhydro-subunits. In some embodiments, the corresponding anhydro-subunit is a product of thermal dehydration of the monosaccharide subunit. In some embodiments, the corresponding anhydro-subunit is a caramelization product of the monosaccharide subunit.

In some embodiments, a herein described oligosaccharide preparation comprises pentose subunits, hexose subunits, or any combination thereof, wherein each of the said pentose or hexose subunit is independently and optionally functionalized and/or replaced with one of its corresponding anhydro-subunits. In some embodiments, the oligosaccharide preparation comprises hexose subunits, wherein each of the said hexose subunits is independently and optionally replaced with one of its corresponding anhydro-subunits.

As used herein, a tetrose refers to a monosaccharide with four carbon atoms, such as erythrose, threose, and erythrulose. As used herein, a pentose refers to a monosaccharide with five carbon atoms, such as arabinose, lyxose, ribose, and xylose. As used herein, a hexose refers to a monosaccharide with six carbon atoms, such as allose, altrose, glucose, mannose, gulose, idose, galactose, talose, psicose, fructose, sorbose, and tagatose. As used herein, a heptose refers to a monosaccharide with seven carbon atoms, such as sedoheptulose and mannoheptulose.

In some embodiments, a herein described oligosaccharide preparation comprises glucose subunit, wherein at least one glucose subunit is optionally replaced with an anhydro-glucose subunit. In some embodiments, a herein described oligosaccharide preparation comprises galactose subunit, wherein at least one galactose subunit is optionally replaced with anhydro-galactose subunit. In some embodiments, a herein described oligosaccharide preparation comprises galactose and glucose subunits, wherein at least one galactose subunit or at least one glucose subunit is optionally replaced with one of its corresponding anhydro-subunits. In some embodiments, a herein described oligosaccharide preparation comprises fructose and glucose subunits, wherein at least one fructose subunit or at least one glucose subunit is optionally replaced with one of its corresponding anhydro-subunits. In some embodiments, a herein described oligosaccharide preparation comprises mannose and glucose subunit, wherein at least one mannose subunit or at least one glucose subunit is optionally replaced with one of its corresponding anhydro-subunits.

In some embodiments, a herein described oligosaccharide preparation comprises a gluco-galactose-oligosaccharide preparation, a gluco-oligosaccharide preparation, a galacto-oligosaccharide preparation, a fructo-oligosaccharide preparation, a manno-oligosaccharide preparation, an arabino-oligosaccharide preparation, a xylo-oligosaccharide preparation, a gluco-fructo-oligosaccharide preparation, a gluco-manno-oligosaccharide preparation, a gluco-arabino-oligosaccharide preparation, a gluco-xylo-oligosaccharide preparation, a galacto-fructo-oligosaccharide preparation, a galacto-manno-oligosaccharide preparation, a galacto-arabino-oligosaccharide preparation, a galacto-xylo-oligosaccharide preparation, a fructo-manno-oligosaccharide preparation, a fructo-arabino-oligosaccharide preparation, a fructo-xylo-oligosaccharide preparation, a manno-arabino-oligosaccharide preparation, a manno-xylo-oligosaccharide preparation, an arabino-xylo-oligosaccharide preparation, a galacto-arabino-xylo-oligosaccharide preparation, a fructo-galacto-xylo-oligosaccharide preparation, an arabino-fructo-manno-xylo-oligosaccharide preparation, a gluco-fructo-galacto-arabino-oligosaccharide preparation, a fructo-gluco-arabino-manno-xylo oligosaccharide preparation, a gluco-galacto-fructo-manno-arabinoxylo-oligosaccharide preparation, or any combinations thereof; wherein each of the monosaccharide subunit within the preparation is independently and optionally functionalized and/or replaced with one of its corresponding anhydro-subunits.

In certain embodiments, a herein described oligosaccharide preparation comprises more than 99% of glucose subunits by weight. In some embodiments, the oligosaccharide preparation comprises only glucose subunits.

In some embodiments, a herein described oligosaccharide preparation comprises about 45% to 55% of glucose subunits and about 55% to 45% of galactose subunits by weight. In some specific embodiments, the oligosaccharide preparation comprises about 50% glucose and 50% galactose subunits by weight.

In some embodiments, a herein described oligosaccharide preparation comprises about 80% to 95% of glucose subunits and about 20% to 5% of mannose subunits by weight. In some embodiments, the oligosaccharide preparation comprises about 85% to 90% of glucose subunits and about 15% to 10% of mannose subunits by weight.

In some embodiments, a herein described oligosaccharide preparation comprises about 80% to 95% of glucose subunits and about 20% to 5% of galactose subunits by weight. In some embodiments, the oligosaccharide preparation comprises about 85% to 90% of glucose subunits and about 15% to 10% of galactose subunits by weight.

In some embodiments, a herein described oligosaccharide preparation comprises about 80% to 95% of glucose subunits, 0% to 8% of galactose subunits, and 5% to 20% of mannose subunits by weight. In some embodiments, the oligosaccharide preparation comprises about 80% to 90% of glucose subunits, 1% to 5% of galactose subunits, and 10% to 15% of mannose subunits by weight.

In some embodiments, an oligosaccharide preparation described herein comprises from about 1 wt % to about 100 wt %, from about 50 wt % to about 100 wt %, from about 80 wt % to about 98 wt %, or from about 85 wt % to about 95 wt % of glucose subunits, or any ranges therebetween. In some embodiments, galactose subunits are present in an oligosaccharide preparation described herein at an amount of from about 0 wt % to about 90 wt %, from about 1 wt % to about 50 wt %, from about 2 wt % to about 20 wt %, or from about 5 wt % to about 15 wt %, or any ranges therebetween. In some embodiments, mannose subunits are present in an oligosaccharide preparation described herein at an amount of from about 0 wt % to about 90 wt %, from about 1 wt % to about 50 wt %, from about 2 wt % to about 20 wt %, or from about 5 wt % to about 15 wt %, or any ranges therebetween.

In some embodiments, a herein described oligosaccharide preparation has a composition of monosaccharide subunits as shown in Table 29.

TABLE 29

Exemplary Compositions of Oligosaccharide Preparations

| Oligo Composition No. | Glucose and anhydro-glucose subunits (wt %) | Galactose and anhydro-galactose subunits (wt %) | Mannose and anhydro-mannose subunits (wt %) | Fructose and anhydro-fructose subunits (wt %) |
|---|---|---|---|---|
| 1 | 87.5 | 12.5 | 0 | 0 |
| 2 | 100 | 0 | 0 | 0 |
| 3 | 85 | 2.5 | 12.5 | 0 |
| 4 | 87.5 | 0 | 12.5 | 0 |
| 5 | 50 | 50 | 0 | 0 |
| 6 | 75 | 0 | 25 | 0 |
| 7 | 9 | 6 | 0 | 0 |
| 8 | 90 | 0 | 10 | 0 |
| 9 | 95 | 5 | 0 | 0 |
| 10 | 97.5 | 2.5 | 0 | 0 |
| 11 | 85 | 5 | 10 | 0 |
| 12 | 85 | 1.5 | 13.5 | 0 |
| 13 | 80 | 10 | 10 | 0 |
| 14 | 85 | 0 | 15 | 0 |
| 15 | 85 | 15 | 0 | 0 |
| 16 | 87.5 | 0 | 0 | 12.5 |

H. D- vs. L-Form

In some embodiments, at least one monosaccharide subunit in an oligosaccharide is in L-form. In some embodiments, at least one monosaccharides subunit in an oligosaccharide is in D-form. In some embodiments, the monosaccharide subunits in a herein described oligosaccharide preparation are in their naturally-abundant form, for example, D-glucose, D-xylose, and L-arabinose.

In some embodiments, a herein described oligosaccharide preparation comprises a mixture of L- and D-forms of monosaccharide subunits. In some embodiments, the ratio of monosaccharide subunits in L- to D- or in D- to L-form is about 1:1, about 1:2, about 1:3, about 1:4, about 1:5, about 1:6, about 1:7, about 1:8, about 1:9, about 1:10, about 1:12, about 1:14, about 1:16, about 1:18, about 1:20, about 1:25, about 1:30, about 1:35, about 1:40, about 1:45, about 1:50, about 1:55, about 1:60, about 1:65, about 1:70, about 1:75, about 1:80, about 1:85, about 1:90, about 1:100 or about 1:150.

I. Functionalized Oligosaccharides

In some embodiments, one or more oligosaccharides in the preparation are independently functionalized. Functionalized oligosaccharides may be produced by, for example, combining one or more sugars with one or more functionalizing compounds in the presence of a catalyst. Methods of producing functionalized oligosaccharides are described in WO 2012/118767, WO 2014/031956, and WO/2016/122887, which are hereby incorporated by reference in their entirety and for their disclosure.

In some embodiments, the functionalizing compound comprises one or more acid groups (e.g., —COOH), hydroxyl groups, or N-containing groups (e.g., —CN, —NO$_2$, and —N(R$_a$)$_2$, wherein R$_a$ is hydrogen, alkyl, alkenyl, alkynyl, haloalkyl, heteroalkyl, cycloalkyl, aryl, heterocycloalkyl, or heteroaryl groups), S-containing groups (e.g., thiol and sulfates), halides (e.g., —Cl), β-containing groups (e.g., phosphate), or any combination thereof. In some embodiments, the functionalizing compound is linked to at least one monosaccharide subunit via an ether, ester, oxygen-sulfur, amine, or oxygen-phosphorous bond. In some embodiments, one or more functionalizing compounds are linked to a monosaccharide subunit via a single linkage. In some embodiments, at least one functionalizing compound is linked to one or two oligosaccharides via two or more linkages.

It is to be understood that for each oligosaccharide in the oligosaccharide preparation, each of the described embodiments is independent and can be combined as if each and every combination were listed separately; thus, any combination of the embodiments are encompassed by the present disclosure. For instance, the various embodiments can be grouped into several categories that include but are not limited to (i) the presence or absence of anhydro-subunit; (ii) the number and level of anhydro-subunit, (iii) the type of species of anhydro-subunit, (iv) the location of anhydro-subunit, (v) the degree of polymerization, (vi) the molecular weight, (vii) the presence or absence of any functional groups, (viii) the type of the oligosaccharide, (ix) the type of glycosidic linkage, and (x) the L- versus D-form. Accordingly, the described oligosaccharide preparation comprises a plurality of oligosaccharides of different species. In some embodiments, a herein described oligosaccharide preparation comprises at least 10, $10^2$, $10^3$, $10^4$, $10^5$, $10^6$, $10^7$, $10^8$, $10^9$, or $10^{10}$ different oligosaccharide species. In some embodiments, the preparation comprises at least $10^3$, $10^4$, $10^5$, $10^6$, or $10^9$ different oligosaccharide species. In some embodiments, the preparation comprises at least $10^3$ different oligosaccharide species.

III. Methods of Manufacturing Oligosaccharide Preparations

In one aspect, provided herein are methods of manufacturing oligosaccharide preparations. In some embodiments, provided herein are methods of manufacturing oligosaccharide preparations suitable for use in a nutritional composition, such as an animal feed composition, or being fed directly to an animal. In one aspect, provided herein are methods of manufacturing an oligosaccharide preparation comprising heating an aqueous composition comprising one or more feed sugars and a catalyst to a temperature and for a time sufficient to induce polymerization, wherein the catalyst is selected from the group consisting of: (+)-camphor-10-sulfonic acid; 2-pyridinesulfonic acid; 3-pyridinesulfonic acid; 8-hydroxy-5-quinolinesulfonic acid hydrate; α-hydroxy-2-pyridinemethanesulfonic acid; (β)-camphor-10-sulfonic acid; butylphosphonic acid; diphenylphosphinic acid; hexylphosphonic acid; methylphosphonic acid; phenylphosphinic acid; phenylphosphonic acid; tert-butylphosphonic acid; SS)-VAPOL hydrogenphosphate; 6-quinolinesulfonic acid, 3-(1-pyridinio)-1-propanesulfonate; 2-(2-pyridinyl)ethanesulfonic acid; 3-(2-pyridyl)-5,6-diphenyl-1,2,4-triazine-p,p'-disulfonic acid monosodium salt hydrate; 1,1'-binaphthyl-2,2'-diyl-hydrogenphosphate; bis(4-methoxyphenyl)phosphinic acid; phenyl(3,5-xylyl)phosphinic acid; L-cysteic acid monohydrate; poly(styrene sulfonic acid-co-divinylbenzene); lysine; Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Palmitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; Tryptophan, and wherein the oligosaccharide preparation comprises at least n fractions of oligosaccharides each having a distinct degree of polymerization selected from 1 (DP1 fraction) to n (DPn fraction), wherein n is an integer greater than 2.

In some embodiments, n is an integer greater than or equal to 3. In some embodiments, n is an integer within a range of 1 to 100, such as 4, 5, 6, 7, 8, 9, 10, 11, 12, 13, 14, 15, 16, 17, 18, 19, 20, 21, 22, 23, 24, 25, 26, 27, 28, 29, 30, 40, or 50. In some embodiments, the polymerization of the feed sugars is achieved by a step-growth polymerization. In some embodiments, the polymerization of the feed sugars is achieved by polycondensation.

A. Feed Sugar

In some embodiments, a method of manufacturing oligosaccharide preparations described herein comprises heating one or more types of feed sugars. In some embodiments, the one or more types of feed sugars comprise monosaccharides, disaccharides, trisaccharides, tetrasaccharides, or any mixtures thereof.

In some embodiments, the one or more feed sugars comprise glucose. In some embodiments, the one or more feed sugars comprise glucose and galactose. In some embodiments, the one or more feed sugars comprise glucose, xylose, and galactose. In some embodiments, the one or more feed sugars comprise glucose and mannose. In some embodiments, the one or more feed sugars comprise glucose and fructose. In some embodiments, the one or more feed sugars comprise glucose, fructose, and galactose. In some embodiments, the one or more feed sugars comprise glucose, galactose, and mannose.

In some embodiments, the one or more feed sugars comprise disaccharides such as lactose, sucrose and cellobiose. In some embodiments, the one or more feed sugars comprise trisaccharides, such as maltotriose or raffinose. In certain embodiments, the one or more feed sugar comprise glucose, mannose, galactose, xylose, malto-dextrin, arabinose, or galactose, or any combinations thereof. In certain embodiments, the one or more feed sugars comprise sugar syrup such as corn syrup. In some embodiments, the one or more feed sugars comprise glucose and lactose. In some embodiments, the one or more feed sugars comprise glucose and sucrose.

In some embodiments, the type of feed sugars can impact the resulting manufactured oligosaccharide preparations. For example, in some variations where the one or more feed sugars are all glucose, the resulting oligosaccharide preparations comprise gluco-oligosaccharides preparations. In other embodiments, where the one or more feed sugars are all mannose, the resulting oligosaccharide preparations comprise manno-oligosaccharide preparations. In some embodiments, wherein the one or more feed sugars comprise glucose and galactose, the resulting oligosaccharide preparations comprise gluco-galacto-oligosaccharide preparations. In yet other embodiments, where the one or more feed sugars comprise xylose, glucose and galactose, the resulting oligosaccharide preparations comprise gluco-galacto-xylo-oligosaccharide preparations.

In some embodiments, each of the one or more feed sugars can be independently in its de-hydrate or hydrate form. In some embodiments, the one or more feed sugars comprise glucose, galactose, fructose, mannose, or any combination thereof, and wherein each of the glucose, galactose, fructose, or mannose is independently in its mono-hydrate or de-hydrate form. In some embodiments, the one or more feed sugars comprise a monosaccharide mono-hydrate such as glucose monohydrate. In some embodiments, the one or more feed sugars comprise a saccharide di-hydrate such as trehalose di-hydrate. In some embodiments, the one or more feed sugars comprise at least one sugar in its de-hydrate form and at least one sugar in its hydrate form.

In some embodiments, the one or more feed sugars can be provided as a sugar solution, in which the sugars are combined with water and fed into the reactor. In some embodiments, the sugars can be fed into the reactor in a solid form and combined with water in the reactor. In some embodiments, the one or more feed sugars are combined and mixed before the addition of water. In other embodiments, the one or more feed sugars are combined into water and mixed thereafter.

In some embodiments, the method comprises combining two or more feed sugars with the catalyst to produce an oligosaccharide preparation. In some embodiments, the two or more feed sugars comprise from glucose, galactose, fructose, mannose, lactose, or any combination thereof. In some embodiments, the method comprises combining a mixture of sugars (e.g., monosaccharides, disaccharides, and/or trisaccharides) with the catalyst to produce an oligosaccharide preparation. In other embodiments, the method comprises combining a mixture of sugars and sugar alcohols with the catalyst to produce an oligosaccharide preparation.

In some embodiments, the one or more feed sugars comprise functionalized or modified sugars. Functionalized or modified sugars may comprise amino sugars, sugar acids, sugar alcohols, sugar amides, sugar ethers, or any combination thereof. In some embodiments, amino sugars refer to sugar molecules in which a hydroxyl group is replaced with an amine group. Exemplary amino sugars include, but are not limited to, N-Acetyl-d-glucosamine, mannosamine, neuraminic acid, muramic acid, N-acetyl-neuramin, N-acetyl-muramic, N-acetyl-galactosamine, N-acetyl-mannosa, N-glycolylneuram, acarviosin, D-glucosamine, and D-galactosamine.

In embodiments, sugar acids refer to sugars with a carboxyl group. Exemplary sugar acids include, but are not limited to, aldonic acids (such as glyceric acid, xylonic acid, gluconic acid, and ascorbic acid), ulosonic acids (such as neuraminic acid and ketodeoxyoctulosonic acid), uronic acids (such as glucuronic acid, galacturonic acid, and iduronic acid), and aldaric acids (such as tartaric acid, mucic acid, and saccharic acid).

In some embodiments, sugar alcohols refer to sugar-derived polyols. Exemplary sugar alcohols include, but are not limited to, ethylene glycol, arabitol, glycerol, erythritol, threitol, xylitol, ribitol, mannitol, sorbitol, galactitol, fucitol, iditol, inositol, and volemitol.

In some embodiments, sugar amides refer to sugar molecules that contain a —C(=O)—N— group. In embodiments, sugar ethers refer to sugar molecules that contain an ether bond, such as glucosides.

In some embodiments, the functionalized or modified sugars comprise glucosamine, N-acetylglucosamine, glucuronic acid, galacturonic acid, glucitol, xylitol, mannitol, sorbitol. In some embodiments, the one of more feed sugars comprise deoxysugars, such as fucose, rhamnose, deoxyribose, or fuculose.

In some embodiments, a herein described method of manufacturing oligosaccharide preparation is performed at gram scale. In some embodiments, a herein described method of manufacturing oligosaccharide preparation is performed at kilogram or higher scale. Accordingly, in some embodiments, the method comprises heating an aqueous composition comprising one or more feed sugars at a quantity of more than 0.5, more than 1, more than 2, more than 3, more than 4, more than 5, more than 6, more than 7, more than 9, more than 10, more than 100, or more than 1000 kg. In some embodiments, the method comprises heating an aqueous composition comprising one or more feed sugars at a quantity of no more than 0.5, 1, 2, 3, 4, 5, 6, 7, 9, 10, 100, 1000, or 1500 kg. In some embodiments, the method comprises heating an aqueous composition comprising one or more feed sugars at a quantity of more than 1 kg.

B. Catalysts

In some embodiments, the catalyst provided herein comprises one or more acids. In some embodiments, the catalyst provided herein comprises mineral acid, carboxylic acid; amino acid; sulfonic acid; boronic acid; phosphonic acid; phosphinic acid; sulfuric acid; phosphoric acid; poly(styrene sulfonic acid-co-vinylbenzyl-imidazolium sulfate-co-divinylbenzene); poly(styrene sulfonic acid-co-divinylbenzene); (+)-camphor-10-sulfonic acid; 2-pyridinesulfonic acid; 3-pyridinesulfonic acid; 8-hydroxy-5-quinolinesulfonic acid hydrate; α-hydroxy-2-pyridinemethanesulfonic acid; (β)-camphor-10-sulfonic acid; butylphosphonic acid; diphenylphosphinic acid; hexylphosphonic acid; methylphosphonic acid; phenylphosphinic acid; phenylphosphonic acid; tert-butylphosphonic acid; SS)-VAPOL hydrogenphosphate; 6-quinolinesulfonic acid; 3-(1-pyridinio)-1-propanesulfonate; 2-(2-pyridinyl)ethanesulfonic acid; 3-(2-pyridyl)-5,6-diphenyl-1,2,4-triazine-p,p'-disulfonic acid monosodium salt hydrate; 1,1'-binaphthyl-2,2'-diyl-hydrogenphosphate; bis(4-methoxyphenyl)phosphinic acid; phenyl(3,5-xylyl)phosphinic acid; L-cysteic acid monohydrate; acetic acid; propionic acid; butanoic acid; glutamic acid; lysine; Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Palmitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; Tryptophan; polymeric acid; carbon-supported acid; or any combination thereof.

In some embodiments, the catalyst provided herein comprises: (+)-camphor-10-sulfonic acid; 2-pyridinesulfonic acid; 3-pyridinesulfonic acid; 8-hydroxy-5-quinolinesulfonic acid hydrate; α-hydroxy-2-pyridinemethanesulfonic acid; (β)-camphor-10-sulfonic acid; butylphosphonic acid; diphenylphosphinic acid; hexylphosphonic acid; methylphosphonic acid; phenylphosphinic acid; phenylphosphonic acid; tert-butylphosphonic acid; SS)-VAPOL hydrogenphosphate; 6-quinolinesulfonic acid, 3-(1-pyridinio)-1-propanesulfonate; 2-(2-pyridinyl)ethanesulfonic acid; 3-(2-pyridyl)-5,6-diphenyl-1,2,4-triazine-p,p'-disulfonic acid monosodium salt hydrate; 1,1'-binaphthyl-2,2'-diyl-hydrogenphosphate; bis(4-methoxyphenyl)phosphinic acid; phenyl(3,5-xylyl)phosphinic acid; L-cysteic acid monohydrate; poly(styrene sulfonic acid-co-divinylbenzene); lysine; Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Palmitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; Tryptophan; or any combination thereof.

In some embodiments, the catalyst provided herein is (+)-camphor-10-sulfonic acid. In some embodiments, the catalyst provided herein is 2-pyridinesulfonic acid. In some embodiments, the catalyst provided herein is 3-pyridinesulfonic acid. In some embodiments, the catalyst provided herein is 8-hydroxy-5-quinolinesulfonic acid hydrate. In some embodiments, the catalyst provided herein is α-hydroxy-2-pyridinemethanesulfonic acid. In some embodiments, the catalyst provided herein is (β)-camphor-10-sulfonic acid. In some embodiments, the catalyst provided herein is butylphosphonic acid. In some embodiments, the catalyst provided herein is diphenylphosphinic acid. In some embodiments, the catalyst provided herein is hexylphosphonic acid. In some embodiments, the catalyst provided herein is methylphosphonic acid. In some embodiments, the catalyst provided herein is phenylphosphinic acid. In some embodiments, the catalyst provided herein is phenylphosphonic acid. In some embodiments, the catalyst provided herein is tert-butylphosphonic acid. In some embodiments, the catalyst provided herein is SS)-VAPOL hydrogenphosphate. In some embodiments, the catalyst provided herein is 6-quinolinesulfonic acid. In some embodiments, the catalyst provided herein is 3-(1-pyridinio)-1-propanesulfonate. In some embodiments, the catalyst provided herein is 2-(2-pyridinyl)ethanesulfonic acid. In some embodiments, the catalyst provided herein is 3-(2-pyridyl)-5,6-diphenyl-1,2,4-triazine-p,p'-disulfonic acid monosodium salt hydrate. In some embodiments, the catalyst provided herein is 1,1'-binaphthyl-2,2'-diyl-hydrogenphosphate. In some embodiments, the catalyst provided herein is bis(4-methoxyphenyl)phosphinic acid. In some embodiments, the catalyst provided herein is phenyl(3,5-xylyl)phosphinic acid. In some embodiments, the catalyst provided herein is L-cysteic acid monohydrate. In some embodiments, the catalyst provided herein is poly(styrene sulfonic acid-co-divinylbenzene). In some embodiments, the catalyst provided herein is lysine.

In some embodiments, the catalyst is Ethanedisulfonic acid. In some embodiments, the catalyst is Ethanesulfonic acid. In some embodiments, the catalyst is Isethionic acid. In some embodiments, the catalyst is Homocysteic acid. In some embodiments, the catalyst is HEPBS (N-(2-Hydroxyethyl)piperazine-N'-(4-butanesulfonic acid)). In some embodiments, the catalyst is HEPES (4-(2-hydroxyethyl)-1-piperazineethanesulfonic acid). In some embodiments, the catalyst is 2-Hydroxy-3-morpholinopropanesulfonic acid. In some embodiments, the catalyst is 2-(N-morpholino)ethanesulfonic acid. In some embodiments, the catalyst is Methanesulfonic acid. In embodiments, the catalyst is Naphthalene-1-sulfonic acid. In some embodiments, the catalyst is some embodiments, the catalyst is Methaniazide. In some Naphthalene-2-sulfonic acid. In some embodiments, the catalyst is Perfluorobutanesulfonic acid. In some embodiments, the catalyst is 6-sulfoquinovose. In some embodiments, the catalyst is Triflic acid. In some embodiments, the catalyst is 2-aminoethanesulfonic acid. In some embodiments, the catalyst is Benzoic acid. In some embodiments, the catalyst is Chloroacetic acid. In some embodiments, the catalyst is Trifluoroacetic acid. In some embodiments, the catalyst is Caproic acid. In some embodiments, the catalyst is Enanthic acid. In some embodiments, the catalyst is Caprylic acid. In some embodiments, the catalyst is Pelargonic acid. In some embodiments, the catalyst is Lauric acid. In some embodiments, the catalyst is Palmitic acid. In some embodiments, the catalyst is Stearic acid. In some embodiments, the catalyst is Arachidic acid. In some embodiments, the catalyst is Aspartic acid. In some embodiments, the catalyst is Glutamic acid. In some embodiments, the catalyst is Serine. In some embodiments, the catalyst is Threonine. In some embodiments, the catalyst is Glutamine. In some embodiments, the catalyst is Cysteine. In some embodiments, the catalyst is Glycine. In some embodiments, the catalyst is Proline. In some embodiments, the catalyst is Alanine. In some embodiments, the catalyst is Valine. In some embodiments, the catalyst is Isoleucine. In some embodiments, the catalyst is Leucine. In some embodiments, the catalyst is Methionine. In some embodiments, the catalyst is Phenylalanine. In some embodiments, the catalyst is Tyrosine. In some embodiments, the catalyst is Tryptophan.

In some embodiments, the catalyst provided herein is a polymeric catalyst or a carbon-supported catalyst disclosed in WO 2016122887, which is hereby incorporated by reference in its entirety and for its disclosure.

In some embodiments, the catalyst provided herein is present in an amount of from about 0.01% to about 5%, from about 0.02% to about 4%, from about 0.03% to about 3%, or from about 0.05% to about 2% of the one or more feed sugars by dry weight. In some embodiments, the catalyst provided herein is present in an amount of from about 1% to 2% of the one or more feed sugars by dry weight. In some embodiments, the catalyst provided herein is present in an amount of about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0% of the one or more feed sugars by dry weight.

In some embodiments, the catalyst provided herein is present in an amount of from about 0.01% to about 5%, from about 0.02% to about 4%, from about 0.03% to about 3%, or from about 0.05% to about 2% of the aqueous composition by dry weight. In some embodiments, the catalyst provided herein is present in an amount of from about 1% to 2% of the aqueous composition by dry weight. In some embodiments, the catalyst provided herein is present in an amount of about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0% of the aqueous composition by dry weight.

In some embodiments, the catalyst provided herein is a combination of two or more different catalysts. In some embodiments, the catalyst comprises a recyclable catalyst such as resins and polymeric catalysts and a non-recyclable catalyst. In some embodiments, where the catalyst comprises at least two different catalysts, each of the catalyst is present in an amount provided herein. In other embodiments, where the catalyst comprises at least two different catalysts, the at least two different catalysts are present in aggregate in an amount provided herein.

In some embodiments, the catalyst is added into the aqueous composition in a dry form. In other embodiments, the catalyst is added into the aqueous composition in a wet form such as in an aqueous solution. In some embodiment, the catalyst is combined with the one or more feed sugars before the addition of water. In other embodiments, the catalyst is dissolved into water before its combining with the one or more feed sugars. In some embodiments, the method provided herein comprises producing an aqueous composition by combining the one or more feed sugars in the de-hydrate form and the catalyst in a wet form (e.g., as an aqueous solution).

C. Addition of Water

In some embodiments, the methods of manufacturing the oligosaccharide preparations comprise adding water to form the aqueous composition. In some embodiments, all or part of the water in the aqueous composition is added as free water. In other embodiments, all of the water in the aqueous composition is added as bonded water, for example, in saccharide mono- or di-hydrate. In some embodiments, all of the water in the aqueous composition is added as bonded water in monosaccharide mono-hydrate, such as glucose mono-hydrate. In certain embodiments, all or part of the water in the aqueous composition is added with the catalyst, i.e., via a catalyst solution.

D. Water Content

As the methods of manufacturing the oligosaccharide preparations proceed, water can be produced through reaction. For example, in some embodiments, water is produced (i) with the formation of a glycosidic bond, (ii) with the formation of an anhydro-subunit, or (iii) through other mechanisms or sources. As the sugar condensation and dehydration reactions both involve water, in some embodiments, the water content influences the composition of the oligosaccharide preparation.

Further, in some embodiments, water content influences the viscosity of the aqueous composition, which in turn may affect the effectiveness of mixing of the aqueous composition. For example, in some embodiments, an overly viscous aqueous composition can lead to an undesirable heterogeneous catalyst distribution in the aqueous composition. Moreover, in some embodiments, very low water content may lead to the solidification of the aqueous composition, which prevents effective mixing. On the other hand, in some other embodiments, exceedingly high water content may impede sugar condensation reaction and lower the level of the anhydro-subunits. Accordingly, the present disclosure describes suitable water content for the manufacturing of oligosaccharide preparations.

In some embodiments, a herein described method of manufacturing oligosaccharide preparation comprises forming and/or heating an aqueous composition. In some embodiments, the aqueous composition comprises from about 0% to about 80%, from about 0% to about 70%, from about 0% to about 60%, from about 0% to about 50%, from about 0% to about 40%, from about 0% to about 35%, from about 0% to about 30%, from about 0% to about 25%, from about 0% to about 20%, from about 0% to about 19%, from about 0% to about 18%, from about 0% to about 17%, from about 0% to about 16%, from about 0% to about 15%, from about 0% to about 14%, from about 0% to about 13%, from about 0% to about 12%, from about 0% to about 11%, from about 0% to about 10%, from about 0% to about 9%, from about 0% to about 8%, from about 0% to about 7%, from about 0% to about 6%, from about 0% to about 5%, from about 0% to about 4%, from about 0% to about 3%, from about 0% to about 2%, or from about 0% to about 1% of water by total weight. In some embodiments, the aqueous composition comprises from about 1% to about 20%, from about 1% to about 18%, from about 1% to about 16%, from about 1% to about 14%, from about 1% to about 12%, from about 1% to about 10%, from about 1% to about 8%, from about 10% to about 6%, or from about 1% to about 4% of water by total weight. In some embodiments, the aqueous composition comprises from about 3% to about 16%, from about 3% to about 14%, from about 3% to about 12%, from about 3% to about 10%, from about 3% to about 8%, from about 3% to about 6%, from about 5% to about 16%, from about 5% to about 14%, from about 5% to about 12%, from about 5% to about 10%, from about 7% to about 16%, from about 7% to about 14%, from about 7% to about 12%, from about 7% to about 10%, or from about 8% to about 10% of water by total weight. In some embodiments, the aqueous composition comprises about 1%, about 2%, about 3%, about 4%, about 5%, about 6%, about 7%, about 8%, about 9%, about 10%, about 11%, about 12%, about 13%, about 14%, or about 15% of water by total weight. In some embodiments, the aqueous composition comprises about 9% water by total weight. It should be understood, however, that the amount of water in the aqueous composition can be adjusted based on the reaction conditions and specific catalyst used. In some embodiments, the water content in the aqueous composition as disclosed above is measured at the beginning of the reaction, for example, before heating the feed sugars. In some embodiments, the water content in the aqueous composition as disclosed above is measured at the end of the polymerization or condensation reaction. In some embodiments, the water content in the aqueous composition as disclosed above is measured as an average water content of the beginning of the reaction and at the end of the reaction.

In certain embodiments, a method described herein can further comprise monitoring the content of water present in the aqueous composition and/or the ratio of water to sugars or catalyst over a period of time. In some embodiments, the method further comprises removing at least a portion of water in the aqueous composition, for example, by distillation. Any method known in the art can be used to remove water from the aqueous composition, including, for example, by vacuum filtration, vacuum distillation, heating, steam, hot air, and/or evaporation.

In some embodiments, herein described oligosaccharide preparations are hygroscopic. Thus, in some embodiments, the hygroscopicity of the feed sugars and the oligosaccharides formed in the polymerization can affect the rate by which the water can be removed from the aqueous composition.

In some embodiments, a herein described method comprises removing at least a portion of water in the aqueous composition such that the water content in the aqueous composition is from about 1% to about 20%, from about 1% to about 18%, from about 1% to about 16%, from about 1% to about 14%, from about 1% to about 12%, from about 1% to about 10%, from about 1% to about 8%, from about 2% to about 16%, from about 2% to about 14%, from about 2% to about 12%, from about 2% to about 10%, from about 2% to about 8%, from about 2% to about 6%, from about 4% to about 16%, from about 4% to about 14%, from about 4% to about 12%, from about 4% to about 10%, from about 4% to about 8%, from about 6% to about 16%, from about 6% to about 12%, from about 6% to about 10%, or from about 6% to about 8% by total weight. In some embodiments, the method comprises removing at least a portion of water in the aqueous composition such that the water content in the aqueous composition is from about 2% to about 10%, from about 2% to about 8%, or from about 4% to about 8% by total weight. In some embodiments, the method comprises removing at least a portion of water in the aqueous composition such that the water content in the aqueous composition is about 2%, about 3%, about 4%, about 5%, about 6%, about 7%, about 8%, about 9%, or about 10% by total weight. In some embodiments, the method comprises removing at least a portion of water in the aqueous composition such that the water content in the aqueous composition is from about 4% to about 8% by total weight. In some embodiments, the method comprises removing at least a portion of water in the aqueous composition such that, at the end of the polymerization and/or condensation reaction, the water content in the aqueous composition is a water content as disclosed above. In some embodiments, the method comprises removing at least a portion of water in the aqueous composition such that, at the beginning of the polymerization and/or condensation reaction, the water content in the aqueous composition is a water content as disclosed above. In some embodiments, the method comprises removing at least a portion of water in the aqueous composition such that, the average water content in the aqueous composition at the beginning and the end of the polymerization and/or condensation reaction is within a range as disclosed above. In some embodiments, the method comprises removing at least a portion of water in the aqueous composition such that, throughout the polymerization and/or condensation reaction, the water content in the aqueous composition remains within a range as disclosed above.

In some embodiments, a herein described method comprises adding at least a portion of water in the aqueous composition such that the water content in the aqueous composition is from about 1% to about 20%, from about 1% to about 18%, from about 1% to about 16%, from about 1% to about 14%, from about 1% to about 12%, from about 1% to about 10%, from about 1% to about 8%, from about 2% to about 16%, from about 2% to about 14%, from about 2% to about 12%, from about 2% to about 10%, from about 2% to about 8%, from about 2% to about 6%, from about 4% to about 16%, from about 4% to about 14%, from about 4% to about 12%, from about 4% to about 10%, from about 4% to about 8%, from about 6% to about 16%, from about 6% to about 12%, from about 6% to about 10%, or from about 6% to about 8% by total weight. In some embodiments, the method comprises adding at least a portion of water in the aqueous composition such that the water content in the aqueous composition is from about 2% to about 10%, from about 2% to about 8%, or from about 4% to about 8% by total weight. In some embodiments, the method comprises adding at least a portion of water in the aqueous composition such that the water content in the aqueous is about 2%, about 3%, about 4%, about 5%, about 6%, about 7%, about 8%, about 9%, or about 10% by total weight. In some embodiments, the method comprises adding at least a portion of water in the aqueous composition such that the water content in the aqueous composition is from about 4% to about 8% by total weight. In some embodiments, the method comprises adding at least a portion of water in the aqueous composition such that, at the end of the polymerization and/or condensation reaction, the water content in the aqueous composition is a water content as disclosed above. In some embodiments, the method comprises adding at least a portion of water in the aqueous composition such that, at the beginning of the polymerization and/or condensation reaction, the water content in the aqueous composition is a water content as disclosed above. In some embodiments, the method comprises adding at least a portion of water in the aqueous composition such that, the average water content in the aqueous composition at the beginning and the end of the polymerization and/or condensation reaction is within a range as disclosed above. In some embodiments, the method comprises adding at least a portion of water in the aqueous composition such that, throughout the polymerization and/or condensation reaction, the water content in the aqueous composition remains within a range as disclosed above.

In some embodiments, the degrees of polymerization of the oligosaccharides and/or the amount and type of the anhydro-subunits within the oligosaccharide preparation can be regulated by adjusting or controlling the content of water present in the aqueous composition throughout the manufacturing process. For example, in some embodiments, the degrees of polymerization of the oligosaccharides and the amount of the anhydro-subunits are increased by decreasing the water content.

Accordingly, in some embodiments, a herein described method comprises in-process control (IPC) of the water content, which can comprise monitoring water content, maintaining water content, increasing water content, decreasing water content, or any combination thereof. In some embodiments, an IPC process comprises maintaining the water content while the aqueous composition is heated to a temperature described herein. In some embodiments, the method comprises maintaining the water content for the time sufficient to induce polymerization. In some embodiments, the method comprises maintaining the water content within a disclosed range by either adding water or removing water from the aqueous composition, or both. In some embodiments, the method comprises maintaining the water content within a disclosed range by distillation. In some embodiments, the method comprises maintaining the water content within a disclosed range by vacuum distillation. In some embodiments, the method comprises maintaining the water content within a disclosed range by distillation under atmosphere pressure.

In some embodiments, the water content of the aqueous composition is maintained within a range of from about 1% to about 20%, from about 1% to about 18%, from about 1% to about 16%, from about 1% to about 14%, from about 10% to about 12%, from about 10% to about 10%, from about 1% to about 8%, from about 2% to about 16%, from about 2% to about 14%, from about 2% to about 12%, from about 2% to about 10%, from about 2% to about 8%, from about 2% to about 6%, from about 4% to about 16%, from about 4% to about 14%, from about 4% to about 12%, from about 4% to about 10%, from about 4% to about 8%, from about 6% to about 16%, from about 6% to about 12%, from about 6% to about 10%, or from about 6% to about 8% by total weight. In some embodiments, the water content of the aqueous composition is maintained within a range of from about 2% to about 10%, from about 2% to about 8%, or from about 4% to about 8% by total weight. In some embodiments, the water content of the aqueous composition is maintained within a range of from about 2% to about 8% by total weight.

The water content of the aqueous composition can be determined by a variety of analytical methods and instruments. In some embodiments, the water content is determined by an evaporation method (e.g., loss on drying technique), a distillation method, or a chemical reaction method (e.g., Karl Fischer titration). In some embodiments, the water content is determined by an analytical instrument such as a moisture analyzer. In some embodiments, the water content is determined by Karl Fischer titration.

In some embodiments, the water content of the aqueous composition is measured during the reaction and is used to implement in-process control (IPC) of the water content. In certain embodiments, the water content of the reaction is measured by Karl-Fisher titration, IR spectroscopy, NIR spectroscopy, conductivity, viscosity, density, mixing torque, or mixing energy. In some embodiments, the measurement of the water content of the reaction is used to control an apparatus that actively adjusts the water content of the reaction, such as a water addition pump or flow valve.

Without being bound by theory, it is believed that water content during the sugar polymerization and/or condensation reaction can affect the level of the anhydro-subunits in a herein described oligosaccharide preparation. For example, as illustrated in FIG. 30, in some embodiments, a higher water content correlates with a lower level of anhydro-subunits. In some embodiments, a lower reaction temperature can correlate with a lower level of anhydro-subunits content.

E. Temperature

In some embodiments, the degrees of polymerization of the oligosaccharides and/or the amount and type of the anhydro-subunits within the oligosaccharide preparation can be regulated by adjusting the temperature, to which the aqueous composition is heated. In some embodiments, a herein described method of manufacturing an oligosaccharide preparation comprises heating the aqueous composition to a temperature of from about 80° C. to about 250° C., from about 90° C. to about 200° C., from about 100° C. to about 200° C., from about 100° C. to about 180° C., from about 110° C. to about 170° C., from about 120° C. to about 160° C., from about 130° C. to about 150° C., or from about 135° C. to about 145° C. In some embodiments, the method of manufacturing an oligosaccharide preparation comprises heating the aqueous composition to a temperature of from about 100° C. to about 200° C., from about 100° C. to about 180° C., from about 110° C. to about 170° C., from about 120° C. to about 160° C., from about 130° C. to about 150° C., or from about 135° C. to about 145° C. In some embodiments, the method of manufacturing an oligosaccharide preparation comprises heating the aqueous composition to a temperature of from about 135° C. to about 145° C. In other embodiments, the method of manufacturing an oligosaccharide preparation comprises heating the aqueous composition to a temperature of from about 125° C. to about 135° C.

F. Reaction Time

In some embodiments, a herein described method of manufacturing an oligosaccharide preparation comprises heating the aqueous composition for a sufficient time. In some embodiments, the degrees of polymerization of the oligosaccharides manufactured according to the methods described herein can be regulated by the reaction time.

In some embodiments, the sufficient time is prescribed by a number of hours. For example, in some embodiments, the sufficient time is at least 30 minutes, at least 1 hour, at least 2 hours, at least 3 hours, at least 4 hours, at least 5 hours, at least 6 hours, at least 7 hour, at least 8 hours, at least 9 hours, or at least 10 hours. In some embodiments, the sufficient time is from about 1 to about 24 hours, from about 1 to about 16 hours, from about 1 to about 8 hours, from about 1 to about 4 hours, from about 1 to about 3 hours, from about 1 to about 2 hours, from about 2 to about 12 hours, from about 2 to about 10 hours, from about 2 to about 8 hours, from about 2 to about 6 hours, from about 2 to about 4 hours, from about 3 to about 8 hours, from about 3 to about 6 hours, from about 3 to about 5 hours, or from about 3 to about 4 hours.

In some embodiments, the sufficient time is determined by measuring one or more chemical or physical properties of the oligosaccharide preparation, for example, water content, viscosity, molecular weight, anhydro-subunit content, and/or the distribution of degrees of polymerization.

In some embodiments, the molecular weight of the oligosaccharide preparation is monitored during polymerization. In some embodiments, the method comprises heating the aqueous composition for a time sufficient for the aqueous composition to reach a number average molecular weight or weight average molecular weight as described herein. In certain embodiments, the method comprises heating the aqueous composition for a time sufficient for the aqueous composition to reach a number average molecular weight within a range of from about 300 to about 5000 g/mol, from about 500 to about 5000 g/mol, from about 700 to about 5000 g/mol, from about 500 to about 2000 g/mol, from about 700 to about 2000 g/mol, from about 700 to about 1500 g/mol, from about 300 to about 1500 g/mol, from about 300 to about 2000 g/mol, from about 400 to about 1000 g/mol, from about 400 to about 900 g/mol, from about 400 to about 800 g/mol, from about 500 to about 900 g/mol, or from about 500 to about 800 g/mol. In certain embodiments, the method comprises heating the aqueous composition for a time sufficient for the aqueous composition to reach a number average molecular weight of from about 500 to about 2000 g/mol. In certain embodiments, the method comprises heating the aqueous composition for a time sufficient for the aqueous composition to reach a weight average molecular weight within a range of from about 300 to about 5000 g/mol, from about 500 to about 5000 g/mol, from about 700 to about 5000 g/mol, from about 500 to about 2000 g/mol, from about 700 to about 2000 g/mol, from about 700 to about 1500 g/mol, from about 300 to about 1500 g/mol, from about 300 to about 2000 g/mol, from about 400 to about 1300 g/mol, from about 400 to about 1200 g/mol, from about 400 to about 1100 g/mol, from about 500 to about 1300 g/mol, from about 500 to about 1200 g/mol, from about 500 to about 1100 g/mol, from about 600 to about 1300 g/mol, from about 600 to about 1200 g/mol, or from about 600 to about 1100 g/mol. In certain embodiments, the method comprises heating the aqueous composition for a time sufficient for the aqueous composition to reach a weight average molecular weight of from about 700 to about 3000 g/mol.

In some embodiments, the sufficient time is the time required for the aqueous composition to reach reaction equilibrium at the respective reaction temperature. Accordingly, in some embodiments, the method comprises heating the aqueous composition for a time sufficient for the aqueous composition to reach equilibrium. For example, in some embodiments, the equilibrium is determined by measuring the molecular weight, viscosity, or DP distribution of the aqueous composition.

In certain embodiments, the equilibrium is determined by measuring the number average or weight average molecular weight of the aqueous composition. In some embodiments, the equilibrium is determined by the number or weight average molecular weight of the aqueous composition that remains essentially unchanged over time. In some embodiments, the equilibrium is determined by a change of the number or weight average molecular weight of the aqueous composition that is less than certain percentage over a period of time. In some embodiments, the molecular weight of the aqueous composition is measured by HPLC or SEC.

In some embodiments, the equilibrium is determined by a change of the number or weight average molecular weight of the aqueous composition of less than 25%, less than 20%, less than 15%, less than 10%, or less than 5% over a period of time. In some embodiments, the equilibrium is determined by a change of the number or weight average molecular weight of the aqueous composition over a period of 3 hours, 2 hours, 1 hour, 30 minutes, 20 minutes, or 10 minutes. In some embodiments, the equilibrium is determined by a change of the weight average molecular weight of the aqueous composition of less than 15% over the period of 1 hour.

In certain embodiments, the equilibrium is determined by measuring the viscosity of the aqueous composition. In some embodiments, the equilibrium is determined by the viscosity of the aqueous composition that remains essentially unchanged over time. In some embodiments, the equilibrium is determined by a change of the viscosity of the aqueous composition that is less than certain percentage over a period of time. In some embodiments, the viscosity of the aqueous composition is measured by a viscometer or rheometer.

In some embodiments, the equilibrium is determined by a change of the viscosity of the aqueous composition of less than 25%, less than 20%, less than 15%, less than 10%, or less than 5% over a period of time. In some embodiments, the equilibrium is determined by a change of the viscosity of the aqueous composition over a period of 3 hours, 2 hours, 1 hour, 30 minutes, 20 minutes, or 10 minutes. In some embodiments, the equilibrium is determined by a change of the viscosity of the aqueous composition of less than 15% over the period of 1 hour.

In certain embodiments, the equilibrium is determined by measuring the DP distribution of the aqueous composition. In some embodiments, the equilibrium is determined by the DP distribution of the aqueous composition that remains essentially unchanged over time. In some embodiments, a change of the DP distribution of the aqueous composition is determined by calculating a series of Km, wherein $$Km = \frac{[DP_m][H_2O]}{[DP_{m-1}][DP1]},$$

wherein [$H_2O$] represents the molar water concentration (mol/L), and [DP1], [$DP_{m-1}$], and [DPm] represent the molar concentrations of oligosaccharides (mol/L) in the DP1, $DP_{m-1}$, and DPm fraction, respectively. For example, K2 equals [DP2][$H_2O$]/[DP1][DP1] according to the above formula. In some embodiments, m is an integer larger than 1 and less than n. In some embodiments, m is an integer larger than 1 and less than or equal to n. In some embodiments, m equals n. In some embodiments, m is 2, 3, 4, 5, 6, 7, 8, 9, or 10.

In some embodiments, the concentration of the oligosaccharides in the DP1, DPm-1, and DPm fractions are determined by SEC, HPLC, FFF, A4F, mass spectrometry, or any other suitable method. In some embodiments, the concentration of the oligosaccharides in the DP1, DPm-1, and DPm fractions are determined by SEC such as GPC. In some embodiments, the concentration of the oligosaccharides in the DP1, DPm-1, and DPm fractions are determined by mass spectrometry such as GC-MS, LC-MS/MS, and MALDI-MS. In some embodiments, the concentration of the oligosaccharides in the DP1, DPm-1, and DPm fractions are determined by HPLC. In some embodiments, the water concentration is determined by an evaporation method (e.g., loss on drying technique), a distillation method, or by a chemical reaction method (e.g., Karl Fischer titration). In some embodiments, the water concentration is determined by any suitable analytical instrument such as a moisture analyzer.

In some embodiments, the method comprises calculating a series of at least 3, at least 4, at least 5, at least 6, at least 7, at least 8, at least 9, at least 10, at least 15, at least 20, at least 30, at least 40, or at least 50 Km numbers. In some embodiments, the method comprises calculating a series of at least 3, at least 4, at least 5, at least 6, at least 7, at least 8, at least 9, at least 10, or at least 15 Km numbers. In some embodiments, the method comprises calculating about 3, 4, 5, 6, 7, 8, 9, 10, or 15 Km numbers. In some embodiments, the method comprises calculating K2 to K4, K2 to K5, K2 to K6, K2 to K7, K2 to K8, K2 to K9, K2 to K10, K2 to K11, K2 to K12, K2 to K13, K2 to K14, K2 to K15, K3 to K5, K3 to K6, K3 to K7, K3 to K8, K3 to K9, K3 to K10, K3 to K11, K3 to K12, K3 to K13, K3 to K14, or K3 to K15. In certain embodiments, the method comprises calculating K2 to K4 or K3 to K5.

In some embodiments, the value of Km depends on the temperature, water concentration, and/or the amount and type of the feed sugars. In some embodiments, Km is from about 0.1 to about 100, from about 0.1 to about 90, from about 0.1 to about 80, from about 0.1 to about 70, from about 0.1 to about 60, from about 0.1 to about 50, from about 0.1 to about 40, from about 0.1 to about 30, from about 0.1 to about 25, from about 0.1 to about 20, or from about 0.1 to about 15. In some embodiments, Km is from about 1 to about 100, from about 1 to about 90, from about 1 to about 80, from about 1 to about 70, from about 1 to about 60, from about 1 to about 50, from about 1 to about 40, from about 1 to about 30, from about 1 to about 25, from about 1 to about 20, from about 1 to about 15, from about 1 to about 10, from about 5 to about 50, from about 5 to about 40, from about 5 to about 30, from about 5 to about 20, from about 5 to about 15, or from about 5 to about 10. In some specific embodiments, Km is from about 1 to about 15 or from about 5 to about 15.

In some embodiments, an average, a standard deviation, and/or a relative standard deviation are determined for the series of Km calculated. As used herein, a relative standard deviation is expressed in percentage, and is obtained by multiplying the standard deviation by 100 and dividing this product by the average.

In some embodiments, the equilibrium is determined by the relative standard deviation of the series of Km of less than 30%, less than 25%, less than 20%, less than 15%, less than 10%, less than 9%, less than 8%, less than 7%, less than 6%, less than 5%, less than 4%, less than 3%, less than 2%, or less than 1%. In some embodiments, the equilibrium is determined by the relative standard deviation of the series of Km of less than 15%, less than 10%, or less than 5%.

G. Post-Reaction Steps

In some embodiments, a herein described method of manufacturing oligosaccharide preparations further comprises one or more additional processing steps after heating the aqueous composition at a temperature and for a sufficient time. In some embodiments, the additional processing steps comprise, for example, separation (such as chromatographic separation), dilution, concentration, drying, filtration, demineralization, extraction, decolorization, or any combination thereof. For example, in some embodiments, the method comprises a dilution step and a decolorization step. In some embodiments, the method comprises a filtration step and a drying step.

In some embodiments, the method comprises a dilution step, where water is added into the oligosaccharide preparation to make a syrup of oligosaccharide preparation. In some embodiments, the concentration of oligosaccharide preparation in the syrup is from about 5% to about 80%, from about 10% to about 70%, from about 10% to about 60%, from about 10% to about 50%, from about 10% to about 40%, from about 10% to about 30%, or from about 15% to about 25%. In other embodiments, the method does not comprise a dilution step, but rather, the oligosaccharide preparation is allowed to solidify. In some embodiments, the method comprises a filtration step. In some embodiments, the method comprises recycling the catalyst by filtration.

In some embodiments, the method described herein further comprises a decolorization step. In some embodiments, the oligosaccharide preparation may undergo a decolorization step using any method known in the art, including, for example, treatment with an absorbent, activated carbon, chromatography (e.g., using ion exchange resin), hydrogenation, and/or filtration (e.g., microfiltration).

In some embodiments, the oligosaccharide preparation is contacted with a material to remove salts, minerals, and/or other ionic species. In certain embodiments, the oligosaccharide preparation is flowed through an anionic/cationic exchange column pair. In one embodiment, the anionic exchange column contains a weak base exchange resin in a hydroxide form and the cationic exchange column contains a strong acid exchange resin in a protonated form.

In some embodiments, the method comprises a concentration step. In some embodiments, the centration step produces an oligosaccharide preparation with increased concentration. For example, in some embodiments, the concentration step comprises evaporation (e.g., vacuum evaporation), drying (e.g., freeze-drying and spray drying) or any combination thereof.

In some embodiments, the method comprises an isolation step, wherein at least a portion of the oligosaccharide preparation is separated. In some embodiments, the isolation step comprises crystallization, precipitation, filtration (e.g., vacuum filtration), and centrifugation, or any combination thereof.

In some embodiments, the method comprises a separation step. In some embodiments, the separation step comprises separating at least a portion of the oligosaccharide preparation from at least a portion of the catalyst, from at least a portion of the unreacted feed sugars, or from both. In some embodiments, the separation step comprises filtration, chromatography, differential solubility, precipitation, extraction, or centrifugation.

H. Reactors

The methods described herein can comprise the use of one or more reactors suitable for sugar condensation, considering the reaction temperature, pH, pressure, and other factors. In some embodiments, the one or more suitable reactors comprise a fed-batch stirred reactor, a batch stirred reactor, a continuous flow stirred reactor, a continuous plug-flow column reactor, an attrition reactor, or a reactor with stirring induced by an electromagnetic field. In some embodiments, the one or more suitable reactors comprise a reactor described in Ryu, S. K., and Lee, J. M., Bioconversion of waste cellulose by using an attrition bioreactor, Biotechnol. Bioeng. 25: 53-65 (1983); Gusakov, A. V., and Sinitsyn, A. P., Kinetics of the enzymatic hydrolysis of cellulose: 1. A mathematical model for a batch reactor process, Enz. Microb. TechnoL, 7: 346-352 (1985); Gusakov, A. V., Sinitsyn, A. P., Davydkin, I. Y., Davydkin, V. Y., Protas, O. V., Enhancement of enzymatic cellulose hydrolysis using a novel type of bioreactor with intensive stirring induced by electromagnetic field, Appl. Biochem. Biotechnol., 56: 141-153 (1996); or Femanda de Castilhos Corazza, Flavio Faria de Moraes, Gisella Maria Zanin and Ivo Neitzel, Optimal control in fed-batch reactor for the cellobiose hydrolysis, Acta Scientiarum. Technology, 25: 33-38 (2003).

In some embodiments, the one or more suitable reactors comprise fluidized bed, upflow blanket, immobilized, or extruder type reactors for hydrolysis and/or fermentation. In some embodiments, the one or more suitable reactors comprise an open reactor, a closed reactor, or both. In some embodiments, where the method comprises a continuous process, the one or more suitable reactors can include a continuous mixer such as a screw mixer.

I. Process

In some embodiments, a herein described method of manufacturing oligosaccharide preparations comprises a batch process, a continuous process, or both. In some embodiments, the method of manufacturing the oligosaccharide preparation comprises a batch process. For example, in some embodiments of the batch process, manufacturing of subsequent batches of the oligosaccharide preparation does not start until the completion of the current batch. In some embodiments, during the batch process, all or a substantial amount of oligosaccharide preparation is removed from the reactor. In some embodiments, during the batch process, all the feed sugars and the catalyst are combined in a reactor before the aqueous composition is heated to the described temperature or before the polymerization is induced. In some embodiments, during the batch process, the feed sugars are added before, after, or simultaneous with the addition of the catalyst.

In some embodiments, the batch process is a fed-batch process, wherein all the feed sugars are not added into the reactor at the same time. In some embodiments of the fed-batch process, at least a portion of the feed sugars are added into the reactor during polymerization or after the aqueous composition is heated to the described temperature. In some embodiments of the fed-batch process, at least 10%, 20%, 30%, 40%, 50%, or 60% by weight of the feed sugars are added into the reactor during polymerization or after the aqueous composition is heated to the described temperature.

In some embodiments, the method of manufacturing the oligosaccharide preparation comprises a continuous process. For example, in some embodiments of the continuous process, the contents of the reactor continuously flow through the reactor. In some embodiments, the combination of the feed sugars with the catalyst and the removal of at least a portion of the oligosaccharide preparation are performed concurrently.

In some embodiments, the method of manufacturing the oligosaccharide preparation comprises a single-pot or multi-pot process. For example, in some embodiments of the single-pot process, the polymerization is performed in a single reactor. For another example, in some embodiments of the multi-pot process, the polymerization is performed in more than one reactor. In some embodiments of the multi-pot process, the method comprises 2, 3, or more reactors. In some embodiments of the multi-pot process, the method comprises a combination step, where the polymerization products from two or more reactors are combined.

IV. Nutritional Compositions Comprising Oligosaccharide Preparations

Provided herein are nutritional compositions comprising an oligosaccharide preparation. In certain embodiments, provided herein are nutritional compositions comprising a described oligosaccharide preparation, wherein the presence and/or concentration of the oligosaccharide preparation within the nutritional compositions may be selectively determined and/or detected. Oligosaccharide preparations, which exhibit complex functional modulation of a microbial community, may be important components of nutritional compositions. Thus, the presence and/or concentration of an oligosaccharide preparation within nutritional compositions may be one of the factors that need to be measured in the quality control and manufacturing process of the nutritional compositions. Accordingly, the provided nutritional compositions are advantageous in terms of quality control and manufacturing purposes as the presence and/or concentration of the oligosaccharide preparation may be selectively determined and/or detected. For example, in some embodiments, the presence and concentration of the oligosaccharide preparation may be determined and/or detected by measuring a signal associated with the anhydro-subunit containing oligosaccharides.

In some embodiments, the nutritional composition is an animal feed composition. In some embodiments, the nutritional composition comprises a base nutritional composition.

A. Base Nutritional Compositions

In some embodiments, the base nutritional composition comprises a carbohydrate source that is different from the oligosaccharide preparation. For example, in some embodiments, the base nutritional composition comprises a naturally occurring carbohydrate source such as starch and plant fibers. In some embodiments, the base nutritional composition comprises starch. In some embodiments, the base nutritional composition comprises plant fibers.

In some embodiments, the base nutritional composition comprises one or more carbohydrate sources that are derived from: seeds, roots, tubers, corn, tapioca, arrowroot, wheat, rice, potatoes, sweet potato, sago, beans (e.g., favas, lentils, mung beans, peas, and chickpeas), maize, cassava, or other starchy foods (e.g., acorns, arrowroot, arracacha, bananas, barley, breadfruit, buckwheat, canna, colacasia, katakuri, kudzu, malanga, millet, oats, oca, polynesian arrowroot, sorghum, rye, taro, chestnuts, water chestnuts, and yams).

In some embodiments, the base nutritional composition comprises one or more carbohydrate sources that are derived from: legumes (e.g., peas, soybeans, lupins, green beans, and other beans), oats, rye, chia, barley, fruits (e.g., figs, avocados, plums, prunes, berries, bananas, apple skin, quinces, and pears), vegetables (e.g., broccoli, carrots, cauliflower, zucchini, celery, nopal, and Jerusalem artichokes), root tubers, root vegetables (e.g., sweet potatoes and onions), psyllium seed husks, seeds (e.g., flax seeds), nuts (e.g., almonds), whole grain foods, wheat, corn bran, lignans, or any combination thereof. In some embodiments, the base nutritional composition comprises one or more plant fibers derived from wheat bran, sugar beet pulp, fuzzy cottonseeds, soy hulls, or any combination thereof.

In some embodiments, the base nutritional composition comprises less than 500 ppm, less than 400 ppm, less than 300 ppm, less than 200 ppm, less than 100 ppm, less than 50 ppm, less than 10 ppm, less than 5 ppm, or less than 1 ppm anhydro-subunits or anhydro-subunit containing oligosaccharides. In some embodiments, the base nutritional composition comprises less than 50 ppm, less than 10 ppm, less than 5 ppm, or less than 1 ppm anhydro-subunits or anhydro-subunit containing oligosaccharides. In some embodiments, the base nutritional composition is essentially free of anhydro-subunits.

In some embodiments, the base nutritional composition lacks a detectable level of anhydro-subunits. Depending on the methods of detecting or determination, an anhydro-subunit level below a certain threshold can be undetectable. For example, in some embodiments, a detectable level of anhydro-subunit can refer to at least 1000 ppm, at least 500 ppm, at least 400 ppm, at least 300 ppm, at least 200 ppm, at least 100 ppm, at least 50 ppm, at least 10 ppm, at least 5 ppm, or at least 1 ppm of anhydro-subunit or anhydro-subunit containing oligosaccharides in the base nutritional composition.

In some embodiments, the base nutritional composition comprises a plurality of oligosaccharides. In some embodiments, the base nutritional composition comprises a glycosidic bond type distribution that is different from the oligosaccharide preparation. For example, in some embodiments, the base nutritional composition comprises a higher percentage of α-(1,4) glycosidic linkages than the oligosaccharide preparation. In some embodiments, the glycosidic linkages such as the α-(1,4) glycosidic linkages in the base nutritional compositions are digestible by one or more enzymes. In some embodiments, the glycosidic linkages in the base nutritional composition are more readily digestible and/or hydrolysable than the glycosidic linkages in the oligosaccharide preparation.

In some embodiments, the level of α-(1,2) glycosidic linkage, α-(1,3) glycosidic linkage, α-(1,6) glycosidic linkage, β-(1,2) glycosidic linkage, β-(1,3) glycosidic linkage, β-(1,4) glycosidic linkage, or β-(1,6) glycosidic linkage in the base nutritional composition is at least 2%, at least 3%, at least 4%, at least 5%, at least 6%, at least 7%, at least 8%, at least 9%, at least 10%, at least 11%, at least 12%, at least 13%, at least 14%, or at least 15% lower than the level of the respective glycosidic linkage in the oligosaccharide preparation. In some embodiments, the level of α-(1,2) glycosidic linkage, α-(1,3) glycosidic linkage, α-(1,6) glycosidic linkage, β-(1,2) glycosidic linkage, β-(1,3) glycosidic linkage, β-(1,4) glycosidic linkage, or β-(1,6) glycosidic linkage in the base nutritional composition is at least 10% lower than the level of the respective glycosidic linkage in the oligosaccharide preparation.

In some embodiments, the level of α-(1,4) glycosidic linkage in the base nutritional composition is at least 50%, at least 40%, at least 35%, at least 30%, at least 25%, at least 20%, at least 15%, at least 10%, at least 5%, or at least 2% higher than the level of α-(1,4) glycosidic linkage in the oligosaccharide preparation. In some embodiments, the level of α-(1,4) glycosidic linkage in the base nutritional composition is at least 10% higher than the level of α-(1,4) glycosidic linkage in the oligosaccharide preparation.

B. Animal Feed Composition

Depending on the type and age of an animal, a nutritional composition can comprise the oligosaccharide preparation and the base nutritional composition at different ratio. For example, the oligosaccharide preparation may be combined with the base nutritional composition at various ratios suitable for the type and age of an animal. In some embodiments, the oligosaccharide preparation is present in the nutritional composition at a concentration of from about 1 to about 10000 ppm, from about 1 to about 5000 ppm, from about 1 to about 3000 ppm, from about 1 to about 2000 ppm, from about 1 to about 1500 ppm, from about 1 to about 1000 ppm, from about 1 to about 500 ppm, from about 1 to about 250 ppm, from about 1 to about 100 ppm, from about 10 to about 5000 ppm, from about 10 to about 3000 ppm, from about 10 to about 2000 ppm, from about 10 to about 1500 ppm, from about 10 to about 1000 ppm, from about 10 to about 500 ppm, from about 10 to about 250 ppm, from about 10 to about 100 ppm, from about 50 to about 5000 ppm, from about 50 to about 3000 ppm, from about 50 to about 2000 ppm, from about 50 to about 1500 ppm, from about 50 to about 1000 ppm, from about 50 to about 500 ppm, from about 50 to about 250 ppm, from about 50 to about 100 ppm, from about 100 to about 5000 ppm, from about 100 to about 3000 ppm, from about 100 to about 2000 ppm, from about 100 to about 1500 ppm, from about 100 to about 1000 ppm, from about 100 to about 500 ppm, from about 100 to about 400 ppm, from about 100 to about 300 ppm, from about 100 to about 200 ppm, from about 200 to about 5000 ppm, from about 200 to about 3000 ppm, from about 200 to about 2500 ppm, from about 200 to about 2000 ppm, from about 200 to about 1500 ppm, from about 200 to about 1000 ppm, from about 200 to about 500 ppm, from about 500 to about 5000 ppm, from about 500 to about 3000 ppm, from about 500 to about 2500 ppm, from about 500 to about 2000 ppm, from about 500 to about 1500 ppm, or from about 500 to about 1000 ppm. In some embodiments, the oligosaccharide preparation is present in the nutritional composition at a concentration of from about 1 to about 5000 ppm, from about 1 to about 1000 ppm, from about 1 to about 500 ppm, from about 10 to about 5000 ppm, from about 10 to about 2000 ppm, from about 10 to about 1000 ppm, from about 10 to about 500 ppm, from about 10 to about 250 ppm, from about 10 to about 100 ppm, from about 50 to about 5000 ppm, from about 50 to about 2000 ppm, from about 50 to about 1000 ppm, from about 50 to about 500 ppm, from about 50 to about 250 ppm, or from about 50 to about 100 ppm. In some embodiments, the oligosaccharide preparation is present in the nutritional composition at a concentration of from about 1 to about 5000 ppm, from about 10 to about 1000 ppm, from about 10 to about 500 ppm, or from about 50 to about 500 ppm.

In some embodiments, the oligosaccharide preparation is present in the nutritional composition at a concentration of greater than 10 ppm, greater than 50 ppm, greater than 100 ppm, greater than 200 ppm, greater than 300 ppm, greater than 400 ppm, greater than 500 ppm, greater than 600 ppm, greater than 1000 ppm, or greater than 2000 ppm. In some embodiments, the oligosaccharide preparation is present in the nutritional composition at a concentration of greater than 10 ppm, greater than 50 ppm, greater than 100 ppm, greater than 200 ppm, or greater than 500 ppm.

In some embodiments, depending on the type and age of an animal, the nutritional composition can further comprise proteins, minerals (such as copper, calcium, and zinc), salts, essential amino acids, vitamins, and/or antibiotics.

Also provided herein is a method of administering a nutritional composition comprising a base nutritional composition and the disclosed oligosaccharide preparation to an animal. In some embodiments, the animal is selected from cattle (e.g., beef cattle and dairy cattle), swine, aquatic animal, and poultry. In some embodiments, the animal is swine, such as sows, piglets, and hogs. In other embodiments, the animal is poultry such as chicken, duck, turkey, goose, quail, and hen. In embodiments, the poultry is a broiler, a breeder, or a layer. In some embodiments, the animal is an aquatic animal such salmon, catfish, bass, eel, tilapia, flounder, shrimp, and crab. In some embodiments, the nutritional composition is administered to an animal in a dry form, a liquid form, a paste, or a combination thereof. In some embodiments, the form of administration, the feeding rate, and the feeding schedule can vary depending on the type and age of the animal.

C. Methods of Producing Nutritional Compositions

Provided herein are methods of manufacturing a nutritional composition comprising: combining an oligosaccharide preparation with a base nutritional composition. In some embodiments, the oligosaccharide preparation comprises anhydro-subunit containing oligosaccharides. In some embodiments, the oligosaccharide preparation comprises a glycosidic bond type distribution that is different from that of the base nutritional composition.

In some embodiments, the oligosaccharide preparation is a synthetic oligosaccharide preparation. In some embodiments, the synthetic oligosaccharide preparation comprises at least n fractions of oligosaccharides each having a distinct degree of polymerization selected from 1 to n (DP1 to DPn fractions). In some embodiments, n is an integer greater than or equal to 2. In some embodiments, n is an integer greater than 2. In some embodiments, n is an integer greater than or equal to 3. In some embodiments, n is an integer within a range of 1 to 100, such as 4, 5, 6, 7, 8, 9, 10, 11, 12, 13, 14, 15, 16, 17, 18, 19, 20, 21, 22, 23, 24, 25, 26, 27, 28, 29, 30, 40, or 50. In some embodiments, each of the DP1 to DPn fraction comprises from 0.1% to 90% anhydro-subunit containing oligosaccharides by relative abundance as measured by mass spectrometry. In some embodiments, the DP1 and DP2 fractions of the oligosaccharide preparation each independently comprises from about 0.10% to about 15% or from about 0.5% to about 10% of anhydro-subunit containing oligosaccharides by relative abundance as measured by mass spectrometry. In some embodiments, the DP1 and DP2 fractions of the oligosaccharide preparation each independently comprises anhydro-subunit containing oligosaccharides within a range of from about 0.1%, 0.5%, 0.6%, 0.7%, 0.8%, 0.9%, 1%, 1.1%, 1.2%, 1.3%, 1.4%, or 1.5% to about 8%, 9%, 10%, 11%, 12%, 15% or 20% by relative abundance as measured by mass spectrometry. In some embodiments, the relative abundance of oligosaccharides in each of the n fractions decreases monotonically with its degree of polymerization. In some embodiments, the relative abundance of oligosaccharides in at least 5, 10, 20, or 30 DP fractions decreases monotonically with its degree of polymerization.

In some embodiments, the method of manufacturing a nutritional composition comprises mixing the oligosaccharide preparation with the base nutritional composition. For example, in some embodiments, the mixing may be performed by an industrial blender and/or mixer such as drum blender, double cone blender, ribbon blender, V blender, shear mixer, and paddle mixer.

In some embodiments, the method of manufacturing a nutritional composition further comprises a herein described quality control step. In some embodiments, the herein described quality control step comprises determining a level of a signal in a sample of the nutritional composition and calculating a concentration of the oligosaccharide preparation in the nutritional composition based on the level of the signal. In some embodiments, the herein described quality control step comprises detecting a signal in a sample of the nutritional composition through analytical instrumentation, and accepting or rejecting a batch of the nutritional composition based on the presence or absence of the signal. In some embodiments, the herein described quality control step comprises detecting, through analytical instrumentation, the presence or absence of a first signal in a first sample of the nutritional composition, and a second signal in a second sample of the nutritional composition, and comparing the first signal and the second signal. In some embodiments, the signal, the first signal, and/or the second signal is/are (i) indicative of one or more anhydro-subunit containing oligosaccharides, (ii) associated with a degree of polymerization (DP) distribution of oligosaccharides, or (iii) associated with α-(1,2) glycosidic linkage, α-(1,3) glycosidic linkage, α-(1,6) glycosidic linkage, β-(1,2) glycosidic linkage, β-(1,3) glycosidic linkage, β-(1,4) glycosidic linkage, or R-(1,6) glycosidic linkage of oligosaccharides.

Additionally, in some embodiments, the method of manufacturing a nutritional composition comprises, after performing the quality control step, further mixing the oligosaccharide preparation with the base nutritional composition, adjusting the level of the oligosaccharide preparation, or a combination thereof. In some embodiments, adjusting the level of the oligosaccharide preparation comprises adding additional oligosaccharide preparation into the nutritional composition or removing a portion of the oligosaccharide preparation from the nutritional composition. In some embodiments, adjusting the level of the oligosaccharide preparation comprises adding additional base nutritional composition into the nutritional composition or removing a portion of the base nutritional composition from the nutritional composition. In some particular embodiments, adjusting the level of the oligosaccharide preparation comprises adding additional oligosaccharide preparation into the nutritional composition.

D. Animal Feed Pre-Mix

In some embodiments, the nutritional composition comprises an animal feed pre-mix comprising a described oligosaccharide preparation.

In some embodiments, the animal feed pre-mix comprises a carrier material, which may be combined with the oligosaccharide preparation to produce the animal feed pre-mix. In some embodiments, the carrier material may be any material in dry or liquid form that is suitable to be combined with the oligosaccharide preparation in the nutritional composition. In some embodiments, the carrier material comprises dried distiller's grains, clay, vermiculite, diatamacious earth, hulls such as ground rice hulls and ground oat hulls, silica such as feed grade silica gel and feed grade fumed silica, corn such as corn gluten feed, corn gluten meal, and milled corn, or any combinations thereof. In some embodiments, the carrier material is milled corn. In other embodiments, the carrier material is ground rice hulls or ground oat hulls.

In some embodiments, the animal feed pre-mix is produced by combining a carrier material with the oligosaccharide preparation, both in a dry form. In some embodiments, the animal feed pre-mix is produced by combining a carrier material with the oligosaccharide preparation; one of the two is in a dry form. In some embodiments, the animal feed pre-mix is produced by combining a carrier material with the oligosaccharide preparation, both in a liquid form. For example, in some embodiments, an oligosaccharide preparation in a liquid form refers to the oligosaccharide in a solution, e.g., an aqueous solution of the oligosaccharides such as syrup.

In some embodiments, the animal feed pre-mix is produced by combining a carrier material with a syrup comprising the oligosaccharide preparation. In some embodiments, the concentration of the oligosaccharide preparation in the syrup is at least 40%, at least 45%, at least 50%, at least 55%, at least 60%, at least 65%, at least 70%, at least 75%, or at least 80% by weight. In some embodiments, the concentration of the oligosaccharide preparation in the syrup is about from 40% to 80%, 50% to 75%, or 60% to 70% by weight.

In some embodiments, the animal feed pre-mix is in a powder (e.g., flowable powder), a slush, a slurry, a pellets form, or a liquid form. In some embodiments, the animal feed pre-mix has a moisture content of less than 40%, 30%, 20%, 15%, 10%, or 5% by weight. In some embodiments, the animal feed pre-mix has a moisture content of less than 10% or 5% by weight. In some embodiments, the animal feed pre-mix has a moisture content of higher than 5%, 10%, 15%, 20%, 25%, or 30% by weight. In further embodiments, the moisture content of the animal feed pre-mix is adjusted to any of the described ranges. For example, in some embodiments, the animal feed pre-mix is dried to increase its moisture content to a described range.

In some embodiments, depending on a specific application, the animal feed pre-mix comprises various levels of the oligosaccharide preparation. In some embodiments, the animal feed pre-mix comprises at least 1%, 5%, 10%, 15%, 20%, 25%, 30%, 40%, 50%, 60%, 70%, 80%, 90%, 95%, or 99% the oligosaccharide preparation by dry weight. In some embodiments, the animal feed pre-mix comprises at most 50%, 60%, 70%, 80%, 90%, 95%, or 99% the oligosaccharide preparation by dry weight.

In some embodiments, the animal feed pre-mix or the carrier material further comprises other animal nutrition such as minerals, fats, and proteins. In some embodiments, the carrier material or the animal feed pre-mix comprises copper, zinc, or both. In some embodiments, the carrier material or the animal feed pre-mix comprises an ionophore or other coccidiostat. In some embodiments, the carrier material or the animal feed pre-mix comprises an antibiotic. In some embodiments, the carrier material comprises a carbohydrate source. In some embodiments, the carbohydrate source in the carrier material does not comprise anhydro-subunits. In some embodiments, the carbohydrate source in the carrier material comprises a glycosidic bond type distribution that is different from the glycosidic bond type distribution of the oligosaccharide preparation.

Accordingly, in some embodiments, the method of manufacturing a nutritional composition comprises combining the animal feed pre-mix with the base nutritional composition.

V. Methods of Providing Oligosaccharide Preparations to Animals

In some embodiments, the methods described herein include providing oligosaccharide preparations to animals. In certain variations, animals are treated by being fed or provided an oligosaccharide preparation. In some embodiments, the animals are provided an oligosaccharide preparation at an intended specific dose. A specific dose may be quantified, for example, as the mass of oligosaccharide preparation consumed by the animal per unit of time (e.g., grams per day), or as the mass of oligosaccharide preparation consumed by the animal per unit of time per unit animal body mass (e.g., mg of oligosaccharide per kg of body mass per day). In certain embodiments, the specific dose of an oligosaccharide preparation is 1, 5, 10, 15, 20, 25, 30, 40, 50, 60, 70, 80, 90, 100, 110, 120, 130, 140, 150, 160, 170, 180, 190, 200, 225, 250, 275, 300, 350, 400, 450, 500, 1000, 1500, 2000, 3000, 4000, 5000, or 10000 mg/kg/day. In some embodiments, the mass of the oligosaccharide preparation is measured as the DP1+ content on a dry solids basis. In some embodiments, the mass of the oligosaccharide preparation is measured as the DP2+ content on a dry solids basis.

In some embodiments, animals are provided oligosaccharide preparations by oral administration via nutritional compositions. In some embodiments, the nutritional composition is formulated to contain an oligosaccharide preparation at a fixed concentration or level of inclusion. The oligosaccharide concentration or level of inclusion in the nutritional composition can be quantified by, for example, the mass fraction of the oligosaccharide preparation per total mass of the final feed or nutritional composition. In some embodiments, the concentration or level of inclusion is measured in parts per million (ppm) of oligosaccharide on a dry solids basis per final nutritional composition on an as-is basis. In some embodiments, the concentration of the oligosaccharide preparation is measured as the mass fraction of DP1+ species on a dry solids basis. In some embodiments, the concentration of the oligosaccharide preparation is measured as the mass fraction of DP2+ species on a dry solids basis.

One of ordinary skill in the art would know various methods and techniques for determining the concentration of the oligosaccharide preparation in the nutritional composition or final feed to achieve an intended specific dose. For example, average daily feed intake as a functional of age is established for different species of broiler chickens and might be used by a nutritionist or veterinarian to determine a desired level of inclusion in final feed.

In some embodiments, animals are provided oligosaccharide preparations by oral administration via consumed liquids. In some embodiments, the oligosaccharide preparations are provided via drinking water. In some embodiments, the concentration of the oligosaccharide preparation in the drinking water is selected to provide an intended specific dose of oligosaccharide preparation to the animal.

VI. Gastrointestinal Barrier Dysfunction

In some embodiments, the methods described herein include preventing or treating dysfunction of a gastrointestinal barrier of an animal. The gastrointestinal barriers of animals comprise a layer of mucus and a layer of epithelial intestinal cells (including, for example, goblet cells). The intestinal epithelium acts as a barrier to prevent the passage of harmful intraluminal entities including foreign antigens, microorganisms and their toxins, and other intestinal content (e.g., food particles). The intestinal epithelium also acts as a selective filter allowing the translocation of essential dietary nutrients, electrolytes, and water from the intestinal lumen into the circulation.

The gastrointestinal epithelium mediates selective permeability via two major routes: transepithelial/transcellular and paracellular. Transcellular permeability is generally associated with solute transport through the epithelial cells and predominantly regulated by selective transporters for amino acids, electrolytes, short chain fatty acids and sugars. Paracellular permeability is associated with transport in the space between epithelial cells, and is regulated by intercellular complexes localized at the apical-lateral membrane junction and along the lateral membrane. Contact between intestinal epithelial cells includes three main components: desmosomes, adherens junctions and tight junctions.

Permeability of the gastrointestinal barriers is regulated by multiple factors including, for example, exogenous factors, epithelial apoptosis, cytokines, immune cells, and the gastrointestinal microbiome. Bacteria of the microbiome and enteric pathogens can disrupt the intestinal barrier directly by binding to cell surface molecules and inducing changes in tight junction protein expression. Bacteria of the microbiome and enteric pathogens can also generate toxins and proteases, which can promote cell damage and apoptosis, alter epithelial ion transport, and disrupt tight junctions and the cytoskeleton.

Dysfunction of the gastrointestinal barrier enables the translocation of intestinal contents into the circulation, including e.g., pathogens and toxins, which can negatively impact the health of the animal and cause disease. Inflammation and/or damage to the epithelial cells can also reduce the ability of the animal to absorb nutrients. Animals with a compromised gastrointestinal barrier therefore exhibit poor nutrition and health outcomes, resulting in reduced weight gain, weight loss, reduced feed efficiency, reduced meat yield, increased feed conversion ratio, lower meat quality, and higher mortality.

A. Methods of Preventing Gastrointestinal Barrier Dysfunction

In some embodiments, the methods described herein include methods of preventing dysfunction of a gastrointestinal barrier in an animal. In some embodiments, the dysfunction of the gastrointestinal barrier is an increase in the permeability of the gastrointestinal barrier above that of a healthy state, which allows for translocation of intestinal contents, including e.g., partially digested food, pathogens, and toxins, into the circulation. In some embodiments, the gastrointestinal barrier dysfunction is hyper-permeability of the gastrointestinal barrier. Hyper-permeability is also known in the art as "leaky gut." As described above, leaky gut can allow toxins, bacteria, and food particles to penetrate the lining of the gastrointestinal tract and enter the body's blood stream. Leaky gut can refer to an acute or a chronic condition. Leaky gut can result in infection, sepsis, or a damaged bowel lining.

Symptoms of a leaky gut can include, but are not limited to, decreased mucus synthesis, decreased mucin synthesis, decreased mucus secretion, decreased mucin secretion, decreased nutrient absorption, increased inflammation, decreased resistance to infection, decreased proliferation of intestinal epithelial cells, decreased maturation of intestinal epithelial cells, malnutrition, decreased weight gain, increased feed conversion ratio, decreased feed efficiency, increased mortality. In some embodiments, the methods described herein prevent one or more symptom of a gastrointestinal barrier dysfunction, such as a symptom of leaky gut.

In some embodiments, the dysfunction is prevented by decreasing the permeability of the gastrointestinal barrier in the animal. In some embodiments, the permeability of the gastrointestinal barrier is about 0.5%, 1%, 2%, 3%, 4%, 5%, 10%, 15%, 20%, 25%, 30%, 40%, or 50% less than the permeability of the gastrointestinal barrier of said animal prior to administration of said synthetic oligosaccharide preparation. In some embodiments, the permeability of the gastrointestinal barrier is about 0.5-40%, 0.5-30%, 0.5-20%, 0.5-10%, 0.5-5%, 0.5-4%, 0.5-3%, 0.5-3%, 0.5-2%, 0.5-1%, 1-40%, 1-30%, 1-20%, 1-10%, 1-5%, 1-4%, 1-3%, 1-2%, 5-40%, 5-30%, 5-20%, 5-10%, 10-40%, 10-30%, or 10-20% less than the permeability of the gastrointestinal barrier of said animal prior to administration of said synthetic oligosaccharide preparation.

In some embodiments, the dysfunction is prevented by decreasing the permeability of the gastrointestinal barrier in the animal. In some embodiments, the permeability of the gastrointestinal barrier is about 0.5%, 1%, 2%, 3%, 4%, 5%, 10%, 15%, 20%, 25%, 30%, 40%, or 50% less than the permeability of the gastrointestinal barrier of an animal administered a nutritional composition lacking the synthetic oligosaccharide preparation. In some embodiments, the permeability of the gastrointestinal barrier is about 0.5-40%, 0.5-30%, 0.5-20%, 0.5-10%, 0.5-5%, 0.5-4%, 0.5-3%, 0.5-3%, 0.5-2%, 0.5-1%, 1-40%, 1-30%, 1-20%, 1-10%, 1-5%, 1-4%, 1-3%, 1-2%, 5-40%, 5-30%, 5-20%, 5-10%, 10-40%, 10-30%, or 10-20% less than the permeability of the gastrointestinal barrier of an animal administered a nutritional composition lacking the synthetic oligosaccharide preparation.

B. Methods of Treating Gastrointestinal Barrier Disfunction

In some embodiments, the methods described herein include methods of treating dysfunction of the gastrointestinal barrier in an animal. In some embodiments, the dysfunction of the gastrointestinal barrier is an increase in the permeability of the gastrointestinal barrier above that of a healthy state, which allows for translocation of intestinal contents, including e.g., partially digested food, pathogens, and toxins, into the circulation.

In some embodiments, the gastrointestinal barrier dysfunction is hyper-permeability of the gastrointestinal barrier. Hyper-permeability is also known in the art as "leaky gut." As described above, leaky gut can allow toxins, bacteria, and food particles to penetrate the lining of the gastrointestinal tract and enter the body's blood stream. Leaky gut can refer to an acute or a chronic condition. Leaky gut can result in infection, sepsis, or a damaged bowel lining.

Symptoms of a leaky gut can include, but are not limited to, decreased mucus synthesis, decreased mucin synthesis, decreased mucus secretion, decreased mucin secretion, decreased nutrient absorption, increased inflammation, decreased resistance to infection, decreased proliferation of intestinal epithelial cells, decreased maturation of intestinal epithelial cells, malnutrition, decreased weight gain, increased feed conversion ratio, decreased feed efficiency, increased mortality. In some embodiments, one or more of the symptoms of leaky gut are ameliorated.

In some embodiments, the dysfunction is prevented by decreasing the permeability of the gastrointestinal barrier in the animal. In some embodiments, the permeability of the gastrointestinal barrier is about 0.5%, 1%, 2%, 3%, 4%, 5%, 10%, 15%, 20%, 25%, 30%, 40%, or 50% less than the permeability of the gastrointestinal barrier of said animal prior to administration of said synthetic oligosaccharide preparation. In some embodiments, the permeability of the gastrointestinal barrier is about 0.5-40%, 0.5-30%, 0.5-20%, 0.5-10%, 0.5-5%, 0.5-4%, 0.5-3%, 0.5-3%, 0.5-2%, 0.5-1%, 1-40%, 1-30%, 1-20%, 1-10%, 1-5%, 1-4%, 1-3%, 1-2%, 5-40%, 5-30%, 5-20%, 5-10%, 10-40%, 10-30%, or 10-20% less than the permeability of the gastrointestinal barrier of said animal prior to administration of said synthetic oligosaccharide preparation.

In some embodiments, the dysfunction is treated by decreasing the permeability of the gastrointestinal barrier in the animal. In some embodiments, the permeability of the gastrointestinal barrier is about 0.5%, 1%, 2%, 3%, 4%, 5%, 10%, 15%, 20%, 25%, or 30% less than the permeability of the gastrointestinal barrier of the animal prior to administration of the nutritional composition lacking the synthetic oligosaccharide preparation. In some embodiments, the permeability of the gastrointestinal barrier is about 0.5-40%, 0.5-30%, 0.5-20%, 0.5-10%, 0.5-5%, 0.5-1%, 1-40%, 1-30%, 1-20%, 1-10%, 1-5%, 1-2%, 5-40%, 5-30%, 5-20%, 5-10%, 10-40%, 10-30%, or 10-20% less than the permeability of the gastrointestinal barrier of the animal prior to administration of the nutritional composition lacking the synthetic oligosaccharide preparation.

C. Methods of Detecting Gastrointestinal Barrier Permeability and Nutrient Absorption Gastrointestinal barrier permeability can be demonstrated by methods known in the art, such as a lactulose-mannitol test, wherein the animal is given a solution containing mannitol and lactulose and urine collected for six hours and tested. Lactulose (a disaccharide) and Mannitol (a monosaccharide) are two water soluble, non-metabolized sugar molecules. Mannitol is easily absorbed, passively penetrating cells, whilst Lactulose, with a larger molecular weight and size, is only partially absorbed by a healthy gastrointestinal barrier. If the levels of mannitol and lactulose in the collected urine sample are high it is indicative that the permeability of the gastrointestinal tract is too high. Low levels of both molecules indicate malabsorption of nutrients. High levels of mannitol and low levels of lactulose indicate that the animal has normal gastrointestinal barrier function.

Gastrointestinal barrier permeability can also be assessed using a digestive stool analysis, which includes the testing of fecal material for digestive function, the extent to which lipids, proteins, carbohydrates and other nutrients are absorbed in the small intestine and colon, as well as for the presence of candida or other bacterial infections, dysbiosis (imbalance in intestinal bacteria), parasitic infection and other indicators of digestive dysfunction. Improvements in bowel function caused by the administration of the synthetic oligosaccharide preparations described herein can also be measured by decreased diarrhea, a decrease in one or more symptoms of leaky gut, increased solid stool, increased production of 5-hydroxy-tryptophan and 5-hydroxytryptamine and 2-methyl-5-hydroxytryptamine, and other neurotransmitter precursors that can be made by bacterial populations (serotonin precursors). Gastrointestinal barrier permeability assessments can also be made using fluorescent tracers (e.g., as described in Droshow et al., "Measurement of gut permeability using fluorescent tracer agent technology," Scientific Reports, 7:108888 (2017)). Other methods include for example those disclosed in Wang et al., "Methods to determine intestinal permeability and bacterial translocation during liver disease," J Immunol Methods, 421:44-53 (2015); Galipeau et al., Neurogastroenterology and Motility, 28:7 (2016); and described in the Examples herein. Gastrointestinal permeability can also be tested using a variety of non-digestible sugars, labeled dextrans, and radio-isotopes known in the art.

Gastrointestinal barrier permeability can also be assessed by histological analysis of a tissue sample or cell sample of said gastrointestinal barrier. In some embodiments one or more stains or labels are used in such an analysis that are known in the art. These include for example, H&E staining, immunofluorescent staining, the use of immunofluorescent antibodies or other targeting agents. Microcopy methods include all of those known in the art, e.g., light microcopy, confocal microscopy, electron microscopy, etc. In some embodiments, the methods described herein comprise evaluating mucosal morphology of said gastrointestinal barrier. In some embodiments, said evaluating comprises determining villus length, crypt length, a level of inflammatory cell infiltration, or any combination thereof.

Similar methods to those described above can be used to assess the ability of the gastrointestinal tract to absorb nutrients. For example, the level of a specific macro or micronutrients can be assessed in a stool sample, e.g., fat. Sweat samples can be analyzed to detect the level of enzymes that are needed to properly direct nutrients. A lactose hydrogen breath test can be sued to determine how much hydrogen is in the animal's breath after a milk sugar (e.g., lactose) solution. Biopsies can be taken of a gastrointestinal barrier in order to assess nutrient absorption. Numerous tests to measure the ability of the gastrointestinal tract to absorb nutrients are known in the art and incorporated herein.

In some embodiments, the level of at least one (e.g., at least 2, 3, 4, 5, 6, 7, 8, 9, or 10) nutrient transporters expressed by a gastrointestinal barrier are analyzed to determine the ability of the gastrointestinal barrier to absorb nutrients generally or a specific macro or micro nutrient. Methods of such analysis are known in the art and incorporated by reference herein. Transporters include, but are not limited to proteins or proteins expressed by SI (sucrase-isomaltase), SLC5A10, SLC34A1, SLC2A2, SLC34A2, SLC23A1, SLC23A2, SLC5A8, SLC16A3, SLC4, SLC4A9, SLC4A2, SLC4A3, NPC1L1, C6orf58, DDC, MCT1, MCT4, NaS1, DTDST, PAT1, DRA, CLD, SAT1, SUT2, SGLT1, GLUT2, B$^0$AT1, ATB0+, SIT1, TAUT, EAAC1, ASCT2, SN1, SN2, PEPT1, SNAT2, GLYT1, y+LAT1, y+LAT2, CD36, LFABP, NPC1L1, ABCG5, ABCG8, SVCT1, SVCT2, SMVT, GIF, AMN, CUBL, MRP1, FOLT, PCFT, FOLR1, OAT10, RFVT1, RFVT2, THTR1, THTR2, VDR, DCYTB, DMT1, HCP1, FPN1, HEPH, HAMP, ZIP4, ZIP11, ZIP8, ZIP14A, ZIP14B, ZnT1, ZnT2, CTR1, SLC3A1, SLC1A4, ALPI, C17orf78, MUC17, DEFA5, RBP2, DEFA6, MLN, MEP1B, LCT, TM4SF20, or FABP6.

Gastrointestinal barrier permeability can be assessed using a variety of samples, e.g., as described herein. For example said samples include, but are not limited to, a tissue sample of a gastrointestinal barrier, a biopsy of gastrointestinal barrier, a cell sample of gastrointestinal barrier, a blood sample, a serum sample, a urine sample, a fecal sample, a cecal (e.g., cecal contents), a sweat sample, or a saliva sample.

Gastrointestinal barriers include any barrier of the gastrointestinal tract, e.g., ileum, cecum, small intestine, colon, stomach, duodenum, jejunum.

D. Goblet Cell Proliferation and Mucus Production

In some embodiments, the methods described herein, include increasing goblet cell proliferation in the gastrointestinal tract of or animal. Goblet cells are simple columnar epithelial cells that that make up part of the epithelial lining of the gastrointestinal barrier. Goblet cells secrete mucus, which contains large glycoproteins called mucins. The mucus layer of the gastrointestinal barrier acts to protect the epithelial cells and prevent breach of the epithelial cells by microorganisms, toxins, etc.

Standard assays known to the skilled artisan can be used to assess goblet cell proliferation. For example, in vitro assays as described in the Examples herein can be used. A variety of molecular or biochemical markers may also be used to assess goblet cell proliferation, including, but not limited to, gene expression or protein expression characteristic of goblet cells, e.g., mucins. Certain mucin genes, e. g., MUC5B, are expressed in the gastrointestinal tract, and have a gene product highly represented in mucus. Therefore, expression of mucin genes provides a suitable marker for determining production of mucus.

Mucin gene expression may be assessed by conventional technology such as northern blot analysis, polymerase chain reaction (PCR), examination of the mucin gene promoter, or in situ analysis. Alternatively, mucin proteins are assessed by conventional methodology, such as western blot analysis, ELISA, immunochemistry and the like, using detectably labeled antibodies. Morphological criteria may also be used to determine the presence or absence of goblet cells in the culture; such as staining for mucins using Alcian blue/PAS staining (Lou et al. (1998) Am. J. Respir. Crit. Care Med. 157:1927-1934). Antibodies to mucins can be examined using ELISA assays.

In vivo assays may also be used to assess the goblet cell proliferation in animals. The gastrointestinal tissue of an animal may be assessed for goblet cell abundance. Gastrointestinal tissue samples of animals may also be assessed for the same molecular and biochemical markers described for the in vitro assays above.

E. Susceptibility to Infection

In some embodiments, the methods described herein, include decreasing the susceptibility of an animal to an infection. Methods also include preventing an infection in an animal or a population of animals. As described above, gastrointestinal barrier dysfunction resulting in an increase in gastrointestinal barrier permeability allows the translocation of pathogenic microorganisms from the intraluminal space to the circulation. Methods described herein prevent infection in an animal by decreasing the gastrointestinal barrier permeability. Methods described herein also decrease the susceptibility of an animal to infection by decreasing the gastrointestinal barrier permeability. The infection can be a result of any pathogenic microorganism present in the lumen of the gastrointestinal tract. The pathogen may access the gastrointestinal tract through contaminated food. In some embodiments, the pathogen is a microorganism. In some embodiments, the pathogen is a bacterium, virus, parasite, or fungus. In some embodiments the pathogen is of the phylum Proteobacteria. In some embodiments, the pathogen is a bacterium and classified as genera *Helicobacter, Escherichia, Salmonella, Vibrio,* or *Yersinia*. In some embodiments, the pathogen is a bacterium and is classified as genera *Treponema, Streptococcus, Staphylococcus, Shigella, Rickettsia, Orientia, Pseudomonas, Neisseria, Mycoplasma, Mycobacterium, Listeria, Leptospira, Legionella, Klebsiella, Haemophilus, Francisella, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium,* and *Bacillus.* Bacterial species include, but are not limited to, *Helicobacter pullo-* rum, *Proteobacteria johnsonii*, *Escherichia coli*, *Campylobacter jejuni*, and *Lactobacillus* crispatus. In some embodiments, the pathogen is *Aeromonas hydrophila*, *Campylobacter fetus*, *Plesiomonas shigelloides*, *Bacillus cereus*, *Campylobacter jejuni*, *Clostridium botulinum*, *Clostridium difficile*, *Clostridium perfringens*, enteroaggregative *Escherichia coli*, enterohemorrhagic *Escherichia coli*, enteroinvasive *Escherichia coli*, enterotoxigenic *Escherichia coli*, *Helicobacter pylori*, *Klebsiella* pneumonia, *Listeria monocytogenes*, *Plesiomonas shigelloides*, *Salmonella* spp., *Salmonella typhi*, *Salmonella paratyphi*, *Shigella* spp., *Staphylococcus* spp., *Staphylococcus aureus*, vancomycin-resistant *enterococcus* spp., *Vibrio* spp., *Vibrio cholerae*, *Vibrio parahaemolyticus*, *Vibrio vulnificus*, and *Yersinia enterocolitica*. In some embodiments, the pathogen is singe or multi drug resistant. Infection of an animal with one or more pathogens can be assessed by standard methods known to the skilled artisan.

In some embodiments, the pathogen is a parasite. In some embodiments, said parasite is an *Eimeria* parasite. In some embodiments, said parasite is *Eimeria acervuline*, *Eimeria maxima*, *Eimeria mitis*, *Eimeria tenella*, *Toxoplasma gondii*, *Hammondia* spp. *Cryptosporidium parvum*, *Cryptosporidium muris*, *Cryptosporidium hominis*, *Isospora canis*, *Isospora ohioensis*, *Isospora burrosi*, *Isospora felis*. In some embodiments, said pathogen is a coccidian protozoa. In some embodiments said coccidian protozoa is *Eimeria acervuline*, *Eimeria maxima*, *Eimeria mitis*, *Eimeria tenella*, *Toxoplasma gondii*, *Hammondia* spp. *Cryptosporidium parvum*, *Cryptosporidium muris*, *Cryptosporidium hominis*, *Isospora canis*, *Isospora ohioensis*, *Isospora burrosi*, or *Isospora felis*.

In some embodiments, the level of at least one pro-inflammatory cytokines or chemokines in the gastrointestinal tract of the animal is increased. Exemplary cytokines and chemokines include, but are not limited to, tumor necrosis factors (TNF) such as TNF-α and TNF-β, TNF superfamily molecules such as FasL, CD27L, CD30L, CD40L, Ox40L, 4-1BBL, TRAIL, TWEAK, and Apo3L, interleukin-1 (IL-1) including IL-1α and IL-1β, IL-2, interferon-γ (IFN-γ), IFN-α/β, IL-6, IL-8, IL-12, IL-15, IL-17, IL-18, IL-21, LIF, CCL5, GROα, MCP-1, MIP-1α, MIP-1β, RANTES, macrophage colony stimulating factor (MCSF), granulocyte macrophage colony stimulating factor (GM-CSF), CXCL2, CCL2, lymphotactin, fractalkine, or GRO/KC, among others.

In some embodiments, the level of at least one anti-inflammatory cytokine or chemokine in the gastrointestinal tract of the animal is decreased. Exemplary anti-inflammatory cytokines and chemokines include, but are not limited to, interleukin (IL)-1 receptor antagonist, IL-4, IL-6, IL-10, IL-11, IL-13, and TGFβ.

In some embodiments, the level of at least one immune cell is increased in the gastrointestinal tract of the animal. In other embodiments, the level of at least one immune cell is increased in the lymphatic system of the animal. In some embodiments, the immune cell is an innate immune cell. In some embodiments, the immune cell is an adaptive immune cell. Exemplary immune cells include, but are not limited to, T cell, B cells, natural killer cells, macrophages, dendritic cells, granulocytes (including e.g., basophils, eosinophils, and neutrophils), mast cells, and monocytes. In some embodiments, the immune cell is a phagocytic cell. Phagocytic immune cells include, but are not limited to, neutrophils, monocytes, macrophages, mast cells, and dendritic cells. In some embodiments, the phagocytic activity of the immune cell is increased. In certain embodiments, immune cell differentiation occurs in Peyer patches.

F. Gastrointestinal Samples

In certain embodiments, the methods described herein include detecting a property (including e.g., the level of mucus, the level of an immune cell, the level of a cytokine, the level of a chemokine, etc.) in the gastrointestinal tract of an animal. In certain embodiments, the property is detected or quantified in a gastrointestinal sample from an animal. Gastrointestinal samples can be obtained from an animal in any standard form which reflects the metabolic contents of the gastrointestinal tract of the animal. Gastrointestinal samples include gastrointestinal tissue samples obtained e.g., by endoscopic biopsy. Gastrointestinal tissues include, e.g., oral tissue, esophagus, stomach, intestine, ileum, cecum, colon or rectum. Samples also feces, saliva, urine, and gastrointestinal ascites. Methods of obtaining gastrointestinal samples are standard and known to the skilled artisan. In some embodiments said sample is a blood or serum sample.

In some embodiments, the sample is a single sample from a single animal. In some embodiments, the sample is a combination of multiple samples from a single animal. In some embodiments, cells or proteins are purified from the sample prior to analysis. In some embodiments, cells or proteins from a single sample are purified. In some embodiments, cells or proteins from multiple samples from a single animal are purified and subsequently combined prior to analysis.

VII. Methods of Enhancing Animal Performance

A. Feed Conversion Ratio

In some embodiments, the methods described herein include reducing the feed conversion ratio of an animal. In some embodiments, an animal administered a synthetic oligosaccharide preparation, a nutritional composition, an animal feed pre-mix, or an animal feed composition as described herein has a lower feed conversion ratio compared to an animal provided a diet that does not include the synthetic oligosaccharide preparation. As used herein the term "feed conversion ratio (FCR)," refers to the ratio of feed mass input (for example consumed by the animal) to the animal output, wherein the animal output is the target animal product. For example, the animal output for dairy animals is milk, whereas the animal output for animals raised for meat is body mass.

In some embodiments, the animal is raised for meat, and the target animal output is body mass. Thus, in some embodiments, the FCR refers to the ratio of the weight of feed consumed compared to the final body weight of the animal prior to processing. In some embodiments, the FCR refers to the ratio of the weight of feed consumed compared to the final body weight gain of the animal prior to processing. It should be understood that FCR may be measured for an animal or population of animals over different time periods. For example, in some embodiments, the FCR is an FCR over the entire lifetime of the animal. In other embodiments, the FCR is a daily FCR, or a weekly FCR, or a cumulative FCR measured up until a particular moment in time (for example, a particular day).

A person of skill in the art would recognize that the performance target minimum FCR (optimal FCR) may be different for different types of animals, and may be different for different breeds of one type animal (for example, different breeds of broiler chickens, or different breeds of swine). The performance target minimum FCR may also be different depending on age of the animal (for example, chickens or swine in a grower phase compared to a finisher phase), or the sex of the animal. It should be clear that the optimal FCR may be different depending on any combination of these factors.

Performance target minimum generally refers to the lowest feed efficiency observed for a given animal and breed under ideal growing conditions, ideal animal health, and ideal dietary nutrition. It is well known to one skilled in the art that under common growing conditions, an animal may not achieve the performance target minimum FCR. An animal may not achieve its performance target minimum FCR due to a variety of health, nutrition, environmental, and/or community influences. An animal may not achieve its performance target minimum FCR when raised in a challenged environment, which may include, for example, environmental pathogenic stress, excessive environmental temperature (heat stress), excessive environmental humidity, crowding, or other social interaction effects, such as difficulty accessing feed or drinking water. In some embodiments, an animal may not achieve its performance target minimum FCR due to disease or environmental pathogenic stress. In other embodiments, an animal may not achieve its performance target minimum FCR due to excessive environmental temperature (heat stress), or excessive environmental humidity. In yet other embodiments, an animal may not achieve its performance target minimum FCR due to crowding, or other social interaction effects, such as difficulty accessing feed or drinking water.

In some embodiments, an animal provided a diet which does not include the synthetic oligosaccharide preparation described herein has an FCR that is at least 1%, 2%, 3%, 4%, 5%, 6%, 7%, 8%, 9%, or 10% higher than the performance target minimum FCR. In certain embodiments, an animal provided a diet which does not include a synthetic oligosaccharide preparation described herein has an FCR that is 1% to 10% higher than the performance target minimum, 2% to 10% higher than the performance target minimum, or 5% to 10% higher than the performance target minimum.

In some embodiments, an animal provided a nutritional composition comprising a synthetic oligosaccharide preparation, a nutritional composition, an animal feed pre-mix, or an animal feed composition as described herein has an FCR that is closer to the performance target minimum compared to an animal provided a diet that does not include the synthetic oligosaccharide preparation. In particular embodiments, the animal provided a synthetic oligosaccharide preparation, nutritional composition, animal feed pre-mix, or animal feed composition as described herein has an FCR that is between 0 to 10% higher than the performance target minimum, between 0 to 5% higher than the performance target minimum, or between 0 to 2% higher than the performance target minimum.

In some embodiments, an animal provided a synthetic oligosaccharide preparation, a nutritional composition, animal feed pre-mix, or animal feed composition as described herein has a lower feed conversion ratio compared to an animal provided a diet that does not include the synthetic oligosaccharide preparation. For example, in certain embodiments, the animal provided a diet comprising the synthetic oligosaccharide preparation consumes less food but has the same animal output as compared to an animal provided a diet that does not include the synthetic oligosaccharide preparation. In other embodiments, the animal provided a diet comprising the synthetic oligosaccharide preparation consumes the same amount of food but has a higher animal output as compared to an animal provided a diet that does not include the synthetic oligosaccharide preparation. In yet other embodiments, the animal provided a diet comprising the synthetic oligosaccharide preparation consumes less food and has a higher animal output as compared to an animal provided a diet that does not include the synthetic oligosaccharide preparation.

In some embodiments, the FCR of an animal provided a synthetic oligosaccharide preparation, nutritional composition, animal feed pre-mix, or animal feed composition as described herein is reduced at least 1%, at least 2%, at least 4%, at least 6%, at least 8%, at least 10%, at least 12%, between 1 to 10%, between 4 to 10%, between 1 to 8%, between 4 to 8%, between 1 to 6%, or between 4 to 6% as compared to an animal provided a diet that does not include the synthetic oligosaccharide preparation. In some embodiments, the animal is poultry. In certain embodiments, the FCR of the poultry is reduced over 0 to 14 days of age, over 15 to 28 days of age, over 29 to 35 days of age, over 35 days, over 42 days, over 6 weeks, over 6.5 weeks, over 0 to 35 days of age, over 0 to 42 days of age, over 0 to 6 weeks of age, over 0 to 6.5 weeks of age, over 15 to 35 days of age, over 36 to 42 days of age, over 15 to 39 days of age, or over 40 to 46 days of age.

In one embodiment, the FCR over 35 days for poultry provided a synthetic oligosaccharide preparation, nutritional composition, animal feed pre-mix, or animal feed composition as described herein is reduced by between 4 to 6% as compared to poultry provided a diet that does not include the synthetic oligosaccharide preparation. For example, in a certain embodiment, the FCR over 35 days for poultry provided a nutritional composition describing a synthetic oligosaccharide preparation, nutritional composition, animal feed pre-mix, or animal feed composition as described herein is 1.53, the FCR over 35 days for poultry provided a diet without the synthetic oligosaccharide preparation is 1.61, and the FCR of the poultry provided the nutritional composition comprising a oligosaccharide preparation, nutritional composition, animal feed pre-mix, or animal feed composition is reduced about 5% compared to the poultry provided a diet without the synthetic oligosaccharide preparation. In some embodiments, the FCR over 42 days, over 6 weeks, or over 6.5 weeks days for poultry provided a synthetic oligosaccharide preparation, nutritional composition, animal feed pre-mix, or animal feed composition as described herein is reduced by between 4 to 6% as compared to poultry provided a diet that does not include the synthetic oligosaccharide preparation.

In some embodiments, an animal population provided a synthetic oligosaccharide preparation, nutritional preparation, animal feed pre-mix, or animal feed composition as described herein has a lower FCR compared to an animal population provided a diet that does not include the synthetic oligosaccharide preparation, wherein the FCR is corrected for mortality in the animal population.

In certain embodiments, an animal provided a synthetic oligosaccharide preparation, animal feed pre-mix, or animal feed composition has a lower FCR than an animal provided a diet that does not include the synthetic oligosaccharide preparation, but which does include one or more antibiotics, one or more ionophores, soluble corn fiber, modified wheat starch, or yeast mannan, or any combinations thereof.

It is known to one skilled in the art, that when determining FCR, the FCR may be adjusted for mortality to reduce noise due to small number statistics. Methods for adjusting FCR for mortality are well known to one skilled in the art.

In some embodiments that may be combined with any of the foregoing embodiments, the poultry is an individual poultry, while in other embodiments the poultry is a poultry population.

In some embodiments, the animal is poultry, and the animal feed composition is poultry feed, wherein the synthetic oligosaccharide preparation, poultry nutritional composition, poultry feed pre-mix, or poultry feed composition feed reduces feed conversion ratio (FCR) by up to about 10%, or about 5%, or between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to poultry as compared to poultry fed a feed composition without the synthetic oligosaccharide preparation.

In certain embodiments, the poultry suffers from a disease or a disorder, or is raised in a challenged environment, wherein the synthetic oligosaccharide preparation, poultry nutritional composition, poultry feed pre-mix, or poultry feed composition feed reduces feed conversion ratio (FCR) by up to about 30%, about 25%, about 20%, about 15%, about 10%, or about 5%, or between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to poultry as compared to poultry fed a feed composition without the synthetic oligosaccharide preparation.

In some embodiments, the animal is swine, and the animal feed composition is swine feed, wherein the synthetic oligosaccharide preparation, swine nutritional composition, swine feed pre-mix, or swine feed composition reduces feed conversion ratio (FCR) by up to about 15%, about 10%, or about 5%, or between 1% and 15%, between 2% and 15%, between 3% and 15%, between 4% and 15%, between 5% and 15%, between 10% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the synthetic oligosaccharide preparation.

In certain embodiments, the swine suffers from a disease or a disorder, or is raised in a challenged environment, wherein the synthetic oligosaccharide preparation, swine nutritional composition, swine feed pre-mix, or swine feed composition reduces feed conversion ratio (FCR) by up to about 40%, about 35% about 30%, about 25%, about 20%, about 15%, about 10%, or about 5%, or between 1% and 40%, between 5% and 40%, between 10% and 40%, between 15% and 40%, between 20% and 40%, between 25% and 40%, between 30% and 40%, between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the synthetic oligosaccharide preparation.

B. Body Weight

In some embodiments, a subject animal that is fed a synthetic oligosaccharide preparation, nutritional composition, animal feed pre-mix, or animal feed composition described herein may experience an increase in weight gain, compared to a control animal that is not fed the oligosaccharide preparation, nutritional composition, animal feed pre-mix, or animal feed composition. In certain embodiments, both the subject animal and the control animal consume the same quantity of feed on a weight basis, but the subject animal provided the synthetic oligosaccharide preparation, nutritional composition, animal feed pre-mix, or animal feed composition experiences an increase in weight gain compared to the control animal that is fed a diet that does not include the synthetic oligosaccharide preparation.

The weight gain of an animal may be determined by any suitable methods known in the art. For example, to determine weight gain of an animal that is subjected to a feeding regimen of the synthetic oligosaccharide preparation, nutritional composition, animal feed pre-mix, or animal feed composition, one of skill in the art can measure the mass of an animal prior to the feeding regimen, measure the mass of the animal after the animal is fed the synthetic oligosaccharide preparation, nutritional composition, animal feed pre-mix, or animal feed composition, and determine the difference between those two measurements.

In some embodiments, the weight gain may be an average daily weight gain (also referred to as average daily gain (ADG)), an average weekly weight gain (AWG), or a final body weight gain (BWG).

C. Average Daily Weight Gain

In some embodiments, providing an animal with a synthetic oligosaccharide preparation, nutritional composition, animal feed pre-mix, or animal feed composition results in an increased average daily weight gain than an animal provided feed without the synthetic oligosaccharide preparation. In some embodiments, providing an animal population with a synthetic oligosaccharide preparation, nutritional composition, animal feed pre-mix, or animal feed composition results in an increased average daily weight gain than an animal population provided feed without the synthetic oligosaccharide preparation.

In one embodiment, the average daily weight gain for an animal is the weight gained each day by an individual animal, averaged over a given period of time. In some embodiments, the average daily weight gain for an animal population is the average daily weight gain for each individual animal, averaged over the population; wherein the average daily weight gain is the weight gained each day by the individual animal, averaged over a given period of time. In yet other embodiments, the average daily weight gain for an animal population is the total weight gained by the population each day, divided by the number of individual animals in the population, averaged over a given period of time. It should be understood that the daily weight gain or average daily weight gain may be further averaged, for example to provide an average daily weight gain across animal populations.

In certain embodiments, the animal is poultry, and the poultry provided a synthetic oligosaccharide preparation, nutritional composition, animal feed pre-mix, or animal feed composition has an average daily weight gain of at least 20 grams per day, at least 30 grams per day, at least 40 grams per day, at least 50 grams per day, at least 60 grams per day, at least 70 grams per day, at least 80 grams per day, at least 90 grams per day, between 20 to 100 grams per day, between 20 to 80 grams per day, between 30 to 50 grams per day, between 40 to 60 grams per day, between 50 to 70 grams per day, or between 70 to 90 grams per day. In one embodiment, the animal is poultry, and the poultry provided a synthetic oligosaccharide preparation, nutritional composition, animal feed pre-mix, or animal feed composition has an average daily weight gain of at least 50 grams per day. In certain embodiments, the poultry provided a synthetic oligosaccharide preparation, nutritional composition, animal feed pre-mix, or animal feed composition has an average daily weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average daily weight gain of poultry provided a diet that does not include the synthetic oligosaccharide preparation.

In certain embodiments, the animal is poultry, and the poultry is between 0 to 14 days of age, and the average daily weight gain is at least 30 grams, at least 40 grams, or at least 50 grams per day.

In other embodiments, the animal is poultry, the poultry is between 14 to 28 days of age, and the average daily weight gain is at least 70 grams, at least 80 grams, or at least 90 grams per day.

In still other embodiments, the animal is poultry, the poultry is between 29 to 35 days of age, and the average daily weight gain is at least 50 grams, at least 60 grams, or at least 70 grams per day.

In some embodiments that may be combined with the foregoing, the animal is poultry, and the animal feed composition is poultry feed, wherein the synthetic oligosaccharide preparation, poultry nutritional composition, poultry feed pre-mix, or poultry feed composition increases average daily gain in poultry by up to about 10%, or about 5%, or between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to the poultry as compared to poultry fed a feed composition without the synthetic oligosaccharide preparation.

In certain embodiments, the poultry suffers from a disease or a disorder, or is raised in a challenged environment, wherein the synthetic oligosaccharide preparation, poultry nutritional composition, poultry feed pre-mix, or poultry feed composition increases average daily gain in poultry by up to about 30%, about 25%, about 20%, about 15%, about 10%, or about 5%, or between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to the poultry as compared to poultry fed a feed composition without the synthetic oligosaccharide preparation.

In some embodiments that may be combined with the foregoing, the animal is swine, and the animal feed composition is swine feed, wherein the synthetic oligosaccharide preparation, swine nutritional preparation, swine feed pre-mix, or swine feed composition increases average daily gain in swine by up to about 15%, about 10%, or about 5%, or between 1% and 15%, between 2% and 15%, between 3% and 15%, between 4% and 15%, between 5% and 15%, between 10% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the synthetic oligosaccharide preparation.

In certain embodiments, the swine suffers from a disease or a disorder, or is raised in a challenged environment, wherein the oligosaccharide preparation, swine nutritional composition, swine feed pre-mix, or swine feed composition increases average daily gain in swine by up to about 40%, about 35% about 30%, about 25%, about 20%, about 15%, about 10%, or about 5%, or between 1% and 40%, between 5% and 40%, between 10% and 40%, between 15% and 40%, between 20% and 40%, between 25% and 40%, between 30% and 40%, between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the synthetic oligosaccharide preparation.

In certain embodiments, the animal is swine, and the swine provided a synthetic oligosaccharide preparation, swine nutritional preparation, swine feed pre-mix, or swine feed composition has an average daily weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average daily weight gain of swine provided a diet that does not include the synthetic oligosaccharide preparation.

D. Average Weekly Weight Gain

In some embodiments, providing an animal with a synthetic oligosaccharide preparation, nutritional composition, animal feed pre-mix, or animal feed composition results in an increased average weekly weight gain than an animal provided feed without the synthetic oligosaccharide preparation. In some embodiments, providing an animal population with a synthetic oligosaccharide preparation, nutritional composition, animal feed pre-mix, or animal feed composition results in an increased average weekly weight gain than an animal population provided feed without the synthetic oligosaccharide preparation.

In one embodiment, the average weekly weight gain for an animal is the weight gained each week by an individual animal, averaged over a given period of time. In some embodiments, the average weekly weight gain for an animal population is the average weekly weight gain for each individual animal, averaged over the population; wherein the average weekly weight gain is the weight gained each week by the individual animal, averaged over a given period of time. In yet other embodiments, the average weekly weight gain for an animal population is the total weight gained by the population each week, divided by the number of individual animals in the population, averaged over a given period of time. It should be understood that the average weekly weight gain may be further averaged, for example to provide an average weekly weight gain across animal populations.

In certain embodiments, the animal is poultry, and poultry provided a synthetic oligosaccharide preparation, nutritional composition, animal feed pre-mix, or animal feed composition has an average weekly weight gain of at least 100 grams per week, at least 200 grams per week, at least 300 grams per week, at least 400 grams per week, at least 500 grams per week, at least 600 grams per week, at least 700 grams per week, at least 800 grams per week, between 100 to 800 grams per week, between 100 to 400 grams per week, between 300 to 600 grams per week, between 500 to 800 grams per week, or between 350 to 550 grams per week. In one embodiment, poultry provided a synthetic oligosaccharide preparation, nutritional composition, animal feed pre-mix, or animal feed composition has an average weekly weight gain of at least 400 grams per week. In certain embodiments, poultry provided a synthetic oligosaccharide preparation, nutritional composition, animal feed pre-mix, or animal feed composition has an average weekly weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average weekly weight gain of poultry provided a diet that does not include the oligosaccharide preparation.

In certain embodiments, the animal is swine, and swine provided a synthetic oligosaccharide preparation, swine nutritional composition, swine feed pre-mix, or swine feed composition has an average weekly weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average weekly weight gain of swine provided a diet that does not include the synthetic oligosaccharide preparation.

E. Final Body Weight Gain

In some embodiments, providing an animal with a synthetic oligosaccharide preparation, nutritional composition, animal feed pre-mix, or animal feed composition results in an increased final body weight gain than an animal provided feed without the synthetic oligosaccharide preparation. In some embodiments, providing an animal population with a synthetic oligosaccharide preparation, nutritional composition, animal feed pre-mix, or animal feed composition results in an increased average final body weight gain than an animal population provided feed without the synthetic oligosaccharide preparation.

In some embodiments, providing an animal or animal population with a synthetic oligosaccharide preparation, nutritional composition, animal feed pre-mix, or animal feed composition results in a final body weight gain or average final body weight gain that is closer to the performance target maximum than an animal or animal population that is provided feed without the synthetic oligosaccharide preparation. The performance target maximum generally refers to the highest practical body weight gain observed for a given type of animal and breed under ideal growing conditions, ideal animal health, and ideal dietary nutrition.

In one embodiment, the final body weight gain is the quantity of weight an individual animal gains over a period of time. For example, in one embodiment, the total body weight gain is the quantity of weight an individual animal gains from 0 days of age until the final weight taken prior to processing of the animal, or the final weight taken on the day of processing of the animal. For example, in one embodiment, the day 0 to 28 total body weight gain for an animal is the quantity of weight an individual animal gains from 0 days of age until 28 days of age.

In another embodiment, the average total body weight gain is the quantity of weight an individual animal gains over a period of time, averaged across an animal population. For example, in one embodiment, the average total body weight gain is the quantity of weight an individual animal gains from 0 days of age until the final weight taken prior to processing of the animal, or the final weight taken on the day of processing of the animal, averaged across the animal population. In yet another embodiment, the average total body weight gain is the quantity of weight an animal population gains over a period of time, divided by the number of individual animals in the population. For example, in one embodiment, the average total body weight gain is the quantity of weight an animal population gains from 0 days of age until the final weight taken prior to processing of the animal population, or the final weight taken on the day of processing of the animal, divided by the number of individual animals in the population.

It should be understood that the values for total body weight gain and average total body weight gain can be further averaged. For example, the average total body weight gain for different populations of the same type of animal may be averaged to obtain an average total body weight gain across populations.

In certain embodiments, the animal is poultry, and poultry provided a synthetic oligosaccharide preparation, nutritional composition, animal feed pre-mix, or animal feed composition has a final body weight gain of at least 3 kg, at least 2.5 kg, at least 2 kg, at least 1.5 kg, at least 1 kg, between 1 to 3 kg, or between 1.5 to 2.5 kg. In one embodiment, poultry provided a synthetic oligosaccharide preparation, animal feed pre-mix, or animal feed composition has a final body weight gain of at least 2 kg. In certain embodiments, poultry provided a synthetic oligosaccharide preparation, animal feed pre-mix, or animal feed composition has a final body weight gain of at least 1%, at least 2%, at least 3%, at least 4%, at least 5%, at least 6%, at least 8%, at least 9%, at least 10%, at least 110%, at least 12%, between 1 to 10%, between 2 to 8%, or between 3 to 5% greater than the final body weight gain of poultry provided a diet that does not include the synthetic oligosaccharide preparation. In certain embodiments, poultry provided a synthetic oligosaccharide preparation, animal feed pre-mix, or animal feed composition has a final body weight gain of at least 0.01 kg, at least 0.02 kg, at least 0.03 kg, at least 0.04 kg, at least 0.05 kg, at least 0.06 kg, at least 0.07 kg, at least 0.08 kg, at least 0.09 kg, at least 0.1 kg, between 0.01 to 0.1 kg, between 0.03 to 0.07 kg, or between 0.04 to 0.06 kg greater than the final body weight gain of poultry provided a diet that does not include the synthetic oligosaccharide preparation.

In certain embodiments, the animal is poultry, and poultry provided a synthetic oligosaccharide preparation, nutritional composition, animal feed pre-mix, or animal feed composition has an average final body weight gain of at least 3 kg, at least 2.5 kg, at least 2 kg, at least 1.5 kg, at least 1 kg, between 1 to 3 kg, or between 1.5 to 2.5 kg. In one embodiment, poultry provided a synthetic oligosaccharide preparation, nutritional composition, animal feed pre-mix, or animal feed composition has an average final body weight gain of at least 2 kg. In certain embodiments, poultry provided a synthetic oligosaccharide preparation, nutritional composition, animal feed pre-mix, or animal feed composition has an average final body weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average final body weight gain of poultry provided a diet that does not include the synthetic oligosaccharide preparation. In certain embodiments, poultry provided a synthetic oligosaccharide preparation, nutritional composition, animal feed pre-mix, or animal feed composition has an average final body weight gain of at least 0.01 kg, at least 0.02 kg, at least 0.03 kg, at least 0.04 kg, at least 0.05 kg, at least 0.06 kg, at least 0.07 kg, at least 0.08 kg, at least 0.09 kg, at least 0.1 kg, between 0.01 to 0.1 kg, between 0.03 to 0.07 kg, or between 0.04 to 0.06 kg greater than the average final body weight gain of poultry provided a diet that does not include the synthetic oligosaccharide preparation.

In some embodiments, the animal is poultry, and the poultry is between 0 to 14 days of age, between 15 to 28 days of age, between 29 to 35 days of age, between 0 to 42 days of age, between 0 to 6 weeks of age, or between 0 to 6.5 weeks of age. In some embodiments, the starter phase is 0 to 14 days of age, the grower phase is 15 to 28 days of age, and the finisher phase is 29 to 35 days of age. In other embodiments, the starter phase is 0 to 14 days of age, the grower phase is 15 to 35 days of age, and the finisher phase is 36 to 42 days of age. In yet other embodiments, the starter phase is 0 to 14 days of age, the grower phase is 15 to 39 days of age, and the finisher phase is 40 to 46 days of age. It should be understood that the length of the starter phase, growing phase, and finisher phase for poultry may change depending on the intended use of the poultry, or the poultry product. For example, in some embodiments the length of the starter phase, grower phase, and finisher phase may be different if the intended use of the poultry is as a broiler chicken, compared to processing for tray-pack chicken meat.

In some embodiments that may be combined with any of the foregoing embodiments, the poultry is an individual poultry, while in other embodiments the poultry is a poultry population.

In certain embodiments, swine provided a synthetic oligosaccharide preparation, swine nutritional composition, swine feed pre-mix, or swine feed composition has a final body weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the final body weight gain of swine provided a diet that does not include the synthetic oligosaccharide preparation.

In certain embodiments, swine provided a synthetic oligosaccharide preparation, swine nutritional composition, swine feed pre-mix, or swine feed composition has an average final body weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average final body weight gain of swine provided a diet that does not include the synthetic oligosaccharide preparation.

In some embodiments that may be combined with any of the foregoing embodiments, the swine is an individual swine, while in other embodiments the swine is a swine population.

F. Yield of Animal Product

In certain embodiments, providing an animal with a synthetic oligosaccharide preparations, nutritional composition, animal feed pre-mix, or animal feed composition as described herein results in an increased yield of animal product, as compared to an animal provided feed that does not include the synthetic oligosaccharide preparation. In some embodiments, the animal provided a synthetic oligosaccharide preparation, nutritional composition, animal feed pre-mix, or animal feed composition yields at least 1%, at least 2%, at least 3%, at least 4%, at least 5%, at least 6%, at least 7%, at least 8%, at least 9%, at least 10%, between 1 to 10%, between 4 to 10%, between 6 to 10%, or between 2 to 8% more animal product compared to an animal provided feed that does not include the synthetic oligosaccharide preparation. For example, in some embodiments, the animal product is the meat of the animal, and an animal provided a synthetic oligosaccharide preparation as described herein yields a greater quantity of meat compared to an animal that is not provided the oligosaccharide preparation. In some embodiments, providing an animal population the synthetic oligosaccharide preparation, nutritional composition, animal feed pre-mix, or animal feed composition results in an increased average yield of animal product, as compared to an animal population provided feed that does not include the synthetic oligosaccharide preparation. In some embodiments, the average animal product yield is the quantity of animal product yielded from each individual animal, averaged across the animal population.

In some embodiments, the animal product is the meat of an animal (e.g., that may be sold to consumers, processed to produce a food product, or consumed by a human). In certain embodiments, the animal is poultry, and the animal product is a poultry eviscerated carcass, leg meat from a poultry eviscerated carcass, breast meat from a poultry eviscerated carcass, drumstick meat from a poultry eviscerated carcass, fat from a poultry eviscerated carcass, breast meat from a poultry deboned carcass, or leg meat from a poultry deboned carcass. In other embodiments, the animal is poultry, and the animal product is white meat, breast meat filets, and breast meat tenders. In another embodiment, the animal is poultry and the product are tray-pack chicken meat. In yet another embodiment, the animal is poultry and the product are whole bird without giblets (WOG).

In some embodiments, the yield of animal product is the yield obtained from an individual animal. In some embodiments, the average yield of animal product is the yield obtained from each individual animal in an animal population, averaged across the population. In yet another embodiment, the average yield of animal product is the total yield of animal product yielded from an animal population, divided by the number of individual animals in the animal population.

In some embodiments, the animal is poultry, the yield of leg meat from a poultry eviscerated carcass is at least 6%, at least 8%, at least 10%, at least 12%, between 6 to 12%, between 8 to 12%, between 10 to 18%, between 12 to 16%, or between 12 to 14% of live weight for poultry provided a synthetic oligosaccharide preparation, nutritional composition, animal feed pre-mix, or animal feed composition. In certain embodiments, the yield of leg meat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the average yield of leg meat from a poultry eviscerated carcass is at least 6%, at least 8%, at least 10%, at least 12%, between 6 to 12%, between 8 to 12%, between 10 to 18%, between 12 to 16%, or between 12 to 14% of live weight for poultry provided a synthetic oligosaccharide preparations, nutritional composition, animal feed pre-mix, or animal feed composition. In certain embodiments, the average yield of leg meat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the yield of breast meat from a poultry eviscerated carcass is at least 10%, at least 12%, at least 15%, at least 16%, at least 18%, at least 20%, at least 22%, at least 24%, at least 28%, between 10 to 18%, between 12 to 16%, between 18 to 29%, between 20 to 27%, or between 20 to 25% of live weight for poultry provided a synthetic oligosaccharide preparations, nutritional composition, animal feed pre-mix, or animal feed composition. In certain embodiments, the yield of breast meat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the average yield of breast meat from a poultry eviscerated carcass is at least 10%, at least 12%, at least 15%, at least 16%, at least 18%, at least 20%, at least 22%, at least 24%, at least 28%, between 10 to 18%, between 12 to 16%, between 18 to 29%, between 20 to 27%, or between 20 to 25% of live weight for poultry provided a synthetic oligosaccharide preparations, nutritional composition, animal feed pre-mix, or animal feed composition. In certain embodiments, the average yield of breast meat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the yield of drumstick meat from a poultry eviscerated carcass is at least 5%, at least 7%, at least 8%, at least 9%, at least 10%, at least 11%, at least 12%, between 5 to 14%, between 7 to 10%, between 7 to 15%, between 9 to 13%, or between 9 to 11% of live weight for poultry provided a synthetic oligosaccharide preparation, nutritional composition, animal feed pre-mix, or animal feed composition. In certain embodiments, the yield of drumstick meat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the average yield of drumstick meat from a poultry eviscerated carcass is at least 5%, at least 7%, at least 8%, at least 9%, at least 10%, at least 11%, at least 12%, between 5 to 14%, between 7 to 10%, between 7 to 15%, between 9 to 13%, or between 9 to 11% of live weight for poultry provided a synthetic oligosaccharide preparation, nutritional composition, animal feed pre-mix, or animal feed composition. In certain embodiments, the average yield of drumstick meat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the yield of breast meat from a poultry deboned carcass is at least 14%, at least 16%, at least 18%, at least 20%, at least 22%, at least 24%, between 14 to 16%, between 18 to 30%, between 20 to 28%, or between 20 to 26% of live weight for poultry provided a synthetic oligosaccharide preparation, nutritional composition, animal feed pre-mix, or animal feed composition. In certain embodiments, the yield of breast meat from a poultry deboned carcass from poultry provided an oligosaccharide preparation, animal feed pre-mix, or animal feed composition as described herein is at least 1%, at least 2%, at least 3%, at least 4%, at least 5%, at least 6%, at least 8%, at least 9%, at least 10%, at least 110%, at least 12%, between 1 to 10%, between 2 to 8%, or between 3 to 5% greater than for poultry provided a diet that does not include the synthetic oligosaccharide preparation.

In some embodiments, the animal is poultry, and the average yield of breast meat from a poultry deboned carcass is at least 14%, at least 16%, at least 18%, at least 20%, at least 22%, at least 24%, between 14 to 16%, between 18 to 30%, between 20 to 28%, or between 20 to 26% of live weight for poultry provided a synthetic oligosaccharide preparations, nutritional composition, animal feed pre-mix, or animal feed composition. In certain embodiments, the average yield of breast meat from a poultry deboned carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the yield of leg meat from a poultry deboned carcass is at least 6%, at least 8%, at least 10%, at least 12%, at least 14%, at least 16%, at least 18%, between 6 to 18%, between 8 to 16%, between 12 to 21%, between 14 to 19%, or between 14 to 17% of live weight for poultry provided a synthetic oligosaccharide preparations, nutritional composition, animal feed pre-mix, or animal feed composition. In certain embodiments, the yield of leg meat from a poultry deboned carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the average yield of leg meat from a poultry deboned carcass is at least 6%, at least 8%, at least 10%, at least 12%, at least 14%, at least 16%, at least 18%, between 6 to 18%, between 8 to 16%, between 12 to 21%, between 14 to 19%, or between 14 to 17% of live weight for poultry provided a synthetic oligosaccharide preparation, nutritional composition, animal feed pre-mix, or animal feed composition. In certain embodiments, the average yield of leg meat from a poultry deboned carcass from poultry provided an oligosaccharide preparation, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the yield of fat from a poultry eviscerated carcass is at least 0.1%, at least 0.2%, at least 0.3%, at least 0.4%, at least 0.5%, at least 0.6%, at least 0.7%, at least 0.8%, at least 0.9%, at least 1%, at least 1.2%, at least 1.4%, at least 1.6%, between 0.1 to 2%, between 0.2 to 1%, between 0.5 to 2%, or between 0.3 to 0.7% of live weight for poultry provided a synthetic oligosaccharide preparation, nutritional composition, animal feed pre-mix, or animal feed composition. In certain embodiments, the yield of fat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the average yield of fat from a poultry eviscerated carcass is at least 0.1%, at least 0.2%, at least 0.3%, at least 0.4%, at least 0.5%, at least 0.6%, at least 0.7%, at least 0.8%, at least 0.9%, at least 1%, at least 1.2%, at least 1.4%, at least 1.6%, between 0.1 to 2%, between 0.2 to 1%, between 0.5 to 2%, or between 0.3 to 0.7% of live weight for poultry provided a synthetic oligosaccharide preparations, nutritional composition, animal feed pre-mix, or animal feed composition. In certain embodiments, the average yield of fat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the yield of a poultry eviscerated carcass is at least 50%, at least 55%, at least 60%, at least 65%, at least 70%, at least 75%, at least 80%, at least 85%, at least 90%, between 50 to 95%, between 60 to 85%, or between 65 to 75% of live weight for poultry provided a synthetic oligosaccharide preparations, nutritional composition, animal feed pre-mix, or animal feed composition. In certain embodiments, the yield of a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the average yield of a poultry eviscerated carcass is at least 50%, at least 55%, at least 60%, at least 65%, at least 70%, at least 75%, at least 80%, at least 85%, at least 90%, between 50 to 95%, between 60 to 85%, or between 65 to 75% of live weight for poultry provided a synthetic oligosaccharide preparations, nutritional composition, animal feed pre-mix, or animal feed composition. In certain embodiments, the average yield of a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

Methods for deboning a poultry carcass are well known to one skilled in the art of poultry processing. It should be understood that meat yielded from poultry may be measured, for example, as the ratio of the mass of recovered meat to the final weight of the bird prior to processing. In some embodiments, the animal is poultry, and the poultry is at least 35 days old, at least 42 days old, at least 6 weeks old, at least 6.5 weeks old before the poultry is processed to produce a poultry eviscerated carcass, poultry deboned carcass, white meat, breast meat filets, and breast meat tenders, tray-pack chicken meat, whole bird without giblets (WOG), or meat as described above.

In other embodiments, the animal is poultry, and the animal product is eggs. In some embodiments, the animal is swine, and the swine product is the meat of swine (e.g., that may be sold to consumers, processed to produce a food product, or consumed by a human). In some embodiments, the yield of swine product is the yield obtained from an individual swine. In some embodiments, the average yield of swine product is the yield obtained from each individual swine in a swine population, averaged across the population. In yet another embodiment, the average yield of swine product is the total yield of swine product yielded from swine population, divided by the number of individual swine in the swine population.

In certain embodiments, an animal or animal population provided a synthetic oligosaccharide preparation, nutritional composition, animal feed pre-mix, or animal feed composition has a higher average daily weight gain, higher average weekly weight gain, higher final body weight gain, higher average final body weight gain, or increased average yield of animal product, or any combinations thereof, than an animal or animal population provided a diet that does not include the synthetic oligosaccharide preparation, but which does include one or more antibiotics, one or more ionophores, soluble corn fiber, modified wheat starch, or yeast mannan, or any combinations thereof.

A person of skill in the art would recognize that the maximum theoretical weight gain may be different for different types of animals and may be different for different breeds of the same type of animal (for example, different types of broiler chickens, or different types of swine).

A person of skill in the art would recognize that the maximum theoretical weight gain may be different for different types of animals and may be different for different breeds of the same type of animal (for example, different types of broiler chickens, or different types of swine).

In some embodiments, the animal is poultry. In some embodiments that may be combined with any of the foregoing embodiments, the poultry is an individual poultry, while in other embodiments the poultry is a poultry population. In other embodiments, the animal is swine. In some embodiments that may be combined with any of the foregoing embodiments, the swine is an individual swine, while in other embodiments the swine is a swine population.

G. Feed Intake

In certain embodiments, providing an animal with a synthetic oligosaccharide preparation, nutritional composition, animal feed pre-mix, or animal feed composition as described herein results in an increased average daily feed intake, as compared to an animal provided feed that does not include the synthetic oligosaccharide preparation.

Average daily feed intake (ADFI) refers to the average mass of feed consumed by an animal over a specified period of time. In certain embodiments, the average daily feed intake is measured by dispensing a known mass of feed to a group of a fixed number of animals, allowing the animals in the group to consume the dispensed feed freely (ad libitum) for a specified number of days, weighing the mass of unconsumed feed at the end of the period, and calculating the average daily feed intake (ADFI) as the difference between the dispensed feed mass minus the residual feed mass, divided by the number of animals in the group, and divided by the number of days in the period. In other embodiments, the average daily feed intake may be corrected for any animals that die or are culled from the group, using methods that are known to one skilled in the art.

In some embodiments, the animal is poultry, and the animal feed composition is poultry feed, wherein the synthetic oligosaccharide preparation, poultry feed pre-mix, or poultry feed composition feed increases average daily feed intake by up to about 10%, or about 5%, or between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to poultry as compared to poultry fed a feed composition without the synthetic oligosaccharide preparation.

In certain embodiments, the poultry suffers from a disease or is raised in a challenged environment, wherein the synthetic oligosaccharide preparation, poultry nutritional composition, poultry feed pre-mix, or poultry feed composition increases average daily feed intake by up to about 30%, about 25%, about 20%, about 15%, about 10%, or about 5%, or between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to poultry as compared to poultry fed a feed composition without the synthetic oligosaccharide preparation.

In some embodiments that may be combined with the foregoing, the animal is swine, and the animal feed composition is swine feed, wherein the oligosaccharide preparation, swine nutritional composition, swine feed pre-mix, or swine feed composition increases average daily feed intake by up to about 15%, about 10%, or about 5%, or between 1% and 15%, between 2% and 15%, between 3% and 15%, between 4% and 15%, between 5% and 15%, between 10% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the synthetic oligosaccharide preparation.

In certain embodiments, the swine suffers from a disease or is raised in a challenged environment, wherein the synthetic oligosaccharide preparation, swine nutritional composition, swine feed pre-mix, or swine feed composition increases average daily feed intake by up to about 40%, about 35% about 30%, about 25%, about 20%, about 15%, about 10%, or about 5%, or between 1% and 40%, between 5% and 40%, between 10% and 40%, between 15% and 40%, between 20% and 40%, between 25% and 40%, between 30% and 40%, between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the synthetic oligosaccharide preparation.

The methods of enhancing growth of an animal or animal population described herein include providing an oligosaccharide preparation, animal feed pre-mix, or animal feed to the animal or animal population. The oligosaccharide preparation, animal feed pre-mix, or animal feed may be provided in any suitable form, to any suitable type of animal, using any suitable feeding schedule to enhance the growth of the animal or animal population.

H. Animal Product Quality

In some embodiments, an animal product, such as animal meat, has enhanced quality. Animal products described herein, include non-meat products, such as milk and eggs. Qualities of animal meat include, for example, color, integrity, texture, flavor, mouth feel, aroma, and tenderness. It is clear to the skilled artisan that qualities of animal meat will depend on the type of animal. Standard assays known to the skilled artisan can be used to assess the qualities of animal meat, including e.g., color, flavor, tenderness, and aroma. Animal meat described herein can be assessed using trained human panelists. The evaluations can involve eyeing, feeling, chewing, and tasting of the product to judge product appearance, color, integrity, texture, flavor, and mouth feel, etc. Panelists can be served samples under red or under white light. Samples can be assigned random three-digit numbers and rotated in ballot position to prevent bias. Sensory judgments can be scaled for "acceptance" or "likeability" or use special terminology. For example, letter scales (A for excellent, B for good, C for poor) or number scales may be used (1=dislike, 2=fair, 3=good; 4=very good; 5=excellent). A scale can be used to rate the overall acceptability or quality of the animal meat or specific quality attributes such texture and flavor. Panelists can be encouraged to rinse their mouths with water between samples, and given opportunity to comment on each sample.

VIII. Animals

The synthetic oligosaccharide preparation, nutritional composition, animal feed pre-mix, or the animal feed composition may be provided to any suitable animal. In some embodiments, the animal is monogastric. It is generally understood that a monogastric animal has a single-chambered stomach. In other embodiments, the animal is a ruminant. It is generally understood that a ruminant has a multi-chambered stomach. In some embodiments, the animal is a ruminant in the pre-ruminant phase. Examples of such ruminants in the pre-ruminant phase include nursery calves.

In some embodiments, the animal is livestock. In some embodiments, the animal is a companion animal. In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human.

In some embodiments, the animal is poultry. Examples of poultry include chicken, duck, turkey, goose, quail, or Cornish game hen. In one variation, the animal is a chicken. In some embodiments, the poultry is a layer hen, a broiler chicken, or a turkey. In other embodiments, the animal is a mammal, including, for example, a cow, a pig, a goat, a sheep, a deer, a bison, a rabbit, an alpaca, a llama, a mule, a horse, a reindeer, a water buffalo, a yak, a guinea pig, a rat, a mouse, an alpaca, a dog, a cat, or a human. In one variation, the animal is a cow. In another variation, the animal is a pig. The animal feed composition may also be used in aquaculture. In some embodiments, the animal is an aquatic animal. Examples of aquatic animals may include a trout, a salmon, a bass, a tilapia, a shrimp, an oyster, a mussel, a clam, a lobster, or a crayfish. In one variation, the animal is a fish.

IX. Administration

In some embodiments, administration comprises providing a synthetic oligosaccharide preparation, a nutritional composition, or an animal feed composition described herein, to an animal such that the animal may ingest the synthetic oligosaccharide preparation, the nutritional composition, or the animal feed composition at will. In such embodiments, the animal ingests some portion of the synthetic oligosaccharide preparation, the nutritional composition, or the animal feed composition.

The synthetic oligosaccharide preparation, nutritional composition, animal feed pre-mix, or animal feed composition may be provided to the animal on any appropriate schedule. In some embodiments, the animal is provided the synthetic oligosaccharide preparation, nutritional composition, animal feed pre-mix, or animal feed composition on a daily basis, on a weekly basis, on a monthly basis, on an every other day basis, for at least three days out of every week, or for at least seven days out of every month. In some embodiments, the animal is provided the oligosaccharide preparation, animal feed pre-mix, or animal feed composition during certain diet phases.

For example, some animals are provided a starter diet between 0 to 14 days of age. In other embodiments, an animal is provided a grower diet between 15 to 28 days of age, between 15 to 35 days of age, or between 15 to 39 days of age. In still other embodiments, an animal is provided a finisher diet between 29 to 35 days of age, between 36 to 42 days of age, or between 40 to 46 days of age.

In certain embodiments, the synthetic oligosaccharide preparation, nutritional composition, animal feed pre-mix, or animal feed composition is provided to the animal during the starter diet phase, the grower diet phase, or the finisher diet phase, or any combinations thereof.

In certain embodiments, the animal is poultry, and the poultry is provided a starter diet between 0 to 15 days of age, a grower diet between 16 to 28 days of age, and a finisher diet between 29 to 35 days of age. In other embodiments, the animal is poultry, and the poultry is provided a starter diet between 0 to 14 days of age, a grower diet between 15 to 35 days of age, and a finisher diet between 36 to 42 days of age. In still other embodiments, the animal is poultry, and the poultry is provided a starter diet between 0 to 14 days of age, a grower diet between 15 to 39 days of age, and a finisher diet between 20 to 46 days of age.

In some embodiments, the synthetic oligosaccharide preparation, nutritional composition, animal feed pre-mix, or animal feed composition is provided to the poultry during the starter diet phase, the grower diet phase, or the finisher diet phase, or any combinations thereof.

The oligosaccharide preparations described herein may be fed to individual animals or an animal population. For example, in one variation where the animal is poultry, the oligosaccharide preparations may be fed to an individual poultry or a poultry population.

The synthetic oligosaccharide preparation, nutritional composition, animal feed pre-mix, or the animal feed composition may be provided to an animal in any appropriate form, including, for example, in solid form, in liquid form, or a combination thereof. In certain embodiments, the oligosaccharide preparation or the animal feed composition is a liquid, such as a syrup or a solution. In other embodiments, the oligosaccharide preparation, animal feed pre-mix, or the animal feed composition is a solid, such as pellets or powder. In yet other embodiments, the oligosaccharide preparation, animal feed pre-mix, or the animal feed composition may be fed to the animal in both liquid and solid components, such as in a mash.

EXAMPLES

Example 1

Synthesis of a Gluco-Galacto-Oligosaccharide Preparation

Synthesis of a gluco-galacto-oligosaccharide preparation was performed in a three-liter reaction vessel using catalyst loadings, reaction times, and reaction temperatures that were selected to enable suitable production at the kg scale.

D-glucose monohydrate (825.16 g), D-lactose monohydrate (263.48 g) and 2-pyridinesulfonic acid (1.0079 g, Sigma-Aldrich, St. Louis, US) were added to a three-liter, three-neck round bottom flask with a center 29/42 ground glass joint and two 24/40 side ground glass joints. A 133 mm Teflon stirring blade was affixed to a glass stir shaft using PTFE tape. The stir rod was secured through the center point using a Teflon bearing adapter and attached to an overhead high-torque mechanical mixer via flexible coupler. The flask was secured inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. When the reaction mixture reached 120° C., the reflux condenser was re-positioned into a distillation configuration, with the distillated collected in a 250 mL round bottom flask placed in an ice bath. The mixture was maintained at 130° C. with continuous mixing for 6 hours, after which the thermocouple box was powered off. The distillation apparatus was removed and 390 g of 60° C. distilled water was gradually added into the three-neck flask. The resulting mixture was left to stir at 40 RPM for 10 hours. Approximately 1,250 g of a viscous, light-amber material was collected and measured by refractive index to have a concentration of 71.6 Brix.

The final water content of the reactor product was measured by Karl Fisher titration for a representative aliquot of the reactor contents drawn at the end of the reaction. At a reaction temperature of 130° C., the water content of the reaction product was determined to be 5.8 wt % water on an as-is basis.

Example 2

Synthesis of a Gluco-Oligosaccharide Preparation

Synthesis of a gluco-oligosaccharide preparation was performed in a three-liter reaction vessel using catalyst loadings, reaction times, and reaction temperatures that were selected to enable suitable production at the kg scale.

D-glucose monohydrate (1,150 g) was added to a three-liter, three-neck round bottom flask with one center 29/42 ground glass joint and two side 24/40 ground glass joints. A 133 mm Teflon stirring blade was affixed to glass stir shaft using PTFE tape. The stir rod was secured through the center port of the flask using a Teflon bearing adapter and attached to an overhead high-torque mechanical mixer via flex coupling. The flask was secured inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4 C by a recirculating bath chiller.

The reaction mixture was gradually heated to 130° C. with continuous mixing with a stir rate of 80-100 rpm. When the reaction temperature increased to between 120° C. and 130° C., (+)-Camphor-10-sulfonic acid (1.16 g, Sigma-Aldrich, St. Louis) was added to the three-neck flask and the apparatus was switched from a reflux condenser to a distillation configuration with a round bottom collection flask placed in an ice bath. This setup was maintained for 1 and a half hours, after which the thermocouple box was powered off, the distillation apparatus was removed, and 390 g of 23 degrees C. distilled water was gradually added into the three-neck flask. The resulting mixture was left to stir at 40 rpm for 10 hours until the moment of collection. Approximately 1300 g of a viscous, dark-amber material was collected and measured to have a concentration of 72.6 brix.

Example 3

Synthesis of a
Gluco-Galacto-Manno-Oligosaccharide Preparation

Synthesis of a gluco-galacto-manno-oligosaccharide preparation was performed in a three-liter reaction vessel using catalyst loadings, reaction times, and reaction temperatures that were selected to enable suitable production at the kg scale.

The gluco-galacto-manno-oligosaccharide was prepared as two separate components synthesized in separate reaction vessels that were independently collected. Each synthesis used different starting reactants but followed the same procedure and methods to completion. The final gluco-galacto-manno-oligosaccharide was a homogeneous syrup formed from the mixing of both synthesis products.

For the synthesis of the first component, 990.54 g of glucose monohydrate, 105.58 g of lactose monohydrate and 1.00 g of 2-pyridinesulfonic acid were added to a three-liter, three-neck round bottom flask with one center 29/42 ground joint flanked by two 24/40 ground joints. A 133 mm Teflon stirring blade was affixed to a 440 mm glass stir shaft using PTFE tape. The stir rod was secured through the center point using a Teflon bearing adapter and attached to an overhead high-torque mechanical mixer via flexible coupler. The flask was placed inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. Once a temperature control box reading between 120 C and 130° C. was observed, the apparatus was switched from a reflux condenser to a distillation configuration with a round bottom collection flask placed in an ice bath. This setup was maintained for approximately 6 hours and 10 minutes, after which the heating mantle was powered off, the distillation apparatus was removed, and 390 g of 60° C. distilled water was gradually added into the three-neck flask. The resulting mixture was left to stir at 40 rpm for 10 hours until the moment of collection. Approximately 1250 g of a viscous, light-amber material was collected and measured by refractive index to have a concentration of 73.1 Brix.

For the synthesis of the second component, 825.04 g of glucose monohydrate, 251.16 g of pure mannose from wood, 25.10 g distilled water, and 1.00 g of 2-pyridinesulfonic acid were added to a three-liter, three-neck round bottom flask with one center 29/42 ground joint flanked by two 24/40 ground joints. The remainder of the second component's synthesis followed the same procedure and methods as those of the first, until the moment of collection. Approximately 1250 g of a viscous, dark-amber material was collected and measured to have a concentration of 72.3 brix.

The entirety of the first and second components were transferred into a suitably sized HDPE container and mixed thoroughly by hand until homogenous. The final syrup mixture was approximately 2.5 kg, dark-amber in color, viscous and was measured to have a concentration of approximately 72 brix.

Example 4

Synthesis of a Gluco-Manno-Oligosaccharide Preparation

Synthesis of a gluco-oligosaccharide preparation was performed in a three-liter reaction vessel using catalyst loadings, reaction times, and reaction temperatures that were selected to enable suitable production at the kg scale.

A gluco-manno-oligosaccharide was prepared as two separate components synthesized in separate reaction vessels that were independently collected. Each synthesis used different starting reactants but followed the same procedure and methods to completion. The final gluco-manno-oligosaccharide was a homogeneous syrup formed from the mixing of both synthesis products.

For the synthesis of the first component, 1264.80 g of glucose monohydrate was added to a three-liter, three-neck round bottom flask with one center 29/42 ground joint flanked by two 24/40 ground joints. A 133 mm Teflon stirring blade was affixed to a 440 mm glass stir shaft using PTFE tape. The stir rod was secured through the center point using a Teflon bearing adapter and attached to an overhead high-torque mechanical mixer via flexible coupler. The flask was placed inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. Once a temperature control box reading between 120° C. and 130° C. was observed, 1.15 g of (+)-camphor-10-sulfonic acid was added to the three-neck flask and the apparatus was switched from a reflux condenser to a distillation configuration with a round bottom collection flask placed in an ice bath. This setup was maintained for approximately 1 hour, after which the thermocouple box was powered off, the distillation apparatus was removed, and 390 g of 23° C. distilled water was gradually added into the three-neck flask. The resulting mixture was left to stir at 40 rpm for 10 hours until the moment of collection. Approximately 1350 g of a viscous, light-amber material was collected and measured to have a concentration of 71.8 brix.

For the synthesis of the second component, 949.00 g of glucose monohydrate, 288.00 g of pure mannose from wood, 27.94 g distilled water, and 1.15 g of 2-pyridinesulfonic acid were added to a three-liter, three-neck round bottom flask with one center 29/42 ground joint flanked by two 24/40 ground joints. The remainder of the second component's synthesis followed the same procedure and methods as those of the first until the moment of collection, except (+)-camphor-10-sulfonic acid was not added as the reflux condenser was switched to a distillation configuration and the resulting setup was maintained for approximately 6 hours. Approximately 1350 g of a viscous, dark-amber material was collected and measured to have a concentration of 72.0 brix.

The entirety of the first and second components were transferred into a suitably sized HDPE container and mixed thoroughly by hand until homogenous. The final syrup mixture was approximately 2.7 kg, dark-amber in color, viscous and was measured by refractive index to have a concentration of approximately 72 Brix.

Example 5

Synthesis of a Gluco-Manno-Oligosaccharide Preparation

Kilogram scale production of the oligosaccharide preparation was performed in a three-liter reaction vessel using catalyst loadings, reaction times, and reaction temperatures found to be suitable for production at the 1 kg scale.

A gluco-manno-oligosaccharide was prepared as two separate components synthesized in separate reaction vessels that were independently collected. Each synthesis used different starting reactants but followed the same procedure and methods to completion. The final gluco-manno-oligosaccharide was a homogeneous syrup formed from the mixing of both synthesis products.

For the synthesis of the first component, 1261.00 g of glucose monohydrate and 1.15 g of 2-pyridinesulfonic acid were added to a three-liter, three-neck round bottom flask with one center 29/42 ground joint flanked by two 24/40 ground joints. A 133 mm Teflon stirring blade was affixed to a 440 mm glass stir shaft using PTFE tape. The stir rod was secured through the center point using a Teflon bearing adapter and attached to an overhead high-torque mechanical mixer via flexible coupler. The flask was secured inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. Once a temperature control box reading between 120° C. and 130° C. was observed, the apparatus was switched from a reflux condenser to a distillation configuration with a round bottom collection flask placed in an ice bath. This setup was maintained for approximately 6 hours, after which the thermocouple box was powered off, the distillation apparatus was removed, and 390 g of 23° C. distilled water was gradually added into the three-neck flask. The resulting mixture was left to stir at 40 rpm for 10 hours until the moment of collection. Approximately 1250 g of a viscous, light-amber material was collected and measured to have a concentration of 73.5 brix.

For the synthesis of the second component, 949.00 g of glucose monohydrate, 288.00 g of pure mannose from wood, 28.94 g distilled water, and 1.15 g of 2-pyridinesulfonic acid were added to a three-liter, three-neck round bottom flask with one center 29/42 ground joint flanked by two 24/40 ground joints. The remainder of the second component's synthesis followed the same procedure and methods as those of the first until the moment of collection. Approximately 1250 g of a viscous, dark-amber material was collected and measured to have a concentration of 73.3 brix.

The entirety of the first and second components were transferred into a suitably sized HDPE container and mixed thoroughly by hand until homogenous. The final syrup mixture was approximately 2.5 kg, dark-amber in color, viscous and was measured to have a concentration of approximately 73 brix.

Example 6

Synthesis of a Gluco-Galacto-Oligosaccharide Preparation

Kilogram scale production of the oligosaccharide preparation was performed in a three-liter reaction vessel using catalyst loadings, reaction times, and reaction temperatures found to be suitable for production at the 1 kg scale.

A 3 L three-neck flask was equipped with an overhead mixer connected via a 10 mm diameter glass stir-shaft to a 14 cm crescent-shaped mixing element. The mixing element was positioned with approximately 5 mm clearance from the walls of the flask. The flask was heated via a hemispherical electric heating mantle powered by a temperature control unit connected to a wand-type thermocouple probe inserted into the reaction flask. The thermocouple probe was placed to provide 5-10 mm clearance above the mixing element. The flask was charged with 576 grams of food-grade dextrose monohydrate and 577 grams of food-grade D-galactose monohydrate and heated to approximately 115° C. to obtain a molten sugar syrup. Once the syrup was obtained, the flask was fitted with a jacketed reflux condenser cooled to 4° C. by circulating chilled glycol/water and the temperature. 31 grams of Dowex Marathon C (moisture content 0.48 g H2O/g resin) were added to the mixture to form a stirred suspension. The condenser was repositioned into distillation configuration and the suspension was heated to 145° C.

A mixing rate of approximately 80 RPM and a temperature of 145° C. was maintained for 3.8 hours, after which the set point on the temperature control unit was reduced to 80° C. and 119 mL of 60° C. deionized water was gradually added to the flask to obtain a dark amber syrup containing residual Dowex resin. The resulting suspension was further diluted to 60 Brix, cooled to room temperature and vacuum filtered through a 0.45 micron filter to remove the resin. 1,200 grams of light-amber syrup at 60 Brix concentration was obtained.

Example 7

Synthesis of a Gluco-Oligosaccharide Preparation

Kilogram scale production of the oligosaccharide preparation was performed in a three-liter reaction vessel using catalyst loadings, reaction times, and reaction temperatures found to be suitable for production at the 1 kg scale.

A 3 L three-neck flask was equipped with an overhead mixer connected via a 10 mm diameter glass stir-shaft to a 14 cm crescent-shaped mixing element. The mixing element was positioned with approximately 5 mm clearance from the walls of the flask. The flask was heated via a hemispherical electric heating mantle powered by a temperature control unit connected to a wand-type thermocouple probe inserted into the reaction flask. The thermocouple probe was placed to provide 5-10 mm clearance above the mixing element. The flask was gradually charged with 1,148 grams of food-grade dextrose monohydrate and heated to approximately 115° C. to obtain a molten sugar syrup. Once the syrup was obtained, the flask was fitted with a jacketed distillation condenser cooled to 4° C. by circulating chilled glycol/water. The reaction temperature was gradually increased to 145° C. Once the temperature was obtained and stable, 31 grams of Dowex Marathon C (moisture content 0.48 g H2O/g resin) was added to the mixture and a mixing rate of approximately 80 RPM and a temperature of 145° C. was maintained for 3.8 hours.

After 3.8 hours, the set point on the temperature control unit was reduced to 80° C. and 119 mL of 60° C. deionized water was gradually added to the flask to obtain a dark amber syrup containing residual Dowex resin. The resulting suspension was further diluted to 60 Brix, cooled to room temperature and vacuum filtered through a 0.45 micron filter to remove the resin. 1,113 grams of dark-amber gluco-oligosaccharide syrup at 60 Brix concentration was obtained.

Example 8

Single-Pot Syntheses of Oligosaccharide Preparations

A single pot (single component) synthesis of the oligosaccharide from Example 3 was demonstrated at 300 gram scale in a one-liter reaction vessel using catalyst loadings, reaction times, and reaction temperatures found to be suitable for the single pot reaction.

30 g of food-grade D-glucose monohydrate from corn, 37.50 g of food grade D-mannose from wood, 15.60 g of food-grade D-lactose monohydrate, 3.96 g of distilled water and 0.270 g of 2-pyridinesulfonic acid (Sigma-Aldrich, St. Louis) were added to a one-liter, three-neck round bottom flask with one center 29/42 ground joint flanked by two 24/40 ground joints. A Teflon stirring blade was affixed to a 220 mm glass stir shaft using PTFE tape. The stir rod was secured through the center point using a Teflon bearing adapter and attached to an overhead high-torque mechanical mixer via flexible coupler. The flask was secured inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. Once a temperature control box reading between 120° C. and 130° C. was observed, the apparatus was switched from a reflux condenser to a distillation configuration with a round bottom collection flask placed in an ice bath. The mixture was maintained at 130° C. with continuous stirring for approximately 5 hours and 40 minutes, after which the heating mantle and distillation apparatus was removed. Approximately 40 g of 23° C. distilled water was gradually added into the three-neck flask. The resulting mixture was left to stir at 40 rpm for 10 hours until the moment of collection. Approximately 389 g of a viscous, dark-amber material was collected and measured to have a concentration of 67.0 brix. Consistency with the oligosaccharide preparation from Example 3 was confirmed by SEC chromatography and 2D HSQC NMR spectroscopy.

Example 9

Characterization of Oligosaccharide Preparations

The methods and procedures from Examples 1-8 were used to prepare replicate batches and blends of the oligosaccharides of Examples 1-7. In preparing the various batches of Examples 9.1-9.7, both multi-pot (multi-component) and single-pot variants of the respective synthetic schemes were employed. The resulting materials were analyzed by HPLC Size Exclusion Chromatography (SEC) to characterize the molecular weight distribution, LC-MS/MS analysis to quantify the DP2 anhydro-sugar content, and 2D ¹H, ¹³C-HSQC NMR to fingerprint the molecular structure of the corresponding oligosaccharide preparations. Materials were prepared as follows:

Example 9.1: eleven batches of the oligosaccharide preparation from Example 1 were prepared and blended into four separate lots to produce oligosaccharide 9.1.

Example 9.2: seven batches of the oligosaccharide preparation from Example 2 were prepared and blended into two separate lots to produce oligosaccharide 9.2.

Example 9.3: twelve batches of the oligosaccharide preparation from Example 3 were prepared and blended into five separate lots to produce oligosaccharide 9.3.

Example 9.4: four batches of the oligosaccharide preparation from Example 4 were prepared and blended into a single lot to produce oligosaccharide 9.4.

Example 9.5: four batches of the oligosaccharide preparation from Example 5 were prepared and blended into a single lot to produce oligosaccharide 9.5.

Example 9.6: two batches of the oligosaccharide preparation from Example 6 were prepared and blended into a single lot to produce oligosaccharide 9.6.

Example 9.7: two batches of the oligosaccharide preparation from Example 7 were prepared and blended into a single lot to produce oligosaccharide 9.7.

Further structural variants of oligosaccharide preparations of Examples 1-7 were synthesized at 300 gram scale using the methods of Examples 1-7 but varying the starting sugar compositions, acid, acid loading, time, and reaction temperature. Oligosaccharide preparations were synthesized as follows:

Example 9.8: 300 grams of sucrose, 3 grams of phosphoric acid, and 27 grams of water were reacted at 125° C. for about one hour to obtain a dark brown oligosaccharide syrup that was then diluted to 60 Brix with distilled water.

Example 9.9: 270 grams of glucose, 30 grams of sucrose, 0.3 grams of phenylphosphonic acid, and 27 grams of water were reacted at 130° C. for between one to four hours to obtain a dark brown oligosaccharide syrup that was then diluted to 60 Brix with distilled water.

Example 9.10: 225 grams of glucose, 75 grams of lactose, 3 grams of butylphosphonic acid and 27 grams of water were reacted at 130° C. for between one to four hours to obtain a dark amber oligosaccharide syrup that was then diluted to 60 Brix with distilled water.

Example 9.11: 225 grams of glucose, 75 grams of lactose, 3 grams of phenylphosphonic acid and 27 grams of water were reacted at 130° C. for between one to five hours to obtain a dark amber oligosaccharide syrup that was then diluted to 60 Brix with distilled water.

Example 9.12: 270 grams of glucose, 30 grams of lactose, 3 grams of phenylphosphinic acid and 27 grams of water were reacted at 130° C. for between three to five hours to obtain a dark brown oligosaccharide syrup that was then diluted to 60 Brix with distilled water.

Example 9.13: 300 grams of glucose, 3 grams of phenylphosphinic acid, and 27 grams of water were reacted at 130° C. for one to three hours to obtain a dark amber oligosaccharide syrup that was then diluted to 60 Brix with distilled water.

Example 9.14: 300 grams of glucose, 2 grams of propionic acid, and 27 grams of water were reacted at 130° C. for one to four hours to obtain an amber oligosaccharide syrup that was then diluted to 60 Brix with distilled water.

Example 9.15: 300 grams of glucose, 0.15 grams of 8-hydroxy-5-quinolinesulfonic acid hydrate, and 27 grams of water were reacted at 130° C. for two to four hours to obtain an amber oligosaccharide syrup that was then diluted to 60 Brix with distilled water.

In the above reactions, all masses refer to the pure component masses, and the total mass of reactant water was inclusive of any carry-along water provided by the moisture content and/or water of hydration of the reactant sugars.

Example 9.16: 10 grams of glucose, 0.01 grams of 8-hydroxy-5-quinolinesulfonic acid hydrate and 1 gram of water were reacted at 130° C. to obtain an amber oligosaccharide syrup that was then diluted to 60 Brix with distilled water.

Example 9.17: Approximately 8 grams of glucose, approximately 2 grams of lactose, 0.01 grams of 2-pyridinesulfonic acid and 1 gram of water were reacted at 130° C. to obtain an amber oligosaccharide syrup that was then diluted to 60 Brix with distilled water.

Characterization of Oligosaccharide Preparations:

The resulting materials were analyzed by HPLC Size Exclusion Chromatography (SEC) to characterize the molecular weight distribution, LC-MS/MS analysis to quantify the DP2 anhydrosugar content, and 2D ¹H, ¹³C-HSQC NMR to fingerprint the molecular structure of the corresponding oligosaccharide preparations.

Polymer Molecular Weight determined by HPLC:

The number average molecular weight (MWn) and weight-average molecular weight (MWw) of the oligosaccharide preparations of Examples 9.1-9.7 were determined by HPLC. SEC analysis was performed on an Agilent 1100 series HPLC with refractive index detection using an Agilent PL aquagel-OH 20 column at 40° C. with distilled water at 0.45 mL/min as the mobile phase. Retention-time to MW calibration was performed using standard solutions with known molecular weight and standard methods from the art were used to determine the various distribution properties from the SEC chromatogram. The MWn and MWw of oligosaccharide preparations with multiple lots are shown below in Table 1.

TABLE 1

| MWn and MWw of Oligosaccharide Preparations | | |
|---|---|---|
| Oligosaccharide Preparation | MWn (g/mol) | MWw (g/mol) |
| 9.1 | 719 ± 11 | 1,063 ± 23 |
| 9.2 | 808 ± 30 | 1,336 ± 122 |
| 9.3 | 757 ± 15 | 1,186 ± 49 |
| 9.4 | 761 | 1,196 |
| 9.5 | 755 | 1,177 |
| 9.6 | 505 | 709 |
| 9.7 | 762 ± 12 | 1,154 ± 14 |

Anhydro-DP2 Content Analysis by GC-MS:

The anhydro DP2 content of oligosaccharide preparations was determined by LC-MS/MS using a Capcell Pak NH2 (Shiseido; 250×4.6 mm, 5 μm) column at a flowrate of 1 mL/min under isocratic conditions of water/acetonitrile 35/65. Prior to MS the flow was split 1:4 and a makeup flow of 50 μL 0.05% NH4OH was added to enhance ionization. For MS detection ESI probe was used in negative mode and MRM method allowed targeted analysis.

The anhydro DP2 contents of the oligosaccharide preparations was first determined relative to that of the oligosaccharide preparation of Example 9.7 as a reference composition. The absolute anhydro DP2 content of the reference oligosaccharide preparation of Example 9.7 was then determined by HPLC-MS/MS to be about 10% and the anhydro DP2 contents of the oligosaccharide preparations of Examples 9.1 to 9.6 were then obtained by calculation. The relative and absolute DP2 contents were determined as described in Table 2.

TABLE 2

Anhydro DP2 content for oligosaccharide preparations with multiple lots

| Oligosaccharide Preparation | Relative Anhydro DP2 Content % Relative to Ex 9.7 | Anhydro DP2 Content (g AHDP2/g total DP2) |
|---|---|---|
| 9.1 | 53% | 5.3% |
| 9.2 | 14% | 1.4% |
| 9.3 | 57% | 5.7% |
| 9.4 | 53% | 5.3% |
| 9.5 | 33% | 3.3% |
| 9.6 | 50% | 5.0% |
| 9.7 | 100% | 10.0% |

Molecular Fingerprint by 2D $^1$H, $^{13}$C-HSQC NMR:

The molecular structures of the oligosaccharide preparations of Example 9 were characterized by 2D $^1$H, $^{13}$C-HSQC NMR spectroscopy. Samples were prepared by drying 125 mg (dry solids basis) of the oligosaccharide preparation at 40° C. and re-dissolving in D$_2$O containing 0.1% acetone. NMR spectra were acquired at 300K on either a Bruker Avance NMR spectrometer operating at a proton frequency of 400 MHz or on a Bruker Avance III NMR spectrometer operating at a proton frequency of 600 MHz equipped with a cryogenically cooled 5 mm TCI probe. FIG. 1 provides an illustrative 2D $^1$H,$^{13}$C HSQC NMR spectrum of the oligosaccharide preparation of oligosaccharide preparation 9.7.

The anomeric region of the $^1$H, $^{13}$C-HSQC spectrum, F2 ($\delta^1$H)=4.2-6.0 ppm and F1 ($\delta^{13}$C)=90-120 ppm, was used to fingerprint the linkage distribution of the oligosaccharide preparations. Each peak in the anomeric region was integrated and its relative abundance was determined relative to that of the total anomeric region. 2D $^1$H,$^{13}$C HSQC fingerprinting was performed on the four lots of the oligosaccharide preparation 9.1.

TABLE 3

Relative Abundances of F2 and F1 Peaks of Oligosaccharide Preparation 9.1

| F2 (ppm) | F1 (ppm) | AUC (Average ± SEM) |
|---|---|---|
| 5.43 | 92.42 | 0.4% ± 0.3% |
| 5.44 | 102.07 | 0.4% ± 0.1% |
| 5.43 | 90.05 | 0.5% ± 0.2% |
| 5.40 | 100.22 | 1.6% ± 0.4% |
| 5.37 | 98.33 | 0.7% ± 0.4% |
| 5.35 | 99.70 | 2.7% ± 0.6% |
| 5.33 | 96.53 | 0.3% ± 0.2% |
| 5.24 | 100.86 | 0.5% ± 0.2% |
| 5.22 | 92.71 | 20.2% ± 3.9% |
| 5.21 | 102.45 | 0.5% ± 0.4% |
| 5.18 | 93.86 | 0.9% ± 0.4% |
| 5.17 | 96.01 | 0.4% ± 0.1% |
| 5.09 | 96.88 | 0.6% ± 0.3% |
| 5.03 | 108.49 | 0.4% ± 0.2% |
| 5.02 | 109.16 | 0.4% ± 0.4% |
| 4.98 | 99.19 | 0.6% ± 0.3% |
| 4.95 | 98.51 | 30.6% ± 4.1% |
| 4.86 | 98.53 | 0.7% ± 0.5% |
| 4.79 | 96.84 | 0.6% ± 0.3% |
| 4.71 | 103.48 | 2.5% ± 0.7% |
| 4.64 | 103.56 | 0.8% ± 0.4% |
| 4.63 | 102.49 | 0.7% ± 0.5% |
| 4.62 | 104.56 | 1.4% ± 0.4% |
| 4.57 | 97.07 | 1.6% ± 0.3% |

TABLE 3-continued

Relative Abundances of F2 and F1 Peaks of Oligosaccharide Preparation 9.1

| F2 (ppm) | F1 (ppm) | AUC (Average ± SEM) |
|---|---|---|
| 4.50 | 103.30 | 25.9% ± 2.2% |
| 4.45 | 103.56 | 2.4% ± 1.3% |

Example 10

Determination of the Anhydro Sugar Subunits of an Oligosaccharide Preparation

The relative abundance of anhydro sugar subunits in the oligosaccharide preparations of Example 9 was determined by MALDI-MS on a Bruker Ultraflex instrument. Samples were dissolved in water to a concentration of 10 mg/ml, from which 5 μl were mixed with matrix solution (30 mg/ml DHB in 80% ethanol and water in a ratio 1:10). Plates were prepared by applying 1 μl of the analyte solution to the target plate and dried at ambient air. In some cases, samples were re-crystalized by applying 1 μl ethanol prior to MS analysis.

Figure 32A:
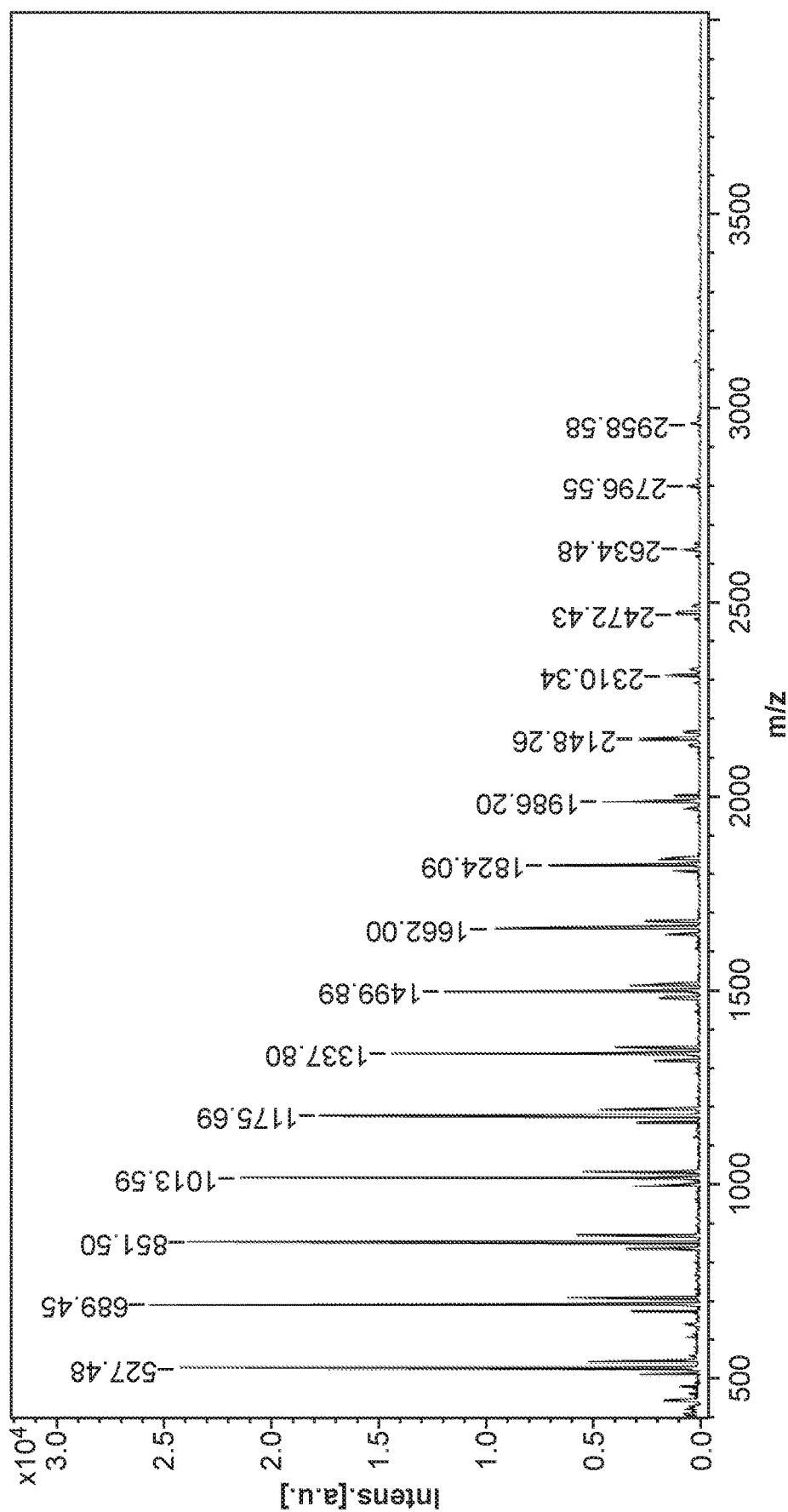
FIG. 32A illustrate a MALDI-MS spectrum of an oligosaccharide preparation from Example 2 that demonstrates the presence of anhydro-subunits.
Figure 32B:
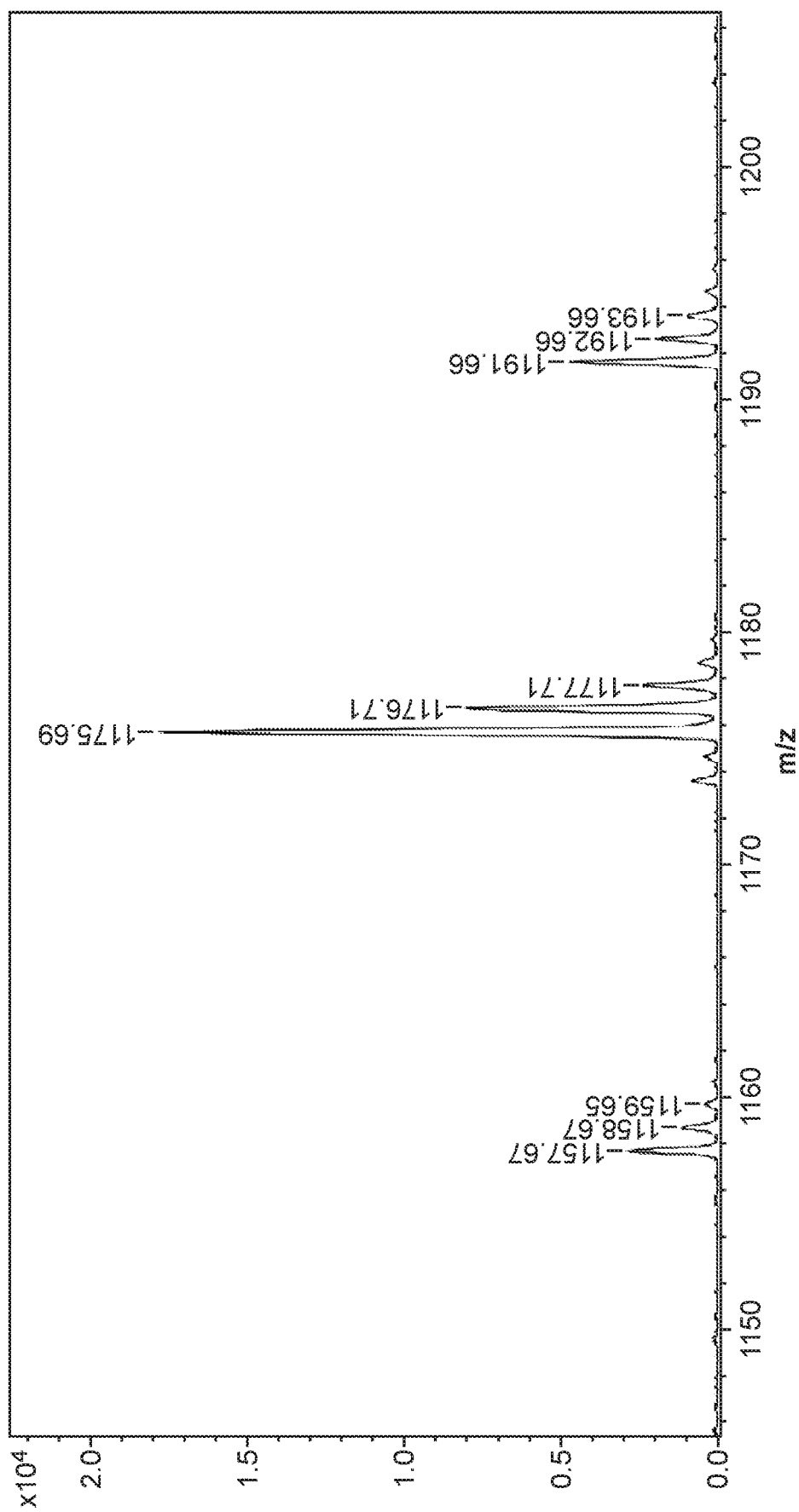
FIG. 32B illustrates a MALDI-MS spectrum of an oligosaccharide preparation from Example 2 that demonstrates the presence of anhydro-subunits.
Figures 33A, 33B, 33C:
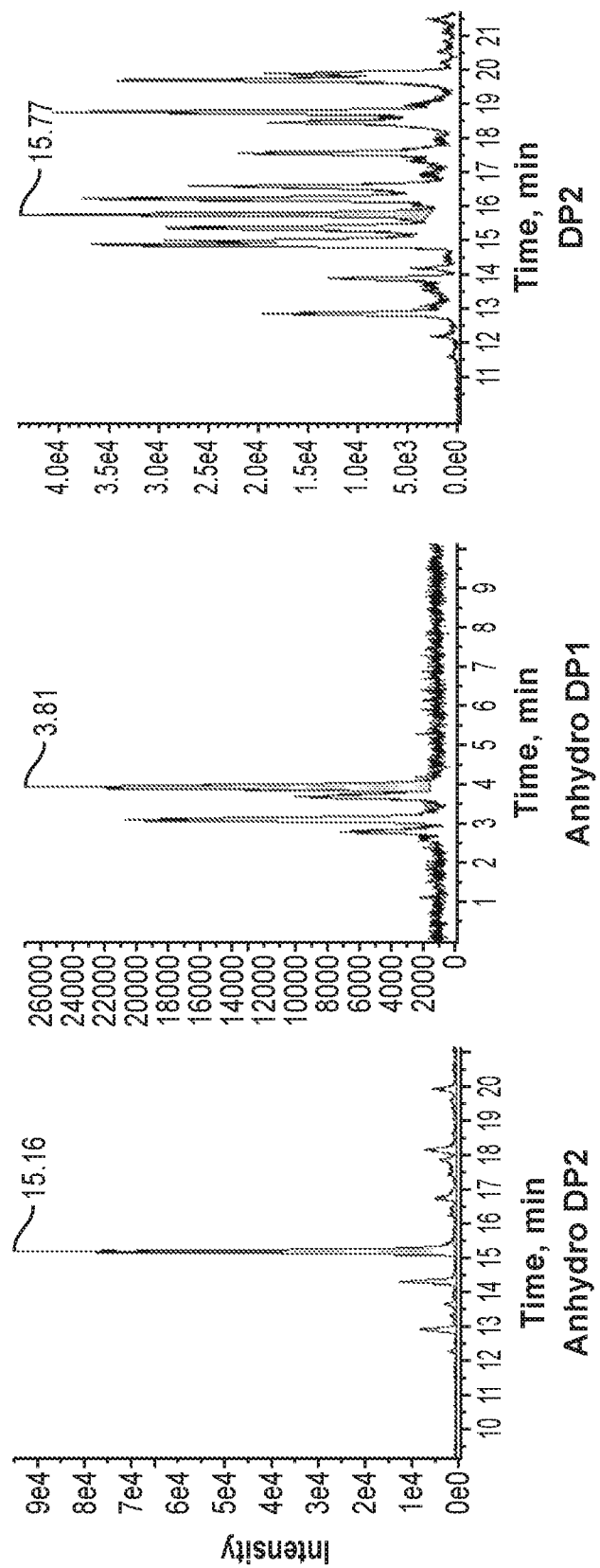
FIG. 33A illustrates LC-MS/MS detection of the anhydro DP2, anhydro DP1, and DP2 species of an oligosaccharide preparation of Example 1.
FIG. 33B illustrates LC-MS/MS detection of the anhydro DP2, anhydro DP1, and DP2 species of an oligosaccharide preparation of Example 1.
FIG. 33C illustrates LC-MS/MS detection of the anhydro DP2, anhydro DP1, and DP2 species of an oligosaccharide preparation of Example 1.
Figures 35A, 35B, 35C:
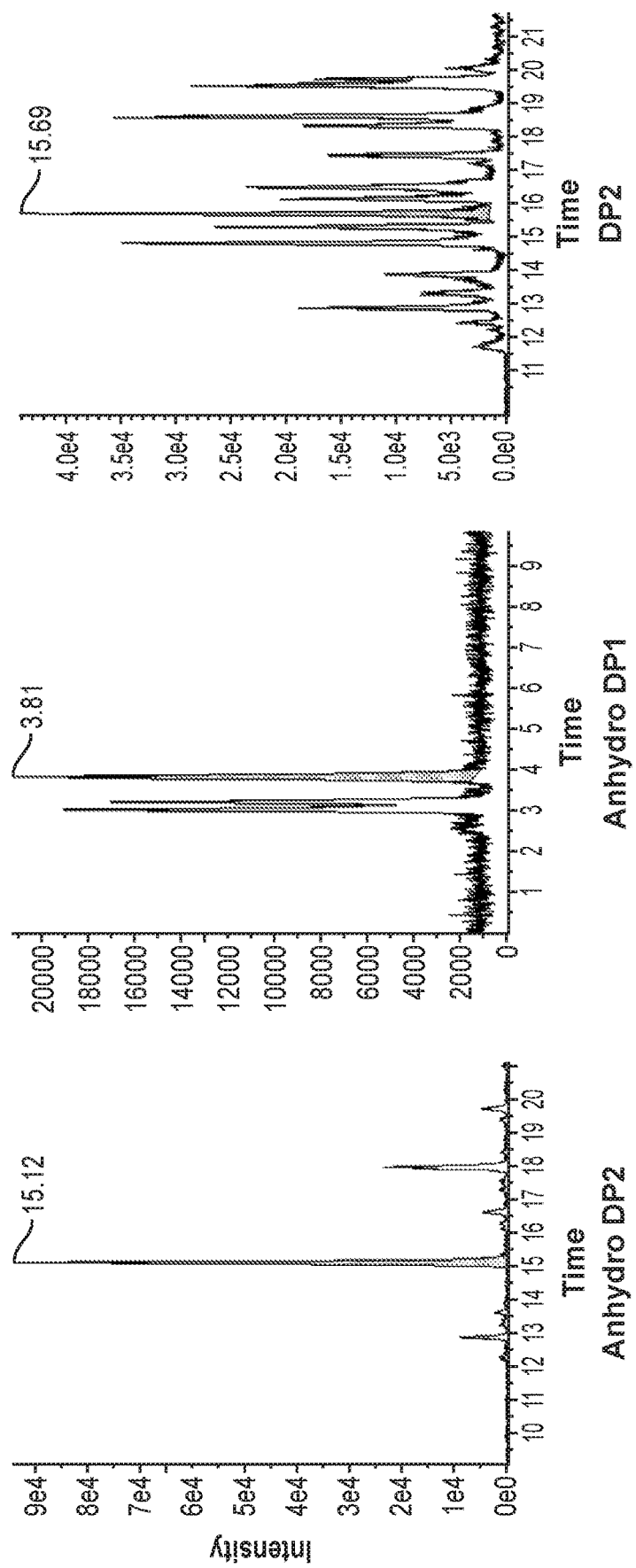
FIG. 35A illustrate LC-MS/MS detection of the anhydro DP2, anhydro DP1, and DP2 species of an oligosaccharide preparation of Example 4.
FIG. 35B illustrate LC-MS/MS detection of the anhydro DP2, anhydro DP1, and DP2 species of an oligosaccharide preparation of Example 4.
FIG. 35C illustrate LC-MS/MS detection of the anhydro DP2, anhydro DP1, and DP2 species of an oligosaccharide preparation of Example 4.
Figures 36A, 36B, 36C:
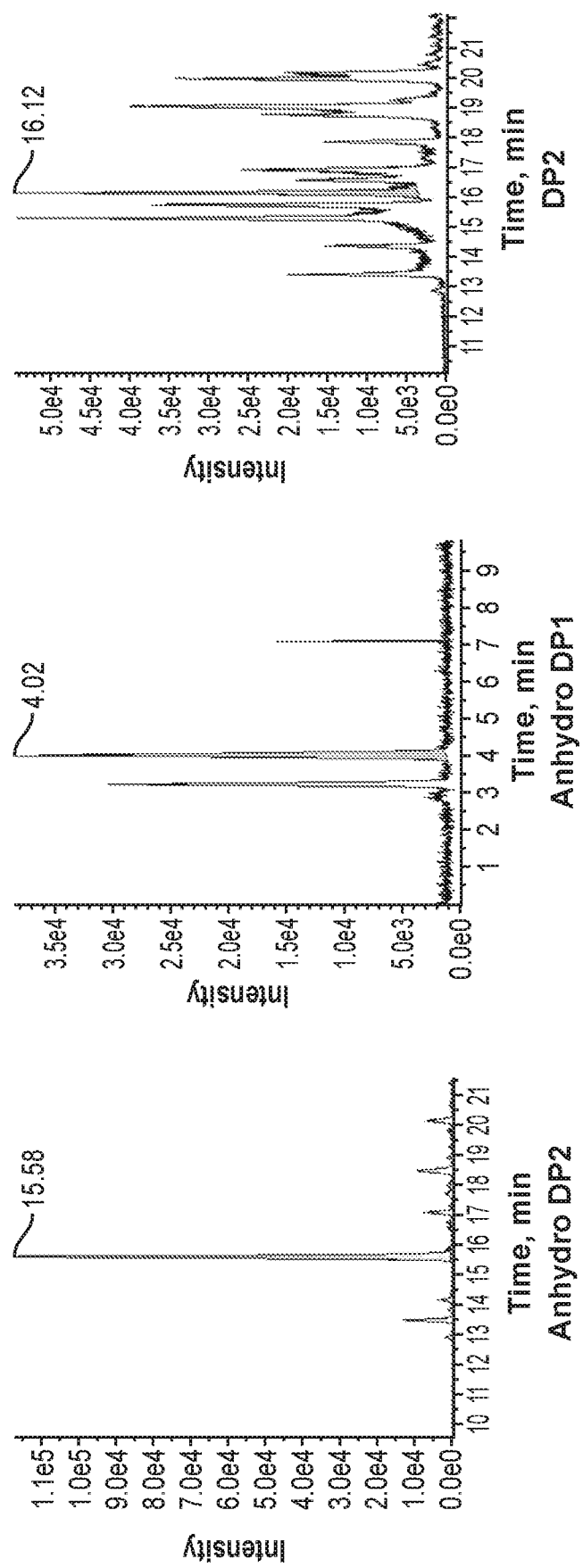
FIG. 36A illustrate LC-MS/MS detection of the anhydro DP2, anhydro DP1, and DP2 species of an oligosaccharide preparation of Example 7.
FIG. 36B illustrate LC-MS/MS detection of the anhydro DP2, anhydro DP1, and DP2 species of an oligosaccharide preparation of Example 7.
FIG. 36C illustrate LC-MS/MS detection of the anhydro DP2, anhydro DP1, and DP2 species of an oligosaccharide preparation of Example 7.
Figure 37A:
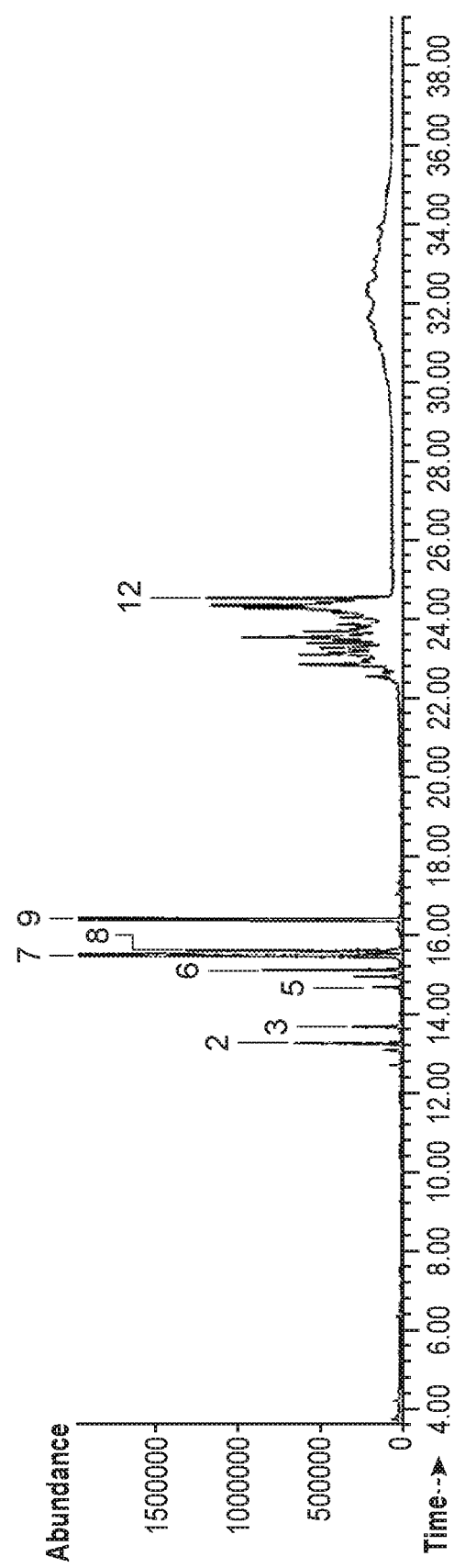
FIG. 37A illustrates GC-MS spectrum detection of the DP1, anhydro DP1, DP2 and anhydro DP2 fractions of an oligosaccharide preparation of Example 1.
Figure 37B:
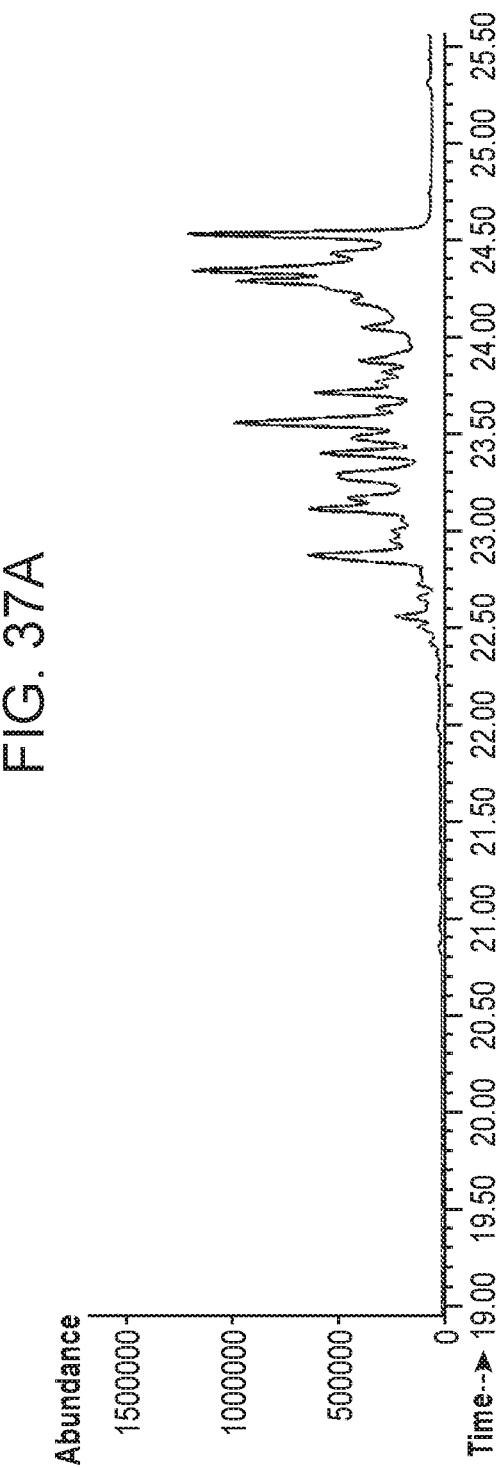
FIG. 37B illustrates an enlargement of the DP2 and anhydro DP 2 fractions as shown in FIG. 37A.
Figure 39A:
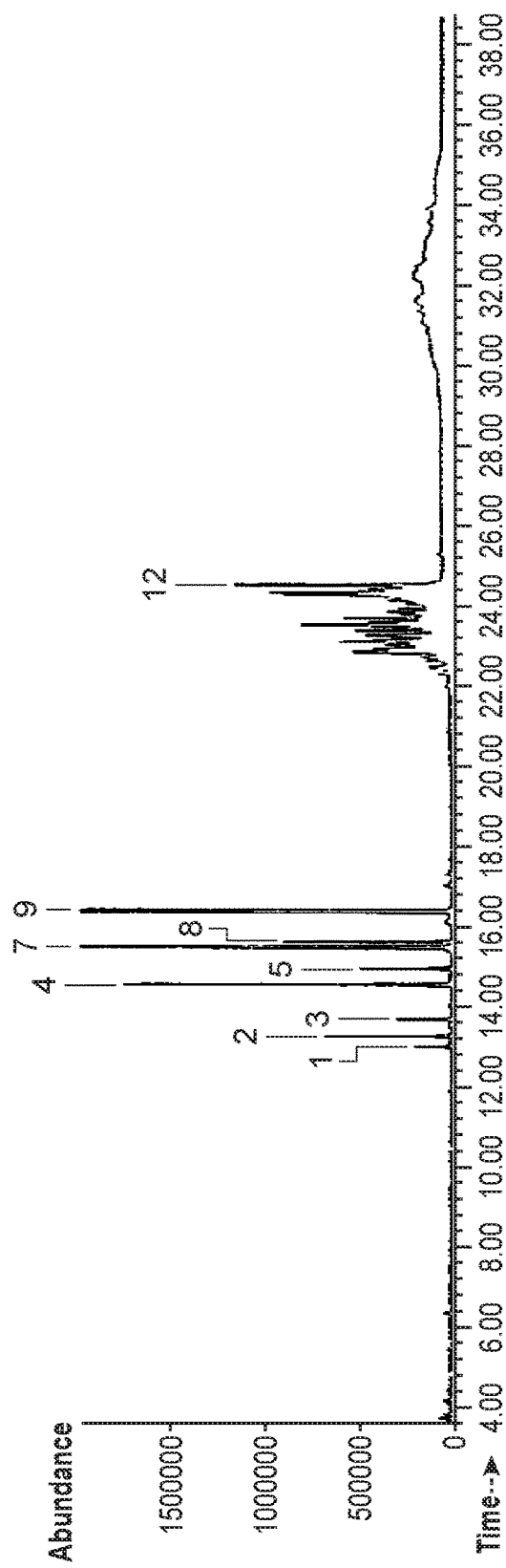
FIG. 39A illustrates GC-MS spectrum detection of the DP1, anhydro DP1, DP2 and anhydro DP2 fractions of an oligosaccharide preparation of Example 4.
Figure 39B:
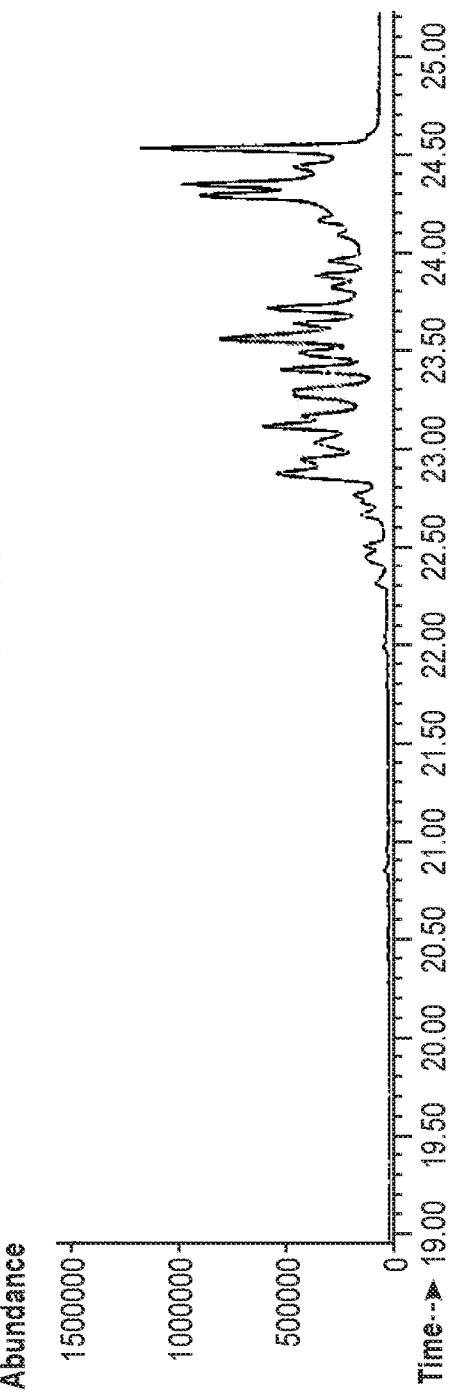
FIG. 39B illustrates an enlargement of the DP2 and anhydro DP 2 fractions as shown in FIG. 39A.
Figure 41:
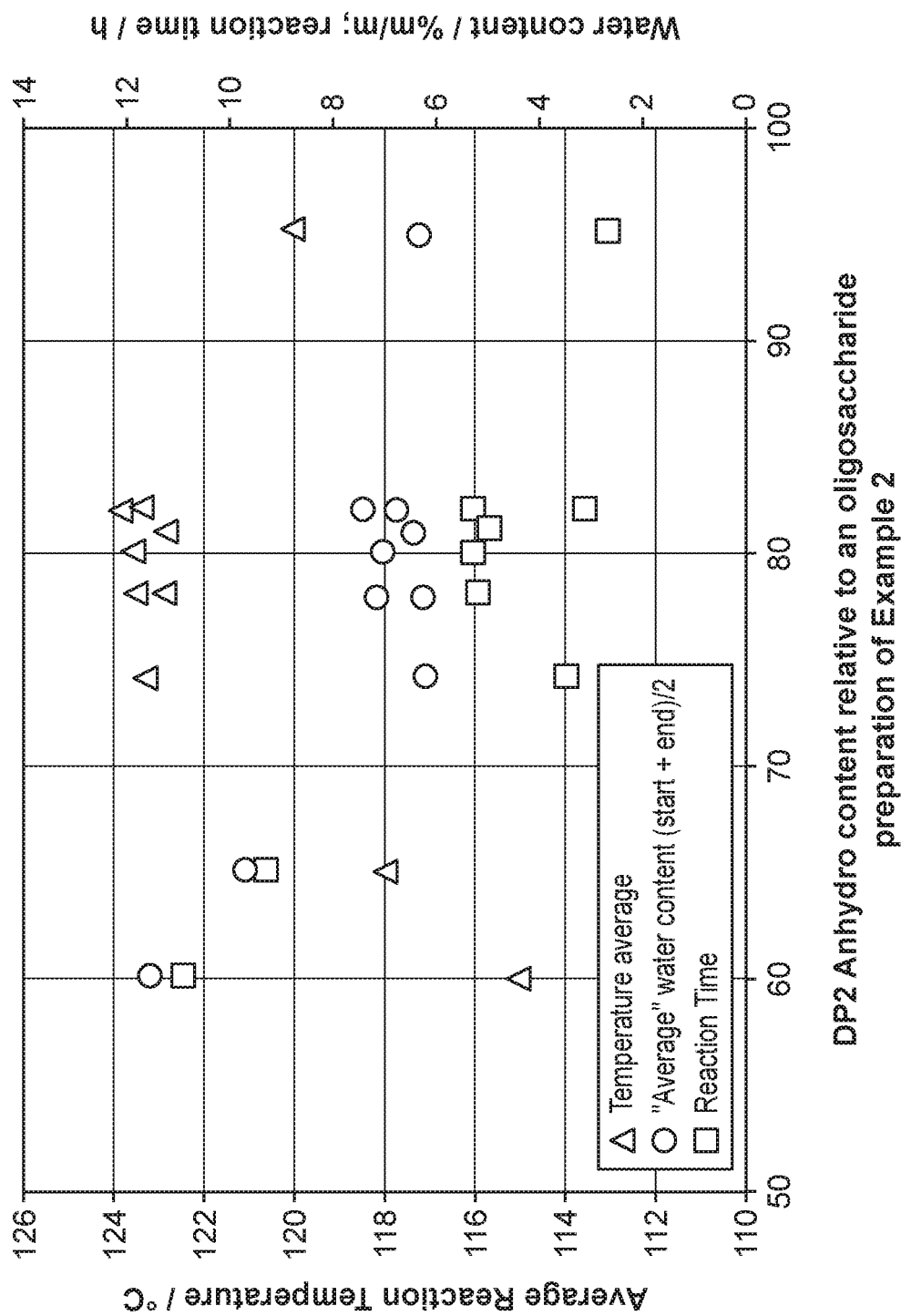
FIG. 41 illustrates the effect of reaction temperature, water content, and reaction time on the content of DP2 anhydro-subunit containing oligosaccharides in the oligosaccharide preparations, as compared to an oligosaccharide preparation according to Example 2.

FIG. 2 provides an illustrative MALDI spectrum of an oligosaccharide preparation from Example 9. Anhydrosugar subunits are clearly observed as offset peaks shifted by −18 g/mol relative to its respective principal DP parent. Offset peaks are observed at all values of DP, indicating that anhydrosugar subunits are detected at all oligosaccharide sizes. The relative intensity of the anhydro subunit peak was determined to be about 10% of the total peak intensity for each DP, from which the total anhydro subunit relative abundance was determined to be about 10%. FIG. 32A and FIG. 32B illustrate MALDI spectra of an oligosaccharide preparation from Example 2. Anhydro-sugar subunits are observed at every DP level with a relative intensity in the range of 5-10%.

Example 11

Characterization of the Anhydro Sub-Units of an Oligosaccharide Preparation

The anhydrosugar subunits of the oligosaccharide preparations of Example 9 were characterized using a combination of LC-MS, GC-MS, LC-MS/MS, and NMR methods.

Figure 3:
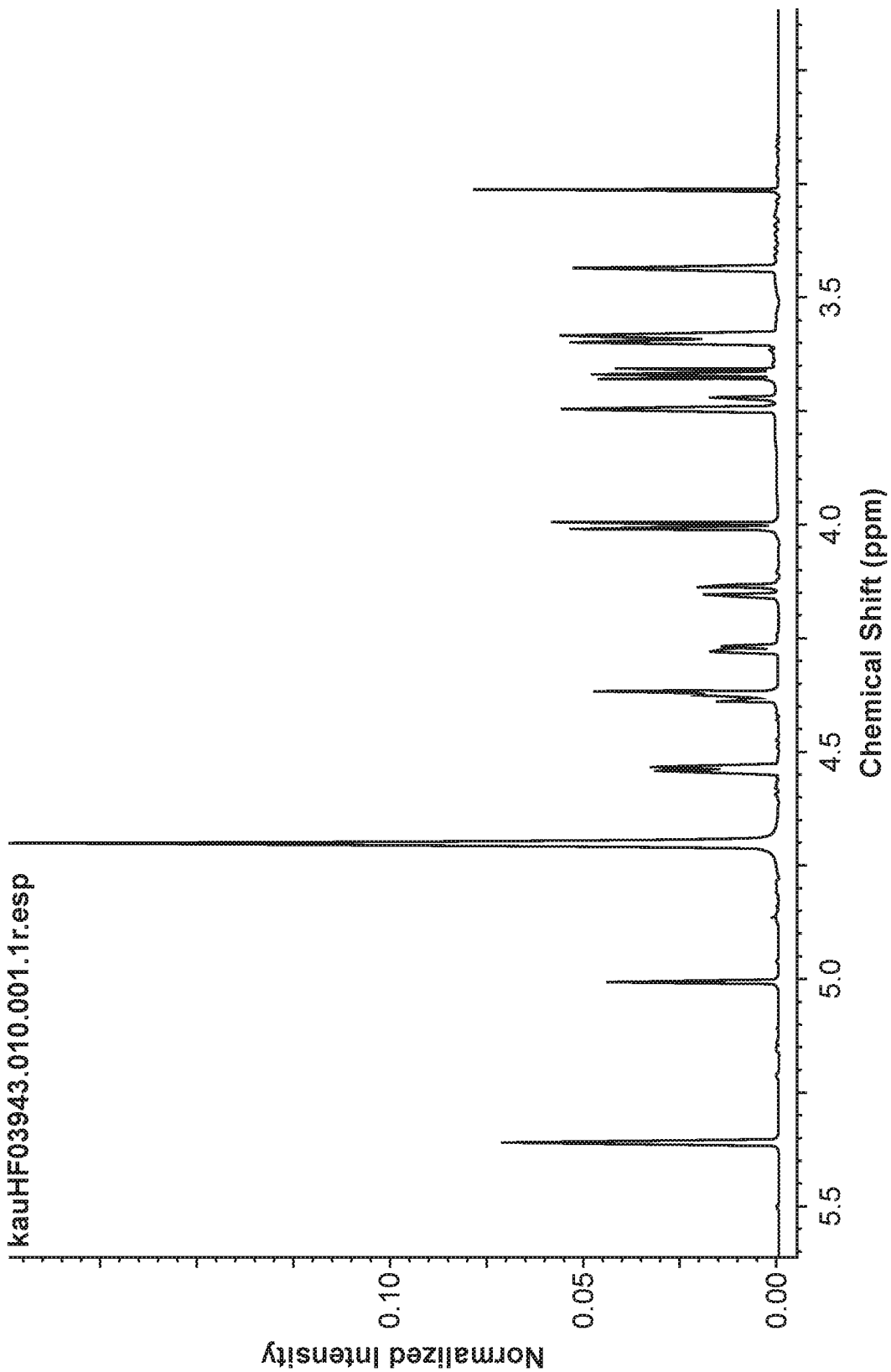
FIG. 3 illustrates a 1D $^1$H-proton NMR spectrum of an anhydro DP1 fraction isolated from an oligosaccharide of Example 9.
Figure 4:
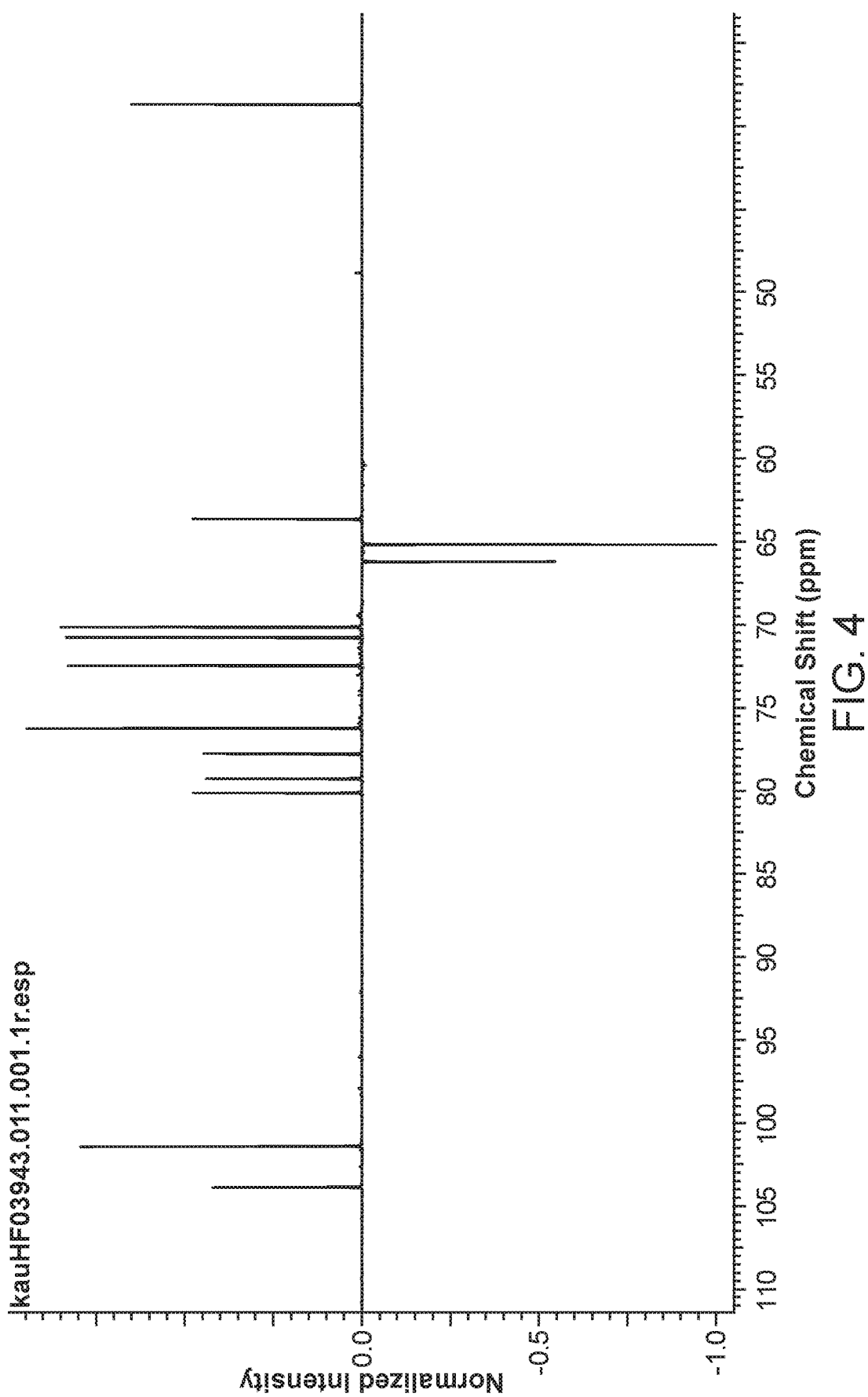
FIG. 4 illustrates a 1D APT $^{13}$C-NMR spectrum of an anhydro DP1 fraction isolated from an oligosaccharide of Example 9.

Characterization of Anhydro-DP1 Components:

The anhydro DP1 component of an oligosaccharide preparation from Example 9 was isolated by preparative liquid chromatography. The isolated anhydro-DP1 component was prepared for NMR by dissolving it in 0.75 mL of D2O. FIG. 3 provides an illustrative 1D $^1$H-NMR spectrum of an anhydro DP1 fraction isolated from an oligosaccharide of Example 9 and FIG. 4 provides an illustrative APT $^{13}$C-NMR spectrum of the same isolated anhydro DP1 fraction.

Using the following peak assignments in Table 4, the ratio of 1,6-anhydro-beta-D-glucofuranose to 1,6-Anhydro-beta-D-glucopyranose was determined by NMR to be 2:1.

TABLE 4

NMR Peak Assignments

| # | 1,6-anhydro-beta-D-glucofuranose | | 1,6-Anhydro-beta-D-glucopyranose | |
|---|---|---|---|---|
| | $^1$H (ppm) | $^{13}$C (ppm) | $^1$H (ppm) | $^{13}$C (ppm) |
| 1 | 5.33 | 101.9 | 5.01 | 104.4 |
| 2 | 3.40 | 70.6 | 4.37 | 79.8 |
| 3 | 3.56 (ov)$^a$ | 73.0 | 4.27 | 78.3 |
| 4 | 3.56 (ov)$^a$ | 71.3 | 4.38 | 80.6 |
| 5 | 4.50 | 76.7 | 3.74 | 64.1 |
| 6 | 3.97, 3.64 | 65.7 | 4.14, 3.72 | 66.7 |

$^a$Ov indicates overlapped signal

Characterization of the Anhydro-DP2 Components

The anhydrosugar subunits of the oligosaccharide preparations of Example 9 were characterized using a combination of LC-MS, GC-MS, LC-MS/MS, and NMR methods. The anhydro DP2 content of the oligosaccharide preparations of Example 9 were determined by GC-MS and LC-MS/MS analysis. Gas chromatography was performed using a 30 m×0.25 mm fused silica column containing HP-5MS stationary phase, with 21.57 psi constant pressure Helium as the carrier gas. Aliquots were pre-derivatized by acetylation by dissolving 20 mg of sample in 0.5 mL pyridine with 0.5 mL acetic anhydride for 30 minutes at 60° C. 1 uL samples were injected at 300° C. with an oven temperature program starting at 70° C. and ramping by 10° C. per minute to 315° C. Detection was performed on an Agilent 5975C MSD with an electron energy of 70 eV.

Figure 5:
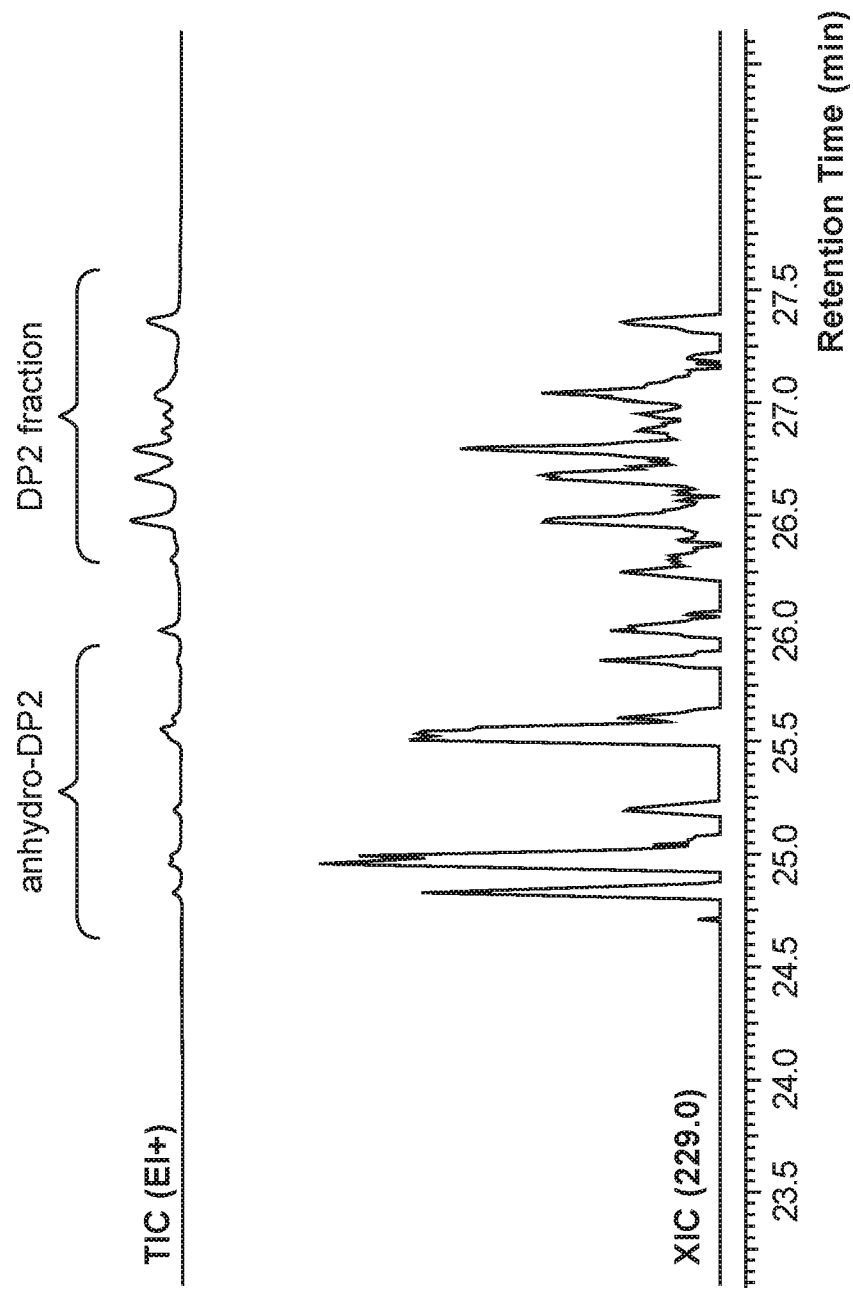
FIG. 5 illustrates the GC-MS chromatogram (TIC and XIC (m/z 229) plots) showing the DP2 and anhydro-DP2 components of oligosaccharide preparation 2.9 following derivatization.

FIG. 5 illustrates an enlargement of the GC-MS chromatogram for the oligosaccharide preparation 9.7. The TIC and XIC (m/z 229) plots demonstrate that the DP2 and anhydro-DP2 components are clearly resolved. FIGS. 37A-37B, 38A-38B, 39A-39B, and 40A-40B illustrate the presence of the DP1, anhydro DP1, DP2 and anhydro DP2 fractions as detected by GC-MS in an oligosaccharide preparation of Example 1, Example 3, Example 4, and Example 7, respectively. As shown in FIGS. 37A-37B, 38A-38B, 39A-39B, and 40A-40B, anhydro DP1 and DP1 fractions have a retention time of from about 12-17 minutes, and anhydro DP2 and DP2 fractions have a retention time of about from 22-25 minutes.

Figure 43:
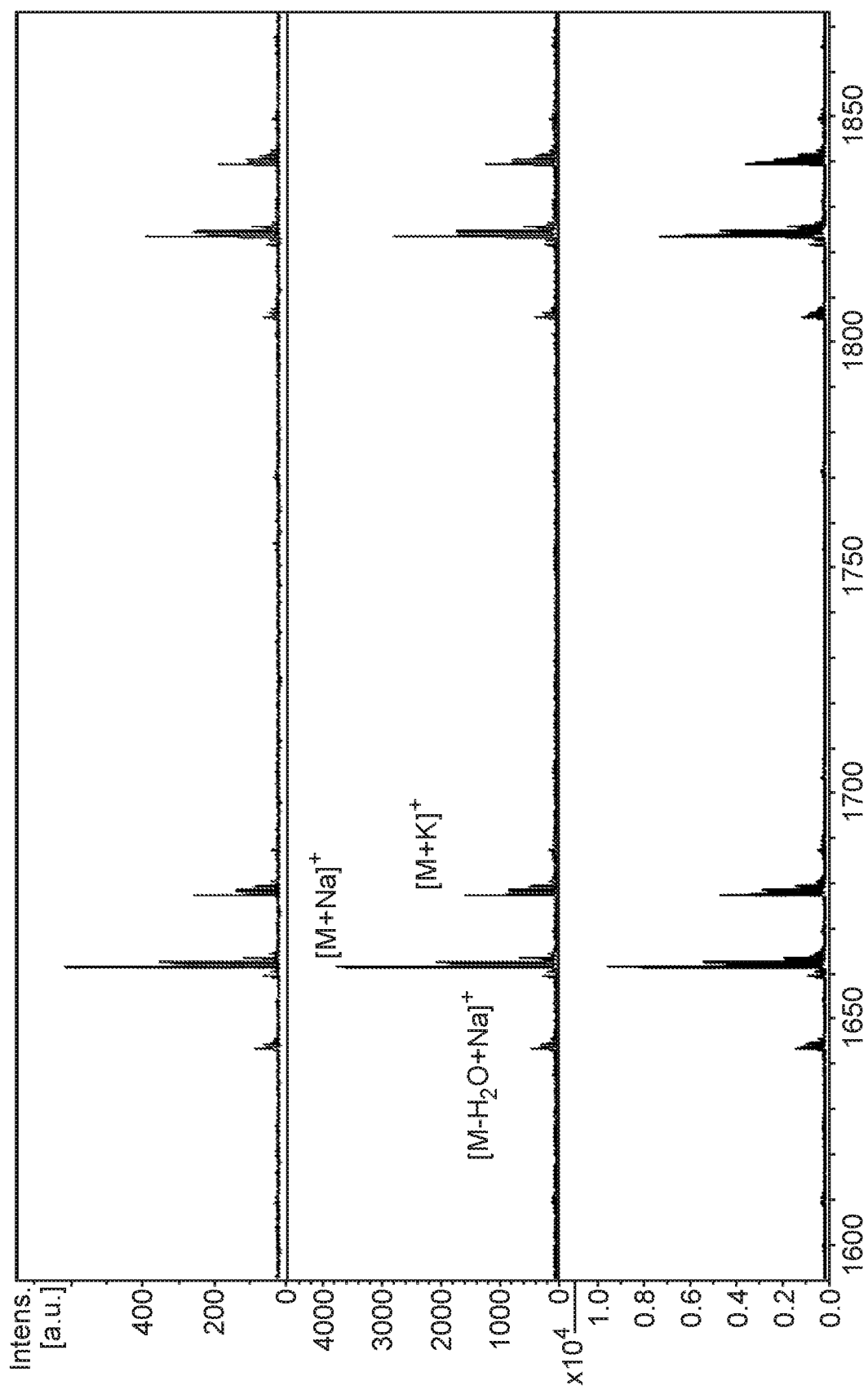
FIG. 43 illustrates MALDI-MS spectra comparing the oligosaccharide preparation from Example 9 at different laser energies.

FIG. 43 illustrates MALDI-MS spectra comparing the oligosaccharide preparation from Example 9 at different laser energies. Relative abundancy of signals was nearly unchanged, demonstrating that no loss of water is introduced by the laser ionization. Hence, proving the presence of anhydro-sugar subunits in the oligosaccharide preparation.

Example 12

Observation of Caramelization Subunits in an Oligosaccharide Preparation

Figure 6:
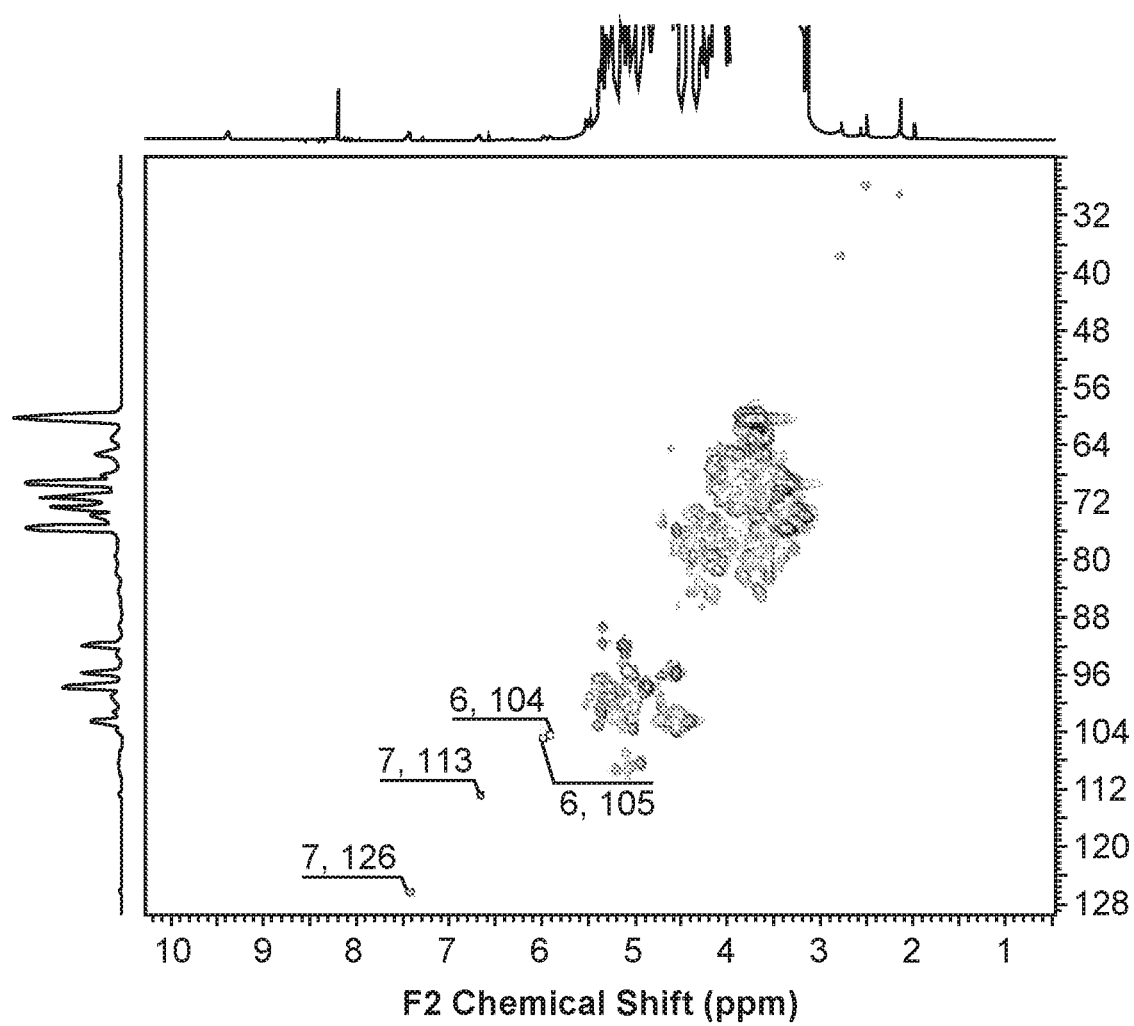
FIG. 6 illustrates a $^1$H, $^{13}$C-HSQC spectrum of an oligosaccharide preparation with a caramelization anhydro-subunit.

An oligosaccharide preparation comprising a 5-hydroxymethylfurfural caramelization subunit was demonstrated by a combination of HPLC analysis and 2D $^1$H,$^{13}$C HSQC NMR. A 50 mg aliquot of an oligosaccharide preparation from Example 9 was dissolved in 0.8 mL D$_2$O. The resulting 2D $^1$H, $^{13}$C HSQC spectrum was analyzed for the presence of a glycosidic linkage between 5-hmf and the anomeric carbon of glucose, with the following peak assignments: $^1$H NMR: δ=9.39 ppm (CHO, m), 7.44 ppm (Ar—H, m), 6.68 ppm (Ar—H, m), 4.60 ppm (CH2, m); and $^{13}$C NMR: δ=180.0, 150.6, 126.2, 112.7, 159.9, 64.5. The absence of free 5-hmf was confirmed by HPLC using an Agilent 1100 HPLC system equipped with a 3000 mm Bio-Rad Aminex 87H using 25 mM aqueous sulfuric acid at 0.65 mL/min isocratic elution and UV detection. 5-hmf was quantified against an authentic sample. No 5-hmf peak was observed in the oligosaccharide preparation of Example 9, but was observed following low-temperature acid hydrolysis of the oligosaccharide preparation under conditions not expected to produce free 5-hmf in the hydrolysate. FIG. 6 provides an illustrative 2D $^1$H, $^{13}$C-HSQC NMR spectrum of an oligosaccharide preparation that incorporates a caramelization subunit.

Example 13

Comparative Example

Figure 7:
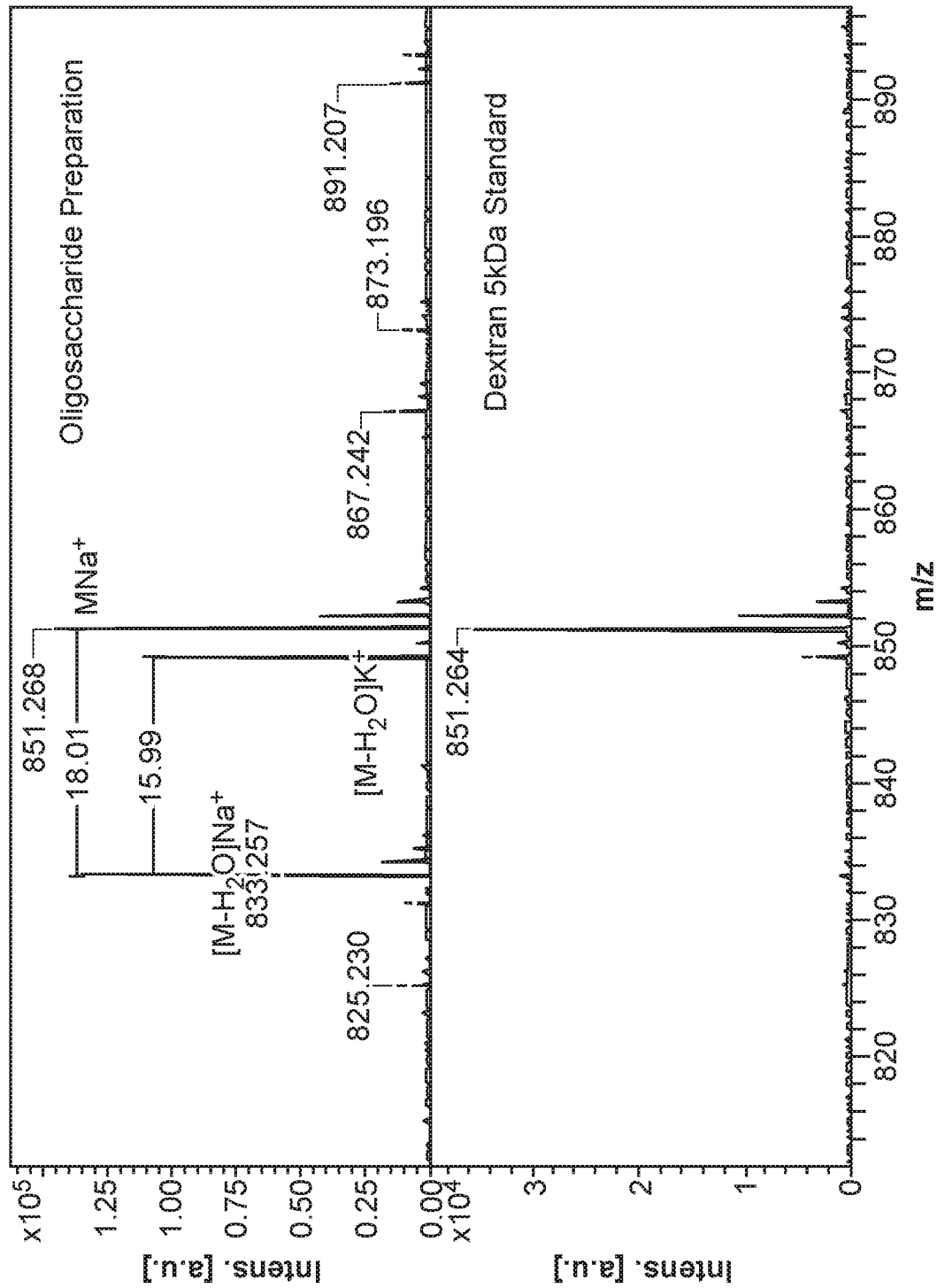
FIG. 7 illustrates a part of a MALDI-MS spectra comparing the oligosaccharide preparation from Example 9 at different laser energies.

A commercial 5 kDa dextran was analyzed by MALDI-MS for the presence of anhydrosugar subunits. FIG. 7 shows the clear presence of the offset peak shifted −18 g/mol from the principal DP peak (Na+ adduct at 851.268 g/mol). By contrast the dextran sample was found to be essentially free of anhydro sugar subunits.

Example 14

Quantification of the Anhydro DP Component by LC-MS/MS

Figure 8A:
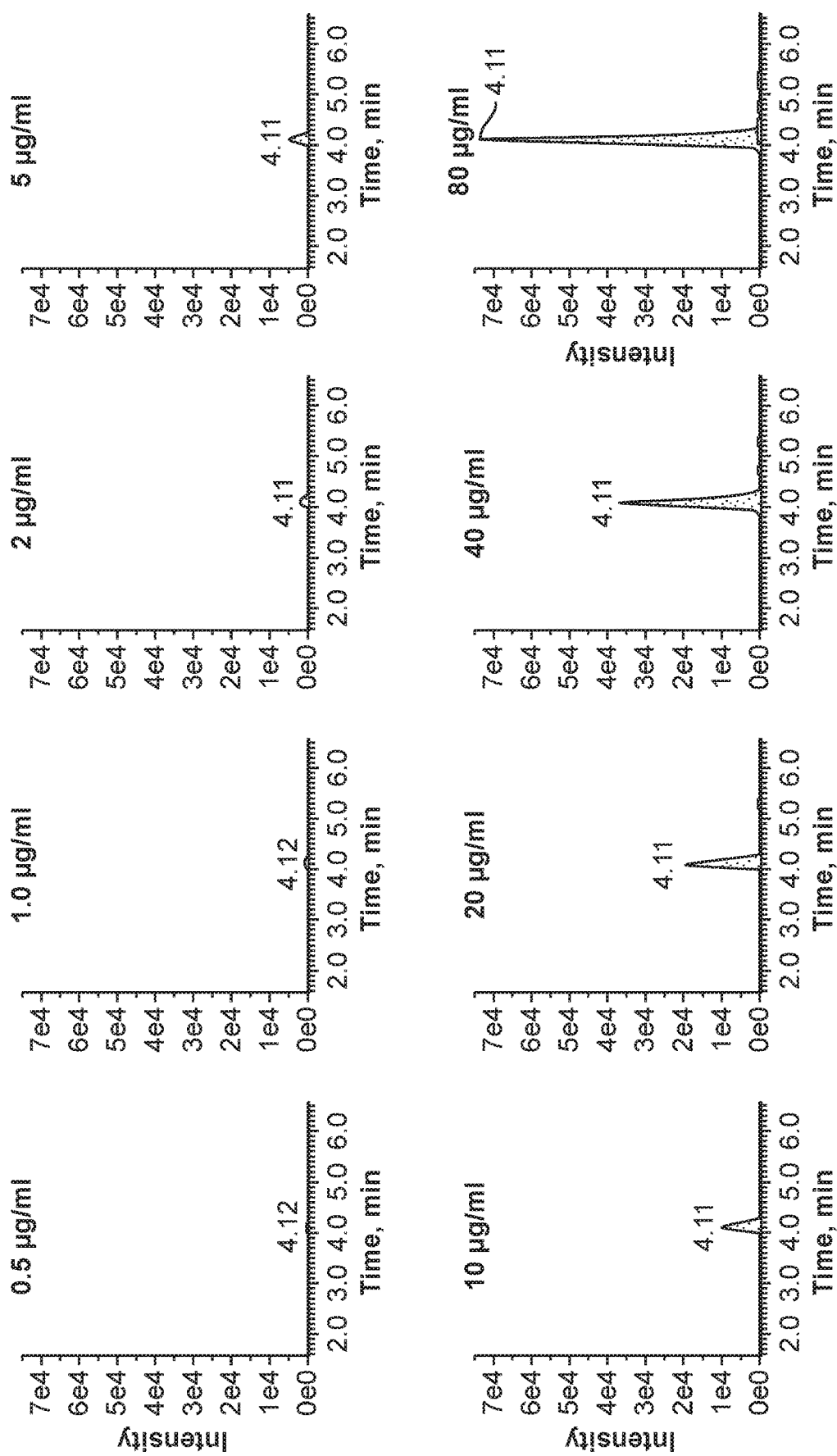
FIG. 8A illustrates LC-MS/MS detection of the anhydro DP2 species at concentration of 1-80 µg/mL of an oligosaccharide preparation in water.
Figure 8B:
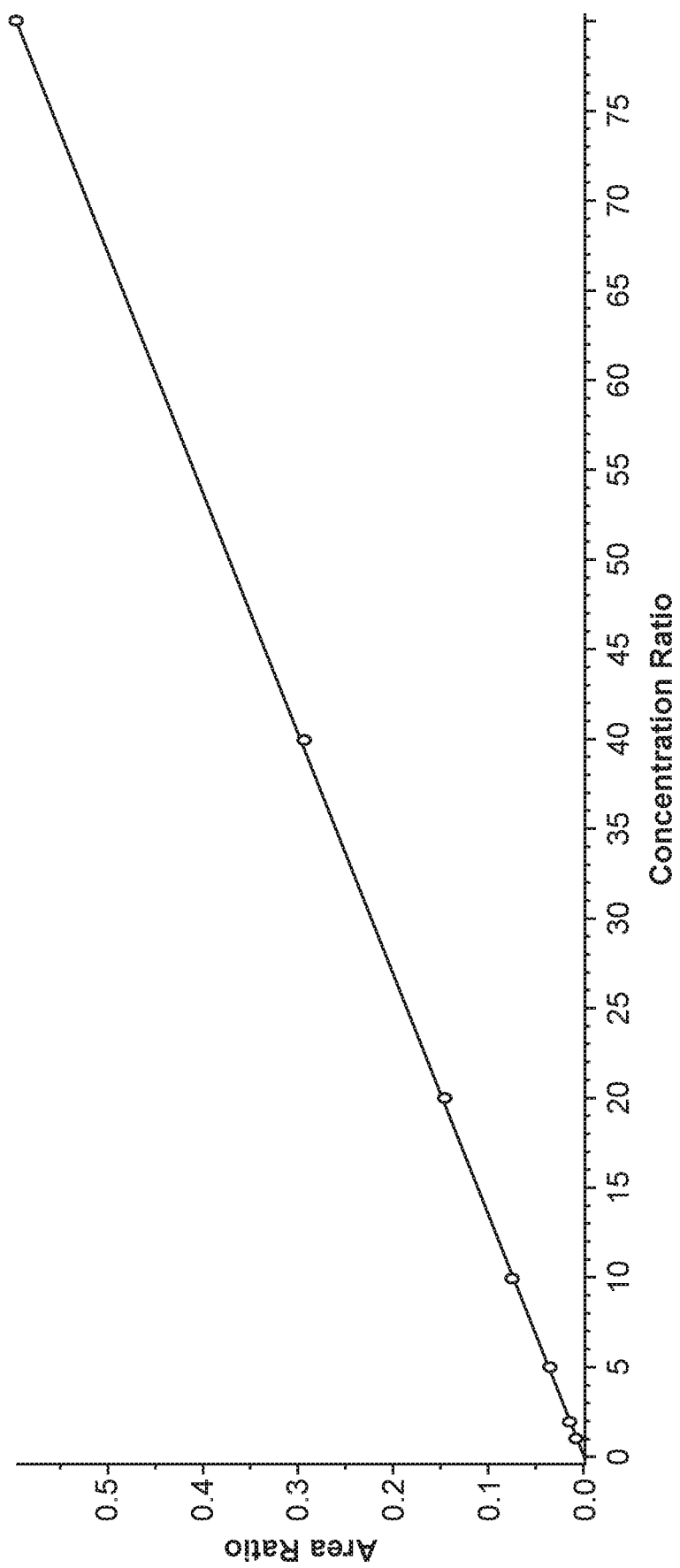
FIG. 8B shows a linear calibration curve resulting from the LC-MS/MS detection of FIG. 8A.

The DP2 fraction of oligosaccharide preparations was isolated by liquid chromatography. Samples were dissolved in water and separated using a Capcell Pak NH2 (Shiseido; 250×4.6 mm, 5 μm) column at a flowrate of 1 mL/min under isocratic conditions of water/acetonitrile 35/65. In some cases, following chromatographic separation, 50 μL 0.05% NH$_4$OH was added to enhance ionization. The anhydro DP2 content was determined by MS/MS detection. For MS detection ESI probe was used in negative mode and MRM method allowed targeted analysis. FIG. 8A illustrates detection an oligosaccharide preparation from Example 9 over a concentration range of 1-80 μg/mL in water, with a linear calibration curve (shown in FIG. 8B) from the area under the LC-MS/MS chromatogram to concentration.

FIGS. 33A-33C, 34A-34C, 35A-35C, and 36A-36C illustrate the presence of the anhydro DP2, anhydro DP1, and DP2 species detected by LC-MS/MS in an oligosaccharide preparation of Example 1, Example 3, Example 4, and Example 7, respectively.

Example 15

Preparation of Feed Comprising Oligosaccharide Preparations

Poultry and swine diets were prepared to demonstrate the incorporation of oligosaccharide preparations into the diet. Control feeds exhibiting a variety of ingredient compositions and corresponding treated feeds obtained by augmenting the respective control feeds with the oligosaccharide preparations of Example 9 were prepared as follows:

Example Feed 15.1: Control Feed 15.1 (CTR) was prepared using 62% corn meal and 32% soybean meal. Treated Feed 15.1 (TRT) was prepared by augmenting the control feed 15.1 (CTR) with 500 mg/kg of an oligosaccharide preparation from Example 9. For the treated diet, the oligosaccharide preparation was provided in a powder form by drying the oligosaccharide onto ground rice hulls as a carrier and adding the powder to the mixer using a micro-ingredient balance prior to pelleting.

Example Feed 15.2: Control Feed 15.2 (CTR) was prepared using 62% corn meal, 3% soybean concentrate, and 26% soybean meal. Treated Feed 15.2 (TRT) was prepared by augmenting the control feed 15.2 (CTR) with 500 mg/kg of an oligosaccharide preparation from Example 9. For the treated diet, the oligosaccharide preparation was provided in a powder form by drying the oligosaccharide onto ground rice hulls as a carrier and adding the powder to the mixer using a micro-ingredient balance prior to pelleting.

Example Feed 15.3: Control Feed 15.3 (CTR) was prepared using 52% corn meal, 6% corn starch, 5% soybean concentrate, 26% soybean meal, and a titanium oxide micro-tracer. Treated Feed 15.3 (TRT) was prepared by augmenting the control feed 15.3 (CTR) with 500 mg/kg of an oligosaccharide preparation. For the treated diet, the oligosaccharide preparation was provided in a powder form by drying the oligosaccharide onto ground rice hulls as a carrier and adding the powder to the mixer using a micro-ingredient balance prior to pelleting.

Example Feed 15.4: Control Feed 15.4 (CTR) was prepared using 55% corn meal and 39% soybean meal. Treated Feed 15.4 (TRT) was prepared by augmenting the control feed 15.4 (CTR) with 1,000 mg/kg of an oligosaccharide preparation. For the treated diet, the oligosaccharide preparation was provided in a powder form by drying the oligosaccharide onto ground rice hulls as a carrier and adding the powder to the mixer using a micro-ingredient balance prior to pelleting.

Example Feed 15.5: Control Feed 15.5 (CTR) was prepared using 62% corn meal, 3% soybean concentrate, and 26% soybean meal. Treated Feed 15.5 (TRT) was prepared by augmenting the control feed 15.5 (CTR) with 500 mg/kg of an oligosaccharide preparation from Example 9. For the treated diet, the oligosaccharide preparation was provided in a powder form and adding the powder to the mixer using a micro-ingredient balance prior to pelleting.

Example Feed 15.6: Control Feed 15.6 (CTR) was a commercial U.S. corn-soy starter poultry feed. Treated Feed 15.6 (TRT) was a commercial U.S. corn-soy starter poultry feed containing 500 ppm of an oligosaccharide preparation. For the treated diet, the oligosaccharide preparation was provided in a powder form and adding the powder to the mixer using a micro-ingredient balance prior to pelleting.

Example Feed 15.7: Control Feed 15.7 (CTR) was a research corn-soy poultry feed with the following diet composition: corn meal 62.39%, soybean meal 31.80%, calcium carbonate 0.15%, bicalcic-phosphate 2.2%, sodium chloride 0.15%, DL-Methionine 0.15%, L-Lysine 0.10%, Soya Oil 2.00%, vitamin-mineral premix 1.00%, and coccidiostat 0.06%. Treated Feed 15.7 (TRT) was obtained by supplementing the control feed 15.7 (CTR) with 1000 ppm of the oligosaccharide preparation of Example 9.1. For the treated diet, the oligosaccharide preparation was provided as 60% syrup in water and was applied by spraying the syrup onto the feed post pelleting.

Example Feed 15.8: Control Feed 15.8 (CTR) was a research corn-soy poultry feed with the following composition: wheat meal 48.45%, soybean meal 32.00%, rye 12%, calcium carbonate 0.20%, bicalcic phosphate 2.00%, sodium chloride 0.20%, DL-methionine 0.15%, soya oil 4.00%, vitamin-mineral premix 1.00%. Treated Feed 15.7 (TRT) was obtained by supplementing the control feed 15.7 (CTR) with 1000 ppm of the oligosaccharide preparation of Example 9.3. For the treated diet, the oligosaccharide preparation was provided as 60% syrup in water and was applied by spraying the syrup onto the feed post pelleting.

As would be understood by one skilled in the art, the 15.1-15.6 also contained industry standard levels of fat, vitamins, minerals, amino acids, other micronutrients and feed enzymes. In some cases the feeds contained a cocciodiostat, but were free in all cases of antibiotic growth promoters. The feeds were provided as either mash, pelletized, or crumbled diets, according to standard practices.

Example 16

Extraction of Feed Samples

Diets prepared according to the procedures of Example 15 were processed by extraction. Feed samples were ground with a mill. Five grams of the resulting milled feed were weighted into a 50 mL volumetric flask and hot water (approx. 80° C.) was added. After shaking, the mixture was incubated in an ultrasonic water bath at 80° C. for 30 minutes. After cooling, the solution was centrifuged for 20 min at 3000×g and the supernatant was filtered through a 1.2 μm filter followed by a 0.45 μm filter (and in some cases by a 0.22 μm filter). The resulting filtered solutions were evaporated to dryness with a rotary evaporator.

In some cases, the extraction was performed using 50 wt % ethanol in water as an alternative extraction solvent. In some cases, the filtration step was performed using a 5,000 Dalton molecular-weight cutoff membrane filter.

Example 17

Enzymatic Processing of Feed Extracts

The feed extracts of Example 16 were subjected to one or more enzymatic hydrolysis steps to digest oligosaccharides naturally present in the feed. A mixture of α-Amylase and amyloglycosidases were used to digest α(1,4) linkages of gluco-oligosaccharides and starch. Invertase and α-galactosidase were used to remove sucrose, raffinose, and other common fiber saccharides.

Enzyme solutions were prepared as follows: Amyloglucosidase (*A. niger*) 36000 U/g solution at 800 U/mL in ammonium acetate buffer (ammonium acetate 0.2 M pH 5 containing 0.5 mM MgCl2 and 200 mM CaCl2)), α-Amylase (Porcine Pancreas) 100000 U/g Megazyme: solution at 800 U/mL in ammonium acetate, Invertase from Backer's yeast (*S. cerevisiae*) 300 U/mg Sigma: solution at 600 U/mL in ammonium acetate buffer, α-Galactosidase from *A. niger* Megazyme 1000 U/mL.

The dry feed extracts of Example 16 were re-suspended in 10 mL ammonium acetate buffer. 50 μl of α-amylase (4 U/mL final), 50 μl of amyl glucosidase (4 U/mL final), 50 μl of invertase (3 U/mL final) were added. 20 μl α-galactosidase (2 U/mL final) was added optionally. The solution was incubated for 4 hours at 60° C. The digested extract was then filtered through an ultrafiltration filter (Vivaspin Turbo 4, 5000 MWCO, Sartorius) before being evaporated to dryness on a nitrogen evaporation system. In variations of the enzymatic digestion, one or more of the above enzymes were used in combinations and the digestion period was varied between 4 hours to overnight digestion. The enzyme concentrations were varied up to twice the above loadings, and the full enzymatic digestion procedure was repeated multiple times in sequence on the same feed.

TABLE 5

List of Feed Samples for Extraction and Digestion

| | Matrix | Extraction solvent | Filtration | Enzyme digestion |
|---|---|---|---|---|
| 1 | Blank feed | Water | 0.22 μM | — |
| 2 | Anhydro-Oligomers feed 1000 mg/kg | Water | 0.22 μM | — |
| 3 | Blank Feed | ethanol/water 50/50 | 0.22 μM | — |
| 4 | Anhydro-Oligomers feed 1000 mg/kg | ethanol/water 50/50 | 0.22 μM | — |
| 5 | Anhydro-Oligomers | Water | 0.22 μM | a + b (4 h 60° C.) |
| 6 | Blank feed | Water | 0.22 μM | a + b (4 h 60° C.) |
| 7 | Anhydro-Oligomers feed 1000 mg/kg | Water | 0.22 μM | a + b (4 h 60° C.) |
| 10 | Blank feed | ethanol/water 50/50 | 0.22 μM | — |
| 11 | Anhydro-Oligomers feed 1000 mg/kg | ethanol/water 50/50 | 0.22 μM | — |
| 12 | Anhydro-Oligomers feed 1000 mg/kg | Water | 0.45 μM | a + b (4 h 60° C.) |
| 13 | Anhydro-Oligomers feed 1000 mg/kg | Water | 0.22 μM | a + b (4 h 60° C.) |
| 14 | Blank starter feed A | Water | 0.45 μM | a + b (4 h 60° C.) |
| 15 | Anhydro-Oligomers starter feed B 2000 mg/kg | Water | 0.45 μM | a + b (4 h 60° C.) |
| 16 | Blank feed | Water | 0.45 μM | a + b + c (4 h 60° C.) |
| 17 | Anhydro-Oligomers feed 1000 mg/kg | Water | 0.45 μM | a + b + c (4 h 60° C.) |
| 18 | Rice spelt/Anhydro-Oligomers | Water | 0.45 μM | — |
| 19 | Rice spelt/Anhydro-Oligomers | ethanol/water 50/50 | 0.45 μM | — |
| 20 | Blank feed | Water | 0.45 μM | a + b + c (4 h 60° C.) |
| 21 | Anhydro-Oligomers feed 1000 mg/kg | Water | 0.45 μM | a + b + c (4 h 60° C.) |
| 22 | Grower feed C (blank) | Water | 0.45 μM | |
| 23 | Grower feed D (Anhydro-Oligomers 2000 mg/kg) | Water | 0.45 μM | |
| 24 | Pre starter feed A (blank) | Water | 0.45 μM | |
| 25 | Pre starter feed D (Anhydro-Oligomers 1000 mg/kg) | Water | 0.45 μM | |
| 26 | Grower feed C (blank) | Water | 0.45 μM | a + b + c + d (4 h 60° C.) |
| 27 | Grower feed D (Anhydro-Oligomers 2000 mg/kg) | Water | 0.45 μM | a + b + c + d (4 h 60° C.) |
| 28 | Pre starter feed A (blank) | Water | 0.45 μM | a + b + c + d (4 h 60° C.) |
| 29 | Pre starter feed D (Anhydro-Oligomers 1000 mg/kg) | Water | 0.45 μM | a + b + c + d (4 h 60° C.) |
| 30 | Maize | Water | 0.45 μM | — |
| 31 | Wheat | Water | 0.45 μM | — |
| 32 | Soy | Water | 0.45 μM | — |
| 33 | Maize | Water | 0.45 μM | a + b + c + d (4 h 60° C.) |
| 34 | Wheat | Water | 0.45 μM | a + b + c + d (4 h 60° C.) |
| 35 | Soy | Water | 0.45 μM | a + b + c + d (4 h 60° C.) |
| 41 | Blank Feed | Water | 0.45 μM | |
| 42 | Anhydro-Oligomers feed 1000 mg/kg | Water | 0.45 μM | |
| 43 | Blank feed | Water | ultra 5000 MWCO | a + b + c × 2 (overnight 60° C.) |
| 44 | Anhydro-Oligomers feed 1000 mg/kg | Water | ultra 5000 MWCO | a + b + c × 2 (overnight 60° C.) |

Anhydro-Oligomers refer to anhydro-subunit containing oligosaccharides.
Blank feeds refer to nutritional compositions without added anhydro-oligomers.
Enzyme a = Amyloglucosidase (*A. niger*) 36000 U/g Megazyme
Enzyme b = α-Amylase (Porcine Pancreas) 100000 U/g Megazyme
Enzyme c = Invertase from Baker's yeast (*S. cerevisiae*) 300 U/mg Sigma
Enzyme d = α-Galactosidase from *A. niger* 620 U/mg Megazyme Example 18

Detection of Oligosaccharide Preparations in Feed

The Control and Treated diets according to Example 15 were assayed to detect the absence or presence of oligosaccharide preparations. After diet manufacture, 1 kg samples were drawn from the final feed. The extractable solids content of the feed was obtained by water extraction using the procedure of Example 16. The resulting extracts were analyzed for the presence of anhydro-DP species by LC-MS/MS according to the procedure of Example 14.

Figure 9:
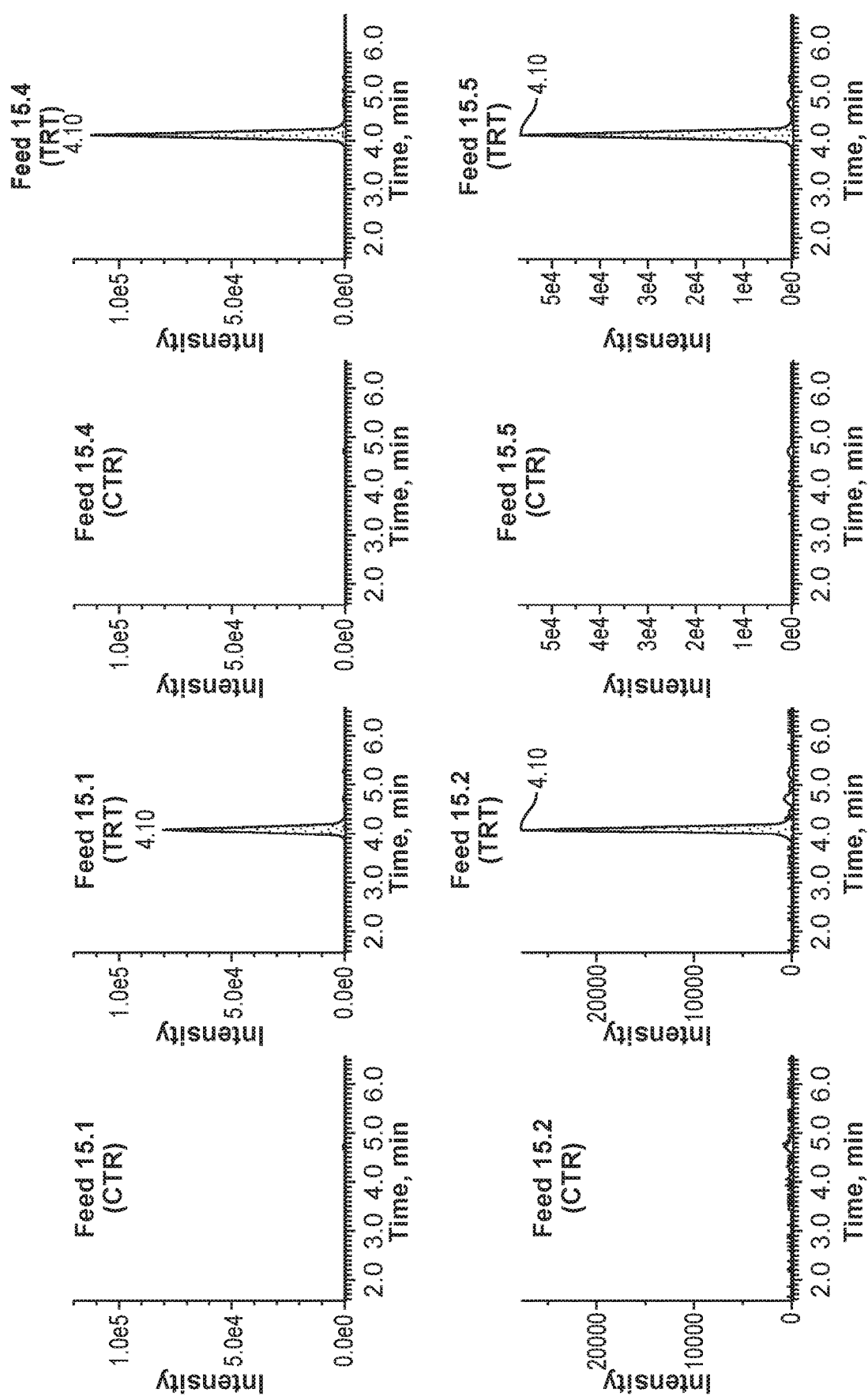
FIG. 9 illustrates the quantification of the anhydro-DP2 content of various control and treated diet compositions.
Figure 9:
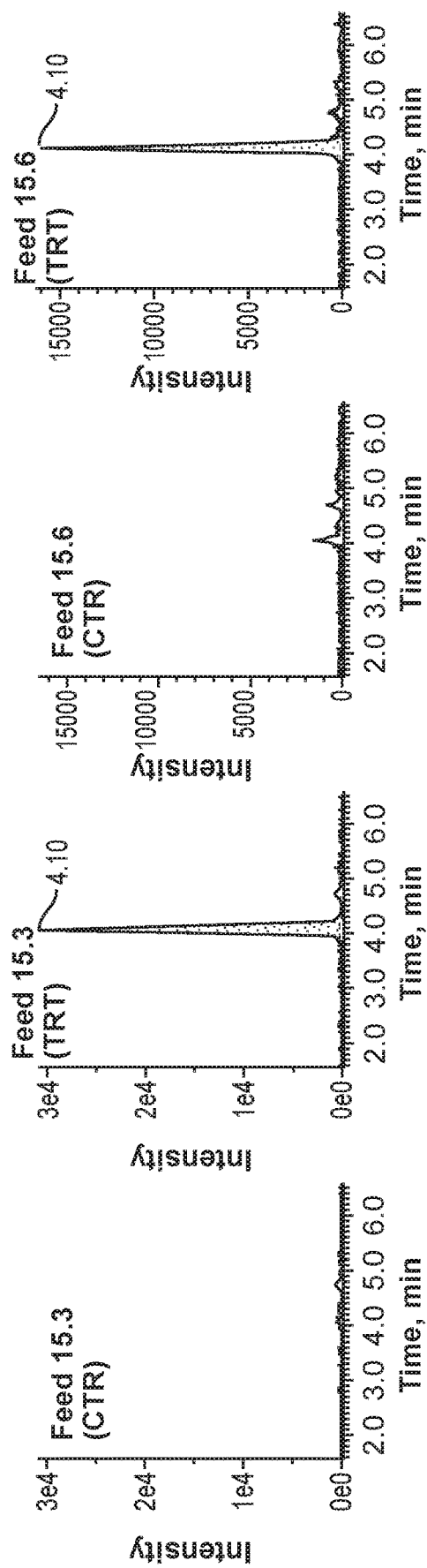

FIG. 9 shows the absence of anhydro-DP2 species in the control feeds of Examples 15.1(CTR)-15.6(CTR) versus the presence of anhydro-DP2 species in the treated feeds of Examples 15.1(TRT)-15.6(TRT). Integration of the resulting LC-MS/MS chromatograms was used to determine the presence of the oligosaccharide preparations of Example 9 in the final feed. Specifically, feeds were determined to contain the respective oligosaccharide preparation if the area under the anhydro-DP2 peak exceeded the limit of detection (or any other suitable threshold established in the method).

Example 19

Quantification of Oligosaccharide Preparations in Feed

The Control and Treated diets according to Example 15 were assayed to determine the concentration of oligosaccharide preparations in the final feed. After diet manufacture, 1 kg samples were drawn from the final feed. The extractable solids content of the feed was obtained by water extraction using the procedure of Example 16. The resulting extracts were analyzed for the presence of anhydro-DP species by LC-MS/MS according to the procedure of Example 14 and the area of the anhydro-DP2 peak was compared against a standard calibration curve to determine the concentration of the oligosaccharide preparation in the feed (Table 6).

TABLE 6

Concentration of Oligosaccharide Preparation in Feed

| Feed | Oligosaccharide Content (ppm) in Control Feed | Oligosaccharide Content (ppm) in Treated Feed |
| --- | --- | --- |
| Example 15.1 | Not detected | 1642 |
| Example 15.2 | Not detected | 953 |
| Example 15.3 | Not detected | 1912 |
| Example 15.4 | Not detected | 549 |
| Example 15.5 | Not detected | 406 |
| Example 15.6 | Trace | 401 |

Example 20

NMR Characterization of Anhydro-Subunit Containing Gluco-Oligosaccharides

Gluco-oligosaccharide preparations comprising anhydro-subunits were characterized by i) the degree of polymerization and ii) the glycosidic linkage distribution of the glucose units.

The relative molar abundances of $\alpha(1,1)\alpha$, $\alpha(1,1)\beta$, $\beta(1,1)\beta$, $\alpha(1,2)$, $\beta(1,2)$, $\alpha(1,3)$, $\beta(1,3)$, $\alpha(1,4)$, $\alpha(1,4)$, $\alpha(1,6)$, and $\alpha(1,6)$ linkages were identified by NMR spectroscopy. $^1$H NMR chemical shifts for the anomeric protons were determined as follows: the region d=4.5-5.5 ppm was considered, with the resonances of C-2 to C-6 covalently bound clustered at ~d 3.2 and 3.9 ppm. Due to coupling with the H-atom at C-2, the anomeric proton appears as a doublet and the axial position appears at higher field than the equatorial position. The sugar conformation was elucidated from the coupling constant of neighboring protons: equatorial-equatorial, equatorial-axial (small coupling constants) or axial-axial (larger coupling constants).

Elucidation of glycosidic linkages was also performed by $^{13}$C NMR. Primary, secondary, tertiary, and quaternary carbons were distinguished by proton off-resonance decoupling or polarization transfer. Carbons attached to methoxy groups resonate at a lower field than corresponding carbon atoms with free hydroxy groups and ring carbon atoms with axial hydroxy groups generally absorb at higher field than corresponding carbons with equatorial hydroxy groups. Thus, following these guidelines, and comparing with reported chemical shifts for both $^1$H and $^{13}$C of analogous sugars in literature most of the signals were assigned.

For the determination of the linkage distribution, J-RES and $^1$H, $^{13}$C-HSQC were used. For some samples, the HSQC method showed a superior performance. For each analysis, approximately 50 mg of freeze-dried product were dissolved in D2O and transferred to a 5 mm NMR tube. Any residual catalyst or solids were removed by filtration. NMR experiments were performed on a Bruker Avance III NMR spectrometer operating at 600 MHz proton corresponding to 150 MHz carbon Larmor frequency. The instrument was equipped with a cryogenically cooled 5 mm TCI probe. All experiments are carried out at 298 K. $^1$H NMR spectra were recorded and calibrated in deuterated water (4.75 ppm). $^{13}$C NMR spectra are calibrated with acetone (30.9 ppm). Data were acquired using TopSpin 3.5 and processed with ACD/Labs running on a personal computer.

Figure 10:
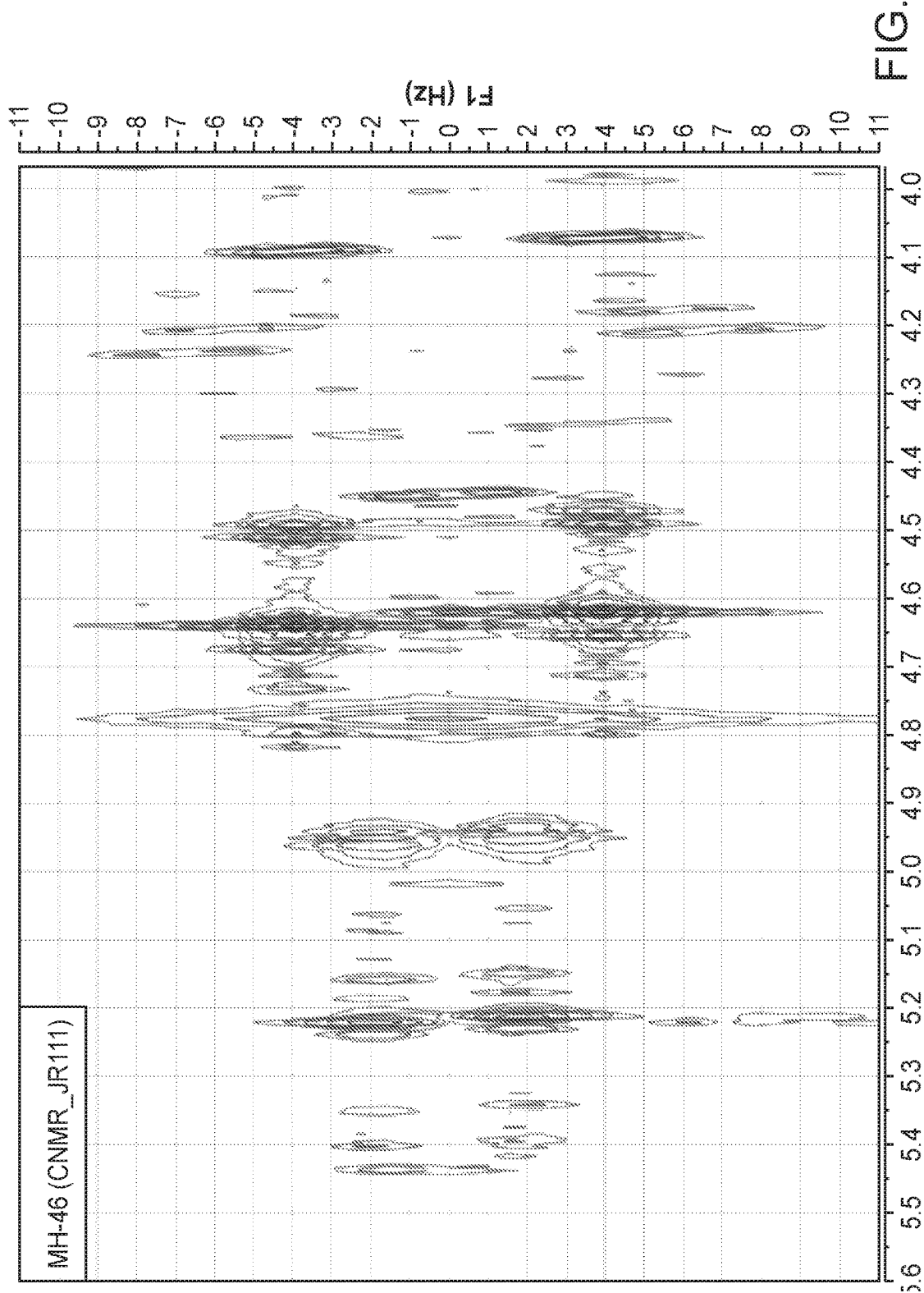
FIG. 10 illustrates a 2D-1H JRES NMR spectrum of an anhydro-subunit containing gluco-oligosaccharides sample.

FIG. 10 provides a representative 2D-1H JRES NMR spectrum of an anhydro-subunit containing gluco-oligosaccharide sample with solvent pre-saturation. Assignments of the different glycosidic linkages were made according to Table 7.

TABLE 7

Relative Molar Abundance for Glycosidic Linkages in an Anhydro-subunit Containing Gluco-oligosaccharides Sample (2D-1H JRES NMR Method)

| Linkage | Relative Molar Abundance Tested in Lab I | Relative Molar Abundance Tested in Lab II |
| --- | --- | --- |
| $\alpha(1, 2)$ | 10.1% | 9.2% |
| $\alpha(1, 4)$ | 2.0% | 17.0% |
| $\alpha(1, 3)$ | 4.5% | 1.3% |
| $\alpha(1, 6)$ | 28.9% | 33.6% |
| $\beta(1, 2)$ | 5.7% | 6.5% |
| $\beta(1, 3)$ | 13.3% | 6.3% |
| $\beta(1, 4)$ | 17.9% | 10.7% |
| $\beta(1, 6)$ | 18.9% | 14.5% |

As shown in Table 7, for some samples, discrepancies were observed between experiments performed by different labs using different instruments for the 2D-$^1$H JRES NMR analysis.

Figure 11:
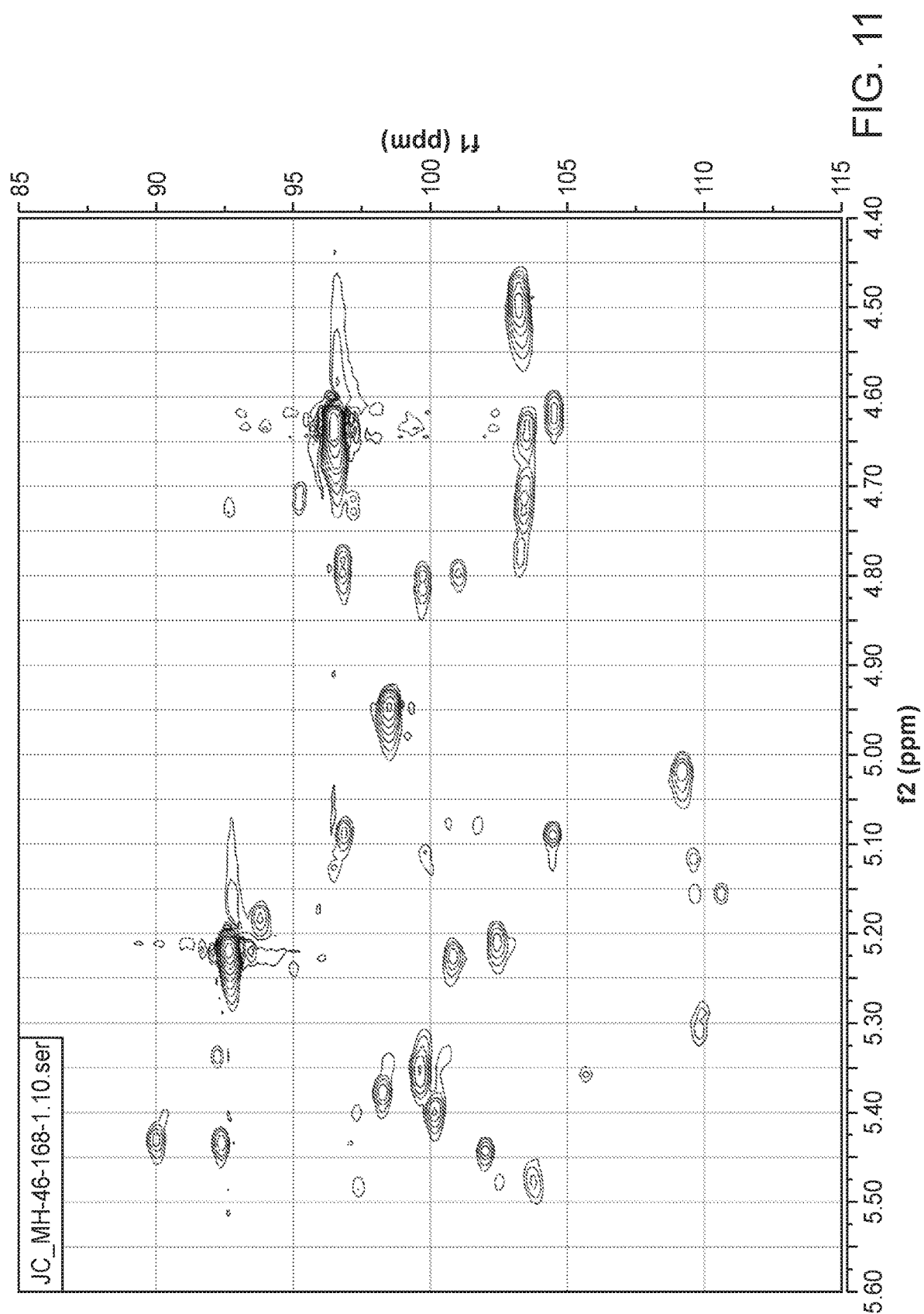
FIG. 11 is a representative $^1$H, $^{13}$C-HSQC NMR spectrum of an anhydro-subunit containing gluco-oligosaccharides sample with relevant resonances and assignments used for linkage distribution.

FIG. 11 provides a representative $^1$H, $^{13}$C-HSQC NMR spectrum of an anhydro-subunit containing gluco-oligosaccharides sample with relevant resonances and assignments used for linkage distribution. By contrast the determination by $^1$H, $^{13}$C-HSQC NMR was found to be consistent between two different labs and instruments, as shown in Table 8.

TABLE 8

Relative Molar Abundance for Glycosidic Linkages in Four Anhydro-subunit Containing Gluco-oligosaccharides Samples ($^1$H, $^{13}$C- HSQC NMR Method)

| Linkage | Sample 1 | | Sample 2 | | Sample 3 | | Sample 4 | |
|---|---|---|---|---|---|---|---|---|
|  | Lab I | Lab II | Lab I | Lab II | Lab I | Lab II | Lab I | Lab II |
| α(1, 2) | 9.2% | 9.2% | 9.0% | 9.5% | 9.1% | 9.9% | 9.1% | — |
| α(1, 4) | 1.4% | 1.3% | 1.2% | 1.3% | 1.3% | 1.3% | 0.0% | — |
| α(1, 3) | 17.7% | 17.0% | 17% | 17.7% | 17.5% | 16.7% | 21.9% | — |
| α(1, 6) | 33.9% | 33.6% | 33.6% | 30.9% | 36.0% | 31.6% | 34.4% | — |
| β(1, 2) | 5.7% | 6.5% | 5.7% | 7.6% | 5.2% | 7.6% | 5.2% | — |
| β(1, 3) | 4.1% | 6.3% | 4.2% | 6.2% | 4.4% | 6.1% | 5.6% | — |
| β(1, 4) | 8.5% | 10.7% | 8.9% | 10.7% | 7.6% | 10.7% | 8.3% | — |
| β(1, 6) | 12.3% | 14.5% | 12.6% | 11.6% | 11.7% | 11.6% | 11.0% | — |

Figure 12:
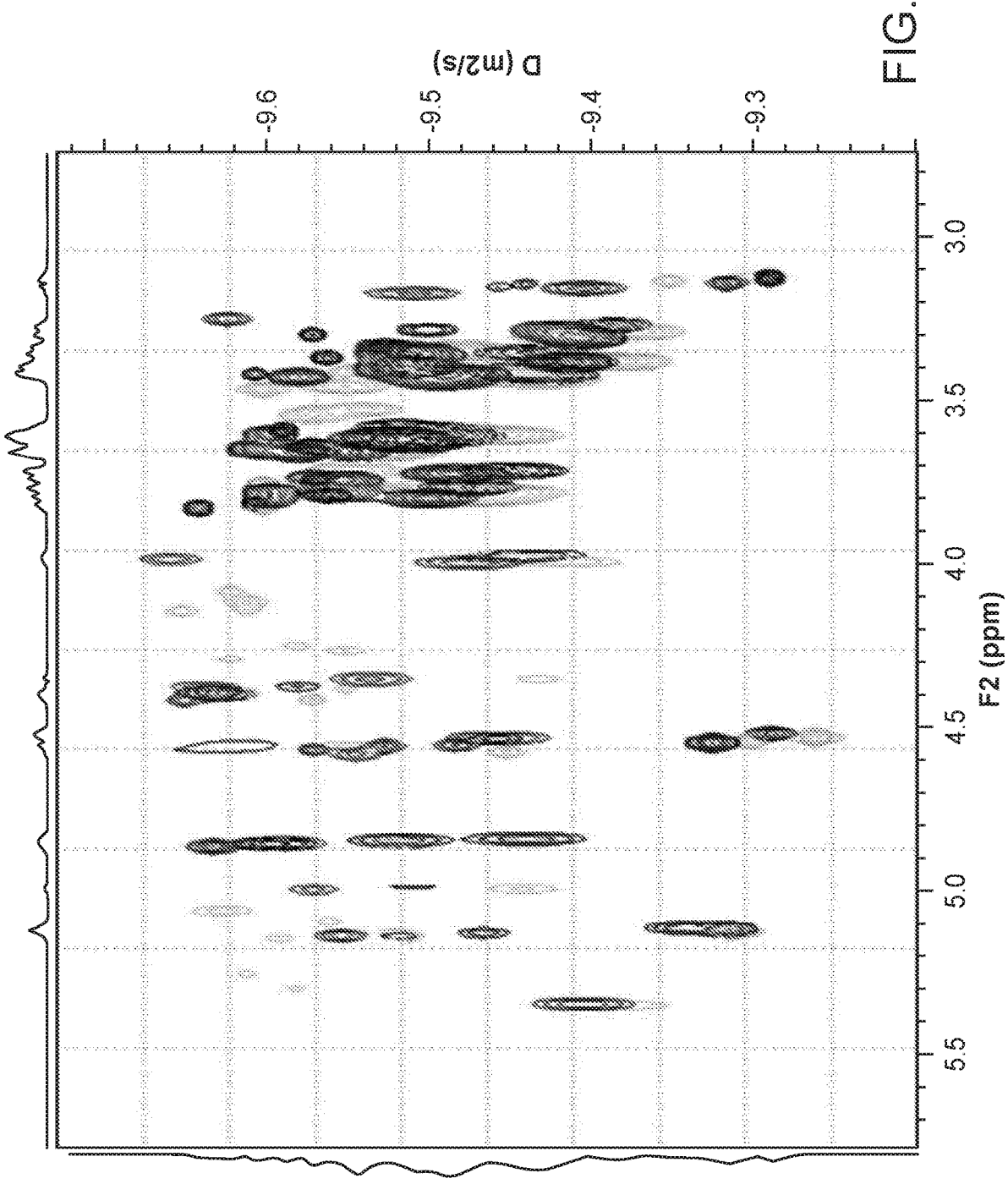
FIG. 12 illustrates an overlay of $^1$H DOSY spectra of three anhydro-subunit containing oligosaccharides.
Figure 13:
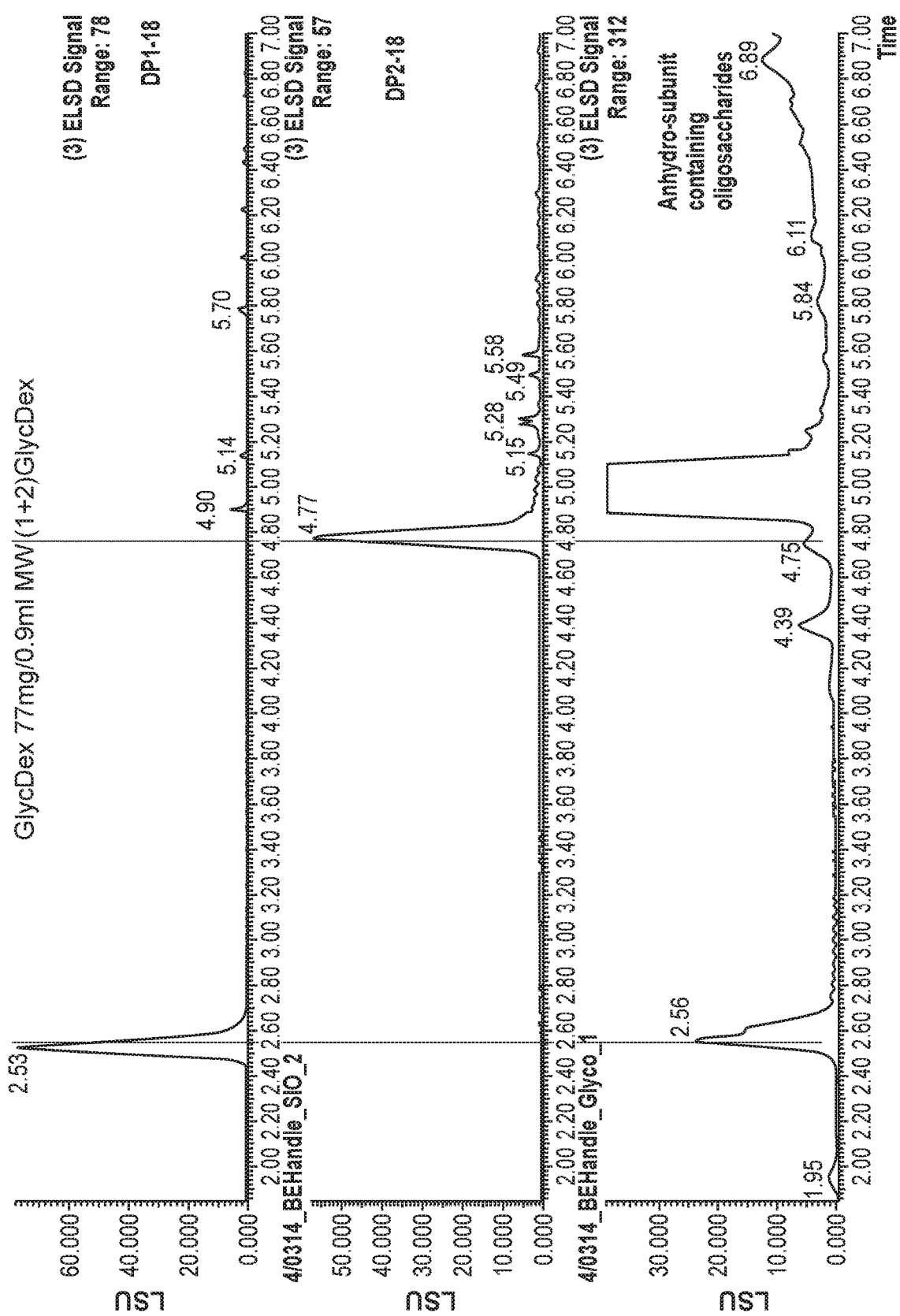
FIG. 13 illustrates a comparison of 1,6-Anhydro-ß-D-glucose (DP1-18), 1,6-Anhydro-ß-D-cellobiose (DP2-18), and an anhydro-subunit containing oligosaccharides sample.
Figure 14:
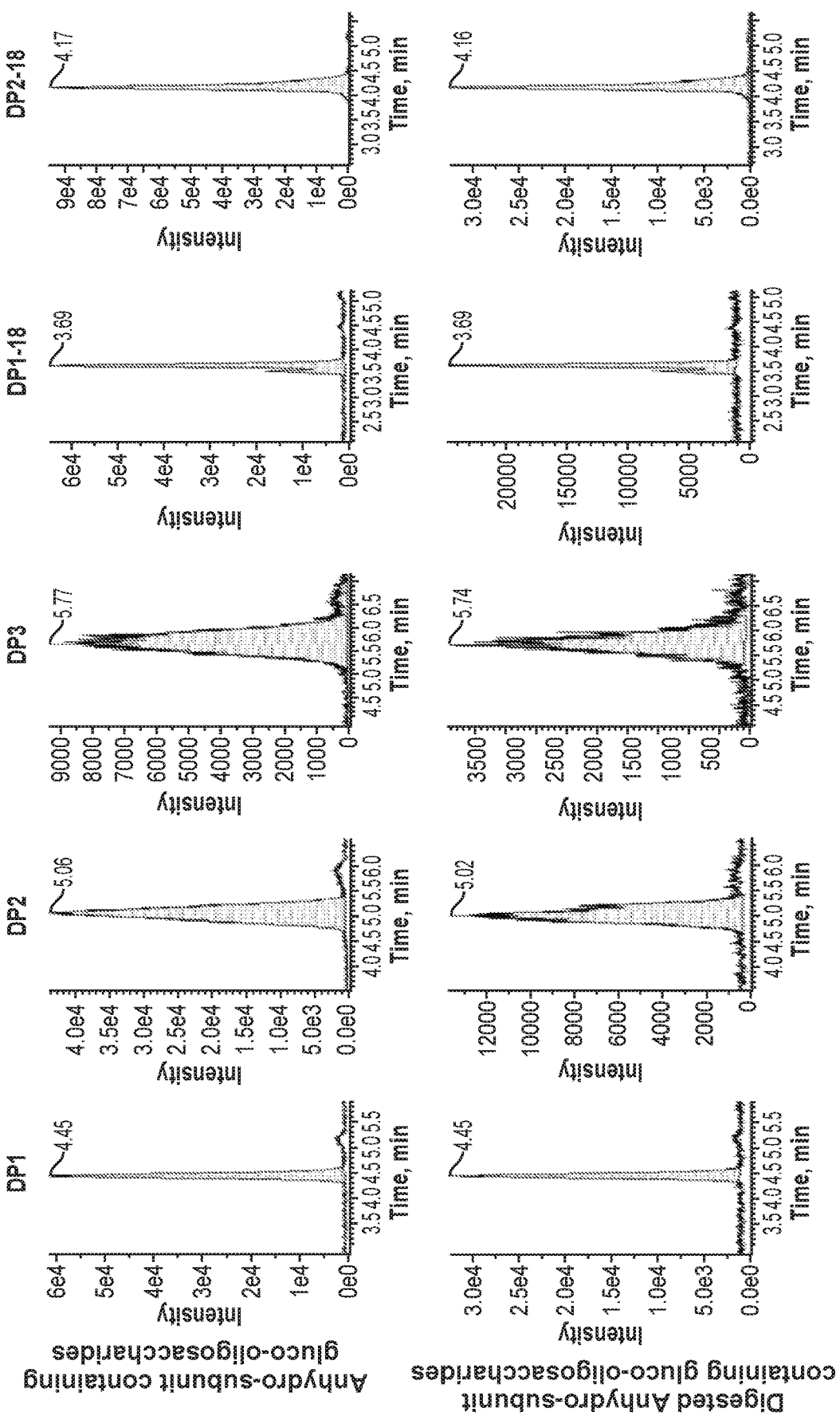
FIG. 14 illustrates mass chromatograms of anhydro-subunit containing oligosaccharides (top) and digested anhydro-subunit containing oligosaccharides (bottom) at selected multiple reaction monitoring (MRM).

Diffusion-Ordered NMR Spectroscopy (DOSY) was performed to separate the NMR signals of different species according to diffusion coefficient and thus MW. Signals at the upper part of the DOSY spectra in FIG. 12 correspond to high DP species, while lower DPs species appear below. FIG. 12 illustrates an overlay of $^1$H DOSY spectra of three anhydro-subunit containing oligosaccharides in Table 8.

Example 21

Semi-Preparative Isolation of DP1 & DP2 Fraction

Preparative isolation of the DP1 fraction was performed by preparative HPLC using a Waters BEH Amide 19×150 mm column. As mobile phase water was used as solvent A and Acetonitrile as solvent B, each with 0.1% ammonia. The applied gradient is shown in Table 9. The collected DP1 fraction of 8 separations were pooled, dried and resolubilized in 0.75 ml D$_2$O for NMR analysis as described before.

For the characterization of the DP2 fraction a 2-step purification was done. The first step was performed on a flash chromatography system, using an ELSD (Evaporative light scattering detector). 2 ml (2.65 g) of an oligosaccharide preparation were diluted with 1 ml DMSO, 0.5 ml water and 0.5 ml Acetonitrile. The solution was mixed and for 15 min sonicated. 1 ml of the solution was injected on a YMC DispoPackAT, NH2, spherical, 25 µm, 120 g column was used. The oligosaccharide preparation was separated running an isocratic gradient method with 75% Acetonitrile in water at 40 ml/min. The DP2 containing fraction was dried with nitrogen and resolubilized in DMSO/water (80:20, v/v).

For the 2$^{nd}$ purification step an analytical UPLC system with a YMC NH$_2$ 4.6×250 mm (5 µm) column at 40° was used. The DP2 fraction was purified with an isocratic gradient (Table 10) and a flow rate of 1 ml/min. A 1:5 post-column spilt was used in order to trigger the collection by ELSD. The DP2 fraction from 12 chromatographic runs were pooled, the Acetonitrile removed by heated nitrogen and the residual water by freeze-drying. The dry fraction was resolubilized for subsequent LC-MS/MS & NMR analysis.

TABLE 9

Gradient Method

| Time (min) | Flow rate (ml/min) | Solvent A | Solvent B |
|---|---|---|---|
| 0 | 25 | 10 | 90 |
| 2.5 | 25 | 10 | 90 |
| 23 | 25 | 25 | 75 |
| 23.1 | 25 | 10 | 90 |
| 47 | 25 | 10 | 90 |

TABLE 10

Isocratic Method

| Time (min) | Flow rate (ml/min) | Water (%) | ACN (%) |
|---|---|---|---|
| 0 | 1 | 25 | 75 |
| 15 | 1 | 25 | 75 |

Example 22

Synthesis of an Oligosaccharide Preparation with a Monotonically Decreasing DP Distribution 330 grams of D-glucose monohydrate and 0.3 grams of (+)-Camphor-10-sulfonic acid were added to a one-liter, three-neck flask with overhead mechanical mixing provided by high-torque mechanical mixer through a flex coupling. The flask was secured inside a hemispherical electric heating mantle operated by a temperature control unit via a wand thermocouple inserted into the reaction mixture. The tip of the thermocouple was adjusted to reside within the reaction mixture with several mm clearance above the mixing element. The flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. When the reaction temperature was increased to between 120° C. and 130° C., the apparatus was switched from a reflux condenser to a distillation configuration with a round bottom receiving flask placed in an ice bath. The reaction was maintained at 130° C. with 120 RPM mixing for sixty minutes and the mass of condensate collected in the receiving flask was recorded as a function time at 10 minute intervals. The reaction was quenched by adding distilled water and removing the heat. After the product mixture cooled to room temperature, an aliquot of the product syrup was diluted to about 1 Brix as determined by refractive index. The diluted aliquot was microfiltered using a 0.2 micron syringe filter and analyzed by HPLC size exclusion chromatography (SEC). SEC analysis was performed on an Agilent 1100 series HPLC with refractive index detection using an Agilent PL aquagel-OH 20 column at 40° C. with distilled water at 0.45 mL/min as the mobile phase. Retention-time to MW calibration was performed using standard solutions with known molecular weight. The DP equilibrium constant was determined to be K=3.3 and the DP distribution was found to be monotonically decreasing. FIG. 15 and FIG. 16 show the shape of the DP distribution of different oligosaccharide preparations of Example 9 as determined by HPLC-SEC.

Example 23

Synthesis of an Oligosaccharide Preparation with a Non-Monotonic DP Distribution 330 grams of D-glucose monohydrate and 0.3 grams of (+)-Camphor-10-sulfonic acid were added to a one-liter, three-neck flask with overhead mechanical mixing provided by high-torque mechanical mixer through a flex coupling. The flask was secured inside a hemispherical electric heating mantle operated by a temperature control unit via a wand thermocouple inserted into the reaction mixture. The tip of the thermocouple was adjusted to reside within the reaction mixture with several mm clearance above the mixing element. The flask was equipped with a reflux condenser cooled by a water-glycol mixture maintained below 4° C. by a recirculating bath chiller.

The reaction mixture was gradually heated to 135° C. with continuous mixing with a stir rate of 80-100 rpm. When the reaction temperature was increased to 130° C., the apparatus was switched from a reflux condenser to a distillation configuration with a round bottom receiving flask placed in an ice bath. The reaction was maintained at 135° C. with 120 RPM mixing for thirty-five minutes. The reaction was quenched by adding distilled water and removing the heat. After the product mixture cooled to room temperature, an aliquot of the product syrup was diluted to about 1 Brix as determined by refractive index. The diluted aliquot was microfiltered using a 0.2 micron syringe filter and analyzed by HPLC size exclusion chromatography (SEC). SEC analysis was performed on an Agilent 1100 series HPLC with refractive index detection using an Agilent PL aquagel-OH 20 column at 40° C. with distilled water at 0.45 mL/min as the mobile phase. Retention-time to MW calibration was performed using standard solutions with known molecular weight. The DP distribution was found to be non-monotonically decreasing. FIG. 16 illustrates that the DP3 content is greater than the DP2 content and that the DP4 and DP5 contents are essentially equal.

Example 24

Fed-Batch Synthesis of an Oligosaccharide Preparation 330 grams of D-glucose monohydrate and 0.3 grams of 2-Pyridinesulfonic acid were added to a one-liter, three-neck flask with overhead mechanical mixing provided by high-torque mechanical mixer through a flex coupling. The flask was secured inside a hemispherical electric heating mantle operated by a temperature control unit via a wand thermocouple inserted into the reaction mixture. The tip of the thermocouple was adjusted to reside within the reaction mixture with several mm clearance above the mixing element. The flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. When the reaction temperature was increased to between 120° C. and 130° C., the apparatus was switched from a reflux condenser to a distillation configuration with a round bottom receiving flask placed in an ice bath. The reaction was maintained at 130° C. with 120 RPM and the mass of condensate collected in the receiving flask was recorded as a function time at 20 minute intervals. After 210 minutes, an additional 110 grams of D-glucose monohydrate were added to the reaction. After 420 minutes, the reaction was quenched by adding distilled water and removing the heat. After the product mixture cooled to room temperature, an aliquot of the product syrup was diluted to about 1 Brix as determined by refractive index. The diluted aliquot was microfiltered using a 0.2 micron syringe filter and analyzed by HPLC size exclusion chromatography (SEC). SEC analysis was performed on an Agilent 1100 series HPLC with refractive index detection using an Agilent PL aquagel-OH 20 column at 40° C. with distilled water at 0.45 mL/min as the mobile phase. Retention-time to MW calibration was performed using standard solutions with known molecular weight. The DP equilibrium constant was determined to be K=0.8 and the DP distribution was found to be monotonically decreasing.

Example 25

Growth Performance of Commercial Broiler Chickens Fed an Oligosaccharide Preparation Broiler chickens were grown on the diets of Example 15.6 to determine the effect of the oligosaccharide preparation on the growth performance of the animals. Specifically, commercial corn-soymeal poultry feeds containing dried distillers grains with solubles (DDGS), a coccidiostat, and a standard micronutrient blend, were manufactured according to industry practices and a three phase feeding program. By proximate analysis, the feed compositions were determined as shown in Table 11.

TABLE 11

| | Feed Compositions | | | |
|---|---|---|---|---|
| Component | Starter | Grower | Withdrawal | Method |
| Moisture | 13.0% | 13.0% | 12.9% | AOAC 930.15 (drafted oven) |
| Crude Protein (CP) | 24.1% | 21.5% | 19.6% | AOAC 992.15; AOAC 990.03 |
| Fat (EE) | 3.2% | 3.8% | 3.9% | AOAC 920.39 (ether extraction) |
| Crude Fiber (CF) | 2.7% | 2.4% | 2.4% | AOAC 962.09 (hydrolysis) |
| Ash (AR) | 5.2% | 4.3% | 4.3% | AOAC 942.05 (muffle furnace) |
| NFE, by difference | 51.9% | 55.1% | 56.9% | Calculated: 1-CP-EE-CF-AR |
| Total | 100.0% | 100.0% | 100.0% | |

Control (CTR) and treated (TRT) diets were prepared for each phase as described in Example 15.6, where the treat diets were prepared by augmenting the control diet with one pound per treated short ton using the oligosaccharide preparation of Example 9.7. In total, about 50 short tons of each diet were manufactured.

Day-of-hatch Hubbard M99×Cobb 500 straight run chicks were obtained from a commercial poultry hatchery and placed randomly into 36 ft×40 ft pens constructed into a tunnel-ventilated, dirt-floor poultry house. Approximately 30,000 birds were placed in total, with an equal number of birds in each pen. The house bedding consisted of built-up litter top-dressed with fresh wood shavings. A standard commercial environmental and lighting program were employed. Animals and housing facilities were inspected daily, including recording the general health status, feed consumption, water supply and temperature of the facility. Any mortalities were recorded daily.

Birds in odd numbered pens were fed the treated diet (i.e., containing the feed additive at 2 lbs/ton inclusion), and birds in the even numbered pens received the control diet. All diets were provided ad libitum via automatic feeders in each pen, and on feeder trays from day one until day 7. Water was provided ad libitum from a nipple drinking line.

The starter phase took place from day 0 to day 13, the grower phase from day 14 to day 27, and the withdrawal phase from day 28 through the end of the study, day 31. Bird weights by pen were recorded on days 0 and 31. The total mass of consumed feed was recorded for each pen. Weight gain and FCR were then determined for each pen according to standard industry practices.

On day 31, six male birds were randomly selected from each pen for blood and cecal sampling. The live weight of each sampled bird was recorded. A blood sample was collected via wing puncture into vacutainer tubes and frozen following coagulation and serum separation. Each sampled bird was then euthanized via cervical dislocation followed by extraction of the ceca using standard veterinary methods. Following dissection, cecal contents were transferred to 15 mL conical tubes, the weight of the cecal contents was recorded, and the contents were flash frozen to −80° C.

From the weights of the sampled birds, the treatment group exhibited an 11 point increase in body weight, significant at $P<0.05$ (by ANOVA).

Example 26

Shotgun Sequencing of Poultry Cecal Microbiota

The relative abundances of identified taxa were determined for a total of 96 sampled birds obtained from the study of Example 25. For each microbiota sample obtained in Example 25, the cecal contents were thawed and DNA was extracted using standard methods. The extracted DNA was analyzed on an Illumina HiSeq-X instrument, with 2×150 bp reads. Standard analyses were performed to process the raw sequencing data, including: trimming (adapter, BBDuk), Entropy filtering (k=5, window=20, min=50, BBDuk), Quality filtering (mean Q20, BBDuk), Gallus filtering (Bowtie2). Taxonomic assignments were made against the MetaPhlAn2 (db_v20) database.

Example 27

Microbial Conversion of Undigested Feed and Oligosaccharide Preparations

The effect of oligosaccharide preparations on the profile of metabolites produced by microbial fermentation of undigested feed was assessed ex vivo in poultry cecal microbiota obtained from the sampled birds of Example 25.

Aliquots of the oligosaccharide preparations to be tested were diluted to 20 wt % oligosaccharide in water, microfiltered through a 0.22 micron PES syringe filter, and degassed under anaerobic conditions. A poultry feed digest (simulated cecal digesta) was prepared and simultaneously sterilized by suspending a 10 g sample of a commercial corn-soy broiler feed in 50 mL of water and then subjecting it to two cycles of autoclaving at 120° C. for 5 minutes followed by aqueous extraction and resuspension. The resulting feed digest was degassed under anaerobic conditions.

The extracted cecal samples were thawed under anaerobic conditions and used to prepare a 20% w/v suspension in pH 7.4 phosphate buffered saline (PBS) containing 15% glycerol. The resulting cecal slurry was analyzed to confirm that its phylogenetic composition closely represented that of the originally sampled microbiota (sequenced in Example 24). The cecal slurry was assessed by 16S rRNA analysis (16Sv4 PCR/Illumina MiSeq sequencing at 2s250 bp) according to a standard 16S rRNA pipeline (USEARCH and SILVA(v4) DB) with a rarefaction cutoff of 12,230 reads per sample. By phylum abundance, the cecal slurry was determined to comprise approximately 70% Firmicutes, 20% Bacteroidetes, 7% Tenericutes, and the remainder as Proteobacteria, Cyanobacteria, Actinobacteria and Verrucomicrobia.

Working under anaerobic conditions, an aliquot of the suspension was centrifuged at 2,000×g, the supernatant was removed by pipette, and the pellet was resuspended to form a 1% w/v cecal slurry in a minimal growth medium consisting of a sterile aqueous mixture of: 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline.

For each oligosaccharide preparation in Example 9, a 25 uL aliquot of the 20 wt % oligosaccharide solution, a 225 uL aliquot of the feed digest and 250 uL of the 1% cecal slurry were loaded in triplicate into the wells of a 96-well deep-well microtiter plate (e.g., Costar 3958 plates). Each plate contained a set of blank wells, prepared by combining 25 uL of water, 225 uL feed digest, and 250 uL of the 1% cecal slurry. The loaded plate was then incubated at 37° C. for 45 hours under anaerobic conditions. Following incubation, the contents of the wells were removed to 1.5 mL Eppendorf tubes, micro-centrifuged at 2000×g for a minimum of 5 minutes, and the resulting supernatants were collected Example 28

Stimulation of Goblet Cell Proliferation by Oligosaccharide Preparations

Goblet cell proliferation in the presence of oligosaccharide preparations from Example 9 was evaluated in vitro. Wells in a 96-well Falcon plate were seeded with 200 uL of growth medium and 40,000 goblet cells and growth for three days. Oligosaccharide preparations from Example 9 were tested in replicate (n=6 wells per oligo) at a concentration of 0.1 mg/mL versus a control (growth medium only). Cells were differentiated for four days, with a full change of the growth media after two days. Plates were then washed with phosphate buffered saline (PBS) and fixed by treating the cells with 4% paraformaldehyde (Cellomics #28906, diluted 1:4 with PBS) for 30 minutes. Plates were then washed twice with PBS and stained with Alcian Blue (Abcam ab150662 pH 2.5) mucin stain. Staining was performed by incubating cells in acetic acid solution for 3 minutes, followed by incubating cells in Alcian Blue solution for 30 minutes at room temperature, and then washing for 2 minutes with water and two final rinses with distilled water.

Nuclei were quantified by Hoechst staining and automated microscopy (10× objective, 49 fields) with a field size of 641×641 microns. At 0.1 mg/mL, the various oligosaccharide preparations produced between about a 1% to about a 5% increase in goblet cell proliferation (Table 12).

TABLE 12

Goblet Cell Count

| Oligosaccharide Preparation | Cell count increase vs control | P-Value | |
|---|---|---|---|
| Ex. 9.1 | 3.2% | 0.003 | *** |
| Ex. 9.3 | 2.3% | 0.007 | *** |
| Ex. 9.4 | 3.1% | 0.002 | *** |
| Ex. 9.5 | 3.6% | 0.001 | *** |
| Ex. 9.6 | 2.7% | 0.007 | *** |
| Ex. 9.7 | 1.2% | 0.115 | |
| Ex. 9.16 | 3.5% | 0.001 | *** |
| Ex. 9.17 | 4.9% | 0.001 | *** |

Example 29

Stimulation of Mucus Production by Oligosaccharide Preparations

The effect of oligosaccharide preparations on mucus production by goblet cells was evaluated in vitro. Wells in a 96-well Falcon plate were seeded with 200 uL of growth medium and 40,000 goblet cells and grown for three days. Oligosaccharide preparations were tested in replicate (n=6 wells per oligo) by augmenting the cell growth medium with the supernatants obtained by ex vivo fermentation of the oligosaccharide preparations in Example 27. For each oligosaccharide preparation, the corresponding supernatant from Example 27 was diluted 1:20 with culture medium and microfiltered. The control was given by a 1:20 dilution of the fermentation medium. Cells were differentiated for four days, with a full change of the growth media after two days. Plates were then washed with phosphate buffered saline (PBS) and fixed by treating with 4% paraformaldehyde (Cellomics #28906, diluted 1:4 with PBS) for 30 minutes. Plates were then washed twice with PBS and stained with Alcian Blue (Abcam ab150662 pH 2.5) mucin stain. Staining was performed by incubating cells in acetic acid solution for 3 minutes, followed by incubating cells in Alcian Blue solution for 30 minutes at room temperature, and then washing for 2 minutes with water and two final rinses with distilled water. Nuclei were quantified by Hoechst staining and automated microscopy (10× objective, 49 fields) with a field size of 641×641 microns.

Mucin production was quantified by absorbance at 600 nm on a Spectramax plate reader. To account for differences in cell counts between wells, absorbance was normalized to OD600 per 100,000 cells. A clear and statistically significant effect on goblet cell mucus production was observed as shown in Table 13.

TABLE 13

Mucus Production

| Oligosaccharide Preparation | Increase in Mucus Production | SEM | P-Value | |
|---|---|---|---|---|
| Ex. 9.2 | 7.9% | 0.2% | 7.21E−05 | *** |
| Ex. 9.1 | 11.1% | 0.4% | 2.4E−05 | *** |
| Ex. 9.6 | 9.1% | 0.3% | 0.00013 | *** |
| Ex. 9.4 | −0.8% | 0.0% | 0.561442 | |
| Ex. 9.7 | 9.7% | 0.4% | 0.000192 | *** |
| Ex. 9.17 | 9.0% | 0.4% | 0.00112 | *** |
| Ex. 9.5 | 9.1% | 0.3% | 2.34E−05 | *** |
| Ex. 9.3 | −4.1% | 0.1% | 0.002309 | *** |

Example 30

Stimulation of Healthy Gut Barrier Integrity

Figure 18:
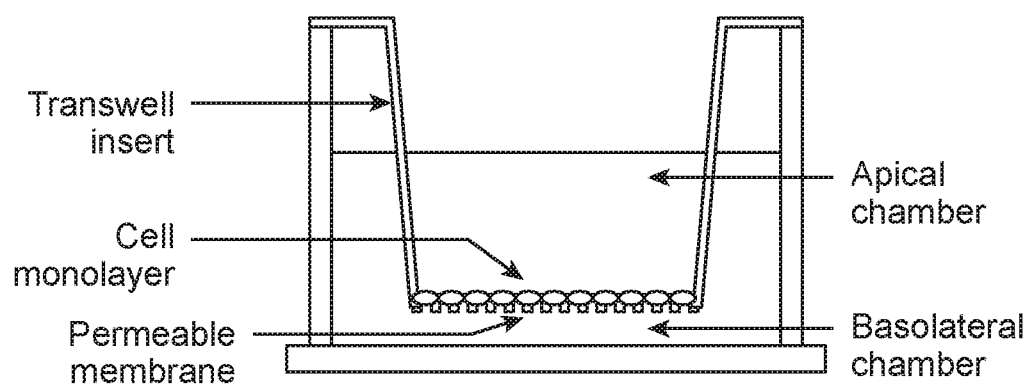
FIG. 18 shows a graphical depiction of an apparatus used for the evaluation of healthy gut barrier integrity.

The effect of oligosaccharide preparations on healthy gut barrier function was evaluated in vitro. Caco-2 cells were co-cultured with goblet cells on a semipermeable membrane, differentiated, and then treated with the microbiome supernatants of Example 27 obtained using the sampled cecal microbiota of Example 25. The change in the trans-endothelial electrical resistance (TEER) was measured relative to control. Specifically, Caco-2 and goblet cells were seeded on a semipermeable insert and placed into a chamber containing a suitable growth medium as illustrated in FIG. 18. Cells were grown for 13 days to achieve a differentiated monolayer exhibiting tight junctions, confirmed by performing a baseline TEER measurement.

Multiple oligosaccharide preparations of Example 9 were analyzed with n=6 replicates. For each oligosaccharide preparation, the corresponding supernatant from Example 27 was diluted 1:20 with growth medium, microfiltered through a 0.2 micron filter, and applied to the apical side of the chamber. The control was provided by applying a 1:20 dilution of the growth medium. After 24 hours, the a TEER measurement was performed for each oligosaccharide preparation. For each, the change in TEER after treatment versus before treatment was determined. The change in TEER for the control was normalized to 100%.

Statistically significant improvements in the healthy gut barrier function as measured by TEER were observed for certain oligosaccharide preparations. The improvement in TEER for the various oligosaccharide preparations varied from about 0% to about 15%, relative to the control. In particular, the oligosaccharide preparation of Example 9.2 provided a 14% increase in TEER relative to the control. The results are shown in Table 14.

TABLE 14

Increase in TEER vs Control for Synthetic Oligosaccharide Preparations

| Oligosaccharide Preparation | Increase in TEER vs Control |
|---|---|
| Ex. 9.1 | 8% ± 2% |
| Ex. 9.2 | 14% ± 1% |
| Ex. 9.3 | 2% ± 1% |
| Ex. 9.4 | 9% ± 2% |
| Ex. 9.6 | 15% ± 1% |
| Ex. 9.7 | 2% ± 1% |

Example 31

Stimulation of Non-Specific Immune Function

The effect of oligosaccharide preparations on non-specific phagocytosis was determined in vitro. Piglet granulocytes were analyzed by flow cytometry for ingestion of opsonized E. coli cells in the presence of the oligosaccharide preparation of Ex. 9.3 at two difference concentrations, 1 mg/mL and 2 mg/mL. The number of granulocytes with ingested pathogens was compared to the number of granulocytes that did not ingest the pathogen to determine the phagocytosis index.

Figure 19:
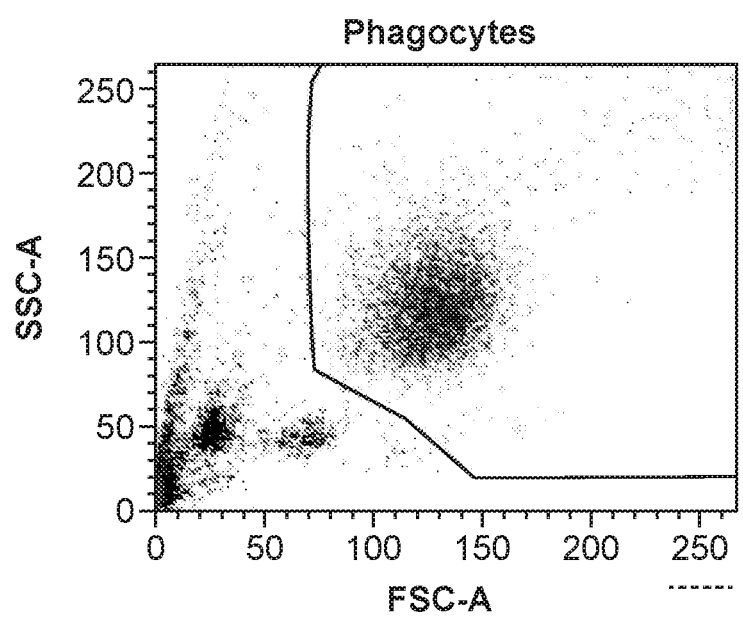
FIG. 19 is a flow cytogram showing granulocytes with and without ingested pathogens.

In the presence of 1 mg/mL of the oligosaccharide preparation Ex. 9.3, the phagocytosis index was determined to be 82, while at a concentration of 2 mg/mL the phagocytosis index was determined to be 106, reflecting a 29% increase in the ingestion of the pathogen. FIG. 19 provides an exemplary flow cytogram illustrating identification of granulocytes with and without ingested pathogens.

The effect of oligosaccharide preparations on immune and inflammatory response was determined in vivo for broiler chickens subjected to common pathogens.

The birds were fed in treatment groups using two background diet types as described in Table 15. Diets comprising oligosaccharide preparations were provided in the Treatment Groups described in Table 16.

TABLE 15

Background Diet Types

| Ingredient | Type 1 (wt %) | Type 2 (wt %) |
|---|---|---|
| Corn | 62.39 | — |
| Soybean Meal | 31.80 | 32.00 |
| Wheat | — | 48.45 |
| Rye | — | 12 |
| Calcium carbonate | 0.15 | 0.20 |
| Bicalcic phosphate | 2.2 | 2.00 |
| NaCl | 0.15 | 0.20 |
| DL-Methionine | 0.15 | 0.15 |
| L-Lysine | 0.10 | — |
| Soya Oil | 2.00 | 4.00 |
| Vitamin and Mineral Premix | 1.00 | 1.00 |
| Coccidiostat | 0.06 | — |

TABLE 16

Treatment Groups

| Treatment Group | Background Diet | Oligosaccharide Preparation | Dose (ppm) |
|---|---|---|---|
| Control 1 | Type 1 | None | |
| Control 2 | Type 2 | None | |
| Treatment 1 | Type 2 | Example 9.17 | 1.000 |
| Treatment 2 | Type 2 | Example 9.6 | 1.000 |
| Treatment 3 | Type 2 | Example 9.1 | 1.000 |
| Treatment 4 | Type 2 | Example 9.4 | 1.000 |
| Treatment 5 | Type 2 | Example 9.8 | 1.000 |
| Treatment 6 | Type 2 | Example 9.3 | 1.000 |

Day-old male Cobb 500 broiler chickens were supplied by a commercial hatchery. On the day of arrival (day −8), the chickens were placed in groups of 50 for a run-in period of 8 days. During the run-in period, animals were fed with the control diet. On day 0, the animals were divided by weight into groups of 8 birds each and a 10× dose of Paracox-5 (MSD Animal Health) attenuated oral coccidiosis vaccine (mixture of E. acervulina, E. maxima, E. mitis and E. tenella) was administrated by individual gavage to all birds on Diet Type 2. Each group was then placed into a battery cage and allocated randomly into the treatment groups, each with two replications per group.

The animals were housed in an environmentally controlled room with the temperature adapted to the age of the birds. Water and all diets were provided ad libitum. On days 7 and 14, birds from each replication were selected at random and euthanized. The sampled birds were immediately dissected. Standard practices were used to obtain samples of ileal digesta, cecal digesta, ileal tissue, and Peyer patch tissue. The tissue samples were analyzed by PCR array for gene expression corresponding to inflammation and immune system cytokines and chemokines.

Figure 20:
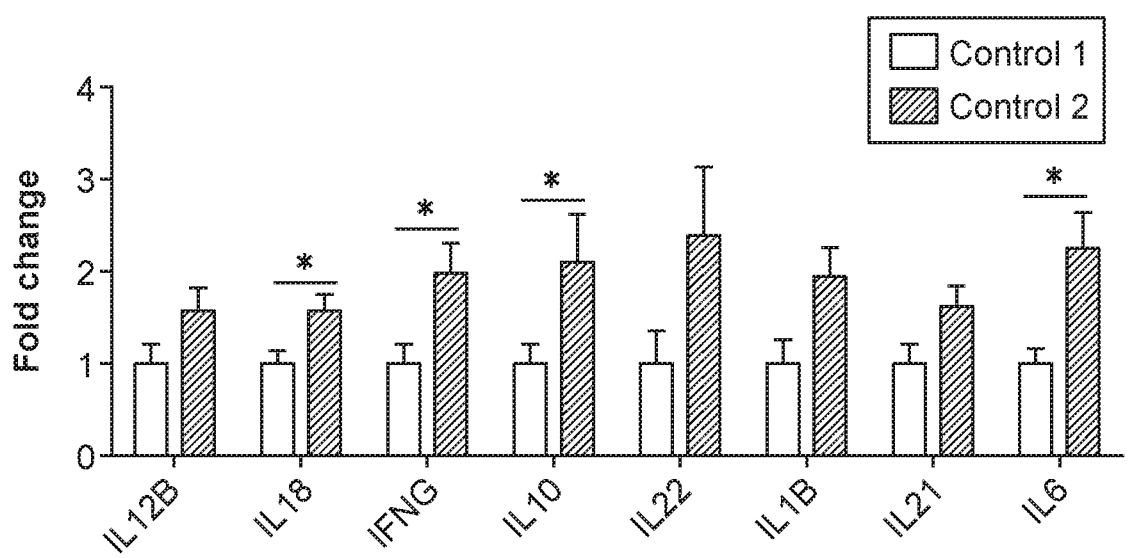
FIG. 20 is a graph showing the fold change of immune and inflammatory cytokine and chemokine expression in Peyer Patch tissue for selected genes with at least a 1.5 fold increase in expression.

Day 7 Peyer patch expression of IL12β, IL18, IFNγ, IL10, IL22, IL1β, IL21 and IL6 for birds in the Control 2 treatment group (Diet Type 2) increased by at least 1.5 fold that of birds in the Control 1 treatment group (Diet Type 1), as illustrated in FIG. 20. Ileal expression of IL12β, IFNγ, IL17α, IL16, IL21, IL8L1 and TNFSF13β were also increased by at least 1.5 fold in the Control 2 treatment group. The cytokine and chemokine expression data were indicative of an inflammatory and immune response for birds in Diet Type 2 exposed to the Eimeria pathogens.

An improved immune response was observed for birds in Treatment Groups 3 and 6, which were fed the oligosaccharide preparations of Examples 9.1 and 9.3, respectively. From cytokine and chemokine expression data, increased adaptive immune system activity corresponding to type-2 T helper cells as well as granulocyte and stem cell stimulation were observed on day 7. Expression data were consistent with increased differentiation of multipotent hematopoietic stem cells into myeloid progenitor cells, increased granulocyte proliferation, and overall activation of T cells, B cells, and mast cells.

By day 14, interleukin expression data were indicative of immune system regulation and anti-inflammatory pathways, including IL9 signaling from regulatory T cells and IL6 anti-inflammatory myokine activity. The expression data were suggestive of an increased adaptive immune response to the Diet Type 2 associated pathogens followed by a more rapid return to homeostasis compared to that of birds in Control Group 2, which were exposed to the pathogenic challenge but not provided oligosaccharide preparations.

Example 32

Restoration of Challenged Gut Barrier Integrity

Multiple oligosaccharide preparations of Example 9 were analyzed with n=6 replicates. For each oligosaccharide preparation, the corresponding supernatant from Example 27 was diluted 1:20 with growth medium, microfiltered through a 0.2 micron filter, and applied to the apical side of the chamber. The control was provided by applying a 1:20 dilution of the growth medium. After 24 hours, a TEER measurement was performed for each oligosaccharide preparation. For each, the change in TEER after treatment versus before treatment was determined. The change in TEER for the control was normalized to 100%.

The effect of oligosaccharides on a leaky gut barrier function was evaluated in vitro. Both the direct effect of the oligosaccharide preparations themselves and the indirect effect of the microbiome products obtained from the oligosaccharide preparations were evaluated. Caco-2 and goblet cells were seeded on a semipermeable insert and inserted into a chamber containing a suitable growth medium and treated with the various oligosaccharide preparations from Example 2 or the corresponding supernatants from Example 3. Barrier integrity was assessed using trans-endothelial electrical resistance and by measuring the permeability of a fluorescent dye.

Figure 21:
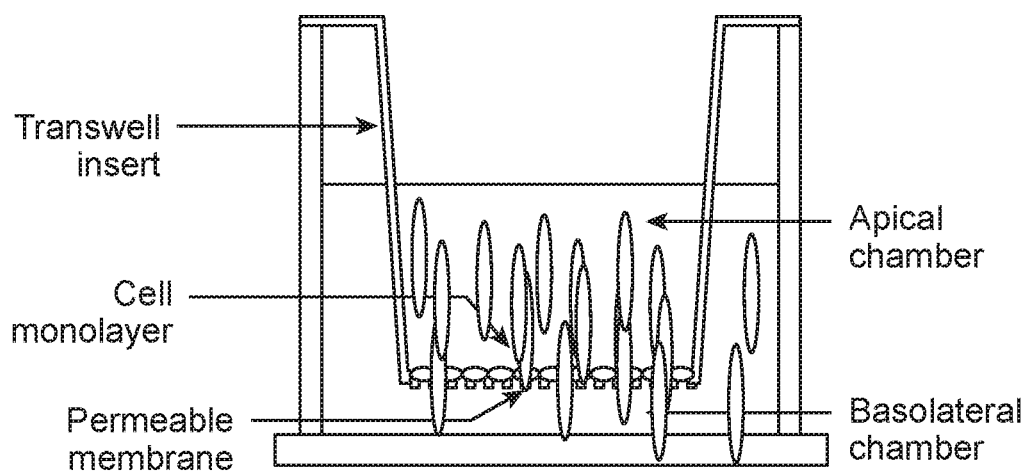
FIG. 21 shows a chamber for in vitro evaluation of the direct and indirect effect of oligosaccharide preparations on disrupted gut barrier function due to a rhamnolipid apical stressor.

Caco-2 and goblet cells were seeded on a semipermeable insert and placed into a chamber containing a suitable growth medium as illustrated in FIG. 21. Oligosaccharide preparations, a negative control comprising only medium, and a positive control comprising only medium were assessed with n=6 replicates. For each, cells were grown for 13 days to achieve a differentiated monolayer. The cells were washed and a TEER measurement was performed to establish the baseline reading. The control was normalized to 100%.

Multiple oligosaccharide preparations of Example 9 were analyzed with n=6 replicates. For each oligosaccharide preparation tested, the corresponding syrup from Example 9 was diluted to 5% with distilled water, further diluted 1:20 with distilled water, microfiltered through a 0.2 micron filter, and applied to the apical side of the chamber. To assess the indirect effect for each oligosaccharide preparation tested, the corresponding supernatant from Example 25 was diluted 1:20 with distilled water, microfiltered through a 0.2 micron filter, and applied to the apical side of the chamber. The control was provided by applying a 1:20 dilution of the growth medium.

Following the baseline TEER reading, a rhamnolipid apical stressor was applied to the apical chamber for each of the oligosaccharide preparations and the positive control. The fluorescent dye Lucifer Yellow was applied to the apical chamber for each of the oligosaccharide preparations, the positive control, and the negative control. After three hours in the presence of the apical stressor and Lucifer Yellow dye, a second TEER measurement was performed to assess the impact of the stressor on the barrier integrity. The barrier permeability was assessed by measuring the extent of Lucifer Yellow permeation from the apical to the basolateral side of the cell layer and membrane.

Statistically significant improvements in the disrupted gut barrier function as measured by TEER and dye permeability were observed for certain oligosaccharide preparations. The improvement in TEER for the various oligosaccharide preparations varied from about 0% to about 30%, relative to the control. Both direct and indirect effects of the oligosaccharide preparations were observed.

In particular, the oligosaccharide preparation of Example 9.3 provided a significant direct reduction in dye permeability relative to the control while the oligosaccharide of Example 9.2 provided a significant indirect reduction in dye permeability relative to control. The oligosaccharide of Example 9.7 provided neither a direct nor indirect reduction in dye permeability and direct application of the oligosaccharide of Example 9.6 exacerbated the barrier function disruption due to the apical stressor.

Example 33

Meta-Analysis of Live Growth Performance Studies in Broiler Chickens

The effect of oligosaccharide preparations on the live growth performance of commercial broiler chickens was assessed in vivo through a series of independent studies conducted across a variety of regions, times of year, background diet types, bird genetics, and management practices including litter handling and coccidiosis-control programs. In each study, birds were allotted to treatment groups including one control group and one or more treated groups. The control group was fed only the background diet. The treated groups were fed the background diet supplemented with a specified dose of the oligosaccharide preparations of Example 9. In selected studies, a commercial feed additive used in the poultry industry was included as a comparative example.

For each study, birds were housed in pens situated within a typical broiler house with a specified number (Hd/Rep) of birds in each pen. Statistical replications were implemented by randomly assigning pens to treatment groups, with a specified number (Reps/Trt) of replications per treatment. Table 17 summarizes the protocol details for each study included in the analysis.

TABLE 17

Protocol details for each study

| Study | Country | Season | Length | Diet Type | Reps/Trt | Hd/Rep | Genetics | Sex | Litter | Cocci Program |
|---|---|---|---|---|---|---|---|---|---|---|
| Ex. 36.1 | USA | Spring | 35 | Corn/Soy | 6 | 14 | Cobb 500 | M/F | Used | Saccox |
| Ex. 36.2 | USA | Winter | 49 | Corn/Soy | 12 | 60 | Cobb 500 | M/F | Used | Maxiban |
| Ex. 36.3 | CA | Winter | 35 | Corn/Soy | 8 | 60 | Ross 708 | M | Used | Saccox |
| Ex. 36.4 | USA | Winter | 49 | Corn/Soy | 12 | 60 | Cobb 500 | M/F | Used | Maxiban |
| Ex. 36.5 | UK | NA | NA | Wheat/Soy | NA | NA | NA | NA | Clean | None |
| Ex. 36.6 | USA | Winter | 33 | Corn/Soy | 12 | 100 | Cobb 500 | M/F | Used | Amprol |
| Ex. 36.7 | USA | Summer | 49 | Corn/Soy | 12 | 18 | Hubbard M99 | M | Used | None |
| Ex. 36.8 | C | Winter | 42 | Corn/Soy | 12 | 17 | Ross308 | Male | Used | Vaccine |
| Ex. 36.9 | GB | Autumn | 42 | Wheat/Soy | 16 | 35 | Ross308 | Male | Fresh | None |
| Ex. 36.10 | FR | Autumn | 42 | Wheat/Soy | 17 | 30 | Ross308 | Male | Fresh | None |
| Ex. 36.11 | US | Autumn | 42 | Corn/Soy | 21 | 40 | Cobb500 | Male | Used | Vaccine |
| Ex. 36.12 | FR | Summer | 36 | Corn/Soy | 12 | 18 | Cobb500 | Male | Fresh | Vaccine |
| Ex. 36.13 | CA | Spring | 42 | Corn/Soy | 10 | 20 | Ross708 | Male | Used | Vaccine |
| Ex. 36.14 | USA | Spring | 42 | Corn/Soy | 14 | 40 | Cobb500 | Male | Used | Vaccine |
| Ex. 36.15 | NZ | Spring | 35 | Wheat/Soy | 12 | 20 | Ross308 | Male | Fresh | Vaccine |

Study outcomes included bird weight (BW), feed intake (FA), feed conversion ratio (FCR), percent mortality (by head), and mortality weight. Pen was the statistical unit. Where possible, spatial blocking was implemented and treatment groups were assigned randomly to blocks.

Background Diets:

Birds were fed in diet phases according to local industry practices for a total study length between 35 and 49 days. Starter phase diets were typically provided as crumble from bird placement through study day 15. All diets were free of antibiotic growth promoters. Starter control diet constructions are described in Table 18 (NA=data not available from site).

TABLE 18

Starter control diet constructions

| Study | % Corn Meal | % Wheat Meal | % Soy Meal | % Corn DDGS | Crude Protein | Crude Fat | AME (kcal/kg) | Lysine (SID) | Methionine (SID) |
|---|---|---|---|---|---|---|---|---|---|
| Ex. 36.1 | 63.5 | NA | 27.4 | NA | 22.1 | NA | 2988 | 1.35 | NA |
| Ex. 36.2 | 0 | NA | 0 | NA | NA | NA | NA | NA | NA |
| Ex. 36.3 | 63.4 | NA | 28.3 | NA | 20.9 | NA | 2940 | 1.14 | NA |
| Ex. 36.4 | NA | NA | NA | NA | NA | NA | NA | NA | NA |
| Ex. 36.5 | NA | NA | NA | NA | NA | NA | NA | NA | NA |
| Ex. 36.6 | 0 | NA | 0 | NA | NA | NA | 3011 | NA | NA |
| Ex. 36.7 | 0 | NA | 0 | NA | NA | NA | NA | NA | NA |
| Ex. 36.8 | 54.52 | 0 | 34.38 | 5 | 22.23 | 2.81 | 2900 | 1.24 | 0.63 |
| Ex. 36.9 | 0 | 51.78 | 30.5 | 0 | 21.31 | 5.74 | 2899 | 1.251 | 0.622 |
| Ex. 36.10 | 0 | 55.1 | 28 | 0 | 22.49 | 5.42 | 2899 | 1.237 | NA |
| Ex. 36.11 | 58.353 | 2.377 | 29.992 | 5 | 20.3 | NA | 2900 | 1.33 | NA |
| Ex. 36.12 | NA | NA | NA | NA | 22 | NA | 3011 | NA | NA |
| Ex. 36.13 | 56.08 | 0 | 34.1 | 5 | 22.23 | 2.31 | 2900 | 1.24 | 0.63 |
| Ex. 36.14 | 58.353 | 0 | 29.992 | 5 | 20.3 | NA | 2900 | 1.33 | NA |
| Ex. 36.15 | 0 | 54.92 | 28.31 | 5 | NA | 6.9 | 2900 | 1.24 | NA |

Grower phase diets were provided as pellets from day 16 through day 24. Grower control diet constructions are detailed in Table 19 (NA=data not available from site).

TABLE 19

Grower phase control diet constructions

| Study | % Corn Meal | % Wheat Meal | % Soy Meal | % Corn DDGS | Crude Protein | Crude Fat | AME (kcal/kg) | Lysine (SID) | Methionine (SID) |
|---|---|---|---|---|---|---|---|---|---|
| Ex. 36.1 | 68.6 | NA | 22 | NA | 19.95 | NA | 3059 | 1.2 | NA |
| Ex. 36.2 | NA | NA | NA | NA | NA | NA | NA | NA | NA |
| Ex. 36.3 | 65.6 | NA | 26.3 | NA | 19.9 | NA | 2988 | 1.06 | NA |
| Ex. 36.4 | NA | NA | NA | NA | NA | NA | NA | NA | NA |
| Ex. 36.5 | NA | NA | NA | NA | NA | NA | NA | NA | NA |
| Ex. 36.6 | NA | NA | NA | NA | NA | NA | 3102 | NA | NA |
| Ex. 36.7 | NA | NA | NA | NA | NA | NA | NA | NA | NA |
| Ex. 36.8 | 54.95 | 0 | 28.31 | 10 | 20.8 | 3.88 | 3000 | 1.11 | 0.56 |
| Ex. 36.9 | 0 | 57.135 | 26 | 0 | 19.01 | 6.55 | 2997 | 1.08 | 0.533 |
| Ex. 36.10 | 0 | 55.77 | 24 | 0 | 20.94 | 7.4 | 2998 | 1.11 | NA |
| Ex. 36.11 | 65.383 | 0.344 | 20.404 | 10 | 17.5 | NA | 3040 | 1.33 | NA |
| Ex. 36.12 | NA | NA | NA | NA | 19 | NA | 3035 | NA | NA |
| Ex. 36.13 | 56.53 | 0 | 28.02 | 10 | 20.8 | 3.39 | 3000 | 1.11 | 0.56 |
| Ex. 36.14 | 65.383 | 0 | 20.404 | 5 | 17.5 | NA | 3040 | 1.14 | NA |
| Ex. 36.15 | 0 | 57.3 | 23.05 | 6 | NA | 6.27 | 3000 | 1.11 | NA |

Finisher phase diets were provided as pellets from day 16 through day 24. Finisher control diet constructions are detailed in Table 20 (NA=data not available from site).

TABLE 20

Finisher phase control diet constructions

| Study | % Corn Meal | % Wheat Meal | % Soy Meal | % Corn DDGS | Crude Protein | Crude Fat | AME (kcal/kg) | Lysine (SID) | Methionine (SID) |
|---|---|---|---|---|---|---|---|---|---|
| Ex. 36.1 | 74.3 | NA | 27.4 | NA | NA | NA | 3155 | 1.06 | NA |
| Ex. 36.2 | NA | NA | NA | NA | NA | NA | NA | NA | NA |
| Ex. 36.3 | 70.8 | NA | 28.3 | NA | NA | NA | 3059 | 0.94 | NA |
| Ex. 36.4 | NA | NA | NA | NA | NA | NA | NA | NA | NA |
| Ex. 36.5 | NA | NA | NA | NA | NA | NA | NA | NA | NA |
| Ex. 36.6 | NA | NA | NA | NA | NA | NA | 3203 | NA | NA |
| Ex. 36.7 | NA | NA | NA | NA | NA | NA | NA | NA | NA |
| Ex. 36.8 | 57.37 | 0 | 24.85 | 10 | 19.4 | 5.16 | 3100 | 1.03 | 0.55 |
| Ex. 36.9 | 0 | 59.94 | 23 | 0 | 17.53 | 7.71 | 3097 | 1.003 | 0.503 |
| Ex. 36.10 | 0 | 87.67 | 21 | 0 | 19.53 | 8.88 | 3099 | 0.994 | NA |
| Ex. 36.11 | 69.41 | 0.12 | 16.879 | 10 | 16 | NA | 3084 | 1.01 | NA |

TABLE 20-continued

Finisher phase control diet constructions

| Study | % Corn Meal | % Wheat Meal | % Soy Meal | % Corn DDGS | Crude Protein | Crude Fat | AME (kcal/kg) | Lysine (SID) | Methionine (SID) |
|---|---|---|---|---|---|---|---|---|---|
| Ex. 36.12 | NA | NA | NA | NA | NA | NA | NA | NA | NA |
| Ex. 36.13 | 58.95 | 0 | 24.56 | 10 | 19.4 | 4.66 | 3100 | 1.03 | 0.55 |
| Ex. 36.14 | 69.41 | 0 | 16.879 | 5 | 16 | NA | 3084 | 1.01 | NA |
| Ex. 36.15 | 0 | 62.02 | 17.62 | 6 | NA | 7.25 | 3100 | 0.99 | NA |

Treatment Groups:

For each study, the treatment groups were designed to compare the effect of oligosaccharide preparations versus the control diet. For selected studies, the treatment groups were designed to assess the dose-response curve for oligosaccharide preparations. Treated diets were obtained by blending a sufficient amount of the corresponding oligosaccharide preparation from Example 9 such that the final oligosaccharide content achieved the specified dose (units of ppm on a dry solids basis). In selected studies, a comparative example (Comp. Ex 36) was provided by a commercial whole yeast product (Diamond V XPC Original). Treatments were allocated according to Table 21.

Live Growth Phase and Sampling:

Feed and water were provided ad libitum. Commercial lighting and temperature programs were implemented in each study according to local industry practices for the corresponding region. Pens were inspected daily and the count and weight of any mortalities was recorded in the study log. No veterinary interventions were required.

For each diet phase, the total pen weight gain, the starting and ending number of birds, and the total feed consumption were measured for each pen. For each pen, the average bird weight (BW) was calculated by dividing the total pen weight by the number of birds in the pen at the time of weighing. For each pen, the feed conversion ratio (FCR) was calculated by dividing the total feed intake over an interval by the total weight gain of the corresponding pen. FCRs were

TABLE 21

Treatment group allocations

| Study | Treatment Group 1 | Treatment Group 2 | Treatment Group 3 | Treatment Group 4 | Treatment Group 5 | Treatment Group 6 | Treatment Group 7 |
|---|---|---|---|---|---|---|---|
| Ex. 36.1 | Control | Ex. 9.7 (500 ppm) | | | | | |
| Ex. 36.2 | Control | Ex. 9.7 (500 ppm) | | | | | |
| Ex. 36.3 | Control | Ex. 9.7 (500 ppm) | | | | | |
| Ex. 36.4 | Control | Ex. 9.7 (500 ppm) | | | | | |
| Ex. 36.5 | Control | Ex. 9.7 (100 ppm) | Ex. 9.7 (500 ppm) | Comp. Ex.36 (1500 ppm) | | | |
| Ex. 36.6 | Control | Ex. 9.7 (500 ppm) | | | | | |
| Ex. 36.7 | Control | Ex. 9.7 (500 ppm) | | | | | |
| Ex. 36.8 | Control | Ex. 9.7 (500 ppm) | Ex. 9.3 (500 ppm) | | | | |
| Ex. 36.9 | Control | Ex. 9.7 (500 ppm) | | | | | |
| Ex. 36.10 | Control | Ex. 9.7 (500 ppm) | Ex. 9.2 (500 ppm) | Ex. 9.3 (500 ppm) | Comp. Ex. 36 (1250 ppm) | | |
| Ex. 36.11 | Control | Ex. 9.7 (500 ppm) | Ex. 9.2 (500 ppm) | Ex. 9.3 (500 ppm) | Ex. 9.4 (500 ppm) | Ex. 9.5 (500 ppm) | Comp. Ex. 36 (1250 ppm) |
| Ex. 36.12 | Control | Ex. 9.7 (500 ppm) | Ex. 9.3 (500 ppm) | | | | |
| Ex. 36.13 | Control | Ex. 9.2 (100 ppm) | Ex. 9.2 (250 ppm) | Ex. 9.2 (500 ppm) | Ex. 9.2 (750 ppm) | Ex. 9.2 (1000 ppm) | |
| Ex. 36.14 | Control (continued, 8-13) | Ex. 9.3 (100 ppm) Ex. 9.2 (100 ppm) | Ex. 9.3 (250 ppm) Ex. 9.2 (250 ppm) | Ex. 9.3 (500 ppm) Ex. 9.2 (500 ppm) | Ex. 9.3 (750 ppm) Ex. 9.2 (750 ppm) | Ex. 9.3 (1000 ppm) Ex. 9.2 (1000 ppm) | Ex. 9.7 (500 ppm) Comp. Ex. 36 (1250 ppm) |
| Ex. 36.15 | Control | Ex. 9.2 (100 ppm) | Ex. 9.2 (250 ppm) | Ex. 9.2 (500 ppm) | Ex. 9.3 (100 ppm) | Ex. 9.3 (250 ppm) | Ex. 9.3 (500 ppm) |

Standard equipment and methods known in the art were used to prepare both the background and treated diets. For the treated diets, oligosaccharide preparations and comparative products were formulated on top of the background diet and added to the mixer pre-pelleting. Oligosaccharide inclusion was confirmed by in-feed assaying.

adjusted for mortalities (FCRma) by adding back the total weight of mortalities during the period. To account for differences in pen weight, FCRma was corrected to a common body weight to obtain the corrected FCR (cFCR) for each pen using methods known in the art. The correction factor was determined for various bird genetics using published BW and FCR performance objectives as a function of growth day for the corresponding genetics.

In selected studies, one bird from each pen was selected randomly for sampling either on day 15 and/or on the final study day. For each sampled bird, 5 mL of blood was drawn from a wing vein into serum vacutainers. After coagulation, serum was recovered by centrifugation, removed, and frozen on dry ice for later processing. Each sampled bird was then euthanized according to local ethical procedures and dissected. Cecal contents were removed to 5 mL conical tubes and immediately flash frozen for microbiome whole genome sequencing and cecal metabolomics. A small resection of ileal tissue was taken, treated to deactivate RNA and frozen for later gene expression analysis.

Example 34

Study Meta-Analysis

A statistical meta-analysis of the in vivo studies of Example 36 was performed to assess the impact of oligosaccharide feed additives and comparative products on bird performance versus birds fed control diets. The analysis employed a mixed linear model with treatment group as the fixed effect and random effects for study nested with block. Statistical analysis was performed in R version 3.4.4 (2018 Mar. 15). Outcomes were assessed by least-squares means, with statistical significance at $P<0.05$. Pairwise comparisons were performed according to Tukey's method and assigned alphabetical labels: a, b, c, d, . . . . Treatments with no common letter in their Tukey grouping label differed significantly under pairwise comparison at $P<0.05$.

Feed Conversion Ratio:

Study effects for cFCR were significant at $P<0.05$. Oligosaccharide treatments provided at least 2.7 pts improvement in cFCR at 500 ppm inclusion over the control diet, versus the comparative example, which provided a 2.2 pts improvement in cFCR at 1250 ppm inclusion. The oligosaccharide of Example 9.4 provided a 6.4 pt improvement in cFCR at 500 ppm inclusion. The results of the meta-analysis for cFCR are presented in Table 22.

TABLE 22

Meta-analysis for cFCR

| Treatment Group | cFCR (lsmean) | SE | df | Tukey Grouping | Δ cFCR (pts vs control) |
|---|---|---|---|---|---|
| Control | 1.6511 | 0.043 | 14 | d | |
| Ex. 9.2 (500 ppm) | 1.6019 | 0.044 | 14 | a | −4.9 |
| Ex. 9.3 (500 ppm) | 1.6106 | 0.044 | 14 | abc | −4.1 |
| Ex. 9.4 (500 ppm) | 1.5876 | 0.044 | 14 | a | −6.4 |
| Ex. 9.5 (500 ppm) | 1.5948 | 0.044 | 14 | ab | −5.6 |
| Ex. 9.7 (500 ppm) | 1.6246 | 0.043 | 14 | bc | −2.7 |
| Comp. Ex. 36 (1250 ppm) | 1.6293 | 0.044 | 14 | c | −2.2 |

Oligosaccharide treatment groups exhibited a higher consistency of effect versus the comparative example, Comp. Ex. 36. For each oligosaccharide included in multiple studies, the consistency of its effect on cFCR was assessed by determining the fraction of studies in which a given value of cFCR improvement versus control was observed. For example, the oligosaccharide of Example 9.2 at 500 ppm inclusion provided at least a 3 pt cFCR benefit in 80% of the studies, at least a 4 pt cFCR benefit in 60% of the studies, at least a 5 pt cFCR benefit in 40% of the studies, and at least a 6 pt cFCR benefit in 40% of the studies. The comparative example at 1250 ppm inclusion provided a 3 pt cFCR benefit in only 25% of the studies, and did not provide a 4 pt cFCR benefit or higher in any of the studies.

TABLE 23

Consistency of effect of treatment group on cFCR

| Treatment Group | 1 pt benefit | 2 pt benefit | 3 pt benefit | 4 pt benefit | 5 pt benefit | 6 pt benefit |
|---|---|---|---|---|---|---|
| Ex. 9.2 (500 ppm) | 100% | 80% | 80% | 60% | 40% | 40% |
| Ex. 9.3 (500 ppm) | 100% | 83% | 67% | 67% | 50% | 33% |
| Ex. 9.7 (500 ppm) | 85% | 85% | 38% | 23% | 15% | 0% |
| Comp. Ex. 36 (1250 ppm) | 100% | 100% | 25% | 0% | 0% | 0% |

A clear dose response between cFCR and the inclusion rate of oligosaccharides in the diet was observed. For the oligosaccharide of Ex. 9.2, a 2.4 pt cFCR benefit was observed at 100 ppm inclusion ($P>0.05$), a 3.7 pt cFCR benefit was observed at 250 ppm inclusion ($P<0.05$), an a 6.4 pt cFCR benefit was observed at 1000 ppm inclusion ($P<0.05$).

Bird Weight

Study effects for BW were significant at $P<0.05$. Oligosaccharide treatments provided at least 48.9 grams increased body weight over the control diet at 500 ppm inclusion, versus the comparative example which provided 39.6 grams increased body weight at 1250 ppm inclusion. The oligosaccharide of Example 9.5 provided 81.8 grams increased BW versus control at 500 ppm inclusion. The results of the meta-analysis for bird weight are presented in Table 24.

TABLE 24

Meta-analysis for Bird Weight

| Treatment Group | BW (lsmean) | SE | df | Tukey Grouping | Δ BW (g vs control) |
|---|---|---|---|---|---|
| Control | 2,755 | 113 | 14 | a | 0 |
| Ex. 9.2 (500 ppm) | 2,817 | 113 | 14 | b | 62.6 |
| Ex. 9.3 (500 ppm) | 2,807 | 113 | 14 | b | 52.6 |
| Ex. 9.4 (500 ppm) | 2,838 | 114 | 14 | b | 83.3 |
| Ex. 9.5 (500 ppm) | 2,837 | 114 | 14 | b | 81.8 |
| Ex. 9.7 (500 ppm) | 2,804 | 113 | 14 | b | 48.9 |
| Comp Ex. 36 (1250 ppm) | 2,794 | 113 | 14 | b | 39.6 |

Flock Uniformity:

Birds fed oligosaccharide preparations at 500 ppm inclusion exhibited improved flock uniformity versus birds fed the control diet. For each treatment group, flock uniformity was assessed by calculating the fraction of bird weights that fell within a range of ±5% around the mean bird weight for its corresponding study. Averaged across all studies 36.1-36.15, 81.7% of birds fed the control diet fell within ±5% of the average bird weight while 91.3% of birds fed diets treated with the oligosaccharide of Ex. 9.2 fell within ±5% of the average bird weight. The uniformity effect was significant at $P<0.01$ as measured by the non-parametric Ansari-Bradley test.

Example 35

Reduced Inflammation and Improved Nutrient Absorption in Broilers Fed Oligosaccharides The effects of oligosaccharides on inflammatory response and nutrient absorption were assessed in vivo in commercial broiler chickens. Day-old male broiler chickens (Cobb 500) were obtained from a commercial hatchery (Joseph Grelier S.A., Elevage avicole de la Bohadière, F-49290 Saint-Laurent de la Plaine, France).

Treatments and Diets:

Birds were fed standard commercial corn/soybean meal diets containing DDGS but free of antibiotic growth promoters and coccidiostats. Diets were fed in two diet phases: Starter Phase diets were fed from days 1 through 22 and were formulated to provide 210 g/kg crude protein and 12.5 MJ/kg ME. Grower Phase diets were fed from days 23 through 36 and were formulated to provide 190 g/kg crude protein and 12.9 MJ/kg ME. All diets were supplemented with phytase feed enzymes (Ronozyme HiPhos) at a standard dose of 100 mg per kg feed.

On the day of arrival (day 1), birds were placed into floor pens with 18 birds per pen and litter provided by wood shavings. Pens were allocated randomly to one of four treatment groups with 12 replicates per treatment. The control group were fed diets containing no added oligosaccharides while treated groups were fed diets obtained by adding oligosaccharides on top of the control diet. The different treatment groups are presented in Table 25.

TABLE 25

Treatment group constructions

| Treatment Group | Oligosaccharide Treatment |
| --- | --- |
| A (Control) | none |
| B | Example 9.1 (500 ppm) |
| C | Example 9.3 (500 ppm) |
| D | Example 9.7 (500 ppm) |

Growth and Sampling:

Birds were housed in an environmentally controlled room with temperature and lighting adapted to the age of the birds. During the first several days of the study an infra-red electric heating lamp was placed in each pen. Feed and water were provided ad libitum, with feed provided as crumbled pellets for the first ten days of the study and as pelleted feed for the remainder of the grow-out. Pen weights and feed intake were recorded on days 1, 22 and 26. Mortalities were recorded daily.

On day 36, one bird was selected randomly from each pen, euthanized and dissected. Ileal contents and cecal contents were collected and immediately frozen for analysis. An approximately 1 square cm of ileal tissue collected about 10 cm below the start of the jejunum and was treated to preserve RNA and genetic material for gene expression analysis.

Figure 22:
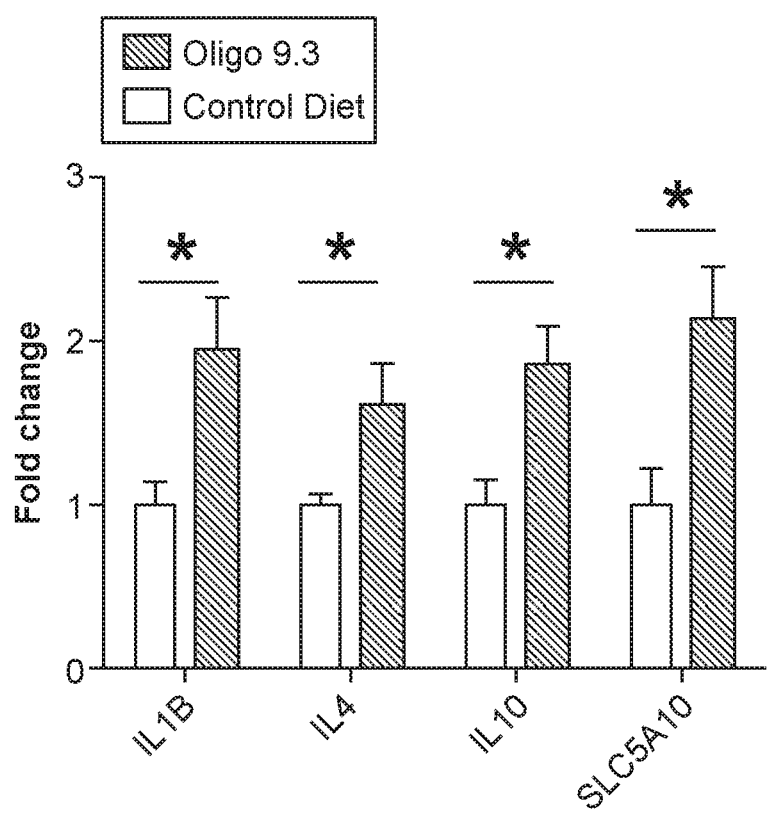
FIG. 22 is a bar graph showing fold change in expression of IL1B, IL4, IL10, and SLC5A10 in birds fed diets containing 500 ppm of the oligosaccharide of Example 9.3 (solid bars) compared to control diet (open bars). The data shows increased gene expression associated with immunity, anti-inflammatory response, and nutrient absorption for birds fed the oligosaccharide of Example 9.3.

Gene Expression Analysis:

Ileal tissue was analyzed using a gut health array to quantify expression levels for 18 genes associated with inflammatory response and immunity, 5 genes associated with gut integrity, and 4 genes associated with nutrient absorption. Gene expression levels were compared between birds fed diets containing oligosaccharides versus those fed the control diet. Statistically significant effects were observed for four genes in birds fed diets containing 500 ppm of the oligosaccharide of Example 9.3 as illustrated in FIG. 22. A 1.5-fold to two-fold increase in the expression of immunity and anti-inflammatory genes IL1B, IL4, IL10 was observed. A two-fold increase in the carbohydrate transporter gene SLC5A10 was observed. These data indicate reduced ileal inflammation and improved nutrient absorption for birds fed the oligosaccharide of Example 9.3 versus birds fed the control diet. By contrast, birds fed diets containing the oligosaccharide of Example 9.1 exhibited an increase in the expression of genes IFNG and IL17B, which are associated with a pro-inflammatory response.

Example 36

Effect of Oligosaccharides on Birds Subject to an Inflammation Challenge

The effects of oligosaccharides on local and systemic immune response, inflammation response, organ health, and gut morphology were assessed in vivo in broiler chickens.

Treatments, Diets, and Inflammatory Challenge

Day-old male birds (Cobb 500) were allocated into battery cages with ten birds per cage. For the first eight days of the study, all birds were fed the same control diet comprising a conventional corn-soy poultry diet supplemented with phytase (Ronozyme HiPhos) at a standard dose of 100 mg per kg feed but free of antibiotic growth promoters and coccidiostats.

Beginning on day 9, cages were assigned to one of four treatment groups with two cages per treatment group. Details of each treatment group are presented in Table 26.

TABLE 26

Treatment group constructions

| Treatment Group | Diet (days 1-8) | Diet (days 9-28) | Inflammatory Challenge | Oligosaccharide Treatment |
| --- | --- | --- | --- | --- |
| A (Control) | Control | Control | None | none |
| B (Challenge) | Control | Challenged | cocci-vac (10x) | none |
| C (Treated 1) | Control | Challenged | cocci-vac (10x) | Example 9.3 (500 ppm) |
| D (Treated 2) | Control | Challenged | cocci-vac (10x) | Example 9.2 (500 ppm) |

Treatment A (the Control Group) continued to receive the same diet as had been fed through day 8. Treatment B (the Challenged Group) was fed the control diet supplemented with 1% potato protein to induce a mild dietary stress on the digestive track. Treatment C was fed the challenged diet supplemented with 500 ppm of the oligosaccharide of Example 9.3. Treatment D was fed the challenged diet supplemented with 500 ppm of the oligosaccharide of Example 9.2.

Birds were housed in an environmentally controlled room with feed and water provided ad libitum. On day 14, all birds in Treatment Groups B, C, and D received a 10× dose of a coccidiosis vaccine (Paracox®-5, MSD Animal Health) to induce a gut inflammatory response by exposure to sporulated oocysts of attenuated *Eimeria acervulina, E. maxima, E. mitis* and *E. tenella*.

Biological Sampling:

On each of days 21 and 28, one cage from each treatment group was removed. The birds from each cage were euthanized and dissected for biological sampling and analysis. Ileal tissue and Peyer patches were collected and processed for gene expression and histological analysis. Blood samples were drawn to analyze the local immune response via lymphocyte phenotyping (Peyer patches) and the systemic immune and inflammation response via measurements of immunoglobin (IgA) and alpha-glycoprotein (an acute phase hepatic response protein). Blood was also analyzed for diamine oxidase (DAO) levels and liver tissue was collected for histology.

By performing the analysis at both one and two weeks following administration of the inflammation challenge provided an assessment of effect of oligosaccharides on both the magnitude and the time-dependence of the animal's immune and inflammatory response.

Ileal Nutrient Absorption

Ileal gene expression analysis revealed that the inflammation challenge of Treatment B significantly degraded ileal absorption of carbohydrate, protein, and phosphorous nutrients. Between a two to three-fold decrease was observed in the expression of transport genes SI, SLC34A2 and SCL15A1 for the challenged group of Treatment B versus the control group of Treatment A at day 21.

Figure 23:
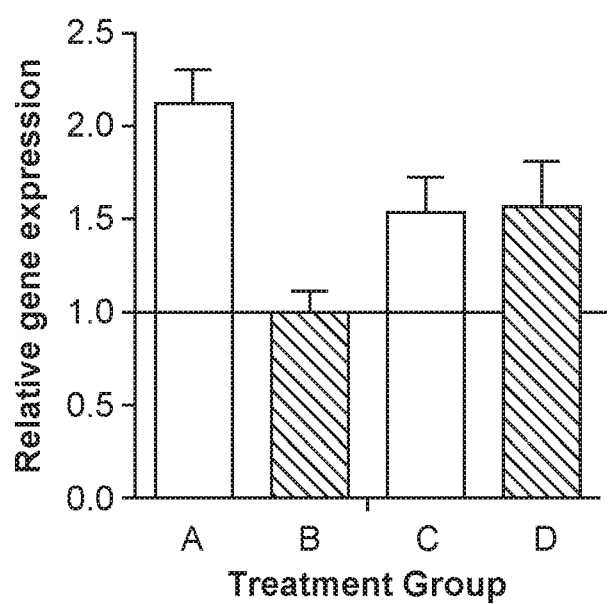
FIG. 23 is a bar graph showing the relative gene expression of SLC34A2 in treatment groups A-B as detailed in Table 26. The data demonstrates that oligosaccharides from Examples 9.2 and 9.3 result in improved ileal absorption of phosphorous as indicated by increased SLC34A2 gene expression analysis.

In contrast, treatment groups C and D, containing the oligosaccharides of Examples 9.3 and 9.2, respectively, exhibited less than half the reduction in ileal absorption. At day 28, phosphorous absorption indicated by SLC34A2 expression for Treatments C and D were statistically similar to the control and improved as shown in FIG. 23.

Ileal Villi Quality and Goblet Cell Counts

Images of ileal tissue sampled from birds in treatment group D versus those in treatment group B are depicted in FIG. 24. Birds in treatment group D exhibited significantly increased villi length and less inflammatory damage as revealed by ileal histology. Therefore, birds fed certain oligosaccharides of Example 9 exhibited an improved resistance to ileal tissue damage resulting from the acute inflammatory challenge compared to birds not fed the oligosaccharides of Example 9.

Figure 25:
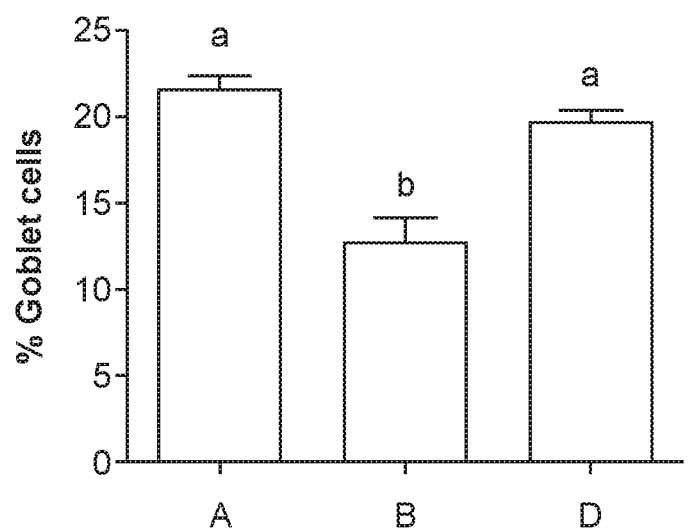
FIG. 25 is a bar graph showing the percentage of goblet cells in treatment Groups A, B, and D (as defined in Table 26). The data shows that oligosaccharides increase goblet cell counts in broilers subject to an inflammatory challenge (Group B).

A significant (P<0.05) increase in ileal goblet cell count was observed in Group D compared to the challenged birds in Group B (FIG. 25). Goblet cells are responsible for mucin production among other key functions of the ileum. Therefore birds fed oligosaccharides fed certain oligosaccharides of Example 9 exhibited improved ability to maintain healthy ileal function resulting from the acute inflammatory challenge compared to birds not fed the oligosaccharides of Example 9.

Figure 26:
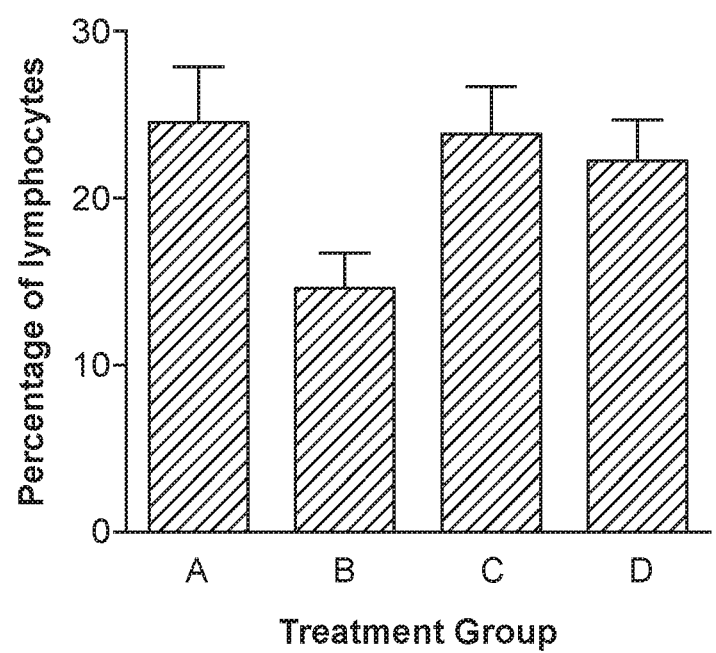
FIG. 26 is a bar graph showing the percentage of lymphocytes from birds in treatment Groups A, B, C, and D (as defined in Table 26). The data shows that broiler chickens treated with selected oligosaccharides of Example 9 promoted increased T-Helper cells, measured as a percentage of total lymphocytes, when subjected to an acute inflammatory challenge.

T-Cell Differentiation:

As illustrated in FIG. 26, birds in Treatment Groups C and D exhibited increased T-Helper cell proliferation compared to those in the challenged Group B. Birds in Group D exhibited a level of T-Helper cells, measured as a percentage of total Peyer Patch lymphocytes, that was statistically indistinguishable from unchallenged birds in Group A. Furthermore, Group C and D birds exhibited a lower percentage of lymphocytes differentiated as T-cytotoxic cells when compared to birds in the challenged Group B.

Figure 27A:
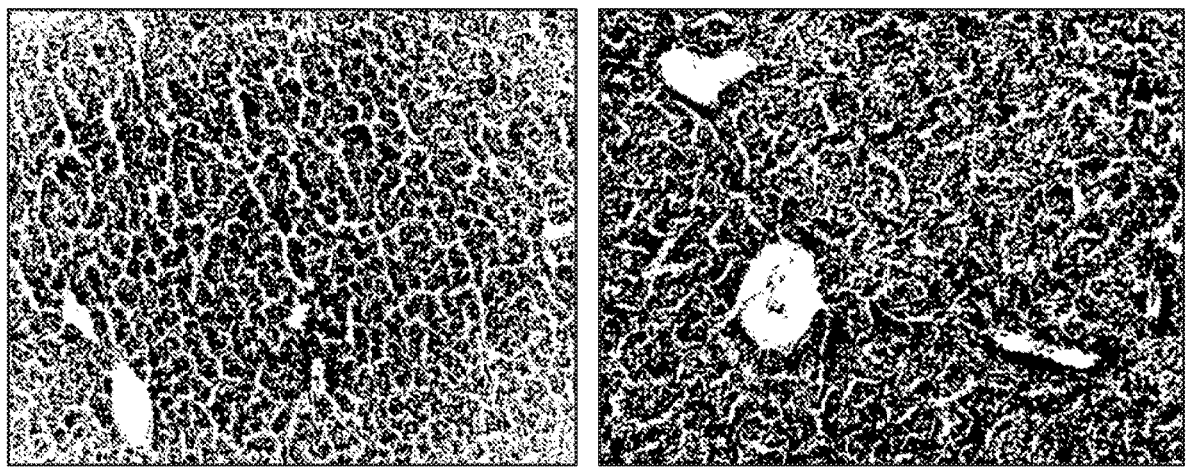
FIG. 27A is a microscopy image of liver tissue from broiler chickens fed a diet containing the oligosaccharide of Example 9.3 with healthy liver tissue (left) and tissue exhibiting inflammatory damage (right).
Figure 27B:
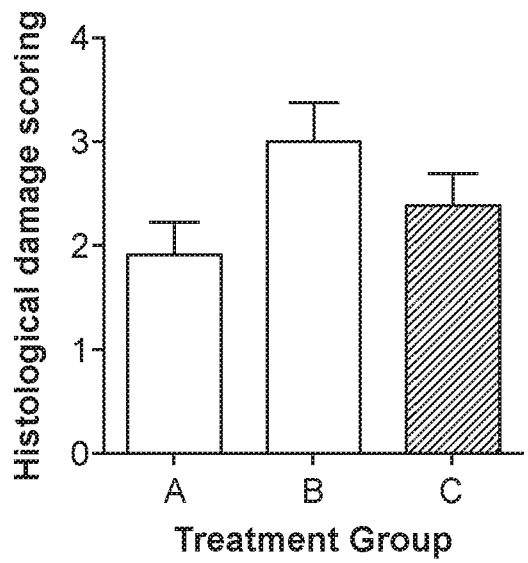
FIG. 27B shows a bar graph of histological damage scoring of liver samples from broilers fed in treatment groups A, B, or C (as defined in Table 26). The data show that treatment Group C (feed containing oligosaccharide of Example 9.3) provides reduced liver damage.
Figure 27C:
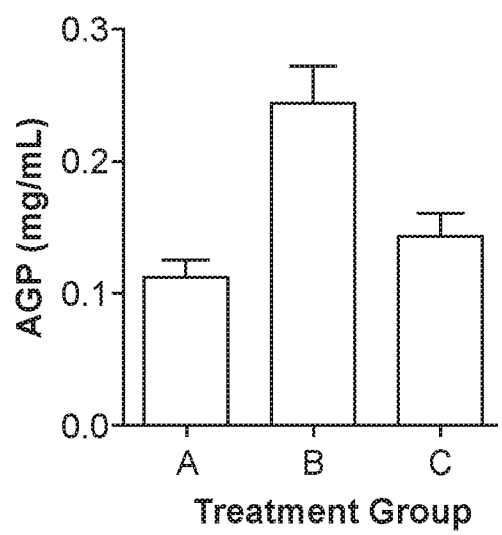
FIG. 27C shows APG level in broiler chickens in treatment Groups A, B, and C (as defined in Table 26). The data shows reduced acute phase hepatic protein AGP when subjected to an inflammatory challenge.
Figure 28A:
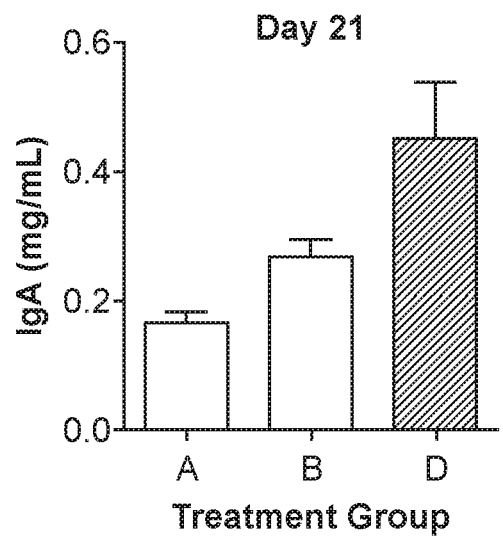
FIG. 28A is a bar graph showing IgA level in blood samples from broiler chicken in treatment Groups A, B, and D at Day 21. The data shows that broiler chickens in treatment Group D exhibited an accelerated immune response at day 21.
Figure 28B:
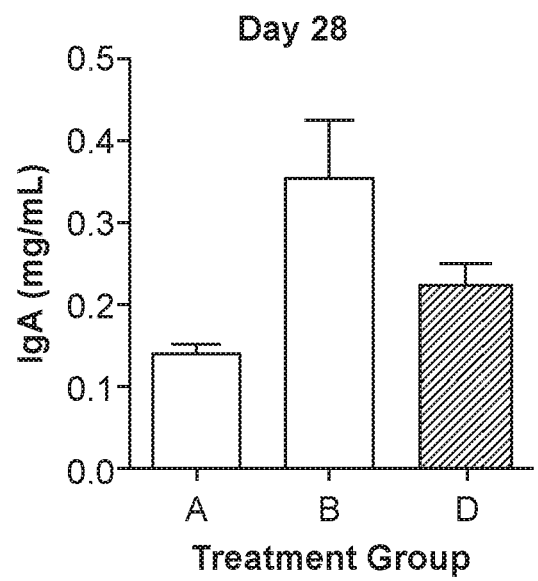
FIG. 28B is a bar graph showing IgA level in blood samples from broiler chicken in treatment Groups A, B, and D at Day 28. The data shows that broiler chickens exhibited a faster recovery toward the control Group A baseline (Day 28) when subjected to an acute inflammation challenge on Day 14.
Figure 29A:
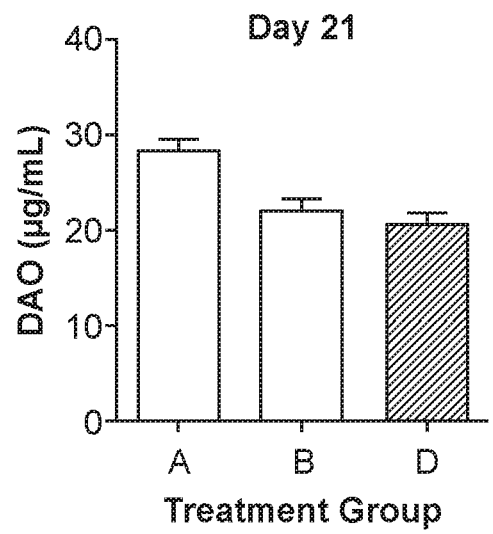
FIG. 29A is a bar graph showing diamine oxidase level in blood samples from broiler chicken in treatment Groups A, B, and D at Day 21. The data shows that broiler chickens exhibited faster recovery toward the control Group A baseline than birds not fed the oligosaccharide when subjected to an acute inflammation challenge on Day 14.
Figure 29B:
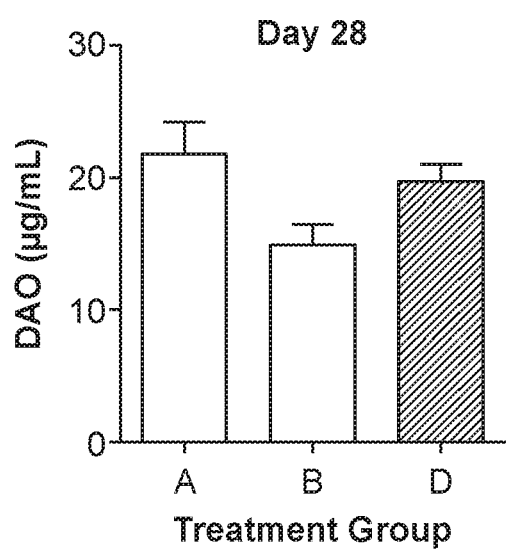
FIG. 29B is a bar graph showing level in blood samples from broiler chicken in treatment Groups A, B, and D at Day 28. The data shows that broiler chickens exhibited faster recovery toward the control Group A baseline than birds not fed the oligosaccharide when subjected to an acute inflammation challenge on Day 14.

Liver Histology and Acute Phase Hepatic Proteins:

Liver histology and blood analysis indicated that birds in Treatment Group C exhibited reduced inflammatory damage compared to those in Group B, indicating that the oligosaccharide of Example 9.3 offered protection against liver damage (FIG. 27A). Histology scoring was performed as illustrated in FIG. 27B. Birds in group C exhibited about a 50% lower increase in liver damage as those in Group B, relative to the unchallenged control Group A. Birds in Group B exhibited a significant increase in circulating the acute phase hepatic alpha-glycoprotein (AGP) (FIG. 27C). By day 28 of the study, birds fed the oligosaccharide of Example 9.3 exhibited blood AGP levels that were statistically indistinguishable from the unchallenged control birds in group A.

Enhanced Recovery Immunoglobin and Diamine Oxidase Levels:

Serum levels of immunoglobin A (IgA) were measured to observe the effect of oligosaccharide preparations on the immune response and speed of recovery of birds subjected to the inflammatory challenge. IgA is an antibody involved in immune function and inflammatory response, particularly of membranes. On day 21, one week following administration of the inflammation challenge, birds in Group B exhibited an increase serum IgA concentration of about 2.25 mg/mL versus about 1.85 mg/mL for the unchallenged control birds in Group A. By contrast, birds in Group D, fed the oligosaccharide preparation of Example 9.2, exhibited an increased IgA response of about 4.4 mg/mL. On day 28, two weeks following administration of the inflammation challenge, birds in Group B exhibited a serum IgA concentration of about 4.35 mg/mL, while birds in Group D exhibited a serum IgA concentration which had decreased to about 2.1 mg/mL. It was concluded that birds fed the oligosaccharide preparation of Example 9.2 exhibited a faster immune response to and a faster recovery from the inflammatory challenge. Serum IgA levels rose faster and decreased back toward the baseline control level of Group A more rapidly than challenged birds in Group B, which were not fed an oligosaccharide preparation.

Serum levels of diamine oxidase (DAO) were measured to observe the effect of oligosaccharide preparations on the inflammatory response and speed of recovery of birds subjected to the inflammatory challenge. DAO involved in histamine regulation and inflammation pathways. On day 21, one week following administration of the inflammation challenge, birds in Groups B and D exhibited about a 25%-30% reduction in serum DAO concentrations relative to a concentration of about 28.5 micrograms/mL for the unchallenged control birds in Group A. The decrease in DAO concentration for Group D birds fed the oligosaccharide of Example 9.2 was numerically greater than those in Group B, which were not fed an oligosaccharide preparation. On day 28, two weeks following administration of the inflammatory challenge, to within experimental error, birds in Group D exhibited a return to the baseline concentration of DAO, as observed in the unchallenged birds of Group A. It was concluded that birds fed the oligosaccharide preparation of Example 9.2 exhibited a similar inflammatory response and a faster recovery to homeostasis compared to birds not fed an oligosaccharide.

Example 37

Microarray Gene Expression Analysis

Ileal gene expression of all known genes in the ileum of broiler chickens was performed by microarray analysis. Ileal tissue from the broilers of Example 36.4 were analyzed to determine the effect of oligosaccharide preparations and doses on ileal gene expression versus that of control birds, which were not fed an oligosaccharide preparation. Tissue samples were obtained according to the methods of Examples 33 and 36.

To prepare for microarray analysis, RNA samples were amplified and labeled in a reaction based on T7 RNA polymerase. The Agilent Low Input Quick Amp Labeling Kit, One-Color was used to generate fluorescent cRNA (complimentary RNA) with a sample input RNA of 100 ng of total RNA for one-color processing. The method employed T7 RNA Polymerase Blend, which simultaneously amplified target material and incorporated Cyanine 3-CTP. Amplification was typically at least 100-fold from total RNA to cRNA.

Double stranded cDNA was generated by reverse transcription is performed in the presence of labeled ribonucleotides, producing microgram quantities of labeled RNA for array hybridization. Labeled cRNA was hybridized onto the microarray slides overnight at a concentration of 1.65 µg per sample. After hybridization (at least 17 hours) the slides are washed and scanned on an Agilent SureScan Microarray Scanner. Data were analyzed using Partek Genomics suite. Mechanistic and ontological grouping was performed as presented in Table 27.

TABLE 27

Mechanistic and ontological grouping

| Mode of Action | Gene Associations |
|---|---|
| Gut Integrity | CLDN1, CLDN2, CLDN3, CLDN5, ZO1, ZO2, MUC2, FOXP1, MUC, OCLN, TFF2, TJP1 |
| Inflammation/ Immunity | ALPI, C5, CCL1, CCL20, CRP, CSF1, CSF2, FASLG, GATA3, IFNG, IL10, IL12A, IL16, IL17A, IL17B, IL18, IL1B, IL2, IL21, IL22, IL3, IL4, IL4, IL5, IL6, IL8L1, LYZ, NoD1, NoS2, TBX21, TGFB2, TLR21, TLR4, TNFSF10, TNFSF13B |
| Nutrient Absorption | SCL15A1, SI, SLC34A2, SLC5A10, MGAM, SLC6A19, SLC6A14, SLC7A9, SLC6A20, SLC6A6, SLC1A1, SLC1A5, SLC38A3, SLC36A1, SLC3A1, SLC38A5 |

Furthermore, an untargeted analysis was performed using a multi-step approach as follows. The ten annotated genes with the highest fold change observed between animals fed the oligosaccharide relative to the control group were identified. The ten annotated genes with the lowest fold change observed between animals fed the oligosaccharide relative to the control group were also identified. Lastly, the ten annotated genes with the highest statistical confidence for differences between animals fed the oligosaccharide versus the control group were analyzed. A pathway analysis was performed against *Gallus gallus* KEGG pathways using genomic and gene expression analysis software (Partek, St. Louis).

Example 38

A Method of Promoting Recovery from Coccidiosis

Coccidiosis is a parasitic disease of the intestinal track of animals caused by exposure to coccidian protozoa, including for example *Eimeria acervuline, Eimeria maxima, Eimeria mitis, Eimeria tenella, Toxoplasma gondii, Hammondia* spp. *Cryptosporidium parvum, Cryptosporidium muris, Cryptosporidium hominis, Isospora canis, Isospora ohioensis, Isospora burrosi, Isospora felis*, and others.

The broiler chickens of Example 36 were exposed to the following levels of sporulated oocysts derived from precocious lines of coccidia: 5,000-6,000 oocysts from *Eimeria acervuline* HP, 2,000-2,300 oocysts of *Eimeria maxima* CP, 1,000-1,300 oocysts of *Eimeria maxima* MFP, 10,000-13,000 oocycsts of *Eimeria mitis* HP, and 5,000-6,500 oocysts of *Eimeria tenella* HP. The exposed birds exhibited a strong inflammatory response, as observed by serum IgA, serum DAO, liver histology, and gut lumen histology of Example 36.

The birds in Group D of Example 36, which were fed 500 ppm of the oligosaccharide preparation of Example 9.2 exhibited significantly reduced intestinal and liver damage and a faster recovery to homeostasis compared to untreated birds. Birds fed oligosaccharide treatments also exhibited improved nutrient absorption and improved T-cell differentiation compared to the untreated challenged birds of Group B.

Example 39

A Method of Improving Tolerance to Coccidiosis Vaccines

The birds of Example 35 exhibited reduced liver damage, improved gut histology, improved nutrient absorption, and a faster inflammatory recovery when exposed to a 10× dose of a commercial coccidiosis vaccine used in the broiler industry.

Example 40

Replicate Batches Scale-Up for Manufacturing

The production scale of oligosaccharide preparations was increased to that of a 720 L overhead-stirred tank reactor. Twelve batch reactions using a scaled-up procedure derived from those of Example 9.2 were performed at the 720 L scale. The resulting oligosaccharide preparations were characterized against pre-determined QC acceptance criteria to perform batch qualification and to assess the process stability.

For the twelve batches, process conditions such as temperature, reaction time, and reaction pressure were varied intentionally in a range around the nominal conditions of Example 9.2 to assess the sensitivities of the resulting product to reasonable variations in the process conditions that might be expected in atypical manufacturing environment. For select batches, an in situ viscosity probe was used to monitor the time dependence of the viscosity of the reactor contents. In certain batches, the reaction stopping time employed an in-process control (IPC) based on the continuous viscosity measurement. Material amounts, including the dispensed quantities of reactants, distillation water, and evolved condensate were measured either by mass via load cells on the reactor and auxiliary tanks or volumetric flow and time.

The final water content of the reactor product was measured by Karl Fisher titration for a representative aliquot of the reactor contents drawn at the end of the reaction, i.e., prior to pH neutralization and dilution. At a reaction temperature of 120° C., the water content of the reaction product was determined to be 8 and 9 wt % water on an as-is basis. At a reaction temperature of 130° C., the water content of the reaction product was determined to be between 5 and 7 wt % water on an as-is basis.

The resulting oligosaccharide syrup appearance of all the batches was determined by visual inspection as a caramel syrup. The total dissolved solids content was determined by Karl-Fisher titration, the residual monomer content, MWn and MWw were determined by HPLC/GPC chromatography, the pH was determined by calibrated pH meter and the anhydro-DP2 content was determined by LC-MS/MS. As shown in Table 28, the following batch characterization data were obtained (N/R="data not reported"):

TABLE 28

Characterization of Oligosaccharide Preparations

| Batch | wt % DS | pH | Residual Catalyst | wt % DP1 | MWn | MWw | Anhydro DP2 Content (g Anhydro DP2/ g total DP2) |
|---|---|---|---|---|---|---|---|
| 27.1 | 66.4 | N/D | N/R | 17.5 | 777 | 1218 | 0.84% |
| 27.2 | 68.8 | 3.3 | N/R | 17.9 | 735 | 1091 | 0.91% |
| 27.3 | 69.4 | 3.1 | 0.095 | 14.8 | 807 | 1276 | N/R |

TABLE 28-continued

Characterization of Oligosaccharide Preparations

| Batch | wt % DS | pH | Residual Catalyst | wt % DP1 | MWn | MWw | Anhydro DP2 Content (g Anhydro DP2/ g total DP2) |
|---|---|---|---|---|---|---|---|
| 27.4 | 71.0 | N/D | 0.068 | 15.5 | 793 | 1241 | 1.04% |
| 27.5 | 70.9 | 3.2 | 0.057 | 15.8 | 777 | 1196 | 1.15% |
| 27.6 | 70.9 | 3.3 | N/R | 16.3 | 773 | 1170 | N/R |
| 27.7 | 70.7 | 3.0 | N/R | 15.7 | 783 | 1226 | 1.13% |
| 27.8 | 70.5 | 3.9 | N/R | 16.1 | 785 | 1182 | 1.09% |
| 27.9 | 71.1 | 4.1 | N/R | 17.1 | 761 | 1169 | 1.09% |
| 27.10 | 70.4 | 4.1 | N/R | 16.3 | 778 | 1193 | 1.15% |
| 27.11 | 70.5 | 4.7 | N/R | 18.6 | 696 | 995 | 1.33% |
| 27.12 | 70.9 | 3.9 | N/R | 16.7 | 769 | 1194 | 1.12% |

Example 41 pH Adjustment of an Oligosaccharide Preparation

The pH of the oligosaccharide preparation of Example 9.2 at 50 wt % solids content was determined in triplicate by diluting 5.00±0.05-gram aliquots of the oligosaccharide preparation with 1.80±0.02 mL of deionized water and mixing by vortex agitation to obtain a uniform concentration. The pH of each aliquot was measured with a calibrated pH meter (VWR, Symphony B30PCI) to obtain an average reading of 2.4 pH units.

To 1.2 kg of the oligosaccharide preparation of Example 9.2 was added 6.53 mL of 1.0 molar aqueous sodium hydroxide solution. The resulting mixture was mixed vigorously to achieve a uniform pH-adjusted syrup. The pH of the resulting adjusted syrup at 50 wt % solids content was then determined in triplicate as described above to obtain an average of 4.1 pH units.

The pH adjustment procedure was repeated for replicate batch syntheses at various scales, but with certain variations in the procedure by which the base was provided to the product oligosaccharide composition. For one batch, the pH adjustment was performed as the final step of the reaction, prior to the dilution of reaction water. In another batch, the pH adjustment was performed concurrently with the dilution step by first dissolving the required amount of base in the dilution water; the base and dilution water were therefore added together to quench the reaction a single step to produce a final syrup at the desired pH. In another batch, the base was provided as food-grade sodium hydroxide pellets. In another batch, 10 ppm of a food-grade silicone emulsion (Dow Xiameter AFE-0100) was added to the reaction prior to dilution and pH adjustment.

Example 42

Preparation of a Glass Powder Formulation of an Oligosaccharide Preparation

Approximately 50 grams of the oligosaccharide preparation of Example 9.1 was dispensed onto a drying tray and placed in a forced-air convection heater at 60° C. to produce a caramel colored brittle glass. The glass was removed from the drying tray and ground with a shear rotary mill to yield a light-orange colored flowable powder. The particle size of the powder was determined by sieving to be between 100 and 2000 microns, with 90% of the mass below 1350 microns. The true density of the coarse milled powder was determined by Helium Pycnometry to be 1.3063 g/mL. The resulting powder was observed to be flowable.

The formulation procedure was repeated using a hammer mill to obtain a fine powder with 90% of the mass of the powder exhibiting a particle size below 196 microns. The true density of the fine milled powder was determined to be 1.5263 g/mL. The resulting powder was neither stable nor flowable.

DSC measurements were performed on the powders using two temperature cycling programs. In the first program, temperature was ramped to 160° C. from 0° C. at a rate of 5° C./min, then annealed back to 0° C. at a rate of −5° C./min, followed by a final heating back to 160° C. In the second program, the temperature was ramped to 50° C. from −50° C. at a rate of 5° C./min, annealed to −60° C. at a rate of −5° C./min and then heated to 60° C. at a rate of 5° C./min. The powder was observed to exhibit a glass transition temperature of between 20 and 40° C., dependent on the residual water content of the solid between 5 and 10 wt % moisture.

The milling formulation process was repeated for each of the oligosaccharide preparations of Example 9.2, Example 9.3, Example 9.4, and Example 9.5. The powders readily re-dissolved in water and alcohol-water mixtures, but were insoluble in acetone, methanol, and anhydrous ethanol.

Example 43

Preparation of a Carrier-Loaded Powder Formulation

Equal masses of a 70 wt % aqueous syrup of the oligosaccharide preparation of Example 9.2 and diatomaceous earth were combined at room temperature to yield a stable, flowable powder. The resulting powder comprised about 35 wt % adsorbed oligosaccharide (dry solids basis) and about 50 wt % carrier. The particle size distribution of the powder was measured by sieving. 10% by weight of the powder exhibited a particle size below 290 micrometers, 50% by weight of the powder exhibited a particle size below 511 micrometers, and 90% by weight of the powder exhibited a particle size below 886 micrometers. The powder was stable to segregation and cohesion, as determined using standard aeration and compressibility tests. The true density of the resulting powder was measured by Helium pycnometry to be 1.8541 g/mL.

The carrier loading formulation was repeated using feed-grade silica to yield a stable, flowable powder with a loading of at least 50 wt % oligosaccharide preparation (dry solids basis) with respect to the final powder. The true density of the resulting powder was measured to be 1.5562 g/mL.

Example 44

Preparation of an Extruded Solid Form

A solid extruded product was prepared by blending 20% of the oligosaccharide preparation of Example 9.2 with semolina and formulated the mixture through a jacketed twin-screw dye extruder to form a flowable powder with a particle size between 0.2 mm and 3.0 mm, with 90% of the mass below 2 mm particle size. The resulting powder was observed to be free-flowing and stable.

Example 45

Preparation of Stable Powder Formulations

The solid formulations, including those of Examples 42-44, were assessed to determine their stability and hygroscopicity. The powders of Examples 43 and 44 were observed to be stable to segregation and agglomeration, while the coarse milled powder of Example 42 was observed to be unstable with respect to segregation.

Sample of each powder formulation to be tested were placed in a sealed climate chambers at 50% relative humidity and 65% relative humidity for up to two-weeks exposure at 25° C. Of the forms tested, several exhibited little or no mass gain upon exposure to humidity and remained flowable after the two-week exposure period. The fine-milled powder of Example 43 was found to be unstable with exposure to humidity.

Example 46

Determination of Residual Catalyst in Oligosaccharide Preparations

The residual acid catalyst content of oligosaccharides preparations was determined by Ion Chromatography. Between 80 and 100 milligrams of a powder formulation of the oligosaccharide preparation (obtained for example as described in Example 42) were dissolved in exactly 1.00 milliliter and centrifuged to remove particulates if necessary. The resulting solution was analyzed by ion chromatography at 30° C. using a Thermo Dionex ICS-3000 System equipped with conductivity detection, a 4×250 mm Ion Pac AS19A column, an Ion Pac AS19G 50 4×50 mm pre-column and a continuously regenerated CR-ATC anion trap column using KOH in water as the eluent. Elution was conducted at 10 mM KOH for the first ten minutes after injection followed by a gradient elution increasing linearly to 55 mM KOH at 25 minutes, then decreasing to 10 mM KOH at 26 minutes, and remaining at 10 mM KOH until the end of the program.

For the oligosaccharide preparation of Example 9.2, the concentration of residual catalyst was determined by reference to a standard calibration curve generated using an authentic sample of (+)-camphor-10-sulfonic acid. A representative batch of the oligosaccharide preparation of Example 9.2 was analyzed and the residual catalyst concentration was determined to be 0.62 mg per gram of 70 wt % syrup.

Example 47

Qualification of the Residual Catalyst Concentration for Batch Acceptance

The residual catalyst determination of Example 46 was compared against a batch acceptance criterion to determine suitability of the batch for further use. The acceptance limit for the concentration of residual catalyst in the product oligosaccharide preparation was preestablished to be <1.0 mg per gram product syrup. The measured value of the residual catalyst was 0.62 mg per gram of product syrup. Therefore, the acceptance criterion was met for the tested batch and the batch was accepted for further use.

Example 48

Formulation of a Syrup Product

The oligosaccharide preparation of Example 9.7 was pH adjusted to a pH of 4.2 with food grade sodium hydroxide according to the procedure of Example 41. The resulting syrup was packaged into a 20 liter carboy with a tamper-resistant cap. Immediately prior to sealing the container, a 500 gram sample was taken and subjected to quality testing. The total solids content of the syrup was confirmed to be greater than 70 wt %, per the methods of FCC APPENDIX X: Carbohydrates (Starches, Sugars, and Related Substances): TOTAL SOLIDS. The reducing sugar content was confirmed to be less than 50% as D-glucose on a dry weight basis according to the method of FCC APPENDIX X: Carbohydrates (Starches, Sugars, and Related Substances): REDUCING SUGARS ASSAY. Sulfated ash was confirmed to be less than 1% on a dry weight basis using the method of FCC APPENDIX II: Physical Tests and Determinations: C. OTHERS: RESIDUE ON IGNITION (Sulfated Ash) Method II (for Liquids). The sulfur dioxide content was confirmed below 40 mg/kg using an optimized Monier Williams method. The lead content was confirmed to be below 1 mg/kg using the method of AOAC International Official Method 2013.06. The total aerobic plate count was confirmed to be below 1000 cfu/g using the methods of CMMEF Chapter 7. Total yeast and mold were confirmed below 100 cfu/g using the method of AACC International Approved Method 42-50. Coliforms were confirmed below 10 MPN/g using the method of the FDA BAM Chapter 4. *E. coli* was confirmed below 3 MPN/g using the method of FDA BAM Chapter 4. *Salmonella* was confirmed to be not detected per a 25 gram sample according to the method of FDA BAM Chapter 5. *Staphylococcus aureus* was confirmed to be below 10 cfu/g using the method of FDA BAM Chapter 12. Color was confirmed by visual inspection to be caramel. The container was sealed, the remaining retention sample was frozen and stored for future reference, and a certificate of analysis was issued for the resulting lot.

Example 49

Preparation of Treated Drinking Water

Drinking water containing 250 ppm of the oligosaccharide preparation of Example 9.7 was prepared as follows. 37 mL of the oligosaccharide syrup of Example 41 and 40 grams of potassium sorbate were added gradually to 50 gallons of potable tap water in a 55 gallon blue-poly drum. The solution was mixed manually using a paddle for 10 minutes at room temperature.

The method was repeated without the incorporation of potassium sorbate.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein can be employed in practicing the invention. It is therefore contemplated that the invention shall also cover any such alternatives, modifications, variations or equivalents.

What is claimed is:

1. A method of treating a gastrointestinal barrier dysfunction or decreasing the permeability of a gastrointestinal barrier, in an animal in need thereof, the method comprising: administering a nutritional composition that comprises a base nutritional composition and a synthetic oligosaccharide preparation to said animal, the synthetic oligosaccharide preparation comprising at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry, wherein said anhydro-subunit containing oligosaccharides are selected from the group consisting of anhydro-glucose, anhydro-galactose, anhydro-mannose and anhydro-fructose, to thereby treat said gastrointestinal barrier dysfunction or decrease the permeability of said gastrointestinal barrier.

2. The method of claim 1, wherein permeability of a gastrointestinal barrier of said animal is decreased relative to permeability of said gastrointestinal barrier of said animal prior to said administering said synthetic oligosaccharide preparation.

3. The method of claim 2, wherein said decrease is at least about a 0.5%, 1%, 2%, 3%, 4%, 5%, 10%, 15%, 20%, 25%, or 30% decrease relative to said permeability of said gastrointestinal barrier of said animal prior to said administering said synthetic oligosaccharide preparation.

4. The method of claim 3, wherein said permeability of said gastrointestinal barrier is determined from a blood, fecal, or urine sample from said animal.

5. The method of claim 4, wherein said permeability is measured by determining a level of at least one microbial species in said blood, fecal, or urine sample.

6. The method of claim 4, wherein said decrease permeability of said gastrointestinal barrier is mediated indirectly by said synthetic oligosaccharide preparation.

7. The method of claim 1, wherein at least one symptom associated with said gastrointestinal barrier dysfunction is ameliorated.

8. The method of claim 1, wherein said gastrointestinal barrier dysfunction is associated with or caused by an infection.

9. A method of treating an infection in an animal in need thereof, the method comprising: administering a nutritional composition comprising a base nutritional composition and a synthetic oligosaccharide preparation to said animal, the synthetic oligosaccharide preparation comprising at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry, wherein said anhydro-subunit containing oligosaccharides are selected from the group consisting of anhydro-glucose, anhydro-galactose, anhydro-mannose and anhydro-fructose, to thereby treat said infection.

10. The method of claim 9, wherein a level of at least one immune cell in a sample from said animal is increased relative to a level of said at least one immune cell in a sample from said animal prior to administration of said nutritional composition that comprises said synthetic oligosaccharide preparation.

11. The method of claim 10, wherein said increase is at least 1%, 2%, 3%, 4%, 5%, 6%, 7%, 8%, 9%, or 10% increased relative to said level of said at least one immune cell prior to administration of said nutritional composition comprising said synthetic oligosaccharide preparation.

12. The method of claim 11, wherein a level of at least one pro-inflammatory cytokine in a sample from said animal is increased relative to a level of said at least one pro-inflammatory cytokine in a sample from said animal prior to administration of said nutritional composition that comprises said synthetic oligosaccharide preparation.

13. The method of claim 12, wherein permeability of a gastrointestinal barrier of said animal is decreased relative to permeability of said gastrointestinal barrier of said animal prior to said administering said synthetic oligosaccharide preparation.

* * * * *